US008975489B2

(12) United States Patent
Craven

(10) Patent No.: US 8,975,489 B2
(45) Date of Patent: Mar. 10, 2015

(54) GRASS FUNGAL ENDOPHYTES AND USES THEREOF

(75) Inventor: Kelly Craven, Ardmore, OK (US)

(73) Assignee: The Samuel Roberts Noble Foundation, Ardmore, OK (US)

( * ) Notice: Subject to any disclaimer, the term of this patent is extended or adjusted under 35 U.S.C. 154(b) by 218 days.

(21) Appl. No.: 13/306,841

(22) Filed: Nov. 29, 2011

(65) Prior Publication Data

US 2012/0144533 A1 Jun. 7, 2012

Related U.S. Application Data

(60) Provisional application No. 61/419,242, filed on Dec. 2, 2010.

(51) Int. Cl.

| | |
|---|---|
| ***A01H 5/00*** | (2006.01) |
| ***A01H 5/10*** | (2006.01) |
| ***A01H 15/00*** | (2006.01) |
| ***A01N 65/44*** | (2009.01) |
| ***C12N 1/14*** | (2006.01) |
| ***A23K 1/00*** | (2006.01) |
| ***A01N 63/04*** | (2006.01) |
| ***C10L 1/02*** | (2006.01) |
| ***C12P 7/10*** | (2006.01) |
| ***C12R 1/645*** | (2006.01) |

(52) U.S. Cl.

CPC ................ *A23K 1/009* (2013.01); *A01N 63/04* (2013.01); *A23K 1/006* (2013.01); *C10L 1/02* (2013.01); *C10L 1/023* (2013.01); *C12P 7/10* (2013.01); *C12R 1/645* (2013.01); *Y02E 50/16* (2013.01); *Y02E 50/30* (2013.01)

USPC ........ 800/320; 435/254.1; 435/267; 435/161; 504/117; 800/278; 800/289; 800/320.1; 800/320.2; 800/320.3

(58) Field of Classification Search

None

See application file for complete search history.

(56) References Cited

U.S. PATENT DOCUMENTS

| | | | | |
|---|---|---|---|---|
| 5,880,343 A * | 3/1999 | Hiruma et al. | ................ | 800/320 |
| 2010/0024076 A1 | 1/2010 | Craven | | |

OTHER PUBLICATIONS

Kawai (GenBank Accession No. AB518683.1, first available online Aug. 30, 2009).*

Dashtban et al (Int J Biochem Mol Biol 1(1):36-50, first available online May 23, 2010).*

Chen et al (Functional Plant Biology, 2004, 31, 235-245).*

Dien et al (Bioenerg. Res. (2009) 2:153-164).*

USDA Technical Notes, Agronomy #35, NRCS- Iowa, published Jan. 2009.*

Gardes et al. "ITS primers with enhanced specificity for Basidimycetes—application to the identification if mycorrhizae and rusts." *Molec Ecol.* 2:113-118, 1993.

Ghimire et al. "Biodiversity of fungal endophyte communities inhabiting switchgrass (*Panicum virgatum* L.) growing in the native tallgrass prairie of northern Oklahoma." *Fungal Diversity.* 47(1), 19-27, 2010.

Khu et al., "QTL mappig of aluminum tolerance in tetraploid alfalfa," Joint Meeting of the 41st North American Alfalfa Improvement Conference & 20th Trifolium Conference, Dallas, Texas, Jun. 2, 2008 (Abstract).

Martin et al. "Fungal-specific PCR primers developed for analysis of the ITS region of environmental DNA extracts." *BMC Microbiol.* 5:28-38, 2005.

Selosse et al., "Sebinales are common mycorrhizal associates of Ericaceae," *New Phytologist*, 174(4):864-878, 2007.

White et al. "Amplification and direct sequencing of fungal ribosomal RNA genes for phylogenetics." In: PCR Protocols: A guide to methods and applications (eds. Innis MA, Gelfand DH, Sninsky JJ, White TJ). Academic Press Inc., New York, 1990.

* cited by examiner

*Primary Examiner* — David T Fox
*Assistant Examiner* — Lee A Visone
(74) *Attorney, Agent, or Firm* — Dentons US LLP

(57) ABSTRACT

The invention provides isolated fungal endophytes and synthetic combinations thereof with host grass plants. Methods for inoculating grass plant with the endophytes, for propagating the grass-endophyte combinations, and for producing feeds and biofuels from grass-endophyte combinations are also provided.

31 Claims, No Drawings

SEQUENCE LISTING

<160> NUMBER OF SEQ ID NOS: 555

<210> SEQ ID NO 1
<211> LENGTH: 573
<212> TYPE: DNA
<213> ORGANISM: Fusarium nygamai

<400> SEQUENCE: 1
ggaagtaaaa gtcgtaacaa ggtctccgtt ggtgaaccag cggagggatc attaccgagt 60
ttacaactcc caaacccctg tgaacatacc aattgttgcc tcggcggatc agcccgctcc 120
cggtaaaacg gaacggcccg ccagaggacc cctaaactct gtttctatat gtaacttctg 180
agtaaaacca taaataaatc aaaactttca acaacggatc tcttggttct ggcatcgatg 240
aagaacgcag caaaatgcga taagtaatgt gaattgcaga attcagtgaa tcatcgaatc 300
tttgaacgca cattgcgccc gccagtattc tggcgggcat gcctgttcga gcgtcatttc 360
aaccctcaag cccccgggtt tggtgttggg gatcggcgag cctcacggca agccggcccc 420
gaaatacagt ggcggtctcg ctgcagcttc cattgcgtag tagtaaaacc ctcgcaactg 480
gtacgcggcg cggccaagcc gttaaacccc caacttctga atgttgacct cggatcaggt 540
aggaataccc gctgaactta agcatatcaa taa 573

<210> SEQ ID NO 2
<211> LENGTH: 598
<212> TYPE: DNA
<213> ORGANISM: Emericellopsis terricola

<400> SEQUENCE: 2
ctattgatat gcttaagttc agcgggtatt cctacctgat ctgaggtcaa ccttgagaag 60
tggggtgttt tacggcgtgg ccagcccgct cgtcccttct gcgaggtagt gttactacgc 120
aggggagtct gtgggagacc gccactgtgt ttcggggacg gccgccgcga ggacggccgg 180
gccccaacgc cagcgccccg cgaacggggg ctgagggttg aaatgacgct cagacaggca 240
tgcccgccag aatactggcg ggcgcaatgt gcgttcaaag attcgatgat tcactgaatt 300
ctgcaattca cattacttat cgcatttcgc tgcgttcttc atcgatgcca gaaccaagag 360
atccgttgct gaaagttttg tttatttttg cttatgccac tcagaggaga cactagaaaa 420
caagagtttg gttccccggc gggcgcctgg atccgggtca cgccacgagg gcgcgccgcg 480
ggacggtccg ccgaagcaac ataggtatgt tcacaggggt ttgggagttg gataactcag 540
taatgatccc tccgctggtt caccaacgga gaccttgtta cgacttttac ttcctcaa 598

<210> SEQ ID NO 3
<211> LENGTH: 579
<212> TYPE: DNA
<213> ORGANISM: Cladosporium colombiae

<400> SEQUENCE: 3
tcttggtcat ttagaggaag taaaagtcgt aacaaggtct ccgtaggtga acctgcggag 60
ggatcattac aagtgacccc ggtttaccac cgggatgttc ataacccttt gttgtccgac 120
tctgttgcct ccggggcgac cctgccttcg ggcgggggct ccgggtggac acttcaaact 180
cttgcgtaac tttgcagtct gagtaaactt aattaataaa ttaaaacttt taacaacgga 240
tctcttggtt ctggcatcga tgaagaacgc agcgaaatgc gataagtaat gtgaattgca 300
gaattcagtg aatcatcgaa tctttgaacg cacattgcgc cccctggtat tccgggggc 360 atgcctgttc gagcgtcatt tcaccactca agcctcgctt ggtattgggc aacgcggtcc 420

```
gccgcgtgcc tcaaatcgac cggctgggtc ttctgtcccc taagcgttgt ggaaactatt    480

cgctaaaggg tgctcgggag gctacgccgt aaaacaaccc catttctaag gttgacctcg    540

gatcaggtag ggatacccgc tgaacttaag catatcata                           579


<210> SEQ ID NO 4
<211> LENGTH: 561
<212> TYPE: DNA
<213> ORGANISM: Uncultured Ascomycete sp.

<400> SEQUENCE: 4

cttattgata tgcttaagtt cagcgggtat ccctacctga tccgaggtca agagtgtaaa     60

aatgtacttt tggacgtcgt cgttgtgagt gcaaagcgcg agatgtactg cgctccgaaa    120

tcaatacgcc ggctgccaat tgttttgagg cgagtctgcg cgcagaggcg agacaaacac    180

ccaacaccaa gcagagcttg aaggtacaaa tgacgctcga acaggcatgc cccatggaat    240

accaaggggc gcaatgtgcg ttcaaagatt cgatgattca ctgaattctg caattcacac    300

tacttatcgc atttcgctgc gttcttcatc gatgccagaa ccaagagatc cgttgttgaa    360

agttgtaact attaagtttg ttcagacgct gattgcaact gcaaatggtt taaattgtcc    420

aatcggcggg cggacccgcc gaggaaacga aggtactcaa aagacatggg taagagatag    480

caggcaaagc ctacaactct aggtaatgat ccttccgcag gttcacctac ggaaaccttg    540

ttacgacttt tacttcctct a                                              561


<210> SEQ ID NO 5
<211> LENGTH: 515
<212> TYPE: DNA
<213> ORGANISM: Phoma glomerata

<400> SEQUENCE: 5

ctacatgatc cgaggtcgag agtgtaaaaa tgtacttttg gacgtcgtcg ttgtgagtgc     60

aaagcgcgag atgtactgcg ctccgaaatc aatacgccgg ctgccaattg ttttgaggcg    120

agtctgcgcg cagaggcgag acaaacaccc aacaccaagc agagcttgaa ggtacaaatg    180

acgctcgaac aggcatgccc catggaatac caaggggcgc aatgtgcgtt caaagattcg    240

atgattcact gaattctgca attcacacta cttatcgcat ttcgctgcgt tcttcatcga    300

tgccagaacc aagagatccg ttgttgaaag ttgtaactat taagtttgtt cagacgctga    360

ttgcaactgc aaatggttta aattgtccaa tcggcgggcg gacccgccga ggaaacgaag    420

gtactcaaaa gacatgggta agagatagca ggcaaagcct acaactctag gtaatgatcc    480

ttccgcaggt tcacctacgg aaaccttgtt acgac                               515


<210> SEQ ID NO 6
<211> LENGTH: 578
<212> TYPE: DNA
<213> ORGANISM: Acremonium sp.

<400> SEQUENCE: 6

ggatctacct gatccgaggt caaccttaaa aaattgggtg ttttacggcg tggtcgttcc     60

gctctccggt gcgaggttgt gctactacgc aggggaggct gcggcgcgac cgccactgaa    120

tttgagggac gggggccgcg agggccgccg atccccagaa ccaggcccgt tcccccggaa    180

gggtgggcct gagggttgaa atgacgctcg gacaggcatg cccgccggag tgccggcggg    240

cgcaatgtgc gttcaaagat tcgatgattc actgaattct gcaattcaca ttacttatcg    300
```

```
catttcgctg cgttcttcat cgatgccaga gccaagagat ccgttgttga aagttttgat    360

tcattttgtt ttcgggcttt cgcccctcag agaaatacga ttaaatcagg gtttggtttt    420

ccccggcgga cgcccggagg cccggaggcc gccgcgcgct gagcccgccg agggaacgtt    480

tggtaagttc acaatgggtt ggagagccta gggcactctg gtaatgatcc ctccgctggt    540

tcaccaacgg agaccttgtt acgactttta cttcctct                            578


<210> SEQ ID NO 7
<211> LENGTH: 621
<212> TYPE: DNA
<213> ORGANISM: Stachybotrys elegans

<400> SEQUENCE: 7

tagaggaagt aaaagtcgta acaaggtctc cgttggtgaa ccagcggagg gatcattacc     60

gagtttacaa ctcccaaacc caatgtgaac atacctcaag ttgcttcggc gggaacgccc    120

cggcgcgccc tccgaccctc ccgtccgcgg ggggatcggg gagcctagcc cggacccagg    180

cgcccgccgg aggtactcaa actcttgtct ttagtatatt cttctgagtg gcaaacgcaa    240

aataaatcaa aactttcaac aacggatctc ttggctctgg catcgatgaa gaacgcagcg    300

aaatgcgata agtaatgtga attgcagaat tcagtgaatc atcgaatctt tgaacgcaca    360

ttgcgcccgc cagcactctg gcgggcatgc ctgtccgagc gtcatttcaa ccctcagccc    420

ccccggggac tggtgttggg gatcggcccg ccctggcgcg gcgccgtccc cgaaatacag    480

tggcggtctc gctgcagcct cccctgcgta gtagcacacc tcgcatcgga gagcggcgcg    540

gccacgccgt gaaaccccaa cttctgatag ttgacctcgg atcaggtagg aatacccgct    600

gaacttaagc atatcaataa g                                              621


<210> SEQ ID NO 8
<211> LENGTH: 592
<212> TYPE: DNA
<213> ORGANISM: Myrothecium melanosporum

<400> SEQUENCE: 8

aattagagga agtaaaagtc gtaacaaggt ctccgttggt gaaccagcgg agggatcatt     60

accgagttta caactcccaa acccaatgtg aacattacct tgacgttgcc tcggcgggac    120

cgccccggcg ccctcaccgg caccggaacc aggcgcccgc cgcagggacc caaacctctg    180

ttttattatg aattctcctc tgagtggatt ttatacaaat aaatcaaaac tttcaacaac    240

ggatctcttg gctctggcat cgatgaagaa cgcagcgaaa tgcgataagt aatgtgaatt    300

gcagaattca gtgaatcatc gaatctttga acgcacattg cgcccgccag cattctggcg    360

ggcatgcctg tccgagcgtc atttcaaccc tcaggctccc gcgcctggcg ttggggatcg    420

gccttcaccg gccggccccg aaatacagtg gcggccccgc cgtagacctc ctctgcgtag    480

tagcacacac ctcgcagcct gggagcgcgg cggcggccac gccggaaaac ccccgacttc    540

tgaaagttga cctcggatca ggtaggaata cccgctgaac ttaagcatat ca            592


<210> SEQ ID NO 9
<211> LENGTH: 571
<212> TYPE: DNA
<213> ORGANISM: Gibberella sp.

<400> SEQUENCE: 9

tagaggaagt aaaagtcgta acaaggtctc cgttggtgaa ccagcggagg gatcattacc     60

gagtttacaa ctcccaaacc cctgtgaaca tacctacatg ttgcctcggc ggatcagccc    120
```

-continued

```
gctccccgta aaacgggacg gcccgccgca ggaaccacaa actctgtttt tagtggaact    180

tctgagtaaa aaaacaaata aatcaaaact ttcaacaacg gatctcttgg ttctggcatc    240

gatgaagaac gcagcaaaat gcgataagta atgtgaattg cagaattcag tgaatcatcg    300

aatctttgaa cgcacattgc gcccgccagt attctggcgg gcatgcctgt tcgagcgtca    360

tttcaaccct caagcccagc ttggtgttgg gagctgtcgt ctgacactcc ccaaatcgat    420

tggcggtcac gtcgagcttc catagcgtag taatttacac atcgttactg gtaatcgtcg    480

cggccacgcc gttaaacccc aacttctgaa tgttgacctc ggatcaggta ggaatacccg    540

ctgaacttaa gcatatcaat aagcggagga a                                    571


<210> SEQ ID NO 10
<211> LENGTH: 573
<212> TYPE: DNA
<213> ORGANISM: Gibberella sp.

<400> SEQUENCE: 10

attagaggaa gtaaaagtcg taacaaggtc tccgttggtg aaccagcgga gggatcatta     60

ccgagtttac aactcccaaa cccctgtgaa catacctaca tgttgcctcg gcggatcagc    120

ccgctccccg taaaacggga cggcccgccg caggaaccac aaactctgtt tttagtggaa    180

cttctgagta aaaaaacaaa taaatcaaaa ctttcaacaa cggatctctt ggttctggca    240

tcgatgaaga acgcagcaaa atgcgataag taatgtgaat tgcagaattc agtgaatcat    300

cgaatctttg aacgcacatt gcgcccgcca gtattctggc gggcatgcct gttcgagcgt    360

catttcaacc ctcaagccca gcttggtgtt gggagctgtc gtctgacact ccccaaatcg    420

attggcggtc acgtcgagct tccatagcgt agtaatttac acatcgttac tggtaatcgt    480

cgcggccacg ccgttaaacc ccaacttctg aatgttgacc tcggatcagg taggaatacc    540

cgctgaactt aagcatatca ataagcggag gaa                                  573


<210> SEQ ID NO 11
<211> LENGTH: 561
<212> TYPE: DNA
<213> ORGANISM: Ascomycete sp.

<400> SEQUENCE: 11

tagaggaagt aaaagtcgta acaaggtctc cgttggtgaa ccagcggagg gatcattacc     60

gagtttacaa ctcccaaacc cctgtgaaca tacctacatg ttgcctcggc ggatcagccc    120

gctccccgta aaacgggacg gcccgccgca ggaaccacaa actctgtttt tagtggaact    180

tctgagtaaa aaaacaaata aatcaaaact ttcaacaacg gatctcttgg ttctggcatc    240

gatgaagaac gcagcaaaat gcgataagta atgtgaattg cagaattcag tgaatcatcg    300

aatctttgaa cgcacattgc gcccgccagt attctggcgg gcatgcctgt tcgagcgtca    360

tttcaaccct caagcccagc ttggtgttgg gagctgtcgt ctgacactcc ccaaatcgat    420

tggcggtcac gtcgagcttc catagcgtag taatttacac atcgttactg gtaatcgtcg    480

cggccacgcc gttaaacccc aacttctgaa tgttgacctc ggatcaggta ggaatacccg    540

ctgaacttaa gcatatcaat a                                              561


<210> SEQ ID NO 12
<211> LENGTH: 598
<212> TYPE: DNA
<213> ORGANISM: Emericellopsis terricola
```

<400> SEQUENCE: 12
tttgatatgc ttaagttcag cgggtattcc tacctgatct gaggtcaacc ttgagaagtg 60
gggtgtttta cggcgtggcc agcccgctcg tcccttctgc gaggtagtgt tactacgcag 120
gggagtctgt gggagaccgc cactgtgttt cggggacggc cgccgcgagg acggccgggc 180
cccaacgcca gcgccccgcg aacgggggct gagggttgaa atgacgctca gacaggcatg 240
cccgccagaa tactggcggg cgcaatgtgc gttcaaagat tcgatgattc actgaattct 300
gcaattcaca ttacttatcg catttcgctg cgttcttcat cgatgccaga accaagagat 360
ccgttgctga aagttttgtt tatttttgct tatgccactc agaggagaca ctagaaaaca 420
agagtttggt tccccggcgg gcgcctgaat ccgggtcacg ccacgagggc gcgccgcggg 480
acggtccgcc gaagcaacat aggtatgttc acaggggttt gggagttgga taactcagta 540
atgatccctc cgctggttca ccaacggaga ccttgttacg acttttactt cctctaat 598

<210> SEQ ID NO 13
<211> LENGTH: 589
<212> TYPE: DNA
<213> ORGANISM: Bionectria rossmaniae

<400> SEQUENCE: 13
tagaggaagt aaaagtcgta acaaggtctc cgttggtgaa ccagcggagg gatcattatc 60
gagtgttaaa actcccaaac cattgtgaat ctaccttttt tcgttgcttc ggcgggatcg 120
ccccgggcgc cattgttgtg ccccggatcc aggcgcccgc cggaggaccc aaacccctgt 180
attctatgtt ttctctgagt ggattacaca aataatcaaa actttcaaca acggatctct 240
tggttctggc atcgatgaag aacgcagcga aatgcgaaaa gtaatgtgaa ttgcagaatt 300
cagtgaatca tcgaatcttt gaacgcacat tgcgcccgcc agtattctgg cgggcatgcc 360
tgtctgagcg tcatttcaac cctcatgccc cagggcgtgg tgttggggaa cggcctggcc 420
ctagcgccgg gccgcccccg aaatatagtg gcggacccgc tgtggcctcc tctgcgtagt 480
agtgataccc cgcaccggaa agcagcgagc ccctgccgta aaaccccaac ttctcaaggt 540
tgacctcaga tcaggtagga atacccgctg aacttaagca tatcaataa 589

<210> SEQ ID NO 14
<211> LENGTH: 573
<212> TYPE: DNA
<213> ORGANISM: F. oxysporum f. sp. vasinfectum

<400> SEQUENCE: 14
tagaggaagt aaaagtcgta acaaggtctc cgttggtgaa ccagcggagg gatcattacc 60
gagtttacaa ctcccaaacc cctgtgaaca taccacttgt tgcctcggcg gatcagcccg 120
ctcccggtaa aacgggacgg cccgccagag gacccctaaa ctctgtttct atatgtaact 180
tctgagtaaa accataaata aatcaaaact ttcaacaacg gatctcttgg ttctggcatc 240
gatgaagaac gcagcaaaat gcgataagta atgtgaattg cagaattcag tgaatcatcg 300
aatctttgaa cgcacattgc gcccgccagt attctggcgg gcatgcctgt tcgagcgtca 360
tttcaaccct caagcacagc ttggtgttgg gactcgcgtt aattcgcgtt cctcaaattg 420
attggcggtc acgtcgagct tccatagcgt agtagtaaaa ccctcgttac tggtaatcgt 480
cgcggccacg ccgttaaacc ccaacttctg aatgttgacc tcggatcagg taggaatacc 540
cgctgaactt aagcatatca ataagccgga gga 573

-continued

<210> SEQ ID NO 15
<211> LENGTH: 600
<212> TYPE: DNA
<213> ORGANISM: Emericellopsis terricola

<400> SEQUENCE: 15
cctattgata tgcttaagtt cagcgggtat tcctacctga tctgaggtca accttgagaa 60
gtggggtgtt ttacggcgtg gccagcccgc tcgtcccttc tgcgaggtag tgttactacg 120
caggggagtc tgtgggagac cgccactgtg tttcggggac ggccgccgcg aggacggccg 180
ggccccaacg ccagcgcccc gcgaacgggg gctgagggtt gaaatgacgc tcagacaggc 240
atgcccgcca gaatactggc gggcgcaatg tgcgttcaaa gattcgatga ttcactgaat 300
tctgcaattc acattactta tcgcatttcg ctgcgttctt catcgatgcc agaaccaaga 360
gatccgttgc tgaaagtttt gtttattttt gcttatgcca ctcagaggag acactagaaa 420
acaagagttt ggttccccgg cgggcgcctg gatccgggtc acgccacgag ggcgcgccgc 480
gggacggtcc gccgaagcaa cataggtatg ttcacagggg tttgggagtt ggataactca 540
gtaatgatcc ctccgctggt tcaccaacgg agaccttgtt acgactttta cttcctctaa 600

<210> SEQ ID NO 16
<211> LENGTH: 553
<212> TYPE: DNA
<213> ORGANISM: F. oxysporum f. sp. vasinfectum

<400> SEQUENCE: 16
tagaggaagt aaaagtcgta acaaggtctc cgttggtgaa ccagcggagg gatcattacc 60
gagtttacaa ctcccaaacc cctgtgaaca taccacttgt tgcctcggcg gatcagcccg 120
ctcccggtaa aacgggacgg cccgccagag gacccctaaa ctctgtttct atatgtaact 180
tctgagtaaa accataaata aatcaaaact ttcaacaacg gatctcttgg ttctggcatc 240
gatgaagaac gcagcaaaat gcgataagta atgtgaattg cagaattcag tgaatcatcg 300
aatctttgaa cgcacattgc gcccgccagt attctggcgg gcatgcctgt tcgagcgtca 360
tttcaaccct caagcacagc ttggtgttgg gactcgcgtt aattcgcgtt cctcaaattg 420
attggcggtc acgtcgagct tccatagcgt agtagtaaaa ccctcgttac tggtaatcgt 480
cgcggccacg ccgttaaacc ccaacttctg aatgttgacc tcggatcagg taggaatacc 540
cgctgaactt aag 553

<210> SEQ ID NO 17
<211> LENGTH: 566
<212> TYPE: DNA
<213> ORGANISM: Uncultured endophytic fungus

<400> SEQUENCE: 17
ttcctccgct tattgatatg cttaagttca gcgggtatcc ctacctgatc cgaggtcaaa 60
agtgagaaag aggctttatg gatgccactg ttgagggact aagacgcaaa atgtgctgcg 120
cttactacca aaacactggc tgccaatgac tttaaggcga gtctttttgta aaaagacaaa 180 acgcccaaca ccaagcagag cttgaaggta caaatgacgc tcgaacaggc atgccccatg 240
gaataccaag gggcgcaatg tgcgttcaaa gattcgatga ttcactgaat tctgcaattc 300
acactactta tcgcatttcg ctgcgttctt catcgatgcc agaaccaaga gatccgttgt 360
tgaaagttgt aattattatg tataattcag acgctgattg aagatttaaa aaaggttata 420
gttttgtcca tccggcaggc aagcccaccg aggaaacaat agtacgcaaa aaacaagggc 480

-continued ataaacaagt agctgggcta ctgaatgtaa tgatccttcc gcaggttcac ctacggaaac 540
cttgttacga cttttacttc ctctaa 566

<210> SEQ ID NO 18
<211> LENGTH: 568
<212> TYPE: DNA
<213> ORGANISM: Uncultured endophytic fungus

<400> SEQUENCE: 18
tgttcctccg cttattgata tgcttaagtt cagcgggtat ccctacctga tccgaggtca 60
aaagtgagaa agaggcttta tggatgccac tgttgaggga ctaagacgca aaatgtgctg 120
cgcttactac caaaacactg gctgccaatg actttaaggc gagtcttttg taaaaagaca 180
aaacgcccaa caccaagcag agcttgaagg tacaaatgac gctcgaacag gcatgcccca 240
tggaatacca aggggcgcaa tgtgcgttca aagattcgat gattcactga attctgcaat 300
tcacactact tatcgcattt cgctgcgttc ttcatcgatg ccagaaccaa gagatccgtt 360
gttgaaagtt gtaattatta tgtataattc agacgctgat tgaagattta aaaaaggtta 420
tagttttgtc catccggcag gcaagcccac cgaggaaaca atagtacgca aaaaacaagg 480
gcataaacaa gtagctgggc tactgaatgt aatgatcctt ccgcaggttc acctacggaa 540
accttgttac gacttttact tcctctaa 568

<210> SEQ ID NO 19
<211> LENGTH: 596
<212> TYPE: DNA
<213> ORGANISM: Myrothecium melanosporum

<400> SEQUENCE: 19
attagaggaa gtaaaagtcg taacaaggtc tccgttggtg aaccagcgga gggatcatta 60
ccgagtttac aactcccaaa cccaatgtga acattacctt gacgttgcct cggcgggacc 120
gccccggcgc cctcaccggc accggaacca ggcgcccgcc gcagggaccc aaacctctgt 180
tttattatga attctcctct gagtggattt tatacaaata aatcaaaact ttcaacaacg 240
gatctcttgg ctctggcatc gatgaagaac gcagcgaaat gcgataagta atgtgaattg 300
cagaattcag tgaatcatcg aatctttgaa cgcacattgc gcccgccagc attctggcgg 360
gcatgcctgt ccgagcgtca tttcaaccct caggctcccg cgcctggcgt tggggatcgg 420
ccttcaccgg ccggccccga aatacagtgg cggccccgcc gtagacctcc tctgcgtagt 480
agcacacacc tcgcagcctg ggagcgcggc ggcggccacg ccggaaaacc cccgacttct 540
gaaagttgac ctcggatcag gtaggaatac ccgctgaact taagcatatc aataag 596

<210> SEQ ID NO 20
<211> LENGTH: 641
<212> TYPE: DNA
<213> ORGANISM: Hypocrea lixii

<400> SEQUENCE: 20
ctattgatat gcttaagttc agcgggtatt cctacctgat ccgaggtcaa catttcagaa 60
gttgggtgtt taacggctgt ggacgcgccg cgctcccgat gcgagtgtgc aaactactgc 120
gcaggagagg ctgcggcgag accgccactg tatttcggag acggccaccc gctaagggag 180
ggccgatccc caacgccgac cccccggagg ggttcgaggg ttgaaatgac gctcggacag 240
gcatgcccgc cagaatactg gcgggcgcaa tgtgcgttca aagattcgat gattcactga 300
attctgcaat tcacattact tatcgcattt cgctgcgttc ttcatcgatg ccagaaccaa 360
gagatccgtt gttgaaagtt ttgattcatt ttcgaaacgc ctacgagagg cgccgagaaa 420
ggctcagatt ataaaaaaac ccgcgagggg gtatacaata agagttttag gttggtcctc 480
cggcgggcgc cttggtccgg ggctgcgacg cacccggggc agagatcccg ccgaggcaac 540
agtttggtaa cgttcacatt gggtttggga gttgtaaact cggtaatgat ccctccgctg 600
gttcaccaac ggagaccttg ttacgacttt tacttcctct a 641

<210> SEQ ID NO 21
<211> LENGTH: 609
<212> TYPE: DNA
<213> ORGANISM: Hypocrea lixii

<400> SEQUENCE: 21
cctgatccga ggtcaacatt tcagaagttg ggtgtttaac ggctgtggac gcgccgcgct 60
cccgatgcga gtgtgcaaac tactgcgcag gagaggctgc ggcgagaccg ccactgtatt 120
tcggagacgg ccacccgcta agggagggcc gatccccaac gccgaccccc cggaggggtt 180
cgagggttga aatgacgctc ggacaggcat gcccgccaga atactggcgg gcgcaatgtg 240
cgttcaaaga ttcgatgatt cactgaattc tgcaattcac attacttatc gcatttcgct 300
gcgttcttca tcgatgccag aaccaagaga tccgttgttg aaagttttga ttcattttcg 360
aaacgcctac gagaggcgcc gagaaaggct cagattataa aaaaacccgc gaggggtat 420 acaataagag ttttaggttg gtcctccggc gggcgccttg gtccggggct gcgacgcacc 480
cggggcagag atcccgccga ggcaacagtt tggtaacgtt cacattgggt ttgggagttg 540
taaactcggt aatgatccct ccgctggttc accaacggag accttgttac gacttttact 600
tcctctaat 609

<210> SEQ ID NO 22
<211> LENGTH: 640
<212> TYPE: DNA
<213> ORGANISM: Hypocrea lixii

<400> SEQUENCE: 22
attagaggaa gtaaaagtcg taacaaggtc tccgttggtg aaccagcgga gggatcatta 60
ccgagtttac aactcccaaa cccaatgtga acgttaccaa actgttgcct cggcgggatc 120
tctgccccgg gtgcgtcgca gccccggacc aaggcgcccg ccggaggacc aaccaaaact 180
ctttttgtat accccctcgc gggtttttta taatctgagc cttctcggcg cctctcgtag 240
gcgtttcgaa aatgaatcaa aactttcaac aacggatctc ttggttctgg catcgatgaa 300
gaacgcagcg aaatgcgata agtaatgtga attgcagaat tcagtgaatc atcgaatctt 360
tgaacgcaca ttgcgcccgc cagtattctg gcgggcatgc ctgtccgagc gtcatttcaa 420
ccctcgaacc cctccggggg gtcggcgttg gggatcggcc ctgcctttgg cggtggccgt 480
ctccgaaata cagtggcggt ctcgccgcag cctctcctgc gcagtagttt gcacactcgc 540
atcgggagcg cggcgcgtcc acagccgtta aacacccaac ttctgaaatg ttgacctcgg 600
atcaggtagg aatacccgct gaacttaagc atatcaatag 640

<210> SEQ ID NO 23
<211> LENGTH: 532
<212> TYPE: DNA
<213> ORGANISM: Buergenerula spartinae

<400> SEQUENCE: 23

```
gggtttctac ctgatccgag tcacctaaga agtttagggg gtttagcggc tggagcccac     60

ctggagctcc cgagcgaggc gcgttttacc gcgagttact gcgctcaggg tcctagcgag    120

accgccgatg tgcttggggg ccccgaccgc cgggcggccg ggtgccccaa caccaagctg    180

ggcttgagtg gtgaaatgac gctcgaacag gcatgcccgc cggaataccg gcgggcgcaa    240

tgtgcgttca aagattcgat gattcactga attctgcaat tcacattact tatcgcattt    300

cgctgcgttc ttcatcgatg ccagaaccaa gagatccgtt gttgaaagtt ttaattattg    360

ttttttttt tttcctcaga gatacaccaa agattcagag tttggaacct ccggcggcct    420

cggggccgca aggcccgtcg cccgccgaag caacagtaaa ggtatgtcca caggggttgg    480

agtttttcaa ctctttaatg atccctccgc tggtcaccaa cgagaccgac gc            532


<210> SEQ ID NO 24
<211> LENGTH: 575
<212> TYPE: DNA
<213> ORGANISM: Gibberella acuminata

<400> SEQUENCE: 24

tcctcccgcc tattgatatg cttaagttca gcgggtattc ctacctgatc cgaggtcaac     60

attcagaagt tggggtttaa cggcgtggcc gcgacgatta ccagtaacga tgtgtaaatt    120

actacgctat ggaagctcga cgtgaccgcc aatcaatttg aggactgtca ataaagacag    180

atcccaacac caagctgggc ttgagggttg aaatgacgct cgaacaggca tgcccgccag    240

aatactggcg ggcgcaatgt gcgttcaaag attcgatgat tcactgaatt ctgcaattca    300

cattacttat cgcatttgc tgcgttcttc atcgatgcca gaaccaagag atccgttgtt    360

gaaagttttg atttatttgt tttttatact cagaagttcc actaaaaaca gagtttaggg    420

tttcctgcgg cgggccgtcc cgttttacag ggcgcgggct gatccgccga ggcaacataa    480

aggtatgttc acaggggttt gggagttgta aactcggtaa tgatccctcc gctggttcac    540

caacggagac cttgttacga cttttacttc ctcta                               575


<210> SEQ ID NO 25
<211> LENGTH: 598
<212> TYPE: DNA
<213> ORGANISM: Emericellopsis terricola

<400> SEQUENCE: 25

tattgatatg cttaagttca gcgggtattc ctacctgatc tgaggtcaac cttgagaagt     60

ggggtgtttt acggcgtggc cagcccgctc gtcccttctg cgaggtagtg ttactacgca    120

ggggagtctg tgggagaccg ccactgtgtt tcggggacgg ccgccgcgag gacggccggg    180

ccccaacgcc agcgccccgc gaacgggggc tgagggttga aatgacgctc agacaggcat    240

gcccgccaga atactggcgg gcgcaatgtg cgttcaaaga ttcgatgatt cactgaattc    300

tgcaattcac attacttatc gcatttcgct gcgttcttca tcgatgccag aaccaagaga    360

tccgttgctg aaagttttgt ttatttttgc ttatgccact cagaggagac actagaaaac    420

aagagtttgg ttccccggcg ggcgcctgga tccgggtcac gccacgaggg cgcgccgcgg    480

gacggtccgc cgaagcaaca taggtatgtt cacaggggtt tgggagttgg ataactcagt    540

aatgatccct ccgctggttc accaacggag accttgttac gacttttact tcctctaa      598


<210> SEQ ID NO 26
<211> LENGTH: 592
<212> TYPE: DNA
<213> ORGANISM: Ascomycete sp.
```

<400> SEQUENCE: 26

```
aattcctccg cttattgata tgcttaagtt cagcgggtat tcctacctga tccgaggtca     60
accttctgta agtttggggg tttaacggca ggggcacgct ggggacctcg ggcgagatgt    120
gttactacgc ccggacctcc agcgggtccg ccactgattt tgagggccta cgctcgcgcg    180
tagtgcccca acaccaagca gggcttgagg gttgaaatga cgctcggaca ggcatgcccg    240
ccagaatgct ggcgggcgca atgtgcgttc aaagattcga tgattcactg aattctgcaa    300
ttcacattac ttatcgcatt tcgctgcgtt cttcatcgat gccagaacca agagatccgt    360
tgttgaaagt tttgattgtt tggaagttac tcagagatgc cactaaatat agttatagtt    420
ttgcgacctg cggcgggcgc ctccgctggg gaggctgcgg ccccgccctg ggccgcccg     480
ccgaggcaac ggtacgggta tgttcacagt ggtttgggag tcgttaaact ctgtaatgat    540
ccctccgctg gttcaccaac ggagaccttg ttacgacttt tacttcctct aa            592
```

<210> SEQ ID NO 27
<211> LENGTH: 597
<212> TYPE: DNA
<213> ORGANISM: Emericellopsis terricola

<400> SEQUENCE: 27

```
ctttgatatg cttaagttca gcgggtattc ctacctgatc tgaggtcaac cttgagaagt     60
ggggtgtttt acggcgtggc cagcccgctc gtcccttctg cgaggtagtg ttactacgca    120
ggggagtctg tgggagaccg ccactgtgtt tcggggacgg ccgccgcgag gacggccggg    180
ccccaacgcc agcgccccgc gaacgggggc tgagggttga aatgacgctc agacaggcat    240
gcccgccaga atactggcgg gcgcaatgtg cgttcaaaga ttcgatgatt cactgaattc    300
tgcaattcac attacttatc gcatttcgct gcgttcttca tcgatgccag aaccaagaga    360
tccgttgctg aaagttttgt ttatttttgc ttatgccact cagaggagac actagaaaac    420
aagagtttgg ttccccggcg ggcgcctgga tccgggtcac gccacgaggg cgcgccgcgg    480
gacggtccgc cgaagcaaca taggtatgtt cacaggggtt tgggagttgg ataactcagt    540
aatgatccct ccgctggttc accaacggag accttgttac gacttttact tcctcta       597
```

<210> SEQ ID NO 28
<211> LENGTH: 579
<212> TYPE: DNA
<213> ORGANISM: Fusarium proliferatum

<400> SEQUENCE: 28

```
ttagaggaag taaaagtcgt aacaaggtct ccgttggtga accagcggag ggatcattac     60
cgagtttaca actcccaaac ccctgtgaac ataccaattg ttgcctcggc ggatcagccc    120
gctcccggta aaacgggacg gcccgccaga ggacccctaa actctgtttc tatatgtaac    180
ttctgagtaa aaccataaat aaatcaaaac tttcaacaac ggatctcttg gttctggcat    240
cgatgaagaa cgcagcaaaa tgcgataagt aatgtgaatt gcagaattca gtgaatcatc    300
gaatctttga acgcacattg cgcccgccag tattctggcg ggcatgcctg ttcgagcgtc    360
atttcaaccc tcaagccccc gggtttggtg ttggggatcg gcgagccctt gcggcaagcc    420
ggccccgaaa tctagtggcg gtctcgctgc agcttccatt gcgtagtagt aaaaccctcg    480
caactggtac gcggcgcggc caagccgtta aacccccaac ttctgaatgt tgacctcgga    540
tcaggtagga atacccgctg aacttaagca tatcaatag                           579
```

-continued

<210> SEQ ID NO 29
<211> LENGTH: 621
<212> TYPE: DNA
<213> ORGANISM: Stachybotrys elegans

<400> SEQUENCE: 29
tagaggaagt aaaagtcgta acaaggtctc gttggtgaac cagcggaggg atcattaccg 60
agtttacaac tcccaaaccc aatgtgaaca tacctcaagt tgcttcggcg ggaacgcccc 120
ggcgcgccct ccgaccctcc cgcccgcggg gggatcgggg agcctagccc ggacccaggc 180
gcccgccgga ggtacccaaa ctcttgtctt cagtatattc ttctgagtgg caaacgcaaa 240
aataaatcaa aactttcaac aacggatctc ttggctctgg catcgatgaa gaacgcagcg 300
aaatgcgata agtaatgtga attgcagaat tcagtgaatc atcgaatctt tgaacgcaca 360
ttgcgcccgc cagcactctg gcgggcatgc ctgtccgagc gtcatttcaa ccctcaggcc 420
ccccggggac tggtgttggg gatcggcccg ccctggcgcg gcgccgtccc cgaaatacag 480
tggcggtctc gctgcagcct cccctgcgta gtagcacacc tcgcatcgga gagcggcgcg 540
gccacgccgt gaaaccccaa cttctgatag ttgacctcgg atcaggtagg aatacccgct 600
gaacttaagc atatcaatag c 621

<210> SEQ ID NO 30
<211> LENGTH: 663
<212> TYPE: DNA
<213> ORGANISM: Eutypa scoparia

<400> SEQUENCE: 30
tagaggaagt aaaagtcgta acaaggtctc cgttggtgaa ccagcggagg gatcattaat 60
gagttttcta aactccaaac ccctgagaac ttacctagtt gcctcggcgg actcgccctg 120
ggacgaccta ccctgcagcg cgttaccctg caactcgcta ccctgtagcg agttgccctg 180
taacaacttg ccctgtaggt gctggccctg tagcctgccc gccggcggcc aacctgaact 240
ctgttttatt gtggcacttc tgaggaccat tctaaatgaa ttaaaacttt caacaacgga 300
tctcttggtt ctggcatcga tgaagaacgc agcgaaatgc gataagtaat gtgaattgca 360
gaattcagtg aatcatcgaa tctttgaacg cacattgcgc ccactagtat tctggtgggc 420
atgcctgttc gagcgtcatt tcaactatca agccctattt gcttggcgtt gggagacttg 480
taggccccgc ctacaagctc cccaaatgga tcggcggagt cgtggcgacc ctcagcgtag 540
taattcttct cgctctaggt gtcggcgccg gcgtctggcc gttaaacccc ctattttttt 600
tagtcttgac ctcggatcag gtaggaatac ccgctgaact taagcatatc aataagcgga 660
gga 663

<210> SEQ ID NO 31
<211> LENGTH: 600
<212> TYPE: DNA
<213> ORGANISM: Sordariomycete sp.

<400> SEQUENCE: 31
tccttcctcc gcttattgat atgcttaagt tcagcgggta ttcctacctg atccgaggtc 60
aacattcaga agttgggggt ttaacggctt ggccgcgccg cgtaccagtt gcgagggttt 120
tactactacg caatggaagc tgcagcgaga ccgccactgt atttcggggc cggcttgccg 180
tgaggctcgc cgatccccaa caccaaaccc gggggcttga gggttgaaat gacgctcgaa 240
caggcatgcc cgccagaata ctggcgggcg caatgtgcgt tcaaagattc gatgattcac 300
tgaattctgc aattcacatt acttatcgca ttttgctgcg ttcttcatcg atgccagaac 360
caagagatcc gttgttgaaa gttttgattt atttatggtt ttactcagaa gttacatata 420
gaaacagagt ttaggggtcc tctggcgggc cgttccgttt taccgggagc gggctgatcc 480
gccgaggcaa caattggtat gttcacaggg gtttgggagt tgtaaactcg gtaatgatcc 540
ctccgctggt tcaccaacgg agaccttgtt acgactttta cttcctctaa atgaccaaga 600

<210> SEQ ID NO 32
<211> LENGTH: 566
<212> TYPE: DNA
<213> ORGANISM: Uncultured soil fungus

<400> SEQUENCE: 32
tttgatatgc ttaagttcag cgggtattcc tacctgatcc gaggtcaaca ttcagaagtt 60
ggggtttaac ggcgtggccg cgacgattac cagtaacgag gtgtatgatt actacgctat 120
ggaagctcga cgtgaccgcc aatcgatttg ggaacgcgg gttaccgcga gtcccaacac 180
caagctgagc ttgagggttg aaatgacgct cgaacaggca tgcccgccag aatactggcg 240
ggcgcaatgt gcgttcaaag attcgatgat tcactgaatt ctgcaattca cattacttat 300
cgcattttgc tgcgttcttc atcgatgcca gaaccaagag atccgttgtt gaaagttttg 360
atttatttgt ttgttttact cagaagttcc actaaaaaca gagtttaggg tcctcgggcg 420
ggccgtcccg ttttacaggg cgcgggctga tccgccgagg caacgtatag gtatgttcac 480
aggggtttgg gagttgtaaa ctcggtaatg atccctccgc tggttcacca acggagacct 540
tgttacgact tttacttcct ctaaat 566

<210> SEQ ID NO 33
<211> LENGTH: 596
<212> TYPE: DNA
<213> ORGANISM: Myrothecium melanosporum

<400> SEQUENCE: 33
ttagaggaag taaaagtcgt aacaaggtct ccgttggtga accagcggag ggatcattac 60
cgagtttaca actcccaaac ccaatgtgaa cattaccttg acgttgcctc ggcgggaccg 120
ccccggcgcc ctcaccggca ccggaaccag gcgcccgccg cagggaccca aacctctgtt 180
ttattatgaa ttctcctctg agtggatttt atacaaataa atcaaaactt tcaacaacgg 240
atctcttggc tctggcatcg atgaagaacg cagcgaaatg cgataagtaa tgtgaattgc 300
agaattcagt gaatcatcga atctttgaac gcacattgcg cccgccagca ttctggcggg 360
catgcctgtc cgagcgtcat ttcaaccctc aggctcccgc gcctggcgtt ggggatcggc 420
cttcaccggc cggccccgaa atacagtggc ggccccgccg tagacctcct ctgcgtagta 480
gcacacacct cgcagcctgg gagcgcggcg gcggccacgc cggaaaaccc ccgacttctg 540
aaagttgacc tcggatcagg taggaatacc cgctgaactt aagcatatca ataagg 596

<210> SEQ ID NO 34
<211> LENGTH: 608
<212> TYPE: DNA
<213> ORGANISM: Leptosphaeria avenaria f. sp. triticea

<400> SEQUENCE: 34
tattgatatg cttaagttca gcgggtatcc ctacctgatc cgaggtcaaa agttataaaa 60
gggcttactg gaggccagca ttgggtaaga atcgcgactt gtgctgcgct tcactaccaa 120

-continued

```
aacactggct gccaatggtt ttaaggcgag tccaaacgct gaggagagga caaacaccca    180

acgccaagca aggcttgagg gtacaaatga cgctcgaaca ggcatgcccc atggaatacc    240

aaggggcgca atgtgcgttc aaagattcga tgattcactg aattctgcaa ttcacactac    300

ttatcgcatt tcgctgcgtt cttcatcgat gccagaacca agagatccgt tgttgaaagt    360

tgtaataatt aggtttttca gacgctgatt gacaattaaa aaggttatag ttgggtccaa    420

tcggcaggca cgcctgccga ggaaacgtgg gtacgcaaaa gacaagggtg gataaaagag    480

gccagctgct catcagcttg cgctatacag actaacagcc ccctttgcag tagtaaacta    540

ctgagtgtaa tgatccttcc gcaggttcac ctacggaaac cttgttacga cttttacttc    600

ctctaatt                                                              608


<210> SEQ ID NO 35
<211> LENGTH: 588
<212> TYPE: DNA
<213> ORGANISM: Acremonium sp.

<400> SEQUENCE: 35

tcttggtcta ttagaggaag taaaagtcgt aacaaggtct ccgttggtga accagcggag     60

ggatcattac cagagtgccc taggctctcc aacccattgt gaacttacca aacgttccct    120

cggcgggctc agcgcgcggc ggcctccggg cctccgggcg tccgccgggg aaaaccaaac    180

cctgatttaa tcgtatttct ctgaggggcg aaagcccgaa aacaaaatga atcaaaactt    240

tcaacaacgg atctcttggc tctggcatcg atgaagaacg cagcgaaatg cgataagtaa    300

tgtgaattgc agaattcagt gaatcatcga atctttgaac gcacattgcg cccgccggca    360

ctccggcggg catgcctgtc cgagcgtcat ttcaaccctc aggcccaccc ttccggggga    420

acgggcctgg ttctggggat cggcggccct cgcggccccc gtccctcaaa ttcagtggcg    480

gtcgcgccgc agcctcccct gcgtagtagc acaacctcgc accggagagc ggaacgacca    540

cgccgtaaaa cacccaattt tttaaggttg acctcggatc aggtagga                 588


<210> SEQ ID NO 36
<211> LENGTH: 597
<212> TYPE: DNA
<213> ORGANISM: Penicillium citreonigrum

<400> SEQUENCE: 36

gaggaagtaa aagtcgtaac aaggtttccg taggtgaacc tgcggaagga tcattaccga     60

gtgagggccc tctgggtcca acctcccacc cgtgtttatc gtaccttgtt gcttcggcgg    120

gcccgccgca aggccgccgg ggggcatctg ccctctggcc cgcgcccgcc gaagacacca    180

ttgaacgctg tctgaagatt gcagtctgag caattagtta aataacttaa aactttcaac    240

aacggatctc ttggttccgg catcgatgaa gaacgcagcg aaatgcgata cgtaatgtga    300

attgcagaat tcagtgaatc atcgagtctt tgaacgcaca ttgcgccccc tggtattccg    360

gggggcatgc ctgtccgagc gtcattgctg ccctcaagca cggcttgtgt gttgggctcc    420

gtcctccttc cgggggacgg gcccgaaagg cagcggcggc accgcgtccg gtcctcgagc    480

gtatggggct tcgtcacccg ctctgcaggc ccggccggcg cttgccgaca catcaatctt    540

ttttccaggt tgacctcgga tcaggtaggg atacccgctg aacttaagca tatcata       597


<210> SEQ ID NO 37
<211> LENGTH: 587
<212> TYPE: DNA
<213> ORGANISM: Fungal endophyte sp.
```

<400> SEQUENCE: 37
tagaggaagt aaaagtcgta acaaggtctc cgttggtgaa ccagcggagg gatcattacc 60
gagtttacaa ctcccaaacc cctgtgaaca taccaattgt tgcctcggcg gatcagcccg 120
ctcccggtaa aacggaacgg cccgccagag gacccctaaa ctctgtttct atatgtaact 180
tctgagtaaa accataaata aatcaaaact ttcaacaacg gatctcttgg ttctggcatc 240
gatgaagaac gcagcaaaat gcgataagta atgtgaattg cagaattcag tgaatcatcg 300
aatctttgaa cgcacattgc gcccgccagt attctggcgg gcatgcctgt tcgagcgtca 360
tttcaaccct caagcccccg ggtttggtgt tggggatcgg cgagcctcac ggcaagccgg 420
ccccgaaata cagtggcggt ctcgctgcag cttccattgc gtagtagtaa aaccctcgca 480
actggtacgc ggcgcggcca agccgttaaa cccccaactt ctgaatgttg acctcggatc 540
aggtaggaat acccgctgaa cttaagcata tcaataaggc ggaggaa 587

<210> SEQ ID NO 38
<211> LENGTH: 579
<212> TYPE: DNA
<213> ORGANISM: Fusarium proliferatum

<400> SEQUENCE: 38
ttagaggaag taaaagtcgt aacaaggtct ccgttggtga accagcggag ggatcattac 60
cgagtttaca actcccaaac ccctgtgaac ataccaattg ttgcctcggc ggatcagccc 120
gctcccggta aaacgggacg gcccgccaga ggacccctaa actctgtttc tatatgtaac 180
ttctgagtaa aaccataaat aaatcaaaac tttcaacaac ggatctcttg gttctggcat 240
cgatgaagaa cgcagcaaaa tgcgataagt aatgtgaatt gcagaattca gtgaatcatc 300
gaatctttga acgcacattg cgcccgccag tattctggcg ggcatgcctg ttcgagcgtc 360
atttcaaccc tcaagccccc gggtttggtg ttggggatcg gcgagccctt gcggcaagcc 420
ggccccgaaa tctagtggcg gtctcgctgc agcttccatt gcgtagtagt aaaaccctcg 480
caactggtac gcggcgcggc caagccgtta aacccccaac ttctgaatgt tgacctcgga 540
tcaggtagga atacccgctg aacttaagca tatcaatag 579

<210> SEQ ID NO 39
<211> LENGTH: 599
<212> TYPE: DNA
<213> ORGANISM: Emericellopsis terricola

<400> SEQUENCE: 39
cctattgata tgcttaagtt cagcgggtat tcctacctga tctgaggtca acctggagaa 60
gtggggtgtt ttacggcgtg gccagcccgc tcgtcccttc tgcgaggtag tgctactacg 120
caggggagtc tgcgggagac cgccactgag tttcggggac ggccgccgcg aggacggccg 180
ggccccaacg ccagcgcccc gcggacgggg gctgagggtt gaaatgacgc tcagacaggc 240
atgcccgcca gaatactggc gggcgcaatg tgcgttcaaa gattcgatga ttcactgaat 300
tctgcaattc acattactta tcgcatttcg ctgcgttctt catcgatgcc agaaccaaga 360
gatccgttgc tgaaagtttt gtttattttt gcttatgcca ctcagaggag acactcgaag 420
acaagagttt ggttccccgg cgggcgcctg ggtccgggtc acgccacgtg ggcgcgccgc 480
gggacggccc gccgaagcaa cataggtatg ttcacagggg tttgggagtt ggataactca 540
gtaatgatcc ctccgctggt tcaccaacgg agaccttgtt acgactttta cttcctcta 599

<210> SEQ ID NO 40
<211> LENGTH: 627
<212> TYPE: DNA
<213> ORGANISM: Emericellopsis terricola

<400> SEQUENCE: 40
tcttggtcat ttagaggaag taaaagtcgt aacaaggtct ccgttggtga accagcggag 60
ggatcattac aaaacgagtg cttcggctct ccaacccatt gtgaacatac ctatcgttcc 120
ctcggcgggc tcagcgcgcg gccggcctcc gggccaccgg gcgtccgccg gggacaacca 180
aacccgaatt tttcgtgtat atctgagggg cgaaagcccg aaaacaaaat gaatcaaaac 240
tttcaacaac ggatctcttg gctctggcat cgatgaagaa cgcagcgaaa tgcgataagt 300
aatgtgaatt gcagaattca gtgaatcatc gaatctttga acgcacattg cgcccgccgg 360
cactccggcg ggcatgcctg tccgagcgtc atttcaaccc tcagggcccc ctttcggggg 420
cggcacctgg ttctggggat cagcggccct tcggggcccc tgtcccccaa attgagtggc 480
ggtcgcgccg cagcctcccc tgcgtagtag cacacctcgc accggagagc ggctcggcca 540
cgccgtaaaa cccccaattt ttacaggttg acctcggatc aggtaggaat acccgctgaa 600
cttaagcata tcaatagccg gaggaaa 627

<210> SEQ ID NO 41
<211> LENGTH: 604
<212> TYPE: DNA
<213> ORGANISM: Acremonium strictum

<400> SEQUENCE: 41
ttcctccgcc ttattgatat gcttaagttc agcgggtatt cctacctgat ctgaggtcaa 60
ccttgagaag tgggggggttt aacggcgtgg ttcaaccgct atcctgccgc gagaggttta 120
attactgcac ggaggagttc gcgagggaac cgccactgga tttcagggcc agccgccgcc 180
aggggcaggc tgatccccaa cgccaggtcc cgcgaacggg tcctgagggt tgaaatgacg 240
ctcagacagg catgcccgcc agaatactgg cgggcgcaat gtgcgttcaa agattcgatg 300
attcactgaa ttctgcaatt cacattactt atcgcatttt gctgcgttct tcatcgatgc 360
cagaaccaag agatccgttg ctgaaagttt tgatttattt gcttatgcca ctcagaaata 420
cactaaaaga caagagtttg gagcctccgg cggacgcctg ggtccgggcc gcgcgaacgc 480
gcccggggcg aggccgccga agcaacagtg gtaggttcac aatggtttgg gagtttttac 540
actcggtaat gatccctccg ctggttcacc aacggagacc ttgttacgac ttttacttcc 600
tcta 604

<210> SEQ ID NO 42
<211> LENGTH: 619
<212> TYPE: DNA
<213> ORGANISM: Emericellopsis minima

<400> SEQUENCE: 42
tcttggtcat ttagaggaag taaaagtcgt aacaaggtct ccgttggtga accagcggag 60
ggatcattac tgagttatcc aactcccaaa cccctgtgaa catacctacg ttgcttcggc 120
gggtcgtccc gcggcgcgcc ctcgcggcgt gacccggacc caggcgcccg ccggggaacc 180
aaactcttgt cttccagtgt ctcctctgag tggcataagc aaaaataaac aaaactttca 240
gcaacggatc tcttggttct ggcatcgatg aagaacgcag cgaaatgcga taagtaatgt 300
gaattgcaga attcagtgaa tcatcgaatc tttgaacgca cattgcgccc gccagtattc 360
tggcgggcat gcctgtctga gcgtcatttc aaccctcagc cccgttcgc ggggcgctgg 420 cgttggggcc cggccgtcct cgcggcggcc gtccccgaaa cacagtggcg gtctcccgca 480
gactcccctg cgtagtagca ctacctcgca gaagggacga gcgggctggc cacgccgtaa 540
aacaccccac ctctccaggt tgacctccag atcaggtagg aatacccgct gaacttaagc 600
atatcaataa gcggaggaa 619

<210> SEQ ID NO 43
<211> LENGTH: 602
<212> TYPE: DNA
<213> ORGANISM: Alternaria mali

<400> SEQUENCE: 43
atttagagga agtaaaagtc gtaacaaggt ctccgtaggt gaacctgcgg agggatcatt 60
acacaaatat gaaggcgggc tggaacctct cggggttaca gccttgctga attattcacc 120
cttgtctttt gcgtacttct tgtttccttg gtgggttcgc ccaccactag gacaaacata 180
aaccttttgt aattgcaatc agcgtcagta acaaattaat aattacaact ttcaacaacg 240
gatctcttgg ttctggcatc gatgaagaac gcagcgaaat gcgataagta gtgtgaattg 300
cagaattcag tgaatcatcg aatctttgaa cgcacattgc gccctttggt attccaaagg 360
gcatgcctgt tcgagcgtca tttgtaccct caagctttgc ttggtgttgg gcgtcttgtc 420
tctagctttg ctggagactc gccttaaagt aattggcagc cggcctactg gtttcggagc 480
gcagcacaag tcgcactctc tatcagcaaa ggtctagcat ccattaagcc ttttttcaa 540 cttttgacct cggatcaggt agggataccc gctgaactta agcatatcaa taagcggagg 600
aa 602

<210> SEQ ID NO 44
<211> LENGTH: 589
<212> TYPE: DNA
<213> ORGANISM: Bipolaris heveae

<400> SEQUENCE: 44
tatgatatgc ttaagttcag cgggtatccc tacctgatcc gaggtcaaaa gtgaaaaacg 60
taaacgtctt gatggagtac cgtccttttc tcctgataca aagcgcaaaa aatgtgctgc 120
gctccgaaac cagtaggccg gctgccaatc gttttaaggc gagtctcccg caaaggagag 180
acaaaaagac gcccaacacc aagcaaagct tgaaggtaca aatgacgctc gaacaggcat 240
gccctttgga ataccaaagg gcgcaatgtg cgttcaaaga ttcgatgatt cactgaattc 300
tgcaattcac actacgtatc gcatttcgct gcgttcttca tcgatgccag aaccaagaga 360
tccgttgttg aaagttgtaa taattacatt gtttttactg acgctgatgg aaactgcata 420
agaaaaaaag gtttatggtt tggtcctggt ggcgggcgag cccgcccagg aaacaacaag 480
tgcgcaaaag acatgggtgg aaaaaatatt tcagccggcc gtgaagccag gccttcctat 540
tttgttgtgt aatgatccct ccgcaggttc acctacggag accttgtta 589

<210> SEQ ID NO 45
<211> LENGTH: 632
<212> TYPE: DNA
<213> ORGANISM: Stachybotrys bisbyi

<400> SEQUENCE: 45
ttagaggaag taaaagtcgt aaacaggtct acgttggtga accagcggag tgatcattac 60

-continued

```
cgagtttaca actcccamac ycaatgtgaa catacctcwa gttgcttcgg sgggaacgcc    120

ccggcgckcc ctccgaccct cccgccccgvk ssrggatcgg ggagcctagc ccggacccag    180

gcgccsgccg gaggtaccca aactyttgtc ttcagtatat tcttctgagt ggcamamrca    240

aaaawraatc aaaactttca amaamrgatc tcttggctck ggcatcratg aagaamgcag    300

mraaatgcga taagtaatgt gaattgcaga attcagtgaa tcatcgaatc tttgaacgca    360

crttgsrccc rccagcaytg ctggcgggca tgcctgtccg agcgtcattt caaccctcrg    420

gccccccggg gactggtgtk ggggatcggm ccgccctggc gcggygccst ccccgaaata    480

crgtggcggt ctcrswgcag cctccccwgc gtagtagcac acmkmgcatc ggagagsggc    540

acgcctacgc cgtgaaaccc caacttctga tagttgacct cggatcaggt aggaataccc    600

gctggaactt aagcatatca tagcggagga aa                                  632
```

<210> SEQ ID NO 46
<211> LENGTH: 614
<212> TYPE: DNA
<213> ORGANISM: Dothideomycete sp.

<400> SEQUENCE: 46

```
tagaggaagt aaaagtcgta acaaggtttc cgtaggtgaa cctgcggaag gatcattatc     60

cataaccaac agcgtgcggt cgcggccccc ggggcaaccc gggtggtttt cgcgccgcat    120

tcctgtatcc ttttttacg agcacctttc gttctccttc ggcggggcaa cctgccgctg    180

gaacttaaca aaaccttttt ttgcatctag cattacctgt tctgatacaa acaatcgtta    240

caactttcaa caatggatct cttggctctg gcatcgatga agaacgcagc gaaatgcgat    300

aagtagtgtg aattgcagaa ttcagtgaat catcgaatct ttgaacgcac attgcgcccc    360

ttggtattcc atggggcatg cctgttcgag cgtcatctac accctcaagc tctgcttggt    420

gttgggcgtc tgtcccgcct ctgcgcgcgg actcgcccca aattcattgg cagcggtctt    480

tgcctcctct cgcgcagcac aattgcgtct gcgggggggc gtggcccgca tccacgaagc    540

aacattaccg tctttgacct cggatcaggt agggataccc gctgaactta agcatatcaa    600

taggcgggag gaaa                                                      614
```

<210> SEQ ID NO 47
<211> LENGTH: 529
<212> TYPE: DNA
<213> ORGANISM: Acremonium strictum

<400> SEQUENCE: 47

```
ctacctgatc cgaggtcacc ttgaaaattg gggtttcac ggcgtggtcg ttccgctctc      60

cggtgcgagg ttgtgctact acgcagggga ggctgcggcg cgaccgccac tgaatttgag    120

ggacgggggc cgcgagggcc gccgatcccc agcaccaggc ccgctccccc ggaagggtgg    180

gcctgagggt tgaaatgacg ctcggacagg catgcccgcc ggagtgccgg cgggcgcaat    240

gtgcgttcaa agattcgatg attcactgaa ttctgcaatt cacattactt atcgcatttc    300

gctgcgttct tcatcgatgc cagagccaag agatccgttg ttgaaagttt tgattcattt    360

tgttttcggc tttcgcccct cagagaaata cgattaaatc agggtttggt tttccccggc    420

ggacgcccgg aggcccggag gccgccgcgc gctgagcccg ccgagggaac gtttggtaag    480

ttcacaatgg gttggagagc ctagggcact ctggtaatga ccctccgct                 529
```

<210> SEQ ID NO 48
<211> LENGTH: 582

<212> TYPE: DNA
<213> ORGANISM: Pleosporaceae sp.

<400> SEQUENCE: 48
ctacctgatc gaggtcaaat gtggatttgt tatagaaaac aaaggcttgc tggatgccgc 60
cccgtggatt ggaaggcgca aatttgtgct gcgctccgaa aaccagtagg tcggctgcca 120
atcgttttaa ggcgagtctc ccccaacaag gggagagaca aaaagacgcc caacaccaag 180
caaagcttga gggtacaaat gacgctcgaa caggcatgcc ctttggaata ccaaagggcg 240
caatgtgcgt tcaaagattc gatgattcac tgaattctgc aattcacact acgtatcgca 300
tttcgctgcg ttcttcatcg atgccagaac caagagatcc gttgttgaaa gttttaataa 360
attgaattat tatactgacg ctgattgcaa ctgcataaaa aaaggtttat ggttgggtcc 420
tggtggcgag cgaactcgcc caggaaacaa aaagtgcgca aaagacatgg gtgaaaaata 480
cttggggcgg acgctgttgc cagcaaacca caccctcata tttttgttgt gtaatgatcc 540
ctccgcaggt tcacctacgg agaccttgtt acgactttta ca 582

<210> SEQ ID NO 49
<211> LENGTH: 570
<212> TYPE: DNA
<213> ORGANISM: Alternaria sp.

<400> SEQUENCE: 49
cctgatccga gggtcaaaag ttgaaaaaaa aggcttaatg gatgctagac ctttgctgat 60
agagagtgcg acttgtgctg cgctccgaaa ccagtaggcc ggctgccaat tactttaagg 120
cgagtctcca gcaaagctag agacaagacg cccaacacca agcaaagctt gagggtacaa 180
atgacgctcg aacaggcatg ccctttggaa taccaaaggg cgcaatgtgc gttcaaagat 240
tcgatgattc actgaattct gcaattcaca ctacttatcg catttcgctg cgttcttcat 300
cgatgccaga accaagagat ccgttgttga aagttgtaat tattaatttg ttactgacgc 360
tgattgcaat tacaaaaggt ttatgtttgt cctagtggtg ggcgaaccca ccaaggaaac 420
aagaagtacg caaaagacaa gggtgaataa ttcagcaagg ctgtaacccc gagaggttcc 480
agcccgcctt catatttgtg taatgatccc tccgcaggtt cacctacggg agaccttgtt 540
acgactttta cttcctctaa atgaccaaga 570

<210> SEQ ID NO 50
<211> LENGTH: 555
<212> TYPE: DNA
<213> ORGANISM: Fusarium moniliformae

<400> SEQUENCE: 50
cgtttgtgac cagcggaggg tcattaccga gtttacaact cccaaacccc tgtgaacata 60
ccaattgttg cctcggcgga tcagcccgct cccggtaaaa cgggacggcc cgccagagga 120
cccctaaact ctgtttctat atgtaacttc tgagtaaaac cataaataaa tcaaaacttt 180
caacaacgga tctcttggtt ctggcatcga tgaagaacgc agcaaaatgc gataagtaat 240
gtgaattgca gaattcagtg aatcatcgaa tctttgaacg cacattgcgc ccgccagtat 300
tctggcgggc atgcctgttc gagcgtcatt tcaaccctca agcccccggg tttggtgttg 360
gggatcggcg agcccttgcg gcaagccggc cccgaaatct agtggcggtc tcgctgcagc 420
ttccattgcg tagtagtaaa accctcgcaa ctggtacgcg gcgcggccaa gccgttaaac 480
ccccaacttc tgaatgttga cctcggatca ggtaggaata cccgctgaac ttaagcaaat 540
caataagcgg aggaa 555

<210> SEQ ID NO 51
<211> LENGTH: 517
<212> TYPE: DNA
<213> ORGANISM: Fusarium moniliformae

<400> SEQUENCE: 51
gcgggtattc ctacctgatc cgaggtcaac attcagaagt tgggggttta acggcttggc 60
cgcgccgcgt accagttgcg agggttttac tactacgcaa tggaagctgc agcgagaccg 120
ccactagatt tcggggccgg cttgccgcaa gggctcgccg atccccaaca ccaaacccgg 180
gggcttgagg gttgaaatga cgctcgaaca ggcatgcccg ccagaatact ggcgggcgca 240
atgtgcgttc aaagattcga tgattcactg aattctgcaa ttcacattac ttatcgcatt 300
ttgctgcgtt cttcatcgat gccagaacca agagatccgt tgttgaaagt tttgatttat 360
ttatggtttt actcagaagt tacatataga aacagagttt aggggtcctc tggcgggccg 420
tcccgtttta ccgggagcgg gctgatccgc cgaggcaaca attggtatgt tcacaggggt 480
ttgggagttg taaactcggt aatgatccct ccgctgg 517

<210> SEQ ID NO 52
<211> LENGTH: 675
<212> TYPE: DNA
<213> ORGANISM: Sporisorium everhartii

<400> SEQUENCE: 52
acctgcagat ggatcatttc gatgaaaacc ttttttctga ggtgtggctc gcacctgtcc 60
aactaaactt gagctacctt tttaacacgg ttgcatcggt tgagagcctg tcaaagaacg 120
cgaaagtgtc cttttggttg ggccctcgac actttacaca aacacttttg atcttctagg 180
atttgaatga caatttatga ctggtaattc ggtcgtttaa atttaaaaac aacttttggc 240
aacggatctc ttggttctcc catcgatgaa gaacgcagcg aattgcgata agtaatgtga 300
attgcagaag tgaatcatcg aatctttgaa cgcaccttgc gctccctgca gatctaatct 360
ggggagcatg cctgtttgag ggccgcgaat tgtttcgaac cactcttttt ttaattaaga 420
agggctggct cggtagtgag ggttttttttg ccattaaccg tggctccctc gaaatacatt 480
agcgcatcca tttgataggc aagaacggac gaaagctcat ctttcgctct ctcttccctg 540
ccgggttttg ataatatcag gacttcggag gcggagaaag ggcaagagct ggacgcaacg 600
atcttgctgt ttggcgtgct tctgaacccc gcccatgctt tgcttcttgc aaagaaggga 660
ttttaataat tcatc 675

<210> SEQ ID NO 53
<211> LENGTH: 644
<212> TYPE: DNA
<213> ORGANISM: Alternaria sp.

<400> SEQUENCE: 53
ggtgacctgc ggagggtcat tacacaaata tgaaggcggg ctggaacctc tcggggttac 60
agccttgctg aattattcac ccttgtcttt tgcgtacttc ttgtttcctt ggtgggttcg 120
cccaccacta ggacaaacat aaaccttttg taattgcaat cagcgtcagt aacaaattaa 180
taattacaac tttcaacaac ggatctcttg gttctggcat cgatgaagaa cgcagcgaaa 240
tgcgataagt agtgtgaatt gcagaattca gtgaatcatc gaatctttga acgcacattg 300
cgccctttgg tattccaaag ggcatgcctg ttcgagcgtc atttgtaccc tcaagctttg 360
cttggtgttg ggcgtcttgt ctctagcttt gctggagact cgccttaaag taattggcag 420
ccggcctact ggtttcggag cgcagcacaa gtcgcactct ctatcagcaa aggtctagca 480
tccattaagc cttttttca acttttgacc tcggatcagg tagggatacc cgctgaactt 540
aagcatatca ataagccgga ggaaacttcg ggaggcggag aaagggcaag agctggacgc 600
aacgatcttt gctgtttggc gtgcttctga accccgccca tgct 644

<210> SEQ ID NO 54
<211> LENGTH: 599
<212> TYPE: DNA
<213> ORGANISM: Fusarium proliferatum

<400> SEQUENCE: 54
tcttggtctt tttataggta gtaaaagtcg taacaaggtc tccgttggtg aaccagcgga 60
gggatcatta ccgagtttac aactcccaaa cccctgtgaa cataccaatt gttgcctcgg 120
cggatcagcc cgctcccggt aaaacgggac ggcccgccag aggaccccta aactctgttt 180
ctatatgtaa cttctgagta aaaccataaa taaatcaaaa ctttcaacaa cggatctctt 240
ggttctggca tcgatgaaga acgcagcaaa atgcgataag taatgtgaat tgcagaattc 300
agtgaatcat cgaatctttg aacgcacatt gcgcccgcca gtattctggc gggcatgcct 360
gttcgagcgt catttcaacc ctcaagcccc cgggtttggt gttggggatc ggcgagccct 420
tgcggcaagc cggccccgaa atctagtggc ggtctcgctg cagcttccat tgcgtagtag 480
taaaaccctc gcaactggta cgcggcgcgg ccaagccgtt aaacccccaa cttctgaatg 540
ttgacctcgg atcaggtagg aatacccgct gaacttaagc atataaataa gcggagaaa 599

<210> SEQ ID NO 55
<211> LENGTH: 550
<212> TYPE: DNA
<213> ORGANISM: Fusarium nygamai

<400> SEQUENCE: 55
tatgggggcg ggtcttcgtt tggtggacca gcggagggat cattaccgag tttacaactc 60
ccaaacccct gtgaacatac caattgttgc ctcgggggat cagcccgctc ccggtaaaac 120
ggaacggccc gccagaggac ccctaaactc tgtttctata tgtaacttct gagtaaaacc 180
ataaataaat yaaaactttc aacamcggat ctctkggtty kggcwtcgat gargaasgca 240
gsmaaatgsg ataagwaatg wgaattgcwg aatycagtga aycmtcgaay cttkgamcgc 300
acaytsckcc cgcccagtat tctggcgggc cagccykwtc ggagsgwyak ttcmaccctc 360
ragcccccgg gtttggggtt ggggttcggg gagcctcacg gcaagccggc cccgaaatac 420
agtggcggtc tcgctgcagc ttccattgcg tagtagtaaa accctcgcaa ctggtacgcg 480
gcgcggccaa gccgttaaac cccaacttc tgaatgttga ccctcggatc agtaggatcc 540
cccccctttt 550

<210> SEQ ID NO 56
<211> LENGTH: 594
<212> TYPE: DNA
<213> ORGANISM: Periconia macrospinosa

<400> SEQUENCE: 56
ttcctccgct tattgatatg cttaagttca gcgggtatcc ctacctgatc cgaggtcaag 60
tcgtgaaagg tcttgctgga gcgcggatcc gccgggcctc cgagaagcgc aaatgtgctg 120

```
cgcgaggggg ccggcacgac cgccgccaat gactttgagg cgagtccgcg cgcgagaacg    180

gcgggacaga cgcccaacac caagctaggc ttgagggtgt aaatgacgct cgaacaggca    240

tggccaaagg aatacctatg gccgcaatgt gcgttcaaag attcgatgat tcactgaatt    300

ctgcaattca cactacttat cgcatttcgc tgcgttcttc atcgatgcca gaaccaagag    360

atccattgtt gaaagttgtg ataatttagg tttgttatca gaagttttcg cgtataatgc    420

aaggggtttc gtgggttcct ggcggcgggc gagcccgccg aggaagctat agaggtacac    480

gtaggcagag ggtgggtgta taaggagcgc cgaagcgccc cgaatgtgta atgatccttc    540

cgcaggttca cctacggaaa ccttgttacg acttttactt cctctaaatg acca          594


<210> SEQ ID NO 57
<211> LENGTH: 553
<212> TYPE: DNA
<213> ORGANISM: Codinaeopsis sp.

<400> SEQUENCE: 57

ttcctccgct tattgatatg cttaagttca gcgggtattc ctacctgatc cgaggtcaac     60

cacttagaaa gttgggggtt ttacggccgg agcgcgcgcc ggaccagaac gagaaagcat    120

tactgcgctc ggttccgggg cgcgcccgcc gctgtctttg ggagcctgcg ctgcgcaggg    180

ctccaacgcc aggcggggcc tgagggttga aatgacgctc ggacaggcat gcccgccaga    240

gtgctggcgg gcgcaatgtg cgttcaaaga ttcgatgatt cactgaattc tgcaattcac    300

attacttatc gcatttcgct gcgttcttca tcgatgccag aaccaagaga tccgttgttg    360

aaagttttga ctcgtttata gtctgctcgg agatgccaac gttacagaga cagagtttag    420

gggccgccgg cgggctggag cgccccggag cgcccgaaga cgcgcccgga gcacccgccg    480

aggcaacggg ttgtaggtaa gttcacagtg gtttacggga gtcttgcgag tcctgtaatg    540

atccctccgc tgg                                                       553


<210> SEQ ID NO 58
<211> LENGTH: 766
<212> TYPE: DNA
<213> ORGANISM: Sporisorium everhartii

<400> SEQUENCE: 58

tattgatatg cttaagttca gcgggtagtc ctaccaatct gaggccgatg aattattaaa     60

atcccttctt tgcaagaagc aaagcatggg cggggttcag aagcacgcca aacagcaaga    120

tcgttgcgtc cagctcttgc cctttctccg cctccgaagt cctgatatta tcaaaacccg    180

gcagggaaga gagagcgaaa gatgagcttt cgtccgttct tgcctatcaa atggatgcgc    240

taatgtattt cgagggagcc acggttaatg gcaaaaaaac cctcactacc gagccagccc    300

ttcttaatta aaaaaagagt ggttcgaaac aattcgcggc cctcaaacag gcatgctccc    360

cagattagat ctgcagggag cgcaaggtgc gttcaaagat tcgatgattc acttctgcaa    420

ttcacattac ttatcgcaat tcgctgcgtt cttcatcgat gggagaacca agagatccgt    480

tgccaaaagt tgtttttaaa tttaaacgac cgaattacca gtcataaatt gtcattcaaa    540

tcctagaaga tcaaaagtgt ttgtgtaaag tgtcgagggc ccaaccaaaa ggacactttc    600

gcgttctttg acaggctctc aaccgatgca accgtgttaa aaaggtagct caagtttagt    660

tggacaggtg cgagccacac ctcagaaaaa aggttttcat cgaaatgatc catctgcagg    720

ttcacctaca gataccttgt tacgactttt acttcctcta aatgga                   766
```

-continued

<210> SEQ ID NO 59
<211> LENGTH: 571
<212> TYPE: DNA
<213> ORGANISM: Fusarium proliferatum

<400> SEQUENCE: 59
gaaaaaaact gggatctacc tgatccgagg tcacattcag aagttggggg tttaacggct 60
tggccgcgcc gcgtaccagt tgcgagggtt ttactactac gcaatggaag ctgcagcgag 120
accgccacta gatttcgggg ccggcttgcc gcaagggctc gccgatcccc aacaccaaac 180
ccgggggctt gagggttgaa atgacgctcg aacaggcatg cccgccagaa tactggcggg 240
cgcaatgtgc gttcaaagat tcgatgattc actgaattct gcaattcaca ttacttatcg 300
cattttgctg cgttcttcat cgatgccaga accaagagat ccgttgttga aagttttgat 360
ttatttatgg ttttactcag aagttacata tagaaacaga gtttaggggt cctctggcgg 420
gccgtcccgt tttaccggga gcgggctgat ccgccgaggc aacaattggt atgttcacag 480
gggtttggga gttgtaaact cggtaatgat ccctccgctg gttcaccaac ggagaccttg 540
ttacgacttt tacttcctct aaatgaccaa g 571

<210> SEQ ID NO 60
<211> LENGTH: 542
<212> TYPE: DNA
<213> ORGANISM: Fusarium moniliformae

<400> SEQUENCE: 60
tacctgatcc gaggtcaaca ttcagaagtt gggggtttaa cggcttggcc gcgccgcgta 60
ccagttgcga gggttttact actacgcaat ggaagctgca gcgagaccgc cactagattt 120
cggggccggc ttgccgcaag ggctcgccga tccccaacac caaacccggg ggcttgaggg 180
ttgaaatgac gctcgaacag gcatgcccgc cagaatactg gcgggcgcaa tgtgcgttca 240
aagattcgat gattcactga attctgcaat tcacattact tatcgcattt tgctgcgttc 300
ttcatcgatg ccagaaccaa gagatccgtt gttgaaagtt ttgatttatt tatggtttta 360
ctcagaagtt acatatagaa acagagttta ggggtcctct ggcgggccgt cccgttttac 420
cgggagcggg ctgatccgcc gaggcaacaa ttggtatgtt cacaggggtt tgggagttgt 480
aaactcggta atgatccctc cgctggttca ccaacggaga ccttgttacg acttttactt 540
ac 542

<210> SEQ ID NO 61
<211> LENGTH: 496
<212> TYPE: DNA
<213> ORGANISM: Fusarium proliferatum

<400> SEQUENCE: 61
tcctacctga tccgaggtca cattcagaag ttgggggttt aacggcttgg ccgcgccgcg 60
taccagttgc gagggtttta ctactacgca atggaagctg cagcgagacc gccactagat 120
ttcggggccg gcttgccgca agggctcgcc gatccccaac accaaacccg ggggcttgag 180
ggttgaaatg acgctcgaac aggcatgccc gccagaatac tggcgggcgc aatgtgcgtt 240
caaagattcg atgattcact gaattctgca attcacatta cttatcgcat tttgctgcgt 300
tcttcatcga tgccagaacc aagagatccg ttgttgaaag ttttgattta tttatggttt 360
tactcagaag ttacatatag aaacagagtt taggggtcct ctggcgggcc gtcccgtttt 420
accgggagcg ggctgatccg ccgaggcaac aattggtatg ttcacagggg tttgggagtt 480
gtaaactcgg taatga 496

<210> SEQ ID NO 62
<211> LENGTH: 573
<212> TYPE: DNA
<213> ORGANISM: Fusarium moniliformae

<400> SEQUENCE: 62
gtcgtaacaa ggtctccgtt ggtgaaccag cggagggatc attaccgagt ttacaactcc 60
caaacccctg tgaacatacc aattgttgcc tcggcggatc agcccgctcc cggtaaaacg 120
ggacggcccg ccagaggacc cctaaactct gtttctatat gtaacttctg agtaaaacca 180
taaataaatc aaaactttca acaacggatc tcttggttct ggcatcgatg aagaacgcag 240
caaaatgcga taagtaatgt gaattgcaga attcagtgaa tcatcgaatc tttgaacgca 300
cattgcgccc gccagtattc tggcgggcat gcctgttcga gcgtcatttc aaccctcaag 360
cccccgggtt tggtgttggg gatcggcgag cccttgcggc aagccggccc cgaaatctag 420
tggcggtctc gctgcagctt ccattgcgta gtagtaaaac cctcgcaact ggtacgcggc 480
gcggccaagc cgttaaaccc ccaacttctg aatgttgacc tcggatcagg taggaatacc 540
cgctgaactt aagcatatca ataagcggag gaa 573

<210> SEQ ID NO 63
<211> LENGTH: 554
<212> TYPE: DNA
<213> ORGANISM: Acremonium strictum

<400> SEQUENCE: 63
acctgatctg aggtcacctt gagaagtggg gggtttaacg gcgtggttca accgctatcc 60
tgccgcgaga ggtttaatta ctgcacggag gagttcgcga gggaaccgcc actggatttc 120
agggccagcc gccgccaggg gcaggctgat ccccaacgcc aggtcccgcg aacgggtcct 180
gagggttgaa atgacgctca gacaggcatg cccgccagaa tactggcggg cgcaatgtgc 240
gttcaaagat tcgatgattc actgaattct gcaattcaca ttacttatcg cattttgctg 300
cgttcttcat cgatgccaga accaagagat ccgttgctga aagttttgat ttatttgctt 360
atgccactca gaaatacact aaaagacaag agtttggagc ctccggcgga cgcctgggtc 420
cgggccgcgc gaacgcgccc ggggcgaggc cgccgaagca acagtggtag gttcacaatg 480
gtttgggagt ttttacactc ggtaatgatc cctccgctgg ttcaccaacg gagaccttgt 540
tacgactttt actt 554

<210> SEQ ID NO 64
<211> LENGTH: 569
<212> TYPE: DNA
<213> ORGANISM: Myrothecium verrucaria

<400> SEQUENCE: 64
ttctacctga tccgaggtca actttcagaa gtggggtgtt taacggcatg gccaccgccg 60
cgttccaact gcgaggttgt gctactacgc agaggaggac tacagcgaga ccgccactag 120
atttcggggc cggcgggctt gacgccctgc tgccgatccc caacaccagg cgctgggggc 180
ctgagggttg aaatgacgct cgaacaggca tgcccgccag aatactggcg ggcgcaatgt 240
gcgttcaaag attcgatgat tcactgaatt ctgcaattca cattacttat cgcatttcgc 300
tgcgttcttc atcgatgcca gaaccaagag atccgttgtt gaaagttttt atttatttgt 360
ttatgtgtca ctcagaggag aaaaccacta aagacatgag ggtttggggc ctccggcggg 420
cgcctggttc cgggcccgag ggcgccgggg cggtcccgcc gaagcaacga tacggtaagg 480
ttcacaaagg gtttgggagt ttgtaaactc ggtaatgatc cctccgctgg ttcaccaacg 540
gagaccttgt tacgactttt acttcctct 569

<210> SEQ ID NO 65
<211> LENGTH: 545
<212> TYPE: DNA
<213> ORGANISM: Fusarium subglutinans

<400> SEQUENCE: 65
tctacctgat ccgaggtcaa cattcagaag ttggggggttt aacggcttgg ccgcgccgcg 60
ataccagttg cgagggtttt actactacgc aatggaagct gcagcgagac cgccactgta 120
tttcggggcc ggcttgccgt gaagacaagc cgaccccccac caccaaaccc gggggggttac 180 ggatgaaaat gacgccggaa tggccttgcc aacacaaaag ggggcggggg gagttggaag 240
ataagatgat tcactgaatt ctgcaattca cattactttt cgtatttcgc tttggtcttc 300
ttcgatgcca gaaccaagag atccgttgtt gaaagttttg atttatttat ggttttactc 360
agaagttaca tatagaaaca gagtttaggg gtcctgtggc gggccgttcc gttttaccgg 420
gagcgggctg atccgccgag gcaacaattg gtatgttcac aggggtttgg gagttgtaaa 480
ctcggtaatg atcctccgct gtgctctccg caggaacacc ttgtgagacc ttgacattcc 540
tttaa 545

<210> SEQ ID NO 66
<211> LENGTH: 545
<212> TYPE: DNA
<213> ORGANISM: Leptosphaeria bicolor

<400> SEQUENCE: 66
cgtaggtgac tgcggaggac attaattacg caagctatcc ccccttcggt gttattgcat 60
ccaccctttg tctactgtac tcttgttgtt tcctcggcag gattgcccgt agctaacaac 120
ccaataaacc cttgtattaa aagcactgaa atctgataac tattaaatta ttacaacttt 180
caacaatgga tctcttggtt ctggcatcaa taaagaacgc aactaaatgc gaaaagtagt 240
gtgaattgca taattccgtg aatcatccaa tctttgaacg ctcattgcgc ccctcggcat 300
tccgtggggc atgcctgttc gagcgtcatt tacaccctca agctctgctt ggtgttgggc 360
gtctgtcccg cttcatgcgt ggactcgccc caaagtcatt ggcagcggtc gtgccagctt 420
ctcgcgcagc acatttgcgt ttcttgaagt ttggtggatc agcatccagt aagctctttt 480
atgacttgac ctcggatcag gtagggatac ccgctgaact taagcataaa aataagcgga 540
ggaaa 545

<210> SEQ ID NO 67
<211> LENGTH: 583
<212> TYPE: DNA
<213> ORGANISM: Acremonium sp.

<400> SEQUENCE: 67
acctgatcga ggtcaacctt aaaaaattgg gtgttttacg gcgtggtcgt tccgctctcc 60
ggtgcgaggt tgtgctacta cgcaggggag gctgcggcgc gaccgccact gaatttgagg 120
gacgggggcc gcgagggccg ccgatcccca gaaccaggcc cgctcccccg gaagggtggg 180
cctgagggtt gaaatgacgc tcggacaggc atgcccgccg gagtgccggc gggcgcaatg 240
tgcgttcaaa gattcgatga ttcactgaat tctgcaattc acattactta tcgcatttcg 300
ctgcgttctt catcgatgcc agagccaaga gatccgttgt tgaaagtttt gattcatttt 360
gttttcgggc tttcgcccct cagagaaata cgattaaatc agggtttggt tttccccggc 420
ggacgcccgg aggcccggag gccaccgcgc gctgagcccg ccgagggaac gtttggtaag 480
ttcacaatgg gttggagagc ctagggcact ctggtaatga tccctccgct ggttcaccaa 540
cggagacctt gttacgactt ttacttcctc taattgacca aga 583

<210> SEQ ID NO 68
<211> LENGTH: 582
<212> TYPE: DNA
<213> ORGANISM: Acremonium strictum

<400> SEQUENCE: 68
gttgtgacca gcggagggac attaccagag tgccctaggc tctccaaccc attgtgaact 60
taccaaacgt tccctcggcg ggctcagcgc gcggtggcct ccgggcctcc gggcgtccgc 120
cggggaaaac caaaccctga tttaatcgta tttctctgag gggcgaaagc ccgaaaacaa 180
aatgaatcaa aactttcaac aacggatctc ttggctctgg catcgatgaa gaacgcagcg 240
aaatgcgata agtaatgtga attgcagaat tcagtgaatc atcgaatctt tgaacgcaca 300
ttgcgcccgc cggcactccg gcgggcatgc ctgtccgagc gtcatttcaa ccctcaggcc 360 caccccttccg gggagcggg cctggttctg gggatcggcg gccctcgcgg cccccgtccc 420
tcaaattcag tggcggtcgc gccgcagcct cccctgcgta gtagcacaac ctcgcaccgg 480
agagcggaac gaccacgccg taaaacaccc aatttttttaa ggttgacctc ggatcaggta 540
ggaatacccg ctgaacttaa gcatatcaat aggcggagga aa 582

<210> SEQ ID NO 69
<211> LENGTH: 769
<212> TYPE: DNA
<213> ORGANISM: Periconia macrospinosa

<400> SEQUENCE: 69
ttcctccgct tattgatatg cttaagttca gcgggtatcc ctacctgatc cgaggtcaag 60
tcgtgaaagg tcttgctgga gcgcggatcc gccgggcctc cgagaagcgc aaatgtgctg 120
cgcgaggggg ccggcacgac cgccgccaat gactttgagg cgagtccgcg cgcgaaaacg 180
gcgggacaga cgcccaacac caagctaggc ttgagggtgt aaatgacgct cgaacaggca 240
tggccaaagg aatacctatg gccgcaatgt gcgttcaaag attcgatgat tcactgaatt 300
ctgcaattca cactacttat cgcatttcgc tgcgttcttc atcgatgcca gaaccaagag 360
atccattgtt gaaagttgtg ataatttagg tttgttatca gaagttttcg cgtataatgc 420
aaggggtttc gtgggttcct ggcggcgggc gagcccgccg aggaagctat agaggtacac 480
gtaggcagag ggtgggtgta taaggagcgc cgaagcgccc cgaatgtgta atgatccttc 540
cgcaggttca cctacggaaa ccttgttacg acttttactt cctctaaatg accaagaaga 600
cactttcgcg ttctttgaca ggctctcaac cgatgcaacc gtgttaaaaa ggtagctcaa 660
gtttagttgg acaggtgcga gccacacctc agaaaaaagg ttttcatcga aatgatccat 720
ctgcaggttc acctacagat accttgttac gacttttact tcctctaaa 769

<210> SEQ ID NO 70
<211> LENGTH: 518
<212> TYPE: DNA
<213> ORGANISM: Fusarium pseudograminearum

<400> SEQUENCE: 70
ttcctacctg atccgaggtc acattcagaa gttggggttt aacggcgtgg ccgcgacgat 60
taccagtaac gatgtgtaaa ttactacgct atggaagctc gacgtgaccg ccaatcgatt 120
tggggagtgt cagacgacag ctcccaacac caagctgggc ttgagggttg aaatgacgct 180
cgaacaggca tgcccgccag aatactggcg ggcgcaatgt gcgttcaaag attcgatgat 240
tcactgaatt ctgcaattca cattacttat cgcattttgc tgcgttcttc atcgatgcca 300
gaaccaagag atccgttgtt gaaagttttg atttatttgt ttttttactc agaagttcca 360
ctaaaaacag agtttgtggt tcctgcggcg ggccgtcccg ttttacgggg agcgggctga 420
tccgccgagg caacatgtag gtatgttcac aggggtttgg gagttgtaaa ctcggtaatg 480
atccctccgc tggttcacca acggagacct tgttacga 518

<210> SEQ ID NO 71
<211> LENGTH: 562
<212> TYPE: DNA
<213> ORGANISM: Acremonium sp.

<400> SEQUENCE: 71
tactgatccg aggtcacctt gtgaaagttg gggtttcac ggcgtggccg agccgctctc 60
cggtgcgagg tgtgctacta cgcaggggag gctgcggcgc gaccgccact gaatttgggg 120
gacaggggcc ccggagggcc gctgatcccc agcaccaggc gccgaacccc cgaaagggtg 180
gccctgaggg ttgaaatgac gctcggacag gcatgcccgc cggagtgccg gcgggcgcaa 240
tgtgcgttca aagattcgat gattcactga attctgcaat tcacattact tatcgcattt 300
cgctgcgttc ttcatcgatg ccagagccaa gagatccgtt gttgaaagtt ttgattcatt 360
ttgttttcgg gctttcgccc ctcagatata cacgaaaaat tcgggtttgg ttgtccccgg 420
cggacgcccg gtggcccgga ggccggccgc gcgctgagcc cgccgaggga acgataggta 480
agttcacaat gggttggaga gccgaagcac tcgttttgta atgatccctc cgctggttca 540
ccaacggaga ccttgttacg ac 562

<210> SEQ ID NO 72
<211> LENGTH: 526
<212> TYPE: DNA
<213> ORGANISM: Fusarium nygamai

<400> SEQUENCE: 72
ctacctgatc gaggtcacat tcagaagttg gggtttaac ggcttggccg cgccgcgtac 60
cagttgcgag ggttttacta ctacgcaatg gaagctgcag cgagaccgcc actgtatttc 120
ggggccggct tgccgtgagg ctcgccgatc cccaacacca aacccggggg cttgagggtt 180
gaaatgacgc tcgaacaggc atgcccgcca gaatactggc gggcgcaatg tgcgttcaaa 240
gattcgatga ttcactgaat tctgcaattc acattactta tcgcattttg ctgcgttctt 300
catcgatgcc agaaccaaga gatccgttgt tgaaagtttt gatttattta tggttttact 360
cagaagttac atatagaaac agagtttagg ggtcctctgg cgggccgttc cgttttaccg 420
ggagcgggct gatccgccga ggcaacaatt ggtatgttca caggggtttg ggagttgtaa 480
actcggtaat gatccctccg ctggttcacc aacggagacc ttgtta 526

<210> SEQ ID NO 73
<211> LENGTH: 547
<212> TYPE: DNA

<213> ORGANISM: Gibberella sp.

<400> SEQUENCE: 73
atctacctga tccgaggtca cattcagaag ttgggggttt aacggcttgg ccgcgccgcg 60
taccagttgc gagggtttta ctactacgca atggaagctg cagcgagacc gccactgtat 120
ttcggggccg gcttgccgtg aggctcgccg atccccaaca ccaaacccgg gggcttgagg 180
gttgaaatga cgctcgaaca ggcatgcccg ccagaatact ggcgggcgca atgtgcgttc 240
aaagattcga tgattcactg aattctgcaa ttcacattac ttatcgcatt ttgctgcgtt 300
cttcatcgat gccagaacca agagatccgt tgttgaaagt tttgatttat ttatggtttt 360
actcagaagt tacatataga aacagagttt aggggtcctc tggcgggccg ttccgtttta 420
ccgggagcgg gctgatccgc cgaggcaaca attggtatgt tcacaggggt ttgggagttg 480
taaactcggt aatgatccct ccgctggttc accaacggag accttgttac gacttttact 540
tcctcta 547

<210> SEQ ID NO 74
<211> LENGTH: 582
<212> TYPE: DNA
<213> ORGANISM: Colletotrichum graminicola

<400> SEQUENCE: 74
cctacctgat cgaggtcaac cagtaaaaag ttgggggttt tacggcaaga gtccctccgg 60
atcccgatgc gagacgttag ttactacgca aaggaggctc cgggagggtc cgccactacc 120
tttaagggcc tacgtacgcc gtagggcccc aacaccaagc ggagcttgag ggttgaaatg 180
acgctcgaac aggcatgccc gccagaatgc tggcgggcgc aatgtgcgtt caaagattcg 240
atgattcact gaattctgca attcacatta cttatcgcat ttcgctgcgt tcttcatcga 300
tgccagaacc aagagatccg ttgttaaaag ttttaattat ttgcttgtgc cactcagaag 360
aaacgtcgtt aaatcagagt ttggttatcc tccggcgggc gccacgcccc gcgagggggc 420
gcggccggga gggcgtcccc ggggagggga ccccctaacc cgccgaagca acagttaggt 480
atgttcacaa agggttatag agcggtaact cagtaatgat ccctccgctg gttcaccaac 540
ggagaccttg ttacgacttt tacttcctct aaatgaacaa ga 582

<210> SEQ ID NO 75
<211> LENGTH: 738
<212> TYPE: DNA
<213> ORGANISM: Sporisorium everhartii

<400> SEQUENCE: 75
ctacctgatc aagctcacat tcagaagttg ggggtttttg cggttggcca gcccgcgtgg 60
gctttgcaag cactccactc cgccagatcg taacctccag cgcttgcgct ttctccgcct 120
ccgaactcct tgtattatca aaacccggcc ggcaacagag agcgaaagag gagcttgggt 180
ggaatcttgc ctataaaatg catgcgctca tgaatttcga gggagccacg gttaatggca 240
aaaaaaccct cactaccgag ccagcccttc ttaattaaaa aaagagtggt tcgaaacaat 300
tcgcggccct caaacaggca tgctccccag ataaaatctt tagggagcgc aaggtgtgtt 360
caaagattcg atgattcact tctgctattc acattactta tcgcaattcg ctgcgttctt 420
catcgatggg agaaccaaga gatccgttgc cagaagttgt ttttaaattt aaacgatcga 480
attaccagtc atgaattgtc attcaaatcc tagcagatca aaagtgtttg tgtaaagtgt 540
cgacggccca accaaaagga cactttcgcg ttctttgaca ggctctcaac cgatgcaacc 600
gtgttaaaaa ggtagctcaa gtttagttgg acaggtgcga gccacacctc agaaaaaagg 660
ttttcatcga aatgatccat ctgcaggttc acctacagat accttgttac gacttttact 720
tcctctaaat gaccaaga 738

<210> SEQ ID NO 76
<211> LENGTH: 568
<212> TYPE: DNA
<213> ORGANISM: Monographella sp.

<400> SEQUENCE: 76
tctactgatc cgaggtcacc attaaaaaag tgcccaatcc cggggggaga ggtgcggttt 60
atggccgtcg accactgcgt tcacacaagc gagatgataa ttactacgct cagagcacag 120
aggactccgc cactggtttt gaggagctgc ggtttagcgc agtctcccaa cactaagcta 180
ggcttaaggg ttgaaatgac gctcgaacag gcatgcccac tagaatacta atgggcgcaa 240
tgtgcgttca aagattcgat gattcactga attctgcaat tcacattact tatcgcattt 300
cgctgcgttc ttcatcgatg ccagaaccaa gagatccgtt gttgaaagtt ttaacttatt 360
tcttagttta gattcagatt tgacaaagtt gacaagagtt tagtttgtcc gccggcggca 420
gcgcccaccc cgagaggggg caccaaccac cgaggcaaca gtggtaagtt cacatggttt 480
ggagagttga aaactcagta atgatccctc cgcaggttca cctacggaga ccttgttacg 540
acttttactt cctctaaatg gaccaaga 568

<210> SEQ ID NO 77
<211> LENGTH: 579
<212> TYPE: DNA
<213> ORGANISM: Myrothecium verrucaria

<400> SEQUENCE: 77
ctacctgatc cgaggtcaac tttcagaagt ggggtgttta acggcatggc caccgccgcg 60
ttccaactgc gaggttgtgc tactacgcag aggaggacta cagcgagacc gccactagat 120
ttcggggccg gcgggcttga cgccctgctg ccgatcccca acaccaggca ctgggggcct 180
gagggttgaa atgacgctcg aacaggcatg cccgccagaa tactggcggg cgcaatgtgc 240
gttcaaagat tcgatgattc actgaattct gcaattcaca ttacttatcg catttcgctg 300
cgttcttcat cgatgccaga accaagagat ccgttgttga aagtttttat ttatttgttt 360
atgtgtcact cagaggagaa aaccactaaa gacatgaggg tttggggcct ccggcgggcg 420
cctggttccg ggcccgaggg cgccggggcg gtcccgccga agcaacgata cggtaaggtt 480
cacaaagggt ttgggagttt gtaaactcgg taatgatccc tccgctggtt caccaacgga 540
gaccttgtta cgacttttac ttcctctaaa tgaccaaga 579

<210> SEQ ID NO 78
<211> LENGTH: 564
<212> TYPE: DNA
<213> ORGANISM: Alternaria arborescens

<400> SEQUENCE: 78
ctacctgatc cgaggtcaca gttggaagta ggcttaatgg atgctagacc tttgctgata 60
gagagtgcga cttgtgctga ctacccaaac cagtaggcag gctgccaatt actttaaggc 120
gagtctccag caaagctaga gacaagacgc ccaacaccaa gcaaagcttg agggtacaaa 180
tgacgctcga acaggcatgc cctttggaat accaaagggc gcaatgtgcg ttcaaagatt 240

```
cgatgattca ctgaattctg caattcacac tacttatcgc atttcgctgc gttcttcatc    300

gatgccagaa ccaagagatc cgttgttgaa agttgtaatt attaatttgt tactgacgct    360

gattgcaatt acaaaaggtt tatgtttgtc ctagtggtgg gcgaacccac caaggaaaca    420

agaagtacgc aaaagacaag ggtgaataat tcagcaaggc tgtaaccccg agaggttcca    480

gcccgccttc atatttgtgt aatgatccct ccgcaggttc acctacggag accttgttac    540

gacttttact tcctctaaat gacc                                           564


<210> SEQ ID NO 79
<211> LENGTH: 745
<212> TYPE: DNA
<213> ORGANISM: Alternaria alternata

<400> SEQUENCE: 79

tactgatcga ggtcaaagtt gaaaaaaagg cttaatggat gctagacctt tgctgataga     60

gagtgcgact tgtgctgcgc tccgaaacca gtaggccggc tgccaattac tttaaggcga    120

gtctccagca aagctagaga caagacgccc aacaccaagc aaagcttgag ggtacaaatg    180

acgctcgaac aggcatgccc tttggaatac caaagggcgc aatgtgcgtt caaagattcg    240

atgattcact gaattctgca attcacacta cttatcgcat ttcgctgcgt tcttcatcga    300

tgccagaacc aagagatccg ttgttgaaag ttgtaattat taatttgtta ctgacgctga    360

ttgcaattac aaaaggttta tgtttgtcct agtggtgggc gaacccacca aggaaacaag    420

aagtacgcaa aagacaaggg tgaataattc agcaaggctg taaccccgag aggttccagc    480

ccgccttcat atttgtgtaa tgatccctcc gcaggttcac ctacggagac cttgttacga    540

cttatacttc ctctaaatga ccaagacgtt ctttgacagg gctctcaacc gatgcaaccg    600

tgttaaaaag gtagctcaag tttagttgga caggtgcgag ccacacctca gaaaaaaagg    660

ttttcatcga aatgatccat ctgcaggttc accctacaga taccttgtta cgaactttta    720

cttcctctaa aatgaccaag gaatg                                          745


<210> SEQ ID NO 80
<211> LENGTH: 560
<212> TYPE: DNA
<213> ORGANISM: Parasarcopodium ceratocaryi

<400> SEQUENCE: 80

ttctacctga tccgaggtca accaaagaaa atagggggg tttaacggct taatcacact     60

atatttccag agcgaggtat agtactacgc agaggaggct acagcgagac tgccactcta    120

tttgggagac ggctacttta cagcagccga tctccaacac cagttctccc gaagaagatc    180

tgagggttga aatgacgctc gaacaggcat gcccgccaga atactagcgg gcgcaatgtg    240

cgttcaaaga ttcgatgatt cactgaattc tgcaattcac attacttatc gcatttcgct    300

gcgttcttca tcgatgccag aaccaagaga tccgttgttg aaagttttga tttatttgta    360

taactcagaa ggatacataa agaatcagag tttactcctt cggcggcatc agtcaagacg    420

agcaagacgt atccgccgaa gcaacaatag gtatgttcac agggggtttt agaggtaaaa    480

aatacactct gtaatgatcc ctccgctggt tcaccaacgg agaccttgtt acgactttta    540

cttcctctaa atgaccaaga                                                560


<210> SEQ ID NO 81
<211> LENGTH: 591
<212> TYPE: DNA
<213> ORGANISM: Acremonium sp.
```

<400> SEQUENCE: 81
atctacctga tccgaggtca accttgtgaa gttgggggtt tcacggcgtg gccgagccgc 60
tctccggtgc gaggtgtgct actacgcagg ggaggctgcg gcgcgaccgc cactgaattt 120
gggggacagg ggccccggag ggccgctgat ccccagcacc aggcgccgaa cccccgaaag 180
ggtggccctg agggttgaaa tgacgctcgg acaggcatgc ccgccggagt gccggcgggc 240
gcaatgtgcg ttcaaagatt cgatgattca ctgaattctg caattcacat tacttatcgc 300
atttcgctgc gttcttcatc gatgccagag ccaagagatc cgttgttgaa agttttgatt 360
cattttgttt tcgggctttc gcccctcaga tatacacgaa aaattcgggt ttggttgtcc 420
ccggcggacg cccggtggcc cggaggccgg ccgcgcgctg agcccgccga gggaacgata 480
ggtaagttca caatgggttg gagagccgaa gcactcgttt tgtaatgatc cctccgctgg 540
ttcaccaacg gagaccttgt tacgactttt acttcctcta aatgaccaag a 591

<210> SEQ ID NO 82
<211> LENGTH: 557
<212> TYPE: DNA
<213> ORGANISM: Acremonium strictum

<400> SEQUENCE: 82
ctacctgatc tgaggtcaac cttgagaagt ggggggttta acggcgtggt tcaaccgcta 60
tcctgccgcg agaggtttaa ttactgcacg gaggagttcg cgagggaacc gccactggat 120
ttcagggcca gccgccgcca ggggcaggct gatccccaac gccaggtccc gcgaacgggt 180
cctgagggtt gaaatgacgc tcagacaggc atgcccgcca gaatactggc gggcgcaatg 240
tgcgttcaaa gattcgatga ttcactgaat tctgcaattc acattactta tcgcattttg 300
ctgcgttctt catcgatgcc agaaccaaga gatccgttgc tgaaagtttt gatttatttg 360
cttatgccac tcagaaatac actaaaagac aagagtttgg agcctccggc ggacgcctgg 420
gtccgggccg cgcgaacgcg cccggggcga ggccgccgaa gcaacagtgg taggttcaca 480
atggtttggg agtttttaca ctcggtaatg atccctccgc tggttcacca acggagacct 540
tgttacgact tttactt 557

<210> SEQ ID NO 83
<211> LENGTH: 740
<212> TYPE: DNA
<213> ORGANISM: Sporisorium everhartii

<400> SEQUENCE: 83
tctaccagtc tcgaggggat gcattattaa gatcccttct ttgcagaagc aaagcccgcg 60
cggcggtcgg aagcgggcca aacaccgcga tcgttgcgtc ccgctcttgc cctttctccg 120
cctccgaagt cctgatatta tcaaaacccg gcagggaaga gagagcgaaa gatgagcttt 180
cgtccgttct tgcctatcaa atggatgcgc taaggtattt cgagggagcc acggttaatg 240
gcaaaaaaac cctcactacc gagccagccc ttcttaatta aaaaaagagt ggttcgaaac 300
aattcgcggc cctcaaacag gcatgctccc caaattagat ctgcagggag cgcatggtgc 360
gttcaaagat tcgatgattc acttctgcaa ttcacattac ttatcgcaat tcgctgcgtt 420
cttcatcgat gggagaacca agagatccgt tgccaaaagt tgtttttaaa tttaaacgac 480
cgaattacca gtcataaatt gtcattcaaa tcctagaaga tcaaaagtgt ttgtgtaaag 540
tgtcgagggc ccaaccaaaa ggacactttc gcgttctttg acaggctctc aaccgatgca 600

```
accgtgttaa aaaggtagct caagtttagt tggacaggtg cgagccacac ctcagaaaaa    660

aggttttcat cgaaatgatc catctgcagg ttcacctaca gataccttgt tacgactttt    720

acttcctcta atgaccaaga                                                740
```

<210> SEQ ID NO 84
<211> LENGTH: 537
<212> TYPE: DNA
<213> ORGANISM: Fusarium nygamai

<400> SEQUENCE: 84

```
tctacctgat ccgaggtcaa cattcagaag ttgggggttt aacggcttgg ccgcgccgcg     60

taccagttgc gagggtttta ctactacgca atggaagctg cagcgagacc gccactgtat    120

ttcggggccg gcttgccgtg aggctcgccg atccccaaca ccaaacccgg gggcttgagg    180

gttgaaatga cgctcgaaca ggcatgcccg ccagaatact ggcgggcgca atgtgcgttc    240

aaagattcga tgattcactg aattctgcaa ttcacattac ttatcgcatt ttgctgcgtt    300

cttcatcgat gccagaacca agagatccgt tgttgaaagt tttgatttat ttatggtttt    360

actcagaagt tacatataga aacagagttt aggggtcctc tggcgggccg ttccgtttta    420

ccgggagcgg gctgatccgc cgaggcaaca attggtatgt tcacaggggt ttgggagttg    480

taaactcggt aatgatccct ccgctggttc accaacggag accttgttac gactttt       537
```

<210> SEQ ID NO 85
<211> LENGTH: 542
<212> TYPE: DNA
<213> ORGANISM: Acremonium sp.

<400> SEQUENCE: 85

```
acctgatcga ggtcaacctt gtgaaagttg ggggtttcac ggcgtggccg agccgctctc     60

cggtgcgagg tgtgctacta cgcaggggag gctgcggcgc gaccgccact gaatttgggg    120

gacaggggcc ccggagggcc gctgatcccc agcaccaggc gccgaacccc cgaaagggtg    180

gccctgaggg ttgaaatgac gctcggacag gcatgcccgc cggagtgccg gcgggcgcaa    240

tgtgcgttca aagattcgat gattcactga attctgcaat tcacattact tatcgcattt    300

cgctgcgttc ttcatcgatg ccagagccaa gagatccgtt gttgaaagtt ttgattcatt    360

ttgttttcgg gctttcgccc ctcagatata cacgaaaaat tcgggtttgg ttgtccccgg    420

cggacgcccg gtggcccgga ggccggccgc gcgctgagcc cgccgaggga acgataggta    480

agttcacaat gggttggaga gccgaagcac tcgttttgta atgatccctc cgctgtcacc    540

aa                                                                   542
```

<210> SEQ ID NO 86
<211> LENGTH: 552
<212> TYPE: DNA
<213> ORGANISM: Alternaria mali

<400> SEQUENCE: 86

```
ctacctgatc gaggtcaaaa gttgaaaaaa aggcttaatg gatgctagac ctttgctgat     60

agagagtgcg acttgtgctg cgctccgaaa ccagtaggcc ggctgccaat tactttaagg    120

cgagtctcca gcaaagctag agacaagacg cccaacacca agcaaagctt gagggtacaa    180

atgacgctcg aacaggcatg ccctttggaa taccaaaggg cgcaatgtgc gttcaaagat    240

tcgatgattc actgaattct gcaattcaca ctacttatcg catttcgctg cgttcttcat    300

cgatgccaga accaagagat ccgttgttga aagttgtaat tattaatttg ttactgacgc    360
```

```
tgattgcaat tacaaaaggt ttatgtttgt cctagtggtg ggcgaaccca ccaaggaaac    420

aagaagtacg caaaagacaa gggtgaataa ttcagcaagg ctgtaacccc gagaggttcc    480

agcccgcctt catatttgtg taatgatccc tccgcaggtt cacctacgga gaccttgtta    540

cgacttttac aa                                                        552
```

```
<210> SEQ ID NO 87
<211> LENGTH: 544
<212> TYPE: DNA
<213> ORGANISM: Gibberella sp.

<400> SEQUENCE: 87

ctacctgatc gaggtcacat tcagaagttg gggtttaacg gcgtggccgc gacgattacc     60

agtaacgagg gttttactac tacgctatgg aagctcggcg tgaccgccaa tcaatttggg    120

gaacgcgatt tgactcgcga gtcccaacac caagctgggc ttgagggttg aaatgacgct    180

cgaacaggca tgcccgccag aatactggcg ggcgcaatgt gcgttcaaag attcgatgat    240

tcactgaatt ctgcaattca cattacttat cgcattttgc tgcgttcttc atcgatgcca    300

gaaccaagag atccgttgtt gaaagttttg atttatttat ggttttactc agaagttaca    360

tatagaaaca gagtttaggg gtcctctggc gggccgtccc gttttaccgg gagcgggctg    420

atccgccgag gcaacaattg gtatgttcac aggggtttgg gagttgtaaa ctcggtaatg    480

atccctccgc tggttcacca acggagacct tgttacgact tttacttcct ctaaatgacc    540

aaga                                                                 544
```

```
<210> SEQ ID NO 88
<211> LENGTH: 561
<212> TYPE: DNA
<213> ORGANISM: Fusarium proliferatum

<400> SEQUENCE: 88

atctacctga tccgaggtca acattcagaa gttgggggtt taacggcttg gccgcgccgc     60

gtaccagttg cgagggtttt actactacgc aatggaagct gcagcgagac cgccactaga    120

tttcggggcc ggcttgccgc aagggctcgc cgatccccaa caccaaaccc gggggcttga    180

gggttgaaat gacgctcgaa caggcatgcc cgccagaata ctggcgggcg caatgtgcgt    240

tcaaagattc gatgattcac tgaattctgc aattcacatt acttatcgca ttttgctgcg    300

ttcttcatcg atgccagaac caagagatcc gttgttgaaa gttttgattt atttatggtt    360

ttactcagaa gttacatata gaaacagagt ttaggggtcc tctggcgggc cgtcccgttt    420

taccgggagc gggctgatcc gccgaggcaa caattggtat gttcacaggg gtttgggagt    480

tgtaaactcg gtaatgatcc ctccgctggt tcaccaacgg agaccttgtt acgactttta    540

aatcctataa agagaccaag a                                              561
```

```
<210> SEQ ID NO 89
<211> LENGTH: 550
<212> TYPE: DNA
<213> ORGANISM: Alternaria mali

<400> SEQUENCE: 89

tactgatccg aggtcaaaag ttgaaaaaaa ggcttaatgg atgctagacc tttgctgata     60

gagagtgcga cttgtgctgc gctccgaaac cagtaggccg gctgccaatt actttaaggc    120

gagtctccag caaagctaga gacaagacgc ccaacaccaa gcaaagcttg agggtacaaa    180
```

```
tgacgctcga acaggcatgc cctttggaat accaaagggc gcaatgtgcg ttcaaagatt    240

cgatgattca ctgaattctg caattcacac tacttatcgc atttcgctgc gttcttcatc    300

gatgccagaa ccaagagatc cgttgttgaa agttgtaatt attaatttgt tactgacgct    360

gattgcaatt acaaaaggtt tatgtttgtc ctagtggtgg gcgaacccac caaggaaaca    420

agaagtacgc aaaagacaag ggtgaataat tcagcaaggc tgtaaccccg agaggttcca    480

gcccgccttc atatttgtgt aatgatccct ccgcaggttc acctacggag accttgttac    540

gacttttact                                                           550


<210> SEQ ID NO 90
<211> LENGTH: 697
<212> TYPE: DNA
<213> ORGANISM: Pseudozyma flocculosa

<400> SEQUENCE: 90

aatctgaggc cgatgaatta ttaaaatccc ttccttcgcc aaaaagcgag gcatgggcgg     60

ggttcagaag cacgccaaac agcaaaaacg ttgcgtcccg ctcgtaccct ttctccgcct    120

ccgaagtcct gatattatca aaacccggca gggaagagag ggcgaaagat gagctttcgt    180

ccgttcttgc ctatcaaatg gatgcgctaa tgtatttcga gggagccacg gttaatggca    240

aagaaaccct cactaccgat ccgtccactt ttaattaaaa aagcgagcgt tcgaaacaat    300

tcgcggccct caaacaggca tgctccccag attagatctg cagggagcgc aaggtgcgtt    360

caaagattcg atgattcact tctgcaattc acattactta tcgcaattcg ctgcgttctt    420

catcgatggg agaaccaaga gatccgttgc caaaagttgt ttttaaattt aaacgaccga    480

attaccagtc ataaattgtc attcaaatcc tagtagatca aaaagtgttt gtgtaaagtg    540

tcgaggcccg tggcaatcaa cgctctcgcg ctttttgaca gggcactcga ccgatgcaac    600

cgtgttgaaa aaggtagctc attttagttg gacaggtgcg agccacacct cagaaaaaag    660

gttttcatcg aaatgatcca tctgcaggtc accctac                             697


<210> SEQ ID NO 91
<211> LENGTH: 545
<212> TYPE: DNA
<213> ORGANISM: Fusarium nygamai

<400> SEQUENCE: 91

ttctactgat ccgaggtcaa cattcagaag ttgggggttt aacggcttgg ccgcgccgcg     60

taccagttgc gagggtttta ctactacgca atggaagctg cagcgagacc gccactgtat    120

ttcggggccg gcttgccgtg aggctcgccg atccccaaca ccaaacccgg gggcttgagg    180

gttgaaatga cgctcgaaca ggcatgcccg ccagaatact ggcgggcgca atgtgcgttc    240

aaagattcga tgattcactg aattctgcaa ttcacattac ttatcgcatt ttgctgcgtt    300

cttcatcgat gccagaacca agagatccgt tgttgaaagt tttgatttat ttatggtttt    360

actcagaagt tacatataga aacagagttt aggggtcctc tggcgggccg ttccgtttta    420

ccgggagcgg gctgatccgc cgaggcaaca attggtatgt tcacaggggt ttgggagttg    480

taaactcggt aatgatccct ccgctggttc accaacggag accttgttac gacttttact    540

tcctc                                                                545


<210> SEQ ID NO 92
<211> LENGTH: 546
<212> TYPE: DNA
<213> ORGANISM: Fusarium nygamai
```

<400> SEQUENCE: 92
aaaagtcgta acaaggtctc cgttggtgaa ccagcggagg gatcattacc gagtttacaa 60
ctcccaaacc cctgtgaaca taccaattgt tgcctcggcg gatcagcccg ctcccggtaa 120
aacggaacgg cccgccagag gacccctaaa ctctgtttct atatgtaact tctgagtaaa 180
accataaata aatcaaaact ttcaacaacg gatctcttgg ttctggcatc gatgaagaac 240
gcagcaaaat gcgataagta atgtgaattg cagaattcag tgaatcatcg aatctttgaa 300
cgcacattgc gcccgccagt attctggcgg gcatgcctgt tcgagcgtca tttcaaccct 360
caagcccccg ggtttggtgt tggggatcgg cgagcctcac ggcaagccgg ccccgaaata 420
cagtggcggt ctcgctgcag cttccattgc gtagtagtaa aaccctcgca actggtacgc 480
ggcgcggcca agccgttaaa cccccaactt ctgaatgtga cctcggatca ggtaggaata 540
cccgct 546

<210> SEQ ID NO 93
<211> LENGTH: 548
<212> TYPE: DNA
<213> ORGANISM: Nigrospora oryzae

<400> SEQUENCE: 93
tcatttagag gaagtaaaag tcgtaacaag gtctccgttg gtgaaccagc ggagggatca 60
ttacagagtt atccaactcc caaacccatg tgaacttatc tctttgttgc ctcggcgcaa 120
gctacccggg acccagcgcc ccgggcggcc cgccggcgga caaaccaaac tcttgttatc 180
ttagttgatt atctgagcgt cttatttaat aagtcaaaac tttcaacaac ggatctcttg 240
gttctggcat cgatgaagaa cgcagcgaaa tgcgataagt aatgtgaatt gcagaattca 300
gtgaatcatc gaatctttga acgcacattg cgcccattag tattctagtg ggcatgcctg 360
ttcgagcgtc atttcaaccc ctaagcacag cttactgttg ggactctacg gcctccgtag 420
ttccctaatg cgattggcgg agtggcagta gtcctctgag cgtagtaatt ctttatctcg 480
cttttgttag gtgctgcccc cccggccgtt aaaccccctt ttttttctgg ttgacctcgg 540
atcaggtg 548

<210> SEQ ID NO 94
<211> LENGTH: 541
<212> TYPE: DNA
<213> ORGANISM: Fusarium nygamai

<400> SEQUENCE: 94
attctacctg atccgaggtc aacattcaga agttgggggt ttaacggctt ggccgcgccg 60
cgtaccagtt gcgagggttt tactactacg caatggaagc tgcagcgaga ccgccactgt 120
atttcggggc cggcttgccg tgaggctcgc cgatccccaa caccaaaccc gggggcttga 180
gggttgaaat gacgctcgaa caggcatgcc cgccagaata ctggcgggcg caatgtgcgt 240
tcaaagattc gatgattcac tgaattctgc aattcacatt acttatcgca ttttgctgcg 300
ttcttcatcg atgccagaac caagagatcc gttgttgaaa gttttgattt atttatggtt 360
ttactcagaa gttacatata gaaacagagt ttaggggtcc tctggcgggc cgttccgttt 420
taccgggagc gggctgatcc gccgaggcaa caattggtat gttcacaggg gtttgggagt 480
tgtaaactcg gtaatgatcc ctccgctggt tcaccaacgg agaccttgtt acgactttta 540
c 541

<210> SEQ ID NO 95
<211> LENGTH: 573
<212> TYPE: DNA
<213> ORGANISM: Acremonium strictum

<400> SEQUENCE: 95
ctacctgatc tgaggtcacc ttgagaagtg gggggtttaa cggcgtggtt caaccgctat 60
cctgccgcga gaggtttaat tactgcacgg aggagttcgc gagggaaccg ccactggatt 120
tcagggccag ccgccgccag gggcaggctg atccccaacg ccaggtcccg cgaacgggtc 180
ctgagggttg aaatgacgct cagacaggca tgcccgccag aatactggcg ggcgcaatgt 240
gcgttcaaag attcgatgat tcactgaatt ctgcaattca cattacttat cgcattttgc 300
tgcgttcttc atcgatgcca gaaccaagag atccgttgct gaaagttttg atttatttgc 360
ttatgccact cagaaataca ctaaaagaca agagtttgga gcctccggcg gacgcctggg 420
tccgggccgc gcgaacgcgc ccggggcgag gccgccgaag caacagtggt aggttcacaa 480
tggtttggga gtttttacac tcggtaatga tccctccgct ggttcaccaa cggagacctt 540
gttacgactt ttacttcctc taaatgacca aga 573

<210> SEQ ID NO 96
<211> LENGTH: 558
<212> TYPE: DNA
<213> ORGANISM: Fusarium proliferatum

<400> SEQUENCE: 96
tctacctgat ccgaggtcaa cattcagaag ttggggggttt aacggcttgg ccgcgccgcg 60
taccagttgc gagggtttta ctactacgca atggaagctg cagcgagacc gccactgtat 120
ttcggggccg gcttgccgtg aggctcgccg atccccaaca ccaaacccgg gggcttgagg 180
gttgaaatga cgctcgaaca ggcatgcccg ccagaatact ggcgggcgca atgtgcgttc 240
aaagattcga tgattcactg aattctgcaa ttcacattac ttatcgcatt ttgctgcgtt 300
cttcatcgat gccagaacca agagatccgt tgttgaaagt tttgatttat ttatggtttt 360
actcagaagt tacatataga aacagagttt aggggtcctc tggcgggccg ttccgtttta 420
ccgggagcgg gctgatccgc cgaggcaaca attggtatgt tcacaggggt ttgggagttg 480
taaactcggt aatgatccct ccgctggttc accaacggag accttgttac gacttttact 540
tcctctaaaa gaccaaga 558

<210> SEQ ID NO 97
<211> LENGTH: 741
<212> TYPE: DNA
<213> ORGANISM: Sporisorium everhartii

<400> SEQUENCE: 97
taccagtctc gagggtgatg tattattaat atcccttctt tgcagaagca aagcatgggc 60
ggggttcgga agcacgccaa acagcaagat cgttgcgtcc agctcttgcc ctttctccgc 120
ctccgaagtc ctgatattat caaaacccgg cagggaagag agagcgaaag atgagctttc 180
gtccgttctt gcctatcaaa tggatgcgct aatgtatttc gagggagcca cggttaatgg 240
caaaaaaacc ctcactaccg agccagccct tcttaattaa aaaaagagtg gttcgaaaca 300
attcgcggcc ctcaaacagg catgctcccc agattagatc tgcagggagc gcaaggtgcg 360
ttcaaagatt cgatgattca cttctgcaat tcacattact tatcgcaatt cgctgcgttc 420
ttcatcgatg ggagaaccaa gagatccgtt gccaaaagtt gtttttaaat ttaaacgacc 480
gaattaccag tcataaattg tcattcaaat cctagaagat caaaagtgtt tgtgtaaagt 540
gtcgagggcc caaccaaaag gacactttcg cgttctttga caggctctca accgatgcaa 600
ccgtgttaaa aaggtagctc aagtttagtt ggacaggtgc gagccacacc tcagaaaaaa 660
ggttttcatc gaaatgatcc atctgcaggt tcacctacag ataccttgtt acgactttta 720
cttcctctaa attgaccaag a 741

<210> SEQ ID NO 98
<211> LENGTH: 566
<212> TYPE: DNA
<213> ORGANISM: Uncultured root-associated fungus

<400> SEQUENCE: 98
tctccgttgt gaccagcgga gggatcatta aagagttgca aaactccaac ccctgtgaac 60
tttacctgta cgttgcttcg gcggccgacg ccgcgcccag ccgggcctgg gggacgccgc 120
cggaggtttt aaaccctgaa ttctagtgta tctctgagga cgaaaaaaac caattaaaac 180
tttcaacaac ggatctcttg gctctggcat cgatgaagaa cgcagcgaaa tgcgataagt 240
aatgtgaatt gcagaattca gtgaatcatc gaatctttga acgcacattg cgcccgccgg 300
tattccggcg ggcatgcctg tccgagcgtc atttcaccac tcaagcccag cttggtgttg 360
gggcacccgg ccgcccggcg gtcggggccc ccaagtacat cggcggtcct gctggggctc 420
cgagcgcagt aacacgcggt aaaacgcgcc ctcgctcggc ggcctcctcg ggcttccagc 480
cgctaaaccc ccagtgacgt ttttcgagtt gacctcggat caggtaggaa tacccgctga 540
acttaagcat atcaataagc ggagga 566

<210> SEQ ID NO 99
<211> LENGTH: 558
<212> TYPE: DNA
<213> ORGANISM: Uncultured endophytic fungus

<400> SEQUENCE: 99
tacctgatct gaggtcaacc ttcgaagaag ttggggggtt taacggctgt ggccgcgccg 60
ctatcctgtt gcgagaggtt tactaccacc ccgtggaagc tgcagagaga ccgccactag 120
attttcgggg ccggttgccg caaggggtcg gcgatcccca acacccaacc cgggcgcttg 180
agggctgaaa tgagaaatga ccaggagaca gggctgcact actgaatact ggcgggtgcg 240
ttgtgcgatt caagaattca tgaatttctg aatttcacat ttcttattac tttttgctgt 300
ttgctgcatc catccccgaa cccagaaacc cgatattgaa agttgaaatt tattatttgt 360
ttgcttctga agttacaaat taaaacaaaa ttcaggagtc cgcagccggg ccgtgacgtt 420
ttaccggggg ccggctgaac cgccgaggca acagttggta taatcacagg ggttagggag 480
ttgtaaactc gggaatgatc catccgctgg tgatccaacg gagaccttgc caccactttc 540
acttccacta ctttaact 558

<210> SEQ ID NO 100
<211> LENGTH: 553
<212> TYPE: DNA
<213> ORGANISM: Gibberella sp.

<400> SEQUENCE: 100
acctgatcga ggtcacattc agaagttggg ggtttaacgg cttggccgcg ccgcgtacca 60
gttgcgaggg ttttactact acgcaatgga agctgcagcg agaccgccac tgtatttcgg 120
ggccggcttg ccgtgaggct cgccgatccc caacaccaaa cccgggggct tgagggttga 180
aatgacgctc gaacaggcat gcccgccaga atactggcgg gcgcaatgtg cgttcaaaga 240
ttcgatgatt cactgaattc tgcaattcac attacttatc gcattttgct gcgttcttca 300
tcgatgccag aaccaagaga tccgttgttg aaagttttga tttatttatg gttttactca 360
gaagttacat atagaaacag agtttagggg tcctctggcg ggccgttccg ttttaccggg 420
agcgggctga tccgccgagg caacaattgg tatgttcaca ggggtttggg agttgtaaac 480
tcggtaatga tccctccgct ggttcaccaa cggagacctt gttacgactt ttacttcctc 540
taaatgacca aga 553

<210> SEQ ID NO 101
<211> LENGTH: 559
<212> TYPE: DNA
<213> ORGANISM: Acremonium strictum

<400> SEQUENCE: 101
gcatctacct gatctgaggt caaccttgag aagtgggggg tttaacggcg tggttcaacc 60
gctatcctgc cgcgagaggt ttaattactg cacggaggag ttcgcgaggg aaccgccact 120
ggatttcagg gccagccgcc gccaggggca ggctgatccc caacgccagg tcccgcgaac 180
gggtcctgag ggttgaaatg acgctcagac aggcatgccc gccagaatac tggcgggcgc 240
aatgtgcgtt caaagattcg atgattcact gaattctgca attcacatta cttatcgcat 300
tttgctgcgt tcttcatcga tgccagaacc aagagatccg ttgctgaaag ttttgattta 360
tttgcttatg ccactcagaa atacactaaa agacaagagt ttggagcctc cggcggacgc 420
ctgggtccgg gccgcgcgaa cgcgcccggg gcgaggccgc cgaagcaaca gtggtaggtt 480
cacaatggtt tgggagtttt tacactcggt aatgatccct ccgctggttc accaacggag 540
accttgttac gacttttac 559

<210> SEQ ID NO 102
<211> LENGTH: 558
<212> TYPE: DNA
<213> ORGANISM: Fusarium proliferatum

<400> SEQUENCE: 102
ctacctgatc cgaggtcaac attcagaagt tgggggttta acggcttggc cgcgccgcgt 60
accagttgcg agggttttac tactacgcaa tggaagctgc agcgagaccg ccactgtatt 120
tcggggccgg cttgccgtga ggctcgccga tccccaacac caaacccggg ggcttgaggg 180
ttgaaatgac gctcgaacag gcatgcccgc cagaatactg gcgggcgcaa tgtgcgttca 240
aagattcgat gattcactga attctgcaat tcacattact tatcgcattt tgctgcgttc 300
ttcatcgatg ccagaaccaa gagatccgtt gttgaaagtt ttgatttatt tatggtttta 360
ctcagaagtt acatatagaa acagagttta ggggtcctct ggcgggccgt tccgttttac 420
cgggagcggg ctgatccgcc gaggcaacaa ttggtatgtt cacaggggtt tgggagttgt 480
aaactcggta atgatccctc cgctggttca ccaacggaga ccttgttacg acttttactt 540
cctctaagaa gaccaaga 558

<210> SEQ ID NO 103
<211> LENGTH: 547
<212> TYPE: DNA
<213> ORGANISM: Fusarium nygamai

<400> SEQUENCE: 103
accagcggag ggatcattac cgagtttaca actcccaaac ccctgtgaac ataccaattg 60
ttgcctcggc ggatcagccc gctcccggta aaacggaacg gcccgccaga ggacccctaa 120
actctgtttc tatatgtaac ttctgagtaa aaccataaat aaatcaaaac tttcaacaac 180
ggatctcttg gttctggcat cgatgaagaa cgcagcaaaa tgcgataagt aatgtgaatt 240
gcagaattca gtgaatcatc gaatctttga acgcacattg cgcccgccag tattctggcg 300
ggcatgcctg ttcgagcgtc atttcaaccc tcaagccccc gggtttggtg ttggggatcg 360
gcgagcctca cggcaagccg gccccgaaat acagtggcgg tctcgctgca gcttccattg 420
cgtagtagta aaaccctcgc aactggtacg cggcgcggcc aagccgttaa acccccaact 480
tctgaatgtt gacctcggat caggtaggaa tacccgctga acttaagcat atcaataggc 540
ggaggaa 547

<210> SEQ ID NO 104
<211> LENGTH: 570
<212> TYPE: DNA
<213> ORGANISM: Acremonium sp.

<400> SEQUENCE: 104
tctactgatc cgaggtcaac cttaaaaaat tgggtgtttt acggcgtggt cgttccgctc 60
tccggtgcga ggttgtgcta ctacgcaggg gaggctgcgg cgcgaccgcc actgaatttg 120
agggacgggg gccgcgaggg ccgccgatcc ccagaaccag gcccgctccc ccggaagggt 180
gggcctgagg gttgaaatga cgctcggaca ggcatgcccg ccggagtgcc ggcgggcgca 240
atgtgcgttc aaagattcga tgattcactg aattctgcaa ttcacattac ttatcgcatt 300
tcgctgcgtt cttcatcgat gccagagcca agagatccgt tgttgaaagt tttgattcat 360
tttgttttcg ggctttcgcc cctcagagaa atacgattaa atcagggttt ggttttcccc 420
ggcggacgcc cggaggcccg gaggccaccg cgcgctgagc ccgccgaggg aacgtttggt 480
aagttcacaa tgggttggag agcctagggc actctggtaa tgatccctcc gctggttcac 540
caacggagac cttgttacga cttttacttc 570

<210> SEQ ID NO 105
<211> LENGTH: 549
<212> TYPE: DNA
<213> ORGANISM: Gibberella sp.

<400> SEQUENCE: 105
gatctacctg atcgaggtca acattcagaa gttggggttt aacggcgtgg ccgcgacgat 60
taccagtaac gagggtttta ctactacgct atggaagctc ggcgtgaccg ccaatcaatt 120
tggggaacgc gatttgactc gcgagtccca acaccaagct gggcttgagg gttgaaatga 180
cgctcgaaca ggcatgcccg ccagaatact ggcgggcgca atgtgcgttc aaagattcga 240
tgattcactg aattctgcaa ttcacattac ttatcgcatt ttgctgcgtt cttcatcgat 300
gccagaacca agagatccgt tgttgaaagt tttgatttat ttatggtttt actcagaagt 360
tacatataga aacagagttt aggggtcctc tggcgggccg tcccgtttta ccgggagcgg 420
gctgatccgc cgaggcaaca attggtatgt tcacaggggt ttgggagttg taaactcggt 480
aatgatccct ccgctggttc accaacggag accttgttac gacttttact tcctctaaat 540
tgaccaaga 549

<210> SEQ ID NO 106

<211> LENGTH: 537
<212> TYPE: DNA
<213> ORGANISM: Gibberella sp.

<400> SEQUENCE: 106

```
tacctgatcg aggtcacatt cagaagttgg gggtttaacg gcttggccgc gccgcgtacc     60

agttgcgagg gttttactac tacgcaatgg aagctgcagc gagaccgcca ctagatttcg    120

gggccggctt gccgcaaggg ctcgccgatc cccaacacca aacccggggg cttgagggtt    180

gaaatgacgc tcgaacaggc atgcccgcca gaatactggc gggcgcaatg tgcgttcaaa    240

gattcgatga ttcactgaat tctgcaattc acattactta tcgcattttg ctgcgttctt    300

catcgatgcc agaaccaaga gatccgttgt tgaaagtttt gatttattta tggttttact    360

cagaagttac atatagaaac agagtttagg ggtcctctgg cgggccgtcc cgttttaccg    420

ggagcgggct gatccgccga ggcaacaatt ggtatgttca caggggtttg ggagttgtaa    480

actcggtaat gatccctccg ctggttcacc aacggagacc ttgttacgac ttttaca       537
```

<210> SEQ ID NO 107
<211> LENGTH: 547
<212> TYPE: DNA
<213> ORGANISM: Gibberella sp.

<400> SEQUENCE: 107

```
tctacctgat ccgaggtcaa cattcagaag ttggggttta acggcgtggc cgcgacgatt     60

accagtaacg agggttttac tactacgcta tggaagctcg gcgtgaccgc caatcaattt    120

ggggaacgcg atttgactcg cgagtcccaa caccaagctg ggcttgaggg ttgaaatgac    180

gctcgaacag gcatgcccgc cagaatactg gcgggcgcaa tgtgcgttca aagattcgat    240

gattcactga attctgcaat tcacattact tatcgcattt tgctgcgttc ttcatcgatg    300

ccagaaccaa gagatccgtt gttgaaagtt ttgatttatt tatggtttta ctcagaagtt    360

acatatagaa acagagttta ggggtcctct ggcgggccgt cccgttttac cgggagcggg    420

ctgatccgcc gaggcaacaa ttggtatgtt cacaggggtt tgggagttgt aaactcggta    480

atgatccctc cgctggttca ccaacggaga ccttgttacg acttttactt cctctaaatg    540

accaaga                                                              547
```

<210> SEQ ID NO 108
<211> LENGTH: 546
<212> TYPE: DNA
<213> ORGANISM: Gibberella sp.

<400> SEQUENCE: 108

```
tctacctgat ccgaggtcaa cattcagaag ttggggttta acggcgtggc cgcgacgatt     60

accagtaacg agggttttac tactacgcta tggaagctcg gcgtgaccgc caatcaattt    120

ggggaacgcg atttgactcg cgagtcccaa caccaagctg ggcttgaggg ttgaaatgac    180

gctcgaacag gcatgcccgc cagaatactg gcgggcgcaa tgtgcgttca aagattcgat    240

gattcactga attctgcaat tcacattact tatcgcattt tgctgcgttc ttcatcgatg    300

ccagaaccaa gagatccgtt gttgaaagtt ttgatttatt tatggtttta ctcagaagtt    360

acatatagaa acagagttta ggggtcctct ggcgggccgt cccgttttac cgggagcggg    420

ctgatccgcc gaggcaacaa ttggtatgtt cacaggggtt tgggagttgt aaactcggta    480

atgatccctc cgctggttca ccaacggaga ccttgttacg actttaactt cctctaaatg    540

accaag                                                               546
```

<210> SEQ ID NO 109
<211> LENGTH: 534
<212> TYPE: DNA
<213> ORGANISM: Fusarium proliferatum

<400> SEQUENCE: 109
attcctacct gatccgaggt caacattcag aagttggggt ttaacggcgt ggccgcgacg 60
attaccagta acgagggttt tactactacg ctatggaagc tcggcgtgac cgccaatcaa 120
tttggggaac gcgatttgac tcgcgagtcc caacaccaag ctgggcttga gggttgaaat 180
gacgctcgaa caggcatgcc cgccagaata ctggcgggcg caatgtgcgt tcaaagattc 240
gatgattcac tgaattctgc aattcacatt acttatcgca ttttgctgcg ttcttcatcg 300
atgccagaac caagagatcc gttgttgaaa gttttgattt atttatggtt ttactcagaa 360
gttacatata gaaacagagt ttaggggtcc tctggcgggc cgtcccgttt taccgggagc 420
gggctgatcc gccgaggcaa caattggtat gttcacaggg gtttgggagt tgtaaactcg 480
gtaatgatcc ctccgctggt tcaccaacgg agaccttgtt acgactttta ctta 534

<210> SEQ ID NO 110
<211> LENGTH: 558
<212> TYPE: DNA
<213> ORGANISM: Alternaria alternata

<400> SEQUENCE: 110
ctacctgatc cgaggtcaaa gttgaaaaaa aggcttaatg gatgctagac ctttgctgat 60
agagagtgcg acttgtgctg cgctccgaaa ccagtaggcc ggctgccaat tactttaagg 120
cgagtctcca gcaaagctag agacaagacg cccaacacca agcaaagctt gagggtacaa 180
atgacgctcg aacaggcatg ccctttggaa taccaaaggg cgcaatgtgc gttcaaagat 240
tcgatgattc actgaattct gcaattcaca ctacttatcg catttcgctg cgttcttcat 300
cgatgccaga accaagagat ccgttgttga aagttgtaat tattaatttg ttactgacgc 360
tgattgcaat tacaaaaggt ttatgtttgt cctagtggtg ggcgaaccca ccaaggaaac 420
aagaagtacg caaaagacaa gggtgaataa ttcagcaagg ctgtaacccc gagaggttcc 480
agcccgcctt catatttgtg taatgatccc tccgcaggtt cacctacgga gaccttgtta 540
cgacttttac tacctcta 558

<210> SEQ ID NO 111
<211> LENGTH: 562
<212> TYPE: DNA
<213> ORGANISM: Sporisorium everhartii

<400> SEQUENCE: 111
cctgatccga ggtcaaccta gtaaaagttg ggggttttac ggctgggccg cgccgcgctc 60
cgcctgcgag aacaagtgct actgcgcaga ggaggctaca gcgagaccgc caatcgtttt 120
aggggacgtc caccgtggag gcgggcgatc cccaacaccg gaggcccccc taaaggggct 180
cccgagggtt gaaatgacgc tcggacaggc atgcccgcca gaatactggc gggcgcaatg 240
tgcgttcaaa gattcgatga ttcactgaat tctgcaattc acattactta tcgcatttcg 300
ctgcgttctt catcgatgcc agaaccaaga gatccgttgt tgaaagtttt gattcatttg 360
tataatccac tcagaagaga cgctgtaaaa tcaagagttt tggtcctccg gcggacgcct 420
gactccgggc agcgctgggc tcccggggcg tgaccgccga agcaacagtg gtaaggttca 480

-continued cacgggtttg ggagttcggt aactcaataa tgatccctcc gctggttcac caacggagac 540
cttgttacga cttttacttc ct 562

<210> SEQ ID NO 112
<211> LENGTH: 565
<212> TYPE: DNA
<213> ORGANISM: Sordariomycete sp.

<400> SEQUENCE: 112
tcttggtcat ttagaggaag taaaagtcgt aacaaggtct ccgttggtga accagcggag 60
ggatcattac cgagtttaca actcccaaac ccctgtgaac ataccaattg ttgcctcggc 120
ggatcagccc gctcccggta aaacggaacg gcccgccaga ggacccctaa actctgtttc 180
tatatgtaac ttctgagtaa aaccataaat aaatcaaaac tttcaacaac ggatctcttg 240
gttctggcat cgatgaagaa cgcagcaaaa tgcgataagt aatgtgaatt gcagaattca 300
gtgaatcatc gaatctttga acgcacattg cgcccgccag tattctggcg ggcatgcctg 360
ttcgagcgtc atttcaaccc tcaagccccc gggtttggtg ttggggatcg gcgagcctca 420
cggcaagccg gccccgaaat acagtggcgg tctcgctgca gcttccattg cgtagtagta 480
aaaccctcgc aactggtacg cggcgcggcc aagccgttaa acccccaact tctgaatgtt 540
gacctcggat caggtaggaa taccc 565

<210> SEQ ID NO 113
<211> LENGTH: 545
<212> TYPE: DNA
<213> ORGANISM: Fusarium proliferatum

<400> SEQUENCE: 113
tctacctgat ccgaggtcaa cattcagaag ttgggggttt aacggcttgg ccgcgccgcg 60
taccagttgc gagggtttta ctactacgca atggaagctg cagcgagacc gccactagat 120
ttcggggccg gcttgccgca agggctcgcc gatccccaac accaaacccg ggggcttgag 180
ggttgaaatg acgctcgaac aggcatgccc gccagaatac tggcgggcgc aatgtgcgtt 240
caaagattcg atgattcact gaattctgca attcacatta cttatcgcat tttgctgcgt 300
tcttcatcga tgccagaacc aagagatccg ttgttgaaag ttttgattta tttatggttt 360
tactcagaag ttacatatag aaacagagtt tagggtcct ctggcgggcc gtcccgtttt 420
accgggagcg ggctgatccg ccgaggcaac aattggtatg ttcacagggg tttgggagtt 480
gtaaactcgg taatgatccc tccgctggtt caccaacgga gaccttgtta cgacttttac 540
ttcct 545

<210> SEQ ID NO 114
<211> LENGTH: 541
<212> TYPE: DNA
<213> ORGANISM: Fusarium moniliformae

<400> SEQUENCE: 114
atctacctga tccgaggtca cattcagaag ttgggggttt aacggcttgg ccgcgccgcg 60
taccagttgc gagggtttta ctactacgca atggaagctg cagcgagacc gccactagat 120
ttcggggccg gcttgccgca agggctcgcc gatccccaac accaaacccg ggggcttgag 180
ggttgaaatg acgctcgaac aggcatgccc gccagaatac tggcgggcgc aatgtgcgtt 240
caaagattcg atgattcact gaattctgca attcacatta cttatcgcat tttgctgcgt 300
tcttcatcga tgccagaacc aagagatccg ttgttgaaag ttttgattta tttatggttt 360

```
tactcagaag ttacatatag aaacagagtt taggggtcct ctggcgggcc gtcccgtttt    420

accgggagcg ggctgatccg ccgaggcaac aattggtatg ttcacagggg tttgggagtt    480

gtaaactcgg taatgatccc tccgctggtt caccaacgga gaccttgtta cgacttttac    540

a                                                                    541


<210> SEQ ID NO 115
<211> LENGTH: 569
<212> TYPE: DNA
<213> ORGANISM: Fusarium nygamai

<400> SEQUENCE: 115

tacctgggat tctacctgat ccgaggtcac attcagaagt tgggggttta acggcttggc     60

cgcgccgcgt accagttgcg agggttttac tactacgcaa tggaagctgc agcgagaccg    120

ccactgtatt tcggggccgg cttgccgtga ggctcgccga tccccaacac caaacccggg    180

ggcttgaggg ttgaaatgac gctcgaacag gcatgcccgc cagaatactg gcgggcgcaa    240

tgtgcgttca aagattcgat gattcactga attctgcaat tcacattact tatcgcattt    300

tgctgcgttc ttcatcgatg ccagaaccaa gagatccgtt gttgaaagtt ttgatttatt    360

tatggtttta ctcagaagtt acatatagaa acagagttta ggggtcctct ggcgggccgt    420

tccgttttac cgggagcggg ctgatccgcc gaggcaacaa ttggtatgtt cacaggggtt    480

tgggagttgt aaactcggta atgatccctc cgctggttca ccaacggaga ccttgttacg    540

acttttactt cctaaaaaga aaaaaaaga                                      569


<210> SEQ ID NO 116
<211> LENGTH: 546
<212> TYPE: DNA
<213> ORGANISM: Fusarium proliferatum

<400> SEQUENCE: 116

ctactgatcc gaggtcaaca ttcagaagtt gggggtttaa cggcttggcc gcgccgcgta     60

ccagttgcga gggttttact actacgcaat ggaagctgca gcgagaccgc cactgtattt    120

cggggccggc ttgccgtgag gctcgccgat ccccaacacc aaacccgggg gcttgagggt    180

tgaaatgacg ctcgaacagg catgcccgcc agaatactgg cgggcgcaat gtgcgttcaa    240

agattcgatg attcactgaa ttctgcaatt cacattactt atcgcatttt gctgcgttct    300

tcatcgatgc cagaaccaag agatccgttg ttgaaagttt tgatttattt atggttttac    360

tcagaagtta catatagaaa cagagtttag gggtcctctg gcgggccgtt ccgttttacc    420

gggagcgggc tgatccgccg aggcaacaat tggtatgttc acaggggttt gggagttgta    480

aactcggtaa tgatccctcc gctggttcac caacggagac cttgttacga cttttacttc    540

ctctaa                                                               546


<210> SEQ ID NO 117
<211> LENGTH: 557
<212> TYPE: DNA
<213> ORGANISM: Fusarium nygamai

<400> SEQUENCE: 117

tacctgatcc gaggtcaaca ttcagaagtt gggggtttaa cggcttggcc gcgccgcgta     60

ccagttgcga gggttttact actacgcaat ggaagctgca gcgagaccgc cactgtattt    120

cggggccggc ttgccgtgag gctcgccgat ccccaacacc aaacccgggg gcttgagggt    180
```

tgaaatgacg ctcgaacagg catgcccgcc agaatactgg cgggcgcaat gtgcgttcaa 240
agattcgatg attcactgaa ttctgcaatt cacattactt atcgcatttt gctgcgttct 300
tcatcgatgc cagaaccaag agatccgttg ttgaaagttt tgatttattt atggttttac 360
tcagaagtta catatagaaa cagagtttag ggtcctctg gcgggccgtt ccgttttacc 420
gggagcgggc tgatccgccg aggcaacaat tggtatgttc acaggggttt gggagttgta 480
aactcggtaa tgatccctcc gctggttcac caacggagac cttgttacga cttttactta 540
ctaaaaaaag accaaga 557

<210> SEQ ID NO 118
<211> LENGTH: 599
<212> TYPE: DNA
<213> ORGANISM: Exserohilum rostratum

<400> SEQUENCE: 118
tactgatcga ggtcaaatgt ggatttgtta tagaaaacaa aggcttgctg gatgccgccc 60
tgtggattgg aaggcgcaaa tttgtgctgc gctccgaaaa ccagtaggtc ggctgccaat 120
cgttttaagg cgagtctccc ccaacaaggg gagagacaaa aagacgccca acaccaagca 180
aagcttgagg gtacaaatga cgctcgaaca ggcatgccct ttggaatacc aaagggcgca 240
atgtgcgttc aaagattcga tgattcactg aattctgcaa ttcacactac gtatcgcatt 300
tcgctgcgtt cttcatcgat gccagaacca agagatccgt tgttgaaagt tttaataaat 360
tgaattatta tactgacgct gattgcaact gcataaaaaa aggtttatgg ttgggtcctg 420
gtggcgagcg aactcgccca ggaaacaaaa agtgcgcaaa agacatgggt gaaaaatact 480
tggggcggac gctgttgcca gcaaaccaca ccctcatatt tttgttgtgt aatgatccct 540
ccgcaggttc acctacggag accttgttac gacaatttac ttcctctaaa tgaccaaga 599

<210> SEQ ID NO 119
<211> LENGTH: 957
<212> TYPE: DNA
<213> ORGANISM: Fusarium proliferatum

<400> SEQUENCE: 119
ttcctccgct tattgatatg cttaagttca gcgggtagtc cctaccaatc tgaggccgat 60
gaattattaa aatcccttct ttgcaagaag caaagcatgg gcggggttca gaagcacgcc 120
aaacagcaag atcgttgcgt ccagctcttg ccctttctcc gcctccgaag tcctgatatt 180
atcaaaattc ctccggctta ttgatatgct taagttcagc gggtattcct acctgatccg 240
aggtcaacat tcagaagttg ggggtttaac ggcttggccg cgccgcgtac cagttgcgag 300
ggttttacta ctacgcaatg gaagctgcag cgagaccgcc actgtatttc ggggccggct 360
tgccgtgagg ctcgccgatc cccaacacca aacccggggg cttgagggtt gaaatgacgc 420
tcgaacaggc atgcccgcca gaatactggc gggcgcaatg tgcgttcaaa gattcgatga 480
ttcactgaat tctgcaattc acattactta tcgcattttg ctgcgttctt catcgatgcc 540
agaaccaaga gatccgttgt tgaaagtttt gatttattta tggttttact cagaagttac 600
atatagaaac agagtttagg ggtcctctgg cgggccgttc cgttttaccg ggagcgggct 660
gatccgccga ggcaacaatt ggtatgttca caggggtttg ggagttgtaa actcggtaat 720
gatccctccg ctggttcacc aacggagacc ttgttacgac ttttacttcc tctaaatgac 780
caaaaggaca ctttcgcgtt ctttgacagg ctctcaaccg atgcaaccgt gttaaaaagg 840
tagctcaagt ttagttggac aggtgcgagc cacacctcag aaaaaaggtt ttcatcgaaa 900
tgatccatct gcaggttcac ctacagatac cttgttacga cttttacttc ctctaaa 957

<210> SEQ ID NO 120
<211> LENGTH: 599
<212> TYPE: DNA
<213> ORGANISM: Fusarium moniliformae

<400> SEQUENCE: 120
tcttggtcac tctatagtaa gtaaaagtcg taacaaggtc tccgttggtg aaccagcgga 60
gggatcatta ccgagtttac aactcccaaa cccctgtgaa cataccaatt gttgcctcgg 120
cggatcagcc cgctcccggt aaaacgggac ggcccgccag aggaccccta aactctgttt 180
ctatatgtaa cttctgagta aaaccataaa taaatcaaaa ctttcaacaa cggatctctt 240
ggttctggca tcgatgaaga acgcagcaaa atgcgataag taatgtgaat tgcagaattc 300
agtgaatcat cgaatctttg aacgcacatt gcgcccgcca gtattctggc gggcatgcct 360
gttcgagcgt catttcaacc ctcaagcccc cgggtttggt gttggggatc ggcgagccct 420
tgcggcaagc cggccccgaa atctagtggc ggtctcgctg cagcttccat tgcgtagtag 480
taaaaccctc gcaactggta cgcggcgcgg ccaagccgtt aaacccccaa cttctgaatg 540
ttgacctcgg atcaggtagg aatacccgct gaacttaaga aaatcaataa gcggaggaa 599

<210> SEQ ID NO 121
<211> LENGTH: 589
<212> TYPE: DNA
<213> ORGANISM: Fusarium moniliformae

<400> SEQUENCE: 121
tcttggtctc tctattggta gtaaaagtcg taacaaggtc tccgttggtg aaccagcgga 60
gggatcatta ccgagtttac aactcccaaa cccctgtgaa cataccaatt gttgcctcgg 120
cggatcagcc cgctcccggt aaaacgggac ggcccgccag aggaccccta aactctgttt 180
ctatatgtaa cttctgagta aaaccataaa taaatcaaaa ctttcaacaa cggatctctt 240
ggttctggca tcgatgaaga acgcagcaaa atgcgataag taatgtgaat tgcagaattc 300
agtgaatcat cgaatctttg aacgcacatt gcgcccgcca gtattctggc gggcatgcct 360
gttcgagcgt catttcaacc ctcaagcccc cgggtttggt gttggggatc ggcgagccct 420
tgcggcaagc cggccccgaa atctagtggc ggtctcgctg cagcttccat tgcgtagtag 480
taaaaccctc gcaactggta cgcggcgcgg ccaagccgtt aaacccccaa cttctgaatg 540
ttgacctcgg atcaggtagg aatacccgct gaacttaagc atatcaata 589

<210> SEQ ID NO 122
<211> LENGTH: 567
<212> TYPE: DNA
<213> ORGANISM: Bipolaris oryzae

<400> SEQUENCE: 122
tgaaaatgta gagtcttgat ggagtaccgt ccttttctcc tgatacaaag cgcaaaaaat 60
gtgctgcgct ccgaaaccag taggccggct gccaatcgtt ttaaggcgag tctcccagaa 120
agagggagac aaaaaaacgc ccaacaccaa gcaaagcttg aaggtacaaa tgacgctcga 180
acaggcatgc cctttggaat accaaagggc gcaatgtgcg ttcaaagatt cgatgattca 240
ctgaattctg caattcacac tacgtatcgc atttcgctgc gttcttcatc gatgccagaa 300
ccaagagatc cgttgttgaa agttgtaata attacattgt ttttactgac gctgatggaa 360
actgcataag aaaaaaaggt ttatggttcg gtcctggtgg cgggcgaacc cgcccaggaa 420
acaacaagtg cgcaaaagac atgggtgaaa aaaatacttc agccggccgc gaaagccagg 480
ccttcatatt ttgttgtgta atgatccctc cgcaggttca cctacggaga ccttgttacg 540
acttttactt cctctaaatt gaccaag 567

<210> SEQ ID NO 123
<211> LENGTH: 545
<212> TYPE: DNA
<213> ORGANISM: Gibberella sp.

<400> SEQUENCE: 123
ctacctgatc cgaggtcaca ttcagaagtt gggggtttaa cggcttggcc gcggccgcgt 60
accagttgcg agggttttac tactacgcaa tggaagctgc agcgagaccg ccactgtatt 120
tcggggccgg cttgccgtga ggctcgccga tccccaacac caaacccggg ggcttgaggg 180
ttgaaatgac gctcgaacag gcatgcccgc cagaatactg gcgggcgcaa tgtgcgttca 240
aagattcgat gattcactga attctgcaat tcacattact tatcgcattt tgctgcgttc 300
ttcatcgatg ccagaaccaa gagatccgtt gttgaaagtt ttgatttatt tatggtttta 360
ctcagaaagt tacatataga aacagagttt aggggtcctc tggcgggccg ttccgtttta 420
ccgggagcgg gctgatccgc cgaggcaaca attggtatgt tcacaggggt ttgggagttg 480
taaactcggt aatgatccct ccgctggttc accaacggag accttgttac gacttttact 540
tcctc 545

<210> SEQ ID NO 124
<211> LENGTH: 580
<212> TYPE: DNA
<213> ORGANISM: Colletotrichum graminicola

<400> SEQUENCE: 124
ctacctgatc caggtcacca gtaaaaagtt aggggtttta cggtaagagt ccctctagat 60
cctaatgtaa gacgttagtt actacgcaaa ggaggctctg ggagggtctg ccactacctt 120
taagggccta cgtacgccgt agggccccaa caccaagcgg agcttgaggg ttaaaataac 180
gctcaaatag gcatgcctac tagaatactg gcgggcgcaa tgtgtgttca aagattcaat 240
gatttactga attctgtaat ttacattact tattatattt cgctacattc ttcattaata 300
ctagaaccaa gagatctatt gttaaaagtt ttaattattt acttatgcca ctcagaagaa 360
acgtcgttaa atcagagttt agttatcctc cggcgggcgc cacgccccgc aagggggcac 420
ggccaggagg gcgtccccgg ggagaggacc ccctaacccg ccaaagcaac agttaggtat 480
attcacaaag ggttatagag cagtaactca gtaataatcc ctccgctagt tcaccaacag 540
agaccttgtt acaactttaa cttcctcaaa atgaccaaga 580

<210> SEQ ID NO 125
<211> LENGTH: 710
<212> TYPE: DNA
<213> ORGANISM: Sporisorium everhartii

<400> SEQUENCE: 125
tctgaggccg atgaattatt aaaatccctt ctttgcaaga agcaaagcat gggcggggtt 60
cagaagcacg ccaaacagca agatcgttgc gtccagctct tgccctttct ccgcctccga 120
agtcctgata ttatcaaaac ccggcaggga agagagagcg aaagatgagc tttcgtccgt 180
tcttgcctat caaatggatg cgctaatgta tttcgaggga gccacggtta atggcaaaaa 240
aaccctcact accgagccag cccttcttaa ttaaaaaaag agtggttcga aacaattcgc 300
ggccctcaaa caggcatgct ccccagatta gatctgcagg gagcgcaagg tgcgttcaaa 360
gattcgatga ttcacttctg caattcacat tacttatcgc aattcgctgc gttcttcatc 420
gatgggagaa ccaagagatc cgttgccaaa agttgttttt aaatttaaac gaccgaatta 480
ccagtcataa attgtcattc aaatcctaga agatcaaaag tgtttgtgta aagtgtcgag 540
ggcccaacca aaaggacact ttcgcgttct ttgacaggct ctcaaccgat gcaaccgtgt 600
taaaaaggta gctcaagttt agttggacag gtgcgagcca cacctcagaa aaaaggtttt 660
catcgaaatg atccatctgc aggttcacct acagatacct tgttacgaca 710

<210> SEQ ID NO 126
<211> LENGTH: 719
<212> TYPE: DNA
<213> ORGANISM: Sporisorium everhartii

<400> SEQUENCE: 126
taccatctga ggccgatgaa ttattaaaat cccttctttg caagaagcaa agcatgggcg 60
gggttcagaa gcacgccaaa cagcaagatc gttgcgtcca gctcttgccc tttctccgcc 120
tccgaagtcc tgatattatc aaaacccggc agggaagaga gagcgaaaga tgagctttcg 180
tccgttcttg cctatcaaat ggatgcgcta atgtatttcg agggagccac ggttaatggc 240
aaaaaaaccc tcactaccga gccagccctt cttaattaaa aaaagagtgg ttcgaaacaa 300
ttcgcggccc tcaaacaggc atgctcccca gattagatct gcagggagcg caaggtgcgt 360
tcaaagattc gatgattcac ttctgcaatt cacattactt atcgcaattc gctgcgttct 420
tcatcgatgg gagaaccaag agatccgttg ccaaaagttg tttttaaatt taaacgaccg 480
aattaccagt cataaattgt cattcaaatc ctagaagatc aaaagtgttt gtgtaaagtg 540
tcgagggccc aaccaaaagg acactttcgc gttctttgac aggctctcaa ccgatgcaac 600
cgtgttaaaa aggtagctca agtttagttg gacaggtgcg agccacacct cagaaaaaag 660
gttttcatcg aaatgatcca tctgcaggtt cacctacaga taccttgtta cgacattta 719

<210> SEQ ID NO 127
<211> LENGTH: 538
<212> TYPE: DNA
<213> ORGANISM: Fusarium moniliformae

<400> SEQUENCE: 127
tctacctgat ccgaggtcaa cattcagaag ttgggggttt aacggcttgg ccgcgccgcg 60
taccagttgc gagggtttta ctactacgca atggaagctg cagcgagacc gccactagat 120
ttcggggccg gcttgccgca agggctcgcc gatccccaac accaaacccg ggggcttgag 180
ggttgaaatg acgctcgaac aggcatgccc gccagaatac tggcgggcgc aatgtgcgtt 240
caaagattcg atgattcact gaattctgca attcacatta cttatcgcat tttgctgcgt 300
tcttcatcga tgccagaacc aagagatccg ttgttgaaag ttttgattta tttatggttt 360
tactcagaag ttacatatag aaacagagtt taggggtcct ctggcgggcc gtcccgtttt 420
accgggagcg ggctgatccg ccgaggcaac aattggtatg ttcacagggg tttgggagtt 480
gtaaactcgg taatgatccc tccgctggtt caccaacgga gaccttgtta cgactttt 538

<210> SEQ ID NO 128
<211> LENGTH: 713
<212> TYPE: DNA

<213> ORGANISM: Sporisorium everhartii

<400> SEQUENCE: 128

```
taccatctga ggcgatgaat tattaaaatc ccttctttgc aagaagcaaa gcatgggcgg      60
ggttcagaag cacgccaaac agcaagatcg ttgcgtccag ctcttgccct ttctccgcct     120
ccgaagtcct gatattatca aaacccggca gggaagagag agcgaaagat gagctttcgt     180
ccgttcttgc ctatcaaatg gatgcgctaa tgtatttcga gggagccacg gttaatggca     240
aaaaaaccct cactaccgag ccagcccttc ttaattaaaa aaagagtggt tcgaaacaat     300
tcgcggccct caaacaggca tgctccccag attagatctg cagggagcgc aaggtgcgtt     360
caaagattcg atgattcact tctgcaattc acattactta tcgcaattcg ctgcgttctt     420
catcgatggg agaaccaaga gatccgttgc caaaagttgt ttttaaattt aaacgaccga     480
attaccagtc ataaattgtc attcaaatcc tagaagatca aaagtgtttg tgtaaagtgt     540
cgagggccca accaaaagga cactttcgcg ttctttgaca ggctctcaac cgatgcaacc     600
gtgttaaaaa ggtagctcaa gtttagttgg acaggtgcga gccacacctc agaaaaaagg     660
ttttcatcga aatgatccat ctgcaggttc acctacagat accttgttac gac            713
```

<210> SEQ ID NO 129
<211> LENGTH: 719
<212> TYPE: DNA
<213> ORGANISM: Sporisorium everhartii

<400> SEQUENCE: 129

```
aaaggagagg ccgatgaatt attaaaatcc cttctttgca agaagcaaag catgggcggg      60
gttcagaagc acgccaaaca gcaagatcgt tgcgtccagc tcttgccctt tctccgcctc     120
cgaagtcctg atattatcaa aacccggcag ggaagagaga gcgaaagatg agctttcgtc     180
cgttcttgcc tatcaaatgg atgcgctaat gtatttcgag ggagccacgg ttaatggcaa     240
aaaaaccctc actaccgagc cagcccttct taattaaaaa aagagtggtt cgaaacaatt     300
cgcggccctc aaacaggcat gctccccaga ttagatctgc agggagcgca aggtgcgttc     360
aaagattcga tgattcactt ctgcaattca cattacttat cgcaattcgc tgcgttcttc     420
atcgatggga gaaccaagag atccgttgcc aaaagttgtt tttaaattta aacgaccgaa     480
ttaccagtca taaattgtca ttcaaatcct agaagatcaa aagtgtttgt gtaaagtgtc     540
gagggcccaa ccaaaaggac actttcgcgt tctttgacag gctctcaacc gatgcaaccg     600
tgttaaaaag gtagctcaag tttagttgga caggtgcgag ccacacctca gaaaaaaggt     660
tttcatcgaa atgatccatc tgcaggttca cctacagata ccttgttacg acttttact      719
```

<210> SEQ ID NO 130
<211> LENGTH: 596
<212> TYPE: DNA
<213> ORGANISM: Sordariomycete sp

<400> SEQUENCE: 130

```
cttggtcatt tagaggaagt aaaagtcgta acaaggtctc cgttggtgaa ccagcggagg      60
gatcattacc gagtttacaa ctcccaaacc cctgtgaaca tatcaattgt tgcctcggcg     120
gatcagcccg ctcccggtaa aacggaacgg cccgccagag gacccctaaa ctctgtttct     180
atatgtaact tctgagtaaa accataaata aatcaaaact ttcaacaacg gatctcttgg     240
ttctggcatc gatgaagaac gcagcaaaat gcgataagta atgtgaattg cagaattcag     300
tgaatcatcg aatctttgaa cgcacattgc gcccgccagt attctggcgg gcatgcctgt     360
```

```
tcgagcgtca tttcaaccct caagcccccg ggtttggtgt tggggatcgg cgagcctcac    420

ggcaagccgg ccccgaaata cagtggcggt ctcgctgcag cttccattgc gtagtagtaa    480

aaccctcgca actggtacgc ggcgcggcca agccgttaaa cccccaactt ctgaatgttg    540

acctcggatc aggtaggaat acccgctgaa cttaagcata tcaataagcg gaggaa        596


<210> SEQ ID NO 131
<211> LENGTH: 663
<212> TYPE: DNA
<213> ORGANISM: Sordariomycete sp

<400> SEQUENCE: 131

aggtgaacct gcggaaggat cattaatgaa tgaatgtaga gtcggttgta gctgacctcc     60

cagtcttggt catttagagg aagtaaaagt cgtaacaagg tctccgttgg tgaaccagcg    120

gagggatcat taccgagttt acaactccca aacccctgtg aacatatcaa ttgttgcctc    180

ggcggatcag cccgctcccg gtaaaacgga acggcccgcc agaggacccc taaactctgt    240

ttctatatgt aacttctgag taaaaccata aataaatcaa aactttcaac aacggatctc    300

ttggttctgg catcgatgaa gaacgcagca aaatgcgata agtaatgtga attgcagaat    360

tcagtgaatc atcgaatctt tgaacgcaca ttgcgcccgc cagtattctg gcgggcatgc    420

ctgttcgagc gtcatttcaa ccctcaagcc cccgggtttg gtgttgggga tcggcgagcc    480

tcacggcaag ccggccccga aatacagtgg cggtctcgct gcagcttcca ttgcgtagta    540

gtaaaaccct cgcaactggt acgcggcgcg gccaagccgt taaacccccca acttctgaat    600

gttgacctcg gatcaggtag gaatacccgc tgaacttaag catatcaata agcggaggaa    660

gat                                                                  663


<210> SEQ ID NO 132
<211> LENGTH: 582
<212> TYPE: DNA
<213> ORGANISM: Fusarium nygamai

<400> SEQUENCE: 132

ggaagtaaaa gtcgtaacaa ggtctccgtt ggtgaaccag cggagggatc attaccgagt     60

ttacaactcc caaacccctg tgaacatacc aattgttgcc tcggcggatc agcccgctcc    120

cggtaaaacg gaacggcccg ccagaggacc cctaaactct gtttctatat gtaacttctg    180

agtaaaacca taaataaatc aaaactttca acaacggatc tcttggttct ggcatcgatg    240

aagaacgcag caaaatgcga taagtaatgt gaattgcaga attcagtgaa tcatcgaatc    300

tttgaacgca cattgcgccc gccagtattc tggcgggcat gcctgttcga gcgtcatttc    360

aaccctcaag cccccgggtt tggtgttggg gatcggcgag cctcacggca agccggcccc    420

gaaatacagt ggcggtctcg ctgcagcttc cattgcgtag tagtaaaacc ctcgcaactg    480

gtacgcggcg cggccaagcc gttaaacccc caacttctga atgttgacct cggatcaggt    540

aggaataccc gctgaactta agcatatcaa taagccggag ga                       582


<210> SEQ ID NO 133
<211> LENGTH: 563
<212> TYPE: DNA
<213> ORGANISM: Fusarium acuminatum

<400> SEQUENCE: 133

aaagtcgtaa caaggtctcc gttggtgaac cagcggaggg atcattaccg agtttacaac     60
```

tcccaaaccc ctgtgaacat acctttatgt tgcctcggcg gatcagcccg cgccccgtaa 120
aacgggacgg cccgccgcag gaaaccctaa actctgtttt tagtggaact tctgagtata 180
aaaaacaaat aaatcaaaac tttcaacaac ggatctcttg gttctggcat cgatgaagaa 240
cgcagcaaaa tgcgataagt aatgtgaatt gcagaattca gtgaatcatc gaatctttga 300
acgcacattg cgcccgccag tattctggcg ggcatgcctg ttcgagcgtc atttcaaccc 360
tcaagcccag cttggtgttg ggatctgtct ttattgacag tcctcaaatt gattggcggt 420
cacgtcgagc ttccatagcg tagtaattta cacatcgtta ctggtaatcg tcgcggccac 480
gccgttaaac cccaacttct gaatgttgac ctcggatcag gtaggaatac ccgctgaact 540
taagcatatc aataagcgga gga 563

<210> SEQ ID NO 134
<211> LENGTH: 546
<212> TYPE: DNA
<213> ORGANISM: Fusarium nygamai

<400> SEQUENCE: 134
ccagcggagg gatcattacc gagtttacaa ctcccaaacc cctgtgaaca tatcaattgt 60
tgcctcggcg gatcagcccg ctcccggtaa aacggaacgg cccgccagag gacccctaaa 120
ctctgtttct atatgtaact tctgagtaaa accataaata aatcaaaact ttcaacaacg 180
gatctcttgg ttctggcatc gatgaagaac gcagcaaaat gcgataagta atgtgaattg 240
cagaattcag tgaatcatcg aatctttgaa cgcacattgc gcccgccagt attctggcgg 300
gcatgcctgt tcgagcgtca tttcaaccct caagcccccg ggtttggtgt tggggatcgg 360
cgagcctcac ggcaagccgg ccccgaaata cagtggcggt ctcgctgcag cttccattgc 420
gtagtagtaa aaccctcgca actggtacgc ggcgcggcca agccgttaaa cccccaactt 480
ctgaatgttg acctcggatc aggtaggaat acccgctgaa cttaagcata tcaataagcg 540
gaggaa 546

<210> SEQ ID NO 135
<211> LENGTH: 567
<212> TYPE: DNA
<213> ORGANISM: Fusarium proliferatum

<400> SEQUENCE: 135
ttagaggaag taaaagtcgt aacaaggtct ccgttggtga accagcggag ggatcattac 60
cgagtttaca actcccaaac ccctgtgaac atatcaattg ttgcctcggc ggatcagccc 120
gctcccggta aaacggaacg gcccgccaga ggacccctaa actctgtttc tatatgtaac 180
ttctgagtaa aaccataaat aaatcaaaac tttcaacaac ggatctcttg gttctggcat 240
cgatgaagaa cgcagcaaaa tgcgataagt aatgtgaatt gcagaattca gtgaatcatc 300
gaatctttga acgcacattg cgcccgccag tattctggcg ggcatgcctg ttcgagcgtc 360
atttcaaccc tcaagccccc gggtttggtg ttggggatcg gcgagcctca cggcaagccg 420
gccccgaaat acagtggcgg tctcgctgca gcttccattg cgtagtagta aaaccctcgc 480
aactggtacg cggcgcggcc aagccgttaa acccccaact tctgaatgtt gacctcggat 540
caggtaggaa tacccgctga acttaag 567

<210> SEQ ID NO 136
<211> LENGTH: 560
<212> TYPE: DNA
<213> ORGANISM: Leaf litter ascomycetes -continued

<400> SEQUENCE: 136
gaagtaaaag tcgtaacaag gtttccgtag gtgaacctgc ggaaggatca ttatcaaaac 60
agcggacttc ggtccttgct gcacccttgt cttttgcgca ccgtattgtt tcctcggcgg 120
gcttgcctgc cggttggaca tcatcaaacc tttttgtagt tgcaatcagc gtcagaaaaa 180
taacaatcgt tacaactttc aacaacggat ctcttggttc tggcatcgat gaagaacgca 240
gcgaaatgcg aaaagtagtg tgaattgcag aattcagtga atcatcgaat ctttgaacgc 300
acattgcgcc ccttggtatt ccatggggca tgcctgttcg agcgtcattt tgtaccctca 360
agcactgctt ggtgttgggc gtttgtcctg ctgaaggact cgcctgaaag cgattggcgg 420
ccaacgtagt cgtggcagag cgcagcacaa tctcgcgtct ctcccctctg cgtcggcgtc 480
catgaagccc ttttttcaac gtttgacctc ggatcaggta gggatacccg ctgaacttaa 540
gcatatcaat aagcggagga 560

<210> SEQ ID NO 137
<211> LENGTH: 611
<212> TYPE: DNA
<213> ORGANISM: Acremonium strictum

<400> SEQUENCE: 137
gtcatttaga ggaagtaaaa gtcgtaacaa ggtctccgtt ggtgaaccag cggagggatc 60
attaccagag tgccctaggc tctccaaccc attgtgaact taccaaacgt tccctcggcg 120
ggctcagcgc gcggtggcct ccgggccgcc gggcgtccgc cggggaaaac caaaccctga 180
tttaatcgta tttctctgag ggcgaaagc ccgaaaacaa aatgaatcaa aactttcaac 240
aacggatctc ttggctctgg catcgatgaa gaacgcagcg aaatgcgata agtaatgtga 300
attgcagaat tcagtgaatc atcgaatctt tgaacgcaca ttgcgcccgc cggcactccg 360
gcgggcatgc ctgtccgagc gtcatttcaa ccctcaggcc caccccttccg ggggagcggg 420 cctggttctg gggatcggcg gccctcgcgg cccccgtccc tcaaattcag tggcggtcgc 480
gccgcagcct cccctgcgta gtagcacaac ctcgcaccgg agagcggaac gaccacgccg 540
taaaacaccc aactttttaa ggttgacctc ggatcaggta ggaatacccg ctgaacttaa 600
gcatatcaat a 611

<210> SEQ ID NO 138
<211> LENGTH: 530
<212> TYPE: DNA
<213> ORGANISM: Fusarium nygamai

<400> SEQUENCE: 138
gagggatcat taccgagttt acaactccca aacccctgtg aacataccaa ttgttgcctc 60
ggcggatcag cccgctcccg gtaaaacgga acggcccgcc agaggacccc taaactctgt 120
ttctatatgt aacttctgag taaaaccata aataaatcaa aactttcaac aacggatctc 180
ttggttctgg catcgatgaa gaacgcagca aaatgcgata agtaatgtga attgcagaat 240
tcagtgaatc atcgaatctt tgaacgcaca ttgcgcccgc cagtattctg gcgggcatgc 300
ctgttcgagc gtcatttcaa ccctcaagcc cccgggtttg gtgttgggga tcggcgagcc 360
tcacggcaag ccggccccga aatacagtgg cggtctcgct gcagcttcca ttgcgtagta 420
gtaaaaccct cgcaactggt acgcggcgcg gccaagccgt taaacccccca acttctgaat 480 gttgacctcg gatcaggtag gaatacccgc tgaacttaag catatcaata 530

<210> SEQ ID NO 139
<211> LENGTH: 551
<212> TYPE: DNA
<213> ORGANISM: Fusarium nygamai

<400> SEQUENCE: 139
tcgtctcgtt ggtgaccagc ggagggatca ttaccgagtt tacaactccc aaacccctgt 60
gaacatatca attgttgcct cggcggatca gcccgctccc ggtaaaacgg aacggcccgc 120
cagaggaccc ctaaactctg tttctatatg taacttctga gtaaaaccat aaataaatca 180
aaactttcaa caacggatct cttggttctg gcatcgatga agaacgcagc aaaatgcgat 240
aagtaatgtg aattgcagaa ttcagtgaat catcgaatct ttgaacgcac attgcgcccg 300
ccagtattct ggcgggcatg cctgttcgag cgtcatttca accctcaagc ccccgggttt 360
ggtgttgggg atcggcgagc ctcacggcaa gccggccccg aaatacagtg gcggtctcgc 420
tgcagcttcc attgcgtagt agtaaaaccc tcgcaactgg tacgcggcgc ggccaagccg 480
ttaaaccccc aacttctgaa tgttgacctc ggatcaggta ggaatacccg ctgaacttaa 540
gcatatcaat a 551

<210> SEQ ID NO 140
<211> LENGTH: 549
<212> TYPE: DNA
<213> ORGANISM: Fusarium nygamai

<400> SEQUENCE: 140
gtgaccagcg gagggakcat taccgagttt acaactccca aacccctgtg aacatatcaa 60
ttgttgcctc ggcggatcag cccgctcccg gtaaaacgga acggcccgcc agaggacccc 120
taaactctgt ttctatatgt aacttctgag taaaaccata aataaatcaa aactttcaac 180
aacggatctc ttggttctgg catcgatgaa gaacgcagca aaatgcgata agtaatgtga 240
attgcagaat tcagtgaatc atcgaatctt tgaacgcaca ttgcgcccgc cagtattctg 300
gcgggcatgc ctgttcgagc gtcatttcaa ccctcaagcc cccgggtttg gtgttgggga 360
tcggcgagcc tcacggcaag ccggccccga aatacagtgg cggtctcgct gcagcttcca 420
ttgcgtagta gtaaaaccct cgcaactggt acgcggcgcg gccaagccgt taaaccccca 480
acttctgaat gttgacctcg gatcaggtag gaatacccgc tgaacttaag catatcaata 540
ggcggagga 549

<210> SEQ ID NO 141
<211> LENGTH: 590
<212> TYPE: DNA
<213> ORGANISM: Stachybotrys elegans

<400> SEQUENCE: 141
tcgttggtga ccagcggagg gatcattacc gagtttacaa ctcccaaacc caatgtgaac 60
atacctcaag ttgcttcggc gggaacgccc cggcgcgccc tccgaccctc ccgtccgcgg 120
ggggatcggg gagcctagcc cggacccagg cgcccgccgg aggtactcaa actcttgtct 180
ttagtatatt cttctgagtg gcaaacgcaa aataaatcaa aactttcaac aacggatctc 240
ttggctctgg catcgatgaa gaacgcagcg aaatgcgata agtaatgtga attgcagaat 300
tcagtgaatc atcgaatctt tgaacgcaca ttgcgcccgc cagcactctg gcgggcatgc 360
ctgtccgagc gtcatttcaa ccctcagccc cccccgggga ctggtgttgg ggatcggccc 420
gccctggcgc ggcgccgtcc ccgaaataca gtggcggtct cgctgcagcc tcccctgcgt 480

```
agtagcacac ctcgcatcgg agagcggcgc ggccacgccg tgaaacccca acttctgata    540

gttgacctcg gatcaggtag gaatacccgc tgaacttaag catatcaata               590
```

<210> SEQ ID NO 142
<211> LENGTH: 579
<212> TYPE: DNA
<213> ORGANISM: Stachybotrys elegans

<400> SEQUENCE: 142

```
ccagcggagg gatcattacc gagtttacaa ctcccaaacc caatgtgaac atacctcaag     60

ttgcttcggc gggaacgccc cggcgcgccc tccgaccctc ccgtccgcgg ggggatcggg    120

gagcctagcc cggacccagg cgcccgccgg aggtactcaa actcttgtct ttagtatatt    180

cttctgagtg gcaaacgcaa aataaatcaa aactttcaac aacggatctc ttggctctgg    240

catcgatgaa gaacgcagcg aaatgcgata agtaatgtga attgcagaat tcagtgaatc    300

atcgaatctt tgaacgcaca ttgcgcccgc cagcactctg gcgggcatgc ctgtccgagc    360

gtcatttcaa ccctcagccc cccccgggga ctggtgttgg ggatcggccc gccctggcgc    420

ggcgccgtcc ccgaaataca gtggcggtct cgctgcagcc tcccctgcgt agtagcacac    480

ctcgcatcgg agagcggcgc ggccacgccg tgaaacccca acttctgata gttgacctcg    540

gatcaggtag gaatacccgc tgaacttaag catatcaaa                           579
```

<210> SEQ ID NO 143
<211> LENGTH: 581
<212> TYPE: DNA
<213> ORGANISM: Stachybotrys elegans

<400> SEQUENCE: 143

```
accagcggag ggatcattac cgagtttaca actcccaaac ccaatgtgaa catacctcaa     60

gttgcttcgg cgggaacgcc ccggcgcgcc ctccgaccct cccgtccgcg gggggatcgg    120

ggagcctagc ccggacccag gcgcccgccg gaggtactca aactcttgtc tttagtatat    180

tcttctgagt ggcaaacgca aaataaatca aaactttcaa caacggatct cttggctctg    240

gcatcgatga agaacgcagc gaaatgcgat aagtaatgtg aattgcagaa ttcagtgaat    300

catcgaatct ttgaacgcac attgcgcccg ccagcactct ggcgggcatg cctgtccgag    360

cgtcatttca accctcagcc ccccccgggg actggtgttg gggatcggcc cgccctggcg    420

cggcgccgtc cccgaaatac agtggcggtc tcgctgcagc ctcccctgcg tagtagcaca    480

cctcgcatcg gagagcggcg cggccacgcc gtgaaacccc aacttctgat agttgacctc    540

ggatcaggta ggaatacccg ctgaacttaa gcatatcaat a                        581
```

<210> SEQ ID NO 144
<211> LENGTH: 573
<212> TYPE: DNA
<213> ORGANISM: Periconia macrospinosa

<400> SEQUENCE: 144

```
tgatatgctt aagttcagcg ggtatcccta cctgatccga ggtcaagtcg tgaaaggtct     60

tgctggagcg cggatccgcc gggcctccga gaagcgcaaa tgtgctgcgc gagggggccg    120

gcacgaccgc cgccaatgac tttgaggcga gtccgcgcgc gagaacggcg ggacagacgc    180

ccaacaccaa gctaggcttg agggtgtaaa tgacgctcga acaggcatgg ccaaaggaat    240

acctatggcc gcaatgtgcg ttcaaagatt cgatgattca ctgaattctg caattcacac    300
```

tacttatcgc atttcgctgc gttcttcatc gatgccagaa ccaagagatc cattgttgaa 360
agttgtgata atttaggttt gttatcagaa gttttcgcgt ataatgcaag ggtttcgtg 420 ggttcctggc ggcgggcgag cccgccgagg aagctataga ggtacacgta ggcagagggt 480
gggtgtataa ggagcgccga agcgccccga atgtgtaatg atccttccgc aggttcacct 540
acggaaacct tgttacgact tttacttcct cta 573

<210> SEQ ID NO 145
<211> LENGTH: 594
<212> TYPE: DNA
<213> ORGANISM: Codinaeopsis sp.

<400> SEQUENCE: 145
ttcctccggc ttattgatat gcttaagttc agcgggtatt cctacctgat ccgaggtcaa 60
ccacttagaa agttgggggt tttacggccg gagcgcgcgc cggaccagaa cgagaaagca 120
ttactgcgct cggttccggg gcgcgcccgc cgctgtcttt gggagcctgc gctgcgcagg 180
gctccaacgc caggcggggc ctgagggttg aaatgacgct cggacaggca tgcccgccag 240
agtgctggcg ggcgcaatgt gcgttcaaag attcgatgat tcactgaatt ctgcaattca 300
cattacttat cgcatttcgc tgcgttcttc atcgatgcca gaaccaagag atccgttgtt 360
gaaagttttg actcgtttat agtctgctcg gagatgccaa cgttacagag acagagttta 420
ggggccgccg gcgggctgga gcgccccgga gcgcccgaag acgcgcccgg agcacccgcc 480
gaggcaacgg gttgtaggta agttcacagt ggtttacggg agtcttgcga gtcctgtaat 540
gatccctccg ctggttcacc aacggagacc ttgttacgac ttttacttcc tcta 594

<210> SEQ ID NO 146
<211> LENGTH: 497
<212> TYPE: DNA
<213> ORGANISM: Fusarium nygamai

<400> SEQUENCE: 146
ccctgtgaac ataccaattg ttgcctcggc ggatcagccc gctcccggta aaacggaacg 60
gcccgccaga ggacccctaa actctgtttc tatatgtaac ttctgagtaa aaccataaat 120
aaatcaaaac tttcaacaac ggatctcttg gttctggcat cgatgaagaa cgcagcaaaa 180
tgcgataagt aatgtgaatt gcagaattca gtgaatcatc gaatctttga acgcacattg 240
cgcccgccag tattctggcg ggcatgcctg ttcgagcgtc atttcaaccc tcaagccccc 300
gggtttggtg ttggggatcg gcgagcctca cggcaagccg gccccgaaat acagtggcgg 360
tctcgctgca gcttccattg cgtagtagta aaaccctcgc aactggtacg cggcgcggcc 420
aagccgttaa acccccaact tctgaatgtt gacctcggat caggtaggaa tacccgctga 480
acttaagcat atcaata 497

<210> SEQ ID NO 147
<211> LENGTH: 589
<212> TYPE: DNA
<213> ORGANISM: Gaeumannomyces incrustans

<400> SEQUENCE: 147
agaggaagta aaagtcgtaa caaggtctcc gttggtgaac cagcggaggg atcattaaag 60
agttgcaaaa ctccaacccc tgtgaacttt acctttactg ttgcttcggc ggttggcgcc 120
ggtgcccaga tgggcctgga ggtcgccgcc ggaggttcga aaccctgaat tctagtgtgt 180
ctctgagaaa agaataaaac aatcaaaact ttcaacaacg gatctcttgg ttctggcatc 240
gatgaagaac gcagcgaaat gcgataagta atgtgaattg cagaattcag tgaatcatcg 300
aatctttgaa cgcacattgc gcccgccggt attccggcgg gcatgcctgt ccgagcgtca 360
tttcaccact caagcacagc ttggtgttgg ggcacccggc cgcctggcgg tcggggcccc 420
caagtacatc ggcggtcccg ctgggggctc cgagcgcagt agcacgcggt aaaacgcgcc 480
ctcgctcggc ggcctcttcg ggcttccagc cgctaaaccc gtccaccgac gcccttcgag 540
ctgacctcgg atcaggtagg aatacccgct gaacttaagc atatcaata 589

<210> SEQ ID NO 148
<211> LENGTH: 573
<212> TYPE: DNA
<213> ORGANISM: Periconia macrospinosa

<400> SEQUENCE: 148
tgatatgctt aagttcagcg ggtatcccta cctgatccga ggtcaagtcg tgaaaggtct 60
tgctggagcg cggatccgcc gggcctccga gaagcgcaaa tgtgctgcgc gagggggccg 120
gcacgaccgc cgccaatgac tttgaggcga gtccgcgcgc gagaacggcg ggacagacgc 180
ccaacaccaa gctaggcttg agggtgtaaa tgacgctcga acaggcatgg ccaaaggaat 240
acctatggcc gcaatgtgcg ttcaaagatt cgatgattca ctgaattctg caattcacac 300
tacttatcgc atttcgctgc gttcttcatc gatgccagaa ccaagagatc cattgttgaa 360
agttgtgata atttaggttt gttatcagaa gttttcgcgt ataatgcaag ggtttcgtg 420 ggttcctggc ggcgggcgag cccgccgagg aagctataga ggtacacgta ggcagagggt 480
gggtgtataa ggagcgccga agcgccccga atgtgtaatg atccttccgc aggttcacct 540
acggaaacct tgttacgact tttacttcct cta 573

<210> SEQ ID NO 149
<211> LENGTH: 506
<212> TYPE: DNA
<213> ORGANISM: Fusarium sp.

<400> SEQUENCE: 149
tattgatatg cttaagttca gcgggtattc ctacctgatt cgaggtcaac attcagaagt 60
tgggtgtttt acggcatggc cgcgccgctc tccagttgcg aggtgttagc tactacgcaa 120
tggaagctgc ggcgggaccg ccactgtatt tgagggacgg cgtgtgccca caggggggctt 180 ccgccgatcc ccaacgccag gcccgggggc ctgagggttg taatgacgct cgaacaggca 240
tgcccgccag aatactggcg ggcgcaatgt gcgttcaaag attcgatgat tcactgaatt 300
ctgcaattca cattacttat cgcatttcgc tgcgttcttc atcgatgcca gagccaagag 360
atccgttgtt gaaagtttta atttatttgc ttgtttactc agaaaaacat tataaaaaca 420
gagttagggg tcctctggcg gggcggcccc gttgttacag ggccgtctgt tcccgccgaa 480
gcaacgtttt aggtatgttc acaggg 506

<210> SEQ ID NO 150
<211> LENGTH: 593
<212> TYPE: DNA
<213> ORGANISM: Gaeumannomyces incrustans

<400> SEQUENCE: 150
ttagaggaag taaaagtcgt aacaaggtct ccgttggtga accagcggag ggatcattaa 60
agagttgcaa aactccaacc cctgtgaact ttacctttac tgttgcttcg gcggttggcg 120
ccggtgccca gatgggcctg gaggtcgccg ccggaggttc gaaaccctga attctagtgt 180
gtctctgaga aaagaataaa acaatcaaaa ctttcaacaa cggatctctt ggttctggca 240
tcgatgaaga acgcagcgaa atgcgataag taatgtgaat tgcagaattc agtgaatcat 300
cgaatctttg aacgcacatt gcgcccgccg gtattccggc gggcatgcct gtccgagcgt 360
catttcacca ctcaagcaca gcttggtgtt ggggcacccg gccgcctggc ggtcggggcc 420
cccaagtaca tcggcggtcc cgctgggggc tccgagcgca gtagcacgcg gtaaaacgcg 480
ccctcgctcg gcggcctctt cgggcttcca gccgctaaac ccgtccaccg acgcccttcg 540
agctgacctc ggatcaggta ggaatacccg ctgaacttaa gcatatcaat aag 593

<210> SEQ ID NO 151
<211> LENGTH: 500
<212> TYPE: DNA
<213> ORGANISM: Fusarium annulatum

<400> SEQUENCE: 151
ccctgtgaac ataccaattg ttgcctcggc ggatcagccc gctcccggta aaacgggacg 60
gcccgccaga ggacccctaa actctgtttc tatatgtaac ttctgagtaa aaccataaat 120
aaatcaaaac tttcaacaac ggatctcttg gttctggcat cgatgaagaa cgcagcaaaa 180
tgcgataagt aatgtgaatt gcagaattca gtgaatcatc gaatctttga acgcacattg 240
cgcccgccag tattctggcg ggcatgcctg ttcgagcgtc atttcaaccc tcaagccctc 300
gggtttggtg ttggggatcg gcgagccctt gcggcaagcc ggccccgaaa tatagtggcg 360
gtctcgctgc agcttccatt gcgtagtagt aaaaccctcg caactggtac gcggcgcggc 420
caagccgtta aacccccaac ttctgaatgt tgacctcgga tcaggtagga atacccgctg 480
aacttaagca tatcaataag 500

<210> SEQ ID NO 152
<211> LENGTH: 499
<212> TYPE: DNA
<213> ORGANISM: Fusarium nygamai

<400> SEQUENCE: 152
ccctgtgaac ataccaattg ttgcctcggc ggatcagccc gctcccggta aaacggaacg 60
gcccgccaga ggacccctaa actctgtttc tatatgtaac ttctgagtaa aaccataaat 120
aaatcaaaac tttcaacaac ggatctcttg gttctggcat cgatgaagaa cgcagcaaaa 180
tgcgataagt aatgtgaatt gcagaattca gtgaatcatc gaatctttga acgcacattg 240
cgcccgccag tattctggcg ggcatgcctg ttcgagcgtc atttcaaccc tcaagccccc 300
gggtttggtg ttggggatcg gcgagcctca cggcaagccg gccccgaaat acagtggcgg 360
tctcgctgca gcttccattg cgtagtagta aaaccctcgc aactggtacg cggcgcggcc 420
aagccgttaa acccccaact tctgaatgtt gacctcggat caggtaggaa tacccgctga 480
acttaagcat atcaatagg 499

<210> SEQ ID NO 153
<211> LENGTH: 517
<212> TYPE: DNA
<213> ORGANISM: Periconia macrospinosa

<400> SEQUENCE: 153
gtttccgtag gtgaacctgc ggaaggatca ttatcaaaag tcaagtcggg ggctgcaaag 60
ccttcgtcta caccccatgt cttttgcgta cttcttgttt cctcggtggc gcaagccgcc 120

```
gattggacaa accaaaacct tttttgtaat tgcaatcagc gtctgaaaat aatctaatta    180

tttacaactt tcaacaacgg atctcttggt tctggcatcg atgaagaacg cagcgaaatg    240

cgataagtag tgtgaattgc agaattcagt gaatcatcga atctttgaac gcacattgcg    300

ccccttggta ttccatgggg catgcctgtt cgagcgtcat ttgtaccctc aagctttgct    360

tggtgttggg cgtcttgtcg tattacgact cgccttaaat acattggcag ccggcacttt    420

ggcctaggag cgccgcacat tttgcgatcg tagcccgttg tactggcgtc catcaagaac    480

atttaccacg tttgacctcg gatcaggtag ggatacc                            517
```

<210> SEQ ID NO 154
<211> LENGTH: 589
<212> TYPE: DNA
<213> ORGANISM: Gaeumannomyces incrustans

<400> SEQUENCE: 154

```
agaggaagta aaagtcgtaa caaggtctcc gttggtgaac cagcggaggg atcattaaag     60

agttgcaaaa ctccaacccc tgtgaacctt acctttactg ttgcttcggc ggttggcgcc    120

ggtgcccaga tgggcctgga ggtcgccgcc ggaggttcga aaccctgaat tctagtgtgt    180

ctctgagaaa agaataaaac aatcaaaact ttcaacaacg gatctcttgg ttctggcatc    240

gatgaagaac gcagcgaaat gcgataagta atgtgaattg cagaattcag tgaatcatcg    300

aatctttgaa cgcacattgc gcccgccggt attccggcgg gcatgcctgt ccgagcgtca    360

tttcaccact caagcacagc ttggtgttgg ggcacccggc cgcctggcgg tcggggcccc    420

caagtacatc ggcggtcccg ctgggggctc cgagcgcagt agcacgcggt aaaacgcgcc    480

ctcgctcggc ggcctcttcg ggcttccagc cgctaaaccc gtccaccgac gcccttcgag    540

ctgacctcgg atcaggtagg aatacccgct gaacttaagc atatcaata                589
```

<210> SEQ ID NO 155
<211> LENGTH: 718
<212> TYPE: DNA
<213> ORGANISM: Coprinus auricomus

<400> SEQUENCE: 155

```
gtcgtaacaa ggtttccgta ggtgaacctg cggaaggatc attatcgaat aaatctgatg     60

tggttgtagc tggcttctag gagcatgtgc acgcccgtca cttttatctt tccacctgtg    120

aaccctctgt agtcctggga taaactctcg cgcgcttcac ggcgtcgcgg atgcgaaggt    180

tgtcgtgcct ctggccggct tcctttgaat ttcctgggtc tacgtctctt aacacacccc    240

taacgaatgt ttaaaagaat gttgatttca aagggctacg gcctatagaa accaaataca    300

actttcagca acggatctct tggctctcgc atcgatgaag aacgcagcga aatgcgataa    360

gtaatgtgaa ttgcagaatt cagtgaatca tcgaatcttt gaacgcacct tgcgctcctt    420

ggtattccga ggagcatgcc tgtttgagtg tcattaaatt ctcaacctca cccagtttgt    480

caaaaccagg tgaaggcttg gacttggggg tcttgcaggc tgcgggtcaa tccgcggttc    540

gctcccctga aatgcattag cgggtctttc ccctccatcc caacggtgtg ataacctatc    600

tacgccgccg gtgttggaga ccttaatggg accagcttct aaccgtccgc aaggacaata    660

ttgaccaaac ttgacctcaa atcaggtagg actacccgct gaacttaagc atatcata      718
```

<210> SEQ ID NO 156
<211> LENGTH: 732
<212> TYPE: DNA

<213> ORGANISM: Coprinus auricomus

<400> SEQUENCE: 156
tagaggaagt aaaagtcgta acaaggtttc cgtaggtgaa cctgcggaag gatcattatc 60
gaataaatct gatgtggttg tagctggctt ctaggagcat gtgcacgccc gtcactttta 120
tctttccacc tgtgaaccct ctgtagtcct gggataaact ctcgcgcgct tcacggcgtc 180
gcggatgcga aggttgtcgt gcctctggcc ggcttccttt gaatttcctg ggtctacgtc 240
tcttaacaca cccctaacga atgtttaaaa gaatgttgat ttcaaarggc tacggcctat 300
agaaaccaaa tacaactttc agcaacggat ctcttggctc tcgcatcgat gaagaacgca 360
gcgaaatgcg ataagtaatg tgaattgcag aattcagtga atcatcgaat ctttgaacgc 420
accttgcgct ccttggtatt ccgaggagca tgcctgtttg agtgtcatta aattctcaac 480
ctcacccagt ttgtcaaaac caggtgaagg cttggacttg ggggtcttgc aggctgcggg 540
tcaatccgcg gttygctccc ctgaaatgca ttagcgggtc tttcccctcc atcccaacgg 600
tgtgataacc tatctacgcc gccggtgttg gagaccttaa tgggaccagc ttctaaccgt 660
ccgcaaggac aatattgacc aaacttgacc tcaaatcagg taggactacc cgctgaactt 720
aagcatatca ta 732

<210> SEQ ID NO 157
<211> LENGTH: 647
<212> TYPE: DNA
<213> ORGANISM: Amyloathelia crassiuscula

<400> SEQUENCE: 157
tagaggaagt aaaagtcgta acaaggtttc cgtaggtgaa cctgcggaag gatcattatt 60
gaattcttcg ggagggggct gctgctggcc ttctggcatg tgcgcgcccc gacccaaaac 120
ccacatacac ttgtgaactc ttgcagggga gtaggctgcc tgacggyggc cgaggaccct 180
gtcttttaac acacgcctta caactatgaa cgtctttttt tgtctgccct aagaagcagg 240
cttaaacata atacaacttt caacaacgga tctcttggct ctcgcatcga tgaagaacgc 300
agcgaaatgc gataagtaat gtgaattgca gaattcagtg aatcatcgaa tctttgaacg 360
caccttgcgc tccctggtat tccggggagc atgcctgttt gagtgtcatt aaattatcaa 420
cccctctggc ttygttgact gaggtggctt ggacttggag cgtgctggcg cgagccggct 480
cctctctaaa tgcattagcg gaacgtctgt tcgcggctag gtgtgataat tatctacgcc 540
ttcagagccg tgtctgggcc cctgcttcta accgtcctta aggacaacca ctttaatgtg 600
tgacctcaaa tcaggtagga ctacccgctg aacttaagca tatcata 647

<210> SEQ ID NO 158
<211> LENGTH: 467
<212> TYPE: DNA
<213> ORGANISM: Alternaria longissima

<400> SEQUENCE: 158
acctgcggaa ggatcattat caaaagtcaa gtcgggggct gcaaagcctt cgtctacacc 60
ccatgtcttt tgcgtacttc ttgtttcctc ggtggcgcaa gccgccgatt ggacaaacca 120
aaaccttttt tgtaattgca atcagcgtct gaaaataatc taattattta caactttcaa 180
caacggatct cttggttctg gcatcgatga agaacgcagc gaaatgcgat aagtagtgtg 240
aattgcagaa ttcagtgaat catcgaatct ttgaacgcac attgcgcccc ttggtattcc 300
atggggcatg cctgttcgag cgtcatttgt accctcaagc tttgcttggt gttgggcgtc 360
ttgtcgtatt acgactcgcc ttaaatacat tggcagccgg cactttggcc taggagcgcc 420
gcacattttg cgatcgtagc ccgttgtact ggcgtccatc aagaaca 467

<210> SEQ ID NO 159
<211> LENGTH: 600
<212> TYPE: DNA
<213> ORGANISM: Kabatiella microsticta

<400> SEQUENCE: 159
agaggaagta aaagtcgtaa caaggtttcc gtaggtgaac ctgcggaagg atcattaaag 60
agtaagggtg ctcagcgccc gacctccaac cctttgttgt taaaactacc ttgttgcttt 120
ggcgggaccg ctcggtctcg agccgctggg gattcgtccc aggcgagcgc ccgccagagt 180
taaaccaaac tcttgttatt taaccggtcg tctgagttaa aattttgaat aaatcaaaac 240
tttcaacaac ggatctcttg gttctcgcat cgatgaagaa cgcagcgaaa tgcgataagt 300
aatgtgaatt gcagaattca gtgaatcatc gaatctttga acgcacattg cgccccttgg 360
tattccgagg ggcatgcctg ttcgagcgtc attacaccac tcaagctatg cttggtattg 420
ggcgtcgtcc ttagttgggc gcgccttaaa gacctcggcg aggccactcc ggctttaggc 480
gtagtagaat ttattcgaac gtctgtcaaa ggagaggaac tccgccgact gaaaccttta 540
tttttctagg ttgacctcgg atcaggtagg gatacccgct gaacttaagc atatcaatag 600

<210> SEQ ID NO 160
<211> LENGTH: 500
<212> TYPE: DNA
<213> ORGANISM: Fusarium annulatum

<400> SEQUENCE: 160
gctattgata tgcttaagtt cagcgggtat tcctacctga tccgaggtca acattcagaa 60
gttgggggtt taacggcttg gccgcgccgc gtaccagttg cgagggtttt actactacgc 120
aatggaagct gcagcgagac cgccactata tttcggggcc ggcttgccgc gagggctcgc 180
cgatccccaa caccaaaccc gagggcttga gggttgaaat gacgctcgaa caggcatgcc 240
cgccagaata ctggcgggcg caatgtgcgt tcaaagattc gatgattcac tgaattctgc 300
aattcacatt acttatcgca ttttgctgcg ttcttcatcg atgccagaac caagagatcc 360
gttgttgaaa gttttgattt atttatggtt ttactcagaa gttacatata gaaacagagt 420
ttaggggtcc tctggcgggc cgtcccgttt taccgggagc gggctgatcc gccgaggcaa 480
caattggtat gttcacaggg 500

<210> SEQ ID NO 161
<211> LENGTH: 497
<212> TYPE: DNA
<213> ORGANISM: Fusarium nygamai

<400> SEQUENCE: 161
ccctgtgaac ataccaattg ttgcctcggc ggatcagccc gctcccggta aaacggaacg 60
gcccgccaga ggacccctaa actctgtttc tatatgtaac ttctgagtaa aaccataaat 120
aaatcaaaac tttcaacaac ggatctcttg gttctggcat cgatgaagaa cgcagcaaaa 180
tgcgataagt aatgtgaatt gcagaattca gtgaatcatc gaatctttga acgcacattg 240
cgcccgccag tattctggcg ggcatgcctg ttcgagcgtc atttcaaccc tcaagccccc 300
gggtttggtg ttggggatcg gcgagcctca cggcaagccg gccccgaaat acagtggcgg 360
tctcgctgca gcttccattg cgtagtagta aaaccctcgc aactggtacg cggcgcggcc 420
aagccgttaa acccccaact tctgaatgtt gacctcggat caggtaggaa tacccgctga 480
acttaagcat atcaata 497

<210> SEQ ID NO 162
<211> LENGTH: 497
<212> TYPE: DNA
<213> ORGANISM: Fusarium nygamai

<400> SEQUENCE: 162
ccctgtgaac ataccaattg ttgcctcggc ggatcagccc gctcccggta aaacggaacg 60
gcccgccaga ggacccctaa actctgtttc tatatgtaac ttctgagtaa aaccataaat 120
aaatcaaaac tttcaacaac ggatctcttg gttctggcat cgatgaagaa cgcagcaaaa 180
tgcgataagt aatgtgaatt gcagaattca gtgaatcatc gaatctttga acgcacattg 240
cgcccgccag tattctggcg ggcatgcctg ttcgagcgtc atttcaaccc tcaagccccc 300
gggtttggtg ttggggatcg gcgagcctca cggcaagccg gccccgaaat acagtggcgg 360
tctcgctgca gcttccattg cgtagtagta aaaccctcgc aactggtacg cggcgcggcc 420
aagccgttaa acccccaact tctgaatgtt gacctcggat caggtaggaa tacccgctga 480
acttaagcat atcaata 497

<210> SEQ ID NO 163
<211> LENGTH: 527
<212> TYPE: DNA
<213> ORGANISM: Alternaria mali

<400> SEQUENCE: 163
tagaggaagt aaaagtcgta acaaggtctc cgtaggtgaa cctgcggagg gatcattaca 60
caaatatgaa ggcgggctgg aacctctcgg ggttacagcc ttgctgaatt attcaccctt 120
gtcttttgcg tacttcttgt ttccttggtg ggttcgccca ccactaggac aaacataaac 180
cttttgtaat tgcaatcagc gtcagtaaca aattaataat tacaactttc aacaacggat 240
ctcttggttc tggcatcgat gaagaacgca gcgaaatgcg ataagtagtg tgaattgcag 300
aattcagtga atcatcgaat ctttgaacgc acattgcgcc ctttggtatt ccaaagggca 360
tgcctgttcg agcgtcattt gtaccctcaa gctttgcttg gtgttgggcg tcttgtctct 420
agctttgctg gagactcgcc ttaaagtaat tggcagccgg cctactggtt tcggagcgca 480
gcacaagtcg cactctctat cagcaaaggt ctagcatcca ttaagcc 527

<210> SEQ ID NO 164
<211> LENGTH: 610
<212> TYPE: DNA
<213> ORGANISM: Fusarium moniliformae

<400> SEQUENCE: 164
tcttggtcaa tttagaggaa gtaaaagtcg taacaaggtc tccgttggtg aaccagcgga 60
gggatcattg ctggaacgcg ccccaggcgc acccagaaac cctttgtgaa cttatacctt 120
actgttgcct cggcgcacgc cggcccccag gggcccctcg gagacgagga gcaggcacgc 180
cggcggccaa gttaactctt gtttttacac tgaaactctg agaaaaaaaa acaaaatgaa 240
tcaaaacttt caacaacgga tctcttggtt ctggcatcga tgaagaacgc agcgaaatgc 300
gataagtaat gtgaattgca gaattcagtg aatcatcgaa tctttgaacg cacattgcgc 360
cctccggtat tccggagggc atgcctgttc gagcgtcatt tcaaccctca agcactgctt 420
ggtgttgggg cactgccttt ttccggaagg caggccctga aattcagtgg cgagctcgcc 480
aggaccccga gcgcagtagt taaaccctcg ctttggaagg ccctggcggt gccctgccgt 540 taaacccccca actcttgaaa atttgacctc ggatcaggta ggaatacccg ctgaacttaa 600
gcatatcaaa 610

<210> SEQ ID NO 165
<211> LENGTH: 573
<212> TYPE: DNA
<213> ORGANISM: Periconia macrospinosa

<400> SEQUENCE: 165
tgatatgctt aagttcagcg ggtatcccta cctgatccga ggtcaagtcg tgaaaggtct 60
tgctggagcg cggatccgcc gggcctccga gaagcgcaaa tgtgctgcgc gagggggccg 120
gcacgaccgc cgccaatgac tttgaggcga gtccgcgcgc gagaacggcg ggacagacgc 180
ccaacaccaa gctaggcttg agggtgtaaa tgacgctcga acaggcatgg ccaaaggaat 240
acctatggcc gcaatgtgcg ttcaaagatt cgatgattca ctgaattctg caattcacac 300
tacttatcgc atttcgctgc gttcttcatc gatgccagaa ccaagagatc cattgttgaa 360
agttgtgata atttaggttt gttatcagaa gttttcgcgt ataatgcaag ggtttcgtg 420 ggttcctggc ggcgggcgag cccgccgagg aagctataga ggtacacgta ggcagagggt 480
gggtgtataa ggagcgccga agcgccccga atgtgtaatg atccttccgc aggttcacct 540
acggaaacct tgttacgact tttacttcct cta 573

<210> SEQ ID NO 166
<211> LENGTH: 565
<212> TYPE: DNA
<213> ORGANISM: Uncultured soil fungus

<400> SEQUENCE: 166
gtaaaagtcg taacaaggtc tccgttggtg aaccagcgga gggatcatta ccgagtttac 60
aactcccaaa cccctgtgaa cataccttac tgttgcctcg gcggatcagc ccgcgcccgg 120
taaaacgggg cggcccgcca gaggacccct aaactctgtt tttattgtaa cttctgagta 180
aaaccataaa taaatcaaaa ctttcaacaa cggatctctt ggttctggca tcgatgaaga 240
acgcagcaaa atgcgataag taatgtgaat tgcagaattc agtgaatcat cgaatctttg 300
aacgcacatt gcgcccgcca gtattctggc gggcatgcct gttcgagcgt catttcaacc 360
ctcaagccct cgggtttggt gttggggatc ggcgagcctt tctggcaagc cggccccgaa 420
atctagtggc ggtctcactg cagcctccat tgcgtagtag ctaacacctc gcaactggaa 480
cgcggtgcgg ccaagccgtt aaacccccca acttctgaat gttgacctcg gatcaggtag 540
gaatacccgc tgaacttaag catat 565

<210> SEQ ID NO 167
<211> LENGTH: 584
<212> TYPE: DNA
<213> ORGANISM: Gaeumannomyces incrustans

<400> SEQUENCE: 167
agaggaagta aaagtcgtaa caaggtctcc gttggtgaac cagcggaggg atcattaaag 60
agttgcaaaa ctccaacccc tgtgaacttt acctgtacgt tgcttcggcg gccgacgccg 120
cgcccagccg ggcctggggg acgccgccgg aggttttaaa ccctgaattc tagtgtatct 180

-continued ctgaggacga aaaaaaccaa ttaaaacttt caacaacgga tctcttggct ctggcatcga 240
tgaagaacgc agcgaaatgc gataagtaat gtgaattgca gaattcagtg aatcatcgaa 300
tctttgaacg cacattgcgc ccgccggtat tccggcgggc atgcctgtcc gagcgtcatt 360
tcaccactca agcccagctt ggtgttgggg cacccggccg cccggcggtc ggggccccca 420
agtacatcgg cggtcccgct ggggctccga gcgcagtaac tcgcggtaaa acgcgccctc 480
gctcggcggc ctcctcgggc ttccagccgc taaaccccca gtgacgtttt tcgagttgac 540
ctcggatcag gtaggaatac ccgctgaact taagcatatc aata 584

<210> SEQ ID NO 168
<211> LENGTH: 485
<212> TYPE: DNA
<213> ORGANISM: Fusarium nygamai

<400> SEQUENCE: 168
caattgttgc ctcggcggat cagcccgctc ccggtaaaac ggaacggccc gccagaggac 60
ccctaaactc tgtttctata tgtaacttct gagtaaaacc ataaataaat caaaactttc 120
aacaacggat ctcttggttc tggcatcgat gaagaacgca gcaaaatgcg ataagtaatg 180
tgaattgcag aattcagtga atcatcgaat ctttgaacgc acattgcgcc cgccagtatt 240
ctggcgggca tgcctgttcg agcgtcattt caaccctcaa gcccccgggt ttggtgttgg 300
ggatcggcga gcctcacggc aagccggccc cgaaatacag tggcggtctc gctgcagctt 360
ccattgcgta gtagtaaaac cctcgcaact ggtacgcggc gcggccaagc cgttaaaccc 420
ccaacttctg aatgttgacc tcggatcagg taggaatacc cgctgaactt aagcatatca 480
atagg 485

<210> SEQ ID NO 169
<211> LENGTH: 650
<212> TYPE: DNA
<213> ORGANISM: Eutypella sp.

<400> SEQUENCE: 169
ggaagtaaaa gtcgtaacaa ggtctccgtt ggtgaaccag cggagggatc attaatgagt 60
tttctaaact ccaaacccct gagaacttac ctagttgcct cggcgggctc gccctgggac 120
gacctaccct gcagcgcgtt accctgcaac tcgctaccct gtagcgagtt gccctgtaac 180
aacttgccct gtaggtgctg gccctgtagc ctgcccgccg gcggccaacc tgaactctgt 240
tttattgtgg cacttctgag gaccattcta aatgaattaa aactttcaac aacggatctc 300
ttggttctgg catcgatgaa gaacgcagcg aaatgcgata agtaatgtga attgcagaat 360
tcagtgaatc atcgaatctt tgaacgcaca ttgcgcccac tagtattctg gtgggcatgc 420
ctgttcgagc gtcatttcaa ctatcaagcc ctatttgctt ggcgttggga gacttgtagg 480
ccccgcctac aagctcccca aatggatcgg cggagtcgtg gcgaccctca gcgtagtaat 540
tcttctcgct ctaggtgtcg gcgccggcgt ctggccgtta aaccccctat ttttttagt 600 cttgacctcg gatcaggtag gaatacccgc tgaacttaag catatcaata 650

<210> SEQ ID NO 170
<211> LENGTH: 573
<212> TYPE: DNA
<213> ORGANISM: Periconia macrospinosa

<400> SEQUENCE: 170
tgatatgctt aagttcagcg ggtatcccta cctgatccga ggtcaagtcg tgaaaggtct 60

```
tgctggagcg cggatccgcc gggcctccga gaagcgcaaa tgtgctgcgc gagggggccg    120
gcacgaccgc cgccaatgac tttgaggcga gtccgcgcgc gagaacggcg ggacagacgc    180
ccaacaccaa gctaggcttg agggtgtaaa tgacgctcga acaggcatgg ccaaaggaat    240
acctatggcc gcaatgtgcg ttcaaagatt cgatgattca ctgaattctg caattcacac    300
tacttatcgc atttcgctgc gttcttcatc gatgccagaa ccaagagatc cattgttgaa    360
agttgtgata atttaggttt gttatcagaa gttttcgcgt ataatgcaag ggtttcgtg     420
ggttcctggc ggcgggcgag cccgccgagg aagctataga ggtacacgta ggcagagggt    480
gggtgtataa ggagcgccga agcgccccga atgtgtaatg atccttccgc aggttcacct    540
acggaaacct tgttacgact tttacttcct cta                                  573
```

<210> SEQ ID NO 171
<211> LENGTH: 499
<212> TYPE: DNA
<213> ORGANISM: Fusarium nygamai

<400> SEQUENCE: 171

```
ccctgtgaac ataccaattg ttgcctcggc ggatcagccc gctcccggta aaacggaacg     60
gcccgccaga ggacccctaa actctgtttc tatatgtaac ttctgagtaa aaccataaat    120
aaatcaaaac tttcaacaac ggatctcttg gttctggcat cgatgaagaa cgcagcaaaa    180
tgcgataagt aatgtgaatt gcagaattca gtgaatcatc gaatctttga acgcacattg    240
cgcccgccag tattctggcg ggcatgcctg ttcgagcgtc atttcaaccc tcaagccccc    300
gggtttggtg ttggggatcg gcgagcctca cggcaagccg gccccgaaat acagtggcgg    360
tctcgctgca gcttccattg cgtagtagta aaaccctcgc aactggtacg cggcgcggcc    420
aagccgttaa acccccaact tctgaatgtt gacctcggat caggtaggaa tacccgctga    480
acttaagcat atcaatagg                                                  499
```

<210> SEQ ID NO 172
<211> LENGTH: 499
<212> TYPE: DNA
<213> ORGANISM: Fusarium nygamai

<400> SEQUENCE: 172

```
ccctgtgaac ataccaattg ttgcctcggc ggatcagccc gctcccggta aaacggaacg     60
gcccgccaga ggacccctaa actctgtttc tatatgtaac ttctgagtaa aaccataaat    120
aaatcaaaac tttcaacaac ggatctcttg gttctggcat cgatgaagaa cgcagcaaaa    180
tgcgataagt aatgtgaatt gcagaattca gtgaatcatc gaatctttga acgcacattg    240
cgcccgccag tattctggcg ggcatgcctg ttcgagcgtc atttcaaccc tcaagccccc    300
gggtttggtg ttggggatcg gcgagcctca cggcaagccg gccccgaaat acagtggcgg    360
tctcgctgca gcttccattg cgtagtagta aaaccctcgc aactggtacg cggcgcggcc    420
aagccgttaa acccccaact tctgaatgtt gacctcggat caggtaggaa tacccgctga    480
acttaagcat atcaatagc                                                  499
```

<210> SEQ ID NO 173
<211> LENGTH: 473
<212> TYPE: DNA
<213> ORGANISM: Fusarium sp.

<400> SEQUENCE: 173

-continued

```
aagttcagcg ggtattccta cctgatccga ggtcaacatt cagaagttgg ggttttacgg      60

cgtggccgcg acgattacca gtaacgaggt gtatgattac tacgctatgg aagctcgacg     120

tgaccgccaa tcgatttggg gaacgcgggt taccgcgagt cccaacacca agctgagctt     180

gagggttgaa atgacgctcg aacaggcatg cccgccagaa tactggcggg cgcaatgtgc     240

gttcaaagat tcgatgattc actgaattct gcaattcaca ttacttatcg cattttgctg     300

cgttcttcat cgatgccaga accaagagat ccgttgttga aagttttgat ttatttgttt     360

gttttactca gaagttccac taaaaacaga gtttaggggt cctcgggcgg gccgtccctt     420

tttacggggc gcgggctgat ccgccgaggc aacgtatagg tatgttcaca ggg            473
```

```
<210> SEQ ID NO 174
<211> LENGTH: 836
<212> TYPE: DNA
<213> ORGANISM: Fungal endophyte

<400> SEQUENCE: 174

tttgctaagc aacagtcctt ctgtagcaga gcttaacgga gaccttgcac ccgagagggg      60

ggaggcgact ataaacaagc ttctagcgca agtcagcact cgctggcaac acaatcgaat     120

tgcggggacg ctttaaagcc taccagtacc aacagccccg gccggggctg ggcgagcgca     180

gctcgaggtc acaatctggg aggatgccac aataagcaat ccgcagcggc tctggccgtc     240

cacagactaa gtggttgtgg gtaggagaac cctatctaag atatagtcgg gcccgaggag     300

agatcctcgg ggcttctgcg tccgtaggtg aacctgcgga aggatcatta aaaaaggata     360

ccgggcaacc ggtagacccc acccgtgtct ctctactctt gttgctttgg caggccgtgg     420

cctccaccgc gggctctgcc tgcgtgtgcc tgccagagga ccaaactctg aattttagtg     480

atgtctgagt actatataat agttaaaact ttcaacaacg gatctcttgg ttctggcatc     540

gatgaagaac gcagcgaaat gcgataagta atgtgaattg cagaattcag tgaatcatcg     600

aatctttgaa cgcacattgc gcccggtggt attccgccgg gcatgcctgt tcgagcgtca     660

ttataaccac tcaagcctgg cttggtattg ggctcgcgg ttccgcggcc cctaaaatca      720

gtggcggtgc cggtgggctc taagcgtagt aaatctcctc gctatagggt ccctccggtt     780

gcctgccaga acccccccat ttttttagg ttgacctcgg atcaggtagg gatacc          836
```

```
<210> SEQ ID NO 175
<211> LENGTH: 497
<212> TYPE: DNA
<213> ORGANISM: Fusarium nygamai

<400> SEQUENCE: 175

ccctgtgaac ataccaattg ttgcctcggc ggatcagccc gctcccggta aaacggaacg      60

gcccgccaga ggacccctaa actctgtttc tatatgtaac ttctgagtaa aaccataaat     120

aaatcaaaac tttcaacaac ggatctcttg gttctggcat cgatgaagaa cgcagcaaaa     180

tgcgataagt aatgtgaatt gcagaattca gtgaatcatc gaatctttga acgcacattg     240

cgcccgccag tattctggcg ggcatgcctg ttcgagcgtc atttcaaccc tcaagccccc     300

gggtttggtg ttggggatcg gcgagcctca cggcaagccg gccccgaaat acagtggcgg     360

tctcgctgca gcttccattg cgtagtagta aaaccctcgc aactggtacg cggcgcggcc     420

aagccgttaa acccccaact tctgaatgtt gacctcggat caggtaggaa tacccgctga     480

acttaagcat atcaata                                                    497
```

<210> SEQ ID NO 176
<211> LENGTH: 527
<212> TYPE: DNA
<213> ORGANISM: Alternaria mali

<400> SEQUENCE: 176
tagaggaagt aaaagtcgta acaaggtctc cgtaggtgaa cctgcggagg gatcattaca 60
caaatatgaa ggcgggctgg aacctctcgg ggttacagcc ttgctgaatt attcaccctt 120
gtcttttgcg tacttcttgt ttccttggtg ggttcgccca ccactaggac aaacataaac 180
cttttgtaat tgcaatcagc gtcagtaaca aattaataat tacaactttc aacaacggat 240
ctcttggttc tggcatcgat gaagaacgca gcgaaatgcg ataagtagtg tgaattgcag 300
aattcagtga atcatcgaat ctttgaacgc acattgcgcc ctttggtatt ccaaagggca 360
tgcctgttcg agcgtcattt gtaccctcaa gctttgcttg gtgttgggcg tcttgtctct 420
agctttgctg gagactcgcc ttaaagtaat tggcagccgg cctactggtt tcggagcgca 480
gcacaagtcg cactctctat cagcaaaggt ctagcatcca ttaagcc 527

<210> SEQ ID NO 177
<211> LENGTH: 497
<212> TYPE: DNA
<213> ORGANISM: Fusarium nygamai

<400> SEQUENCE: 177
ccctgtgaac ataccaattg ttgcctcggc ggatcagccc gctcccggta aaacggaacg 60
gcccgccaga ggacccctaa actctgtttc tatatgtaac ttctgagtaa aaccataaat 120
aaatcaaaac tttcaacaac ggatctcttg gttctggcat cgatgaagaa cgcagcaaaa 180
tgcgataagt aatgtgaatt gcagaattca gtgaatcatc gaatctttga acgcacattg 240
cgcccgccag tattctggcg ggcatgcctg ttcgagcgtc atttcaaccc tcaagccccc 300
gggtttggtg ttggggatcg gcgagcctca cggcaagccg gccccgaaat acagtggcgg 360
tctcgctgca gcttccattg cgtagtagta aaaccctcgc aactggtacg cggcgcggcc 420
aagccgttaa acccccaact tctgaatgtt gacctcggat caggtaggaa tacccgctga 480
acttaagcat atcaata 497

<210> SEQ ID NO 178
<211> LENGTH: 484
<212> TYPE: DNA
<213> ORGANISM: Fusarium nygamai

<400> SEQUENCE: 178
caattgttgc ctcggcggat cagcccgctc ccggtaaaac ggaacggccc gccagaggac 60
ccctaaactc tgtttctata tgtaacttct gagtaaaacc ataaataaat caaaactttc 120
aacaacggat ctcttggttc tggcatcgat gaagaacgca gcaaaatgcg ataagtaatg 180
tgaattgcag aattcagtga atcatcgaat ctttgaacgc acattgcgcc cgccagtatt 240
ctggcgggca tgcctgttcg agcgtcattt caaccctcaa gcccccgggt ttggtgttgg 300
ggatcggcga gcctcacggc aagccggccc cgaaatacag tggcggtctc gctgcagctt 360
ccattgcgta gtagtaaaac cctcgcaact ggtacgcggc gcggccaagc cgttaaaccc 420
ccaacttctg aatgttgacc tcggatcagg taggaatacc cgctgaactt aagcatatca 480
atag 484

<210> SEQ ID NO 179

<211> LENGTH: 577
<212> TYPE: DNA
<213> ORGANISM: Microdochium sp.

<400> SEQUENCE: 179
tagaggaagt aaaagtcgta acaaggtctc cgtaggtgaa cctgcggagg gatcattact 60
gagttttcaa ctctccaaac catgtgaact taccactgtt gcctcggtgg ttagtgctct 120
ccttcggggg agtgctgccg ccggtggact actaaactct tgttaatttt tggcattctg 180
aatcataact aagaaataag ttaaaacttt caacaacgga tctcttggtt ctggcatcga 240
tgaagaacgc agcgaaatgc gataagtaat gtgaattgca gaattcagtg aatcatcgaa 300
tctttgaacg cacattgcgc ccattagtat tctagtgggc atgcctgttc gagcgtcatt 360
tcaaccctta agcctagctt agcgttggga gactgcacta aaccgcagct cctcaaaacc 420
agtggcggag tcctcttgtg ctctgagcgt agtaattcat tatctcgctt ctgtaagtac 480
agtggatcac agccataaac cgcacccttc gggggcactt tttaatggtt gacctcggat 540
caggtaggaa tacccgctga acttaagcat atcaata 577

<210> SEQ ID NO 180
<211> LENGTH: 497
<212> TYPE: DNA
<213> ORGANISM: Fusarium nygamai

<400> SEQUENCE: 180
ccctgtgaac ataccaattg ttgcctcggc ggatcagccc gctcccggta aaacggaacg 60
gcccgccaga ggacccctaa actctgtttc tatatgtaac ttctgagtaa aaccataaat 120
aaatcaaaac tttcaacaac ggatctcttg gttctggcat cgatgaagaa cgcagcaaaa 180
tgcgataagt aatgtgaatt gcagaattca gtgaatcatc gaatctttga acgcacattg 240
cgcccgccag tattctggcg ggcatgcctg ttcgagcgtc atttcaaccc tcaagccccc 300
gggtttggtg ttggggatcg gcgagcctca cggcaagccg gccccgaaat acagtggcgg 360
tctcgctgca gcttccattg cgtagtagta aaaccctcgc aactggtacg cggcgcggcc 420
aagccgttaa acccccaact tctgaatgtt gacctcggat caggtaggaa tacccgctga 480
acttaagcat atcaata 497

<210> SEQ ID NO 181
<211> LENGTH: 498
<212> TYPE: DNA
<213> ORGANISM: Fusarium nygamai

<400> SEQUENCE: 181
ccctgtgaac ataccaattg ttgcctcggc ggatcagccc gctcccggta aaacggaacg 60
gcccgccaga ggacccctaa actctgtttc tatatgtaac ttctgagtaa aaccataaat 120
aaatcaaaac tttcaacaac ggatctcttg gttctggcat cgatgaagaa cgcagcaaaa 180
tgcgataagt aatgtgaatt gcagaattca gtgaatcatc gaatctttga acgcacattg 240
cgcccgccag tattctggcg ggcatgcctg ttcgagcgtc atttcaaccc tcaagccccc 300
gggtttggtg ttggggatcg gcgagcctca cggcaagccg gccccgaaat acagtggcgg 360
tctcgctgca gcttccattg cgtagtagta aaaccctcgc aactggtacg cggcgcggcc 420
aagccgttaa acccccaact tctgaatgtt gacctcggat caggtaggaa tacccgctga 480
acttaagcat atcaatag 498

<210> SEQ ID NO 182
<211> LENGTH: 498
<212> TYPE: DNA
<213> ORGANISM: Fusarium nygamai

<400> SEQUENCE: 182
ccctgtgaac ataccaattg ttgcctcggc ggatcagccc gctcccggta aaacggaacg 60
gcccgccaga ggacccctaa actctgtttc tatatgtaac ttctgagtaa aaccataaat 120
aaatcaaaac tttcaacaac ggatctcttg gttctggcat cgatgaagaa cgcagcaaaa 180
tgcgataagt aatgtgaatt gcagaattca gtgaatcatc gaatctttga acgcacattg 240
cgcccgccag tattctggcg ggcatgcctg ttcgagcgtc atttcaaccc tcaagccccc 300
gggtttggtg ttggggatcg gcgagcctca cggcaagccg gccccgaaat acagtggcgg 360
tctcgctgca gcttccattg cgtagtagta aaaccctcgc aactggtacg cggcgcggcc 420
aagccgttaa acccccaact tctgaatgtt gacctcggat caggtaggaa tacccgctga 480
acttaagcat atcaatag 498

<210> SEQ ID NO 183
<211> LENGTH: 573
<212> TYPE: DNA
<213> ORGANISM: Periconia macrospinosa

<400> SEQUENCE: 183
tgatatgctt aagttcagcg ggtatcccta cctgatccga ggtcaagtcg tgaaaggtct 60
tgctggagcg cggatccgcc gggcctccga gaagcgcaaa tgtgctgcgc gagggggccg 120
gcacgaccgc cgccaatgac tttgaggcga gtccgcgcgc gagaacggcg ggacagacgc 180
ccaacaccaa gctaggcttg agggtgtaaa tgacgctcga acaggcatgg ccaaaggaat 240
acctatggcc gcaatgtgcg ttcaaagatt cgatgattca ctgaattctg caattcacac 300
tacttatcgc atttcgctgc gttcttcatc gatgccagaa ccaagagatc cattgttgaa 360
agttgtgata atttaggttt gttatcagaa gttttcgcgt ataatgcaag ggtttcgtg 420 ggttcctggc ggcgggcgag cccgccgagg aagctataga ggtacacgta ggcagagggt 480
gggtgtataa ggagcgccga agcgccccga atgtgtaatg atccttccgc aggttcacct 540
acggaaacct tgttacgact tttacttcct cta 573

<210> SEQ ID NO 184
<211> LENGTH: 517
<212> TYPE: DNA
<213> ORGANISM: Uncultured Ascomycete sp.

<400> SEQUENCE: 184
ggtatcccta cctgatccga ggtcaaacgt ggtaaatgtt cttgatggac gccagtacaa 60
cgggctacga tcgcaaaatg tgcggcgctc ctaggccaaa gtgccggctg ccaatgaatt 120
taaggcgagt cgtaatacga caagacgccc aacaccaagc aaagcttgag ggtacaaatg 180
acgctcgaac aggcatgccc catggaatac caaggggcgc aatgtgcgtt caaagattcg 240
atgattcact gaattctgca attcacacta cttatcgcat ttcgctgcgt tcttcatcga 300
tgccagaacc aagagatccg ttgttgaaag ttgtaaataa ttagattatt ttcagacgct 360
gattgcaatt acaaaaaagg ttttggtttg tccaatcggc agcttgcgcc accgaggaaa 420
caagaagtac gcaaaagaca tggggtgtag acgagagctt tacagccccc gacttgactt 480
ttgataatga tccttccgca ggttcaccta cggaaac 517

<210> SEQ ID NO 185
<211> LENGTH: 517
<212> TYPE: DNA
<213> ORGANISM: Uncultured Ascomycete sp.

<400> SEQUENCE: 185
ggtatcccta cctgatccga ggtcaaacgt ggtaaatgtt cttgatggac gccagtacaa 60
cgggctacga tcgcaaaatg tgcggcgctc ctaggccaaa gtgccggctg ccaatgaatt 120
taaggcgagt cgtaatacga caagacgccc aacaccaagc aaagcttgag ggtacaaatg 180
acgctcgaac aggcatgccc catggaatac caaggggcgc aatgtgcgtt caaagattcg 240
atgattcact gaattctgca attcacacta cttatcgcat ttcgctgcgt tcttcatcga 300
tgccagaacc aagagatccg ttgttgaaag ttgtaaataa ttagattatt ttcagacgct 360
gattgcaatt acaaaaaagg ttttggtttg tccaatcggc agcttgcgcc accgaggaaa 420
caagaagtac gcaaaagaca tggggtgtag acgagagctt tacagccccc gacttgactt 480
ttgataatga tccttccgca ggttcaccta cggaaac 517

<210> SEQ ID NO 186
<211> LENGTH: 617
<212> TYPE: DNA
<213> ORGANISM: Uncultured Ascomycete sp.

<400> SEQUENCE: 186
tattgatatg cttaagttca gcgggtatcc ctacctgatc cgaggtcaac ctgtaaaaat 60
tgggggttgc tggcaagtaa acctaccgga ctcaatcgcg aggagtatta ctacgcgtag 120
agccgacagg caccgccact gattttaggg gccgcgaaac cgcgaacccc aataccaagc 180
gagagcttga gtggttataa tgacgctcga acaggcatgc cccccggaat accagagggc 240
gcaatgtgcg ttcaaagatt cgatgattca ctgaattctg caattcacat tacttatcgc 300
atttcgctgc gttcttcatc gatgccagaa ccaagagatc cgttgttgaa agttttaact 360
attatatagt actcagacat cactaaaaac aagagttgtg gtcctctggc gggcactcaa 420
cagccgaagc cgctggcgcg aggcggcccg ccaaagcaac aaaggtaatt tattcaaggg 480
tggagttcag gaccgagctt cttcgagagg cccgacgaca accctaccga agcagggctg 540
tctatccttt gctctagtaa tgatccttcc gcaggttcac ctacggaaac cttgttacga 600
cttttacttc ctctaat 617

<210> SEQ ID NO 187
<211> LENGTH: 567
<212> TYPE: DNA
<213> ORGANISM: Uncultured Ascomycete sp.

<400> SEQUENCE: 187
tagaggaagt aaaagtcgta acaaggtttc cgtaggtgaa cctgcggaag gatcattatc 60
aaaagtcaag tcgggggctg taaagctctc gtctacaccc catgtctttt gcgtactctt 120
gtttcctcgg tggcgcaagc tgccgattgg acaaaccaaa accttttttg taattgcaat 180
cagcgtctga aaataatcta attatttaca actttcaaca acggatctct tggttctggc 240
atcgatgaag aacgcagcga aatgcgataa gtagtgtgaa ttgcagaatt cagtgaatca 300
tcgaatcttt gaacgcacat tgcgcccctt ggtattccat ggggcatgcc tgttcgagcg 360
tcatttgtac cctcaagctt tgcttggtgt tgggcgtctt gtcgtattac gactcgcctt 420
aaattcattg gcagccggca ctttggccta ggagcgcagc acattttgcg atcgtagccc 480
gttgtactgg cgtccatcaa gaacatttac cacgtttgac ctcggatcag gtagggatac 540
ccgctgaact taagcatatc ataggcc 567

<210> SEQ ID NO 188
<211> LENGTH: 497
<212> TYPE: DNA
<213> ORGANISM: Fusarium nygamai

<400> SEQUENCE: 188
ccctgtgaac ataccaattg ttgcctcggc ggatcagccc gctcccggta aaacggaacg 60
gcccgccaga ggacccctaa actctgtttc tatatgtaac ttctgagtaa aaccataaat 120
aaatcaaaac tttcaacaac ggatctcttg gttctggcat cgatgaagaa cgcagcaaaa 180
tgcgataagt aatgtgaatt gcagaattca gtgaatcatc gaatctttga acgcacattg 240
cgcccgccag tattctggcg ggcatgcctg ttcgagcgtc atttcaaccc tcaagccccc 300
gggtttggtg ttggggatcg gcgagcctca cggcaagccg gccccgaaat acagtggcgg 360
tctcgctgca gcttccattg cgtagtagta aaaccctcgc aactggtacg cggcgcggcc 420
aagccgttaa acccccaact tctgaatgtt gacctcggat caggtaggaa tacccgctga 480
acttaagcat atcaaag 497

<210> SEQ ID NO 189
<211> LENGTH: 483
<212> TYPE: DNA
<213> ORGANISM: Fusarium nygamai

<400> SEQUENCE: 189
caattgttgc ctcggcggat cagcccgctc ccggtaaaac ggaacggccc gccagaggac 60
ccctaaactc tgtttctata tgtaacttct gagtaaaacc ataaataaat caaaactttc 120
aacaacggat ctcttggttc tggcatcgat gaagaacgca gcaaaatgcg ataagtaatg 180
tgaattgcag aattcagtga atcatcgaat ctttgaacgc acattgcgcc cgccagtatt 240
ctggcgggca tgcctgttcg agcgtcattt caaccctcaa gcccccgggt ttggtgttgg 300
ggatcggcga gcctcacggc aagccggccc cgaaatacag tggcggtctc gctgcagctt 360
ccattgcgta gtagtaaaac cctcgcaact ggtacgcggc gcggccaagc cgttaaaccc 420
ccaacttctg aatgttgacc tcggatcagg taggaatacc cgctgaactt aagcatatca 480
ata 483

<210> SEQ ID NO 190
<211> LENGTH: 482
<212> TYPE: DNA
<213> ORGANISM: Fusarium sp.

<400> SEQUENCE: 190
gatatgctta agttcagcgg gtattcctac ctgatccgag gtcaacattc agaagttggg 60
gttttacggc gtggccgcga cgattaccag taacgaggtg tatgattact acgctatgga 120
agctcgacgt gaccgccaat cgatttgggg aacgcgggtt accgcgagtc ccaacaccaa 180
gctgagcttg agggttgaaa tgacgctcga acaggcatgc ccgccagaat actggcgggc 240
gcaatgtgcg ttcaaagatt cgatgattca ctgaattctg caattcacat tacttatcgc 300
attttgctgc gttcttcatc gatgccagaa ccaagagatc cgttgttgaa agttttgatt 360
tatttgtttg ttttactcag aagttccact aaaaacagag tttaggggtc ctcgggcggg 420

-continued

```
ccgtcccttt ttacggggcg cgggctgatc cgccgaggca acgtataggt atgttcacag    480

gg                                                                   482


<210> SEQ ID NO 191
<211> LENGTH: 572
<212> TYPE: DNA
<213> ORGANISM: Fusarium nygamai

<400> SEQUENCE: 191

gaagtaaaag tcgtaacaag gtctccgttg gtgaaccagc ggagggatca ttaccgagtt     60

tacaactccc aaacccctgt gaacatacca attgttgcct cggcggatca gcccgctccc    120

ggtaaaacgg aacggcccgc cagaggaccc ctaaactctg tttctatatg taacttctga    180

gtaaaaccat aaataaatca aaactttcaa caacggatct cttggttctg gcatcgatga    240

agaacgcagc aaaatgcgat aagtaatgtg aattgcagaa ttcagtgaat catcgaatct    300

ttgaacgcac attgcgcccg ccagtattct ggcgggcatg cctgttcgag cgtcatttca    360

accctcaagc ccccgggttt ggtgttgggg atcggcgagc ctcacggcaa gccggccccg    420

aaatacagtg gcggtctcgc tgcagcttcc attgcgtagt agtaaaaccc tcgcaactgg    480

tacgcggcgc ggccaagccg ttaaaccccc aacttctgaa tgttgacctc ggatcaggta    540

ggaatacccg ctgaacttaa gcatatcaat ag                                  572


<210> SEQ ID NO 192
<211> LENGTH: 498
<212> TYPE: DNA
<213> ORGANISM: Fusarium nygamai

<400> SEQUENCE: 192

ccctgtgaac ataccaattg ttgcctcggc ggatcagccc gctcccggta aaacggaacg     60

gcccgccaga ggacccctaa actctgtttc tatatgtaac ttctgagtaa aaccataaat    120

aaatcaaaac tttcaacaac ggatctcttg gttctggcat cgatgaagaa cgcagcaaaa    180

tgcgataagt aatgtgaatt gcagaattca gtgaatcatc gaatctttga acgcacattg    240

cgcccgccag tattctggcg ggcatgcctg ttcgagcgtc atttcaaccc tcaagccccc    300

gggtttggtg ttggggatcg gcgagcctca cggcaagccg gccccgaaat acagtggcgg    360

tctcgctgca gcttccattg cgtagtagta aaaccctcgc aactggtacg cggcgcggcc    420

aagccgttaa acccccaact tctgaatgtt gacctcggat caggtaggaa tacccgctga    480

acttaagcat atcaatag                                                  498


<210> SEQ ID NO 193
<211> LENGTH: 493
<212> TYPE: DNA
<213> ORGANISM: Fusarium nygamai

<400> SEQUENCE: 193

ccctgtgaac ataccaattg ttgcctcggc ggatcagccc gctcccggta aaacggaacg     60

gcccgccaga ggacccctaa actctgtttc tatatgtaac ttctgagtaa aaccataaat    120

aaatcaaaac tttcaacaac ggatctcttg gttctggcat cgatgaagaa cgcagcaaaa    180

tgcgataagt aatgtgaatt gcagaattca gtgaatcatc gaatctttga acgcacattg    240

cgcccgccag tattctggcg ggcatgcctg ttcgagcgtc atttcaaccc tcaagccccc    300

gggtttggtg ttggggatcg gcgagcctca cggcaagccg gccccgaaat acagtggcgg    360

tctcgctgca gcttccattg cgtagtagta aaaccctcgc aactggtacg cggcgcggcc    420
```

aagccgttaa acccccaact tctgaatgtt gacctcggat caggtaggaa tacccgctga 480
acttaagcat atc 493

<210> SEQ ID NO 194
<211> LENGTH: 584
<212> TYPE: DNA
<213> ORGANISM: Gaeumannomyces incrustans

<400> SEQUENCE: 194
agaggaagta aaagtcgtaa caaggtctcc gttggtgaac cagcggaggg atcattaaag 60
agttgcaaaa ctccaacccc tgtgaacttt acctgtacgt tgcttcggcg gccgacgccg 120
cgcccagccg ggcctggggg acgccgccgg aggttttaaa ccctgaattc tagtgtatct 180
ctgaggacga aaagaaccaa ttaaaacttt caacaacgga tctcttggct ctggcatcga 240
tgaagaacgc agcgaaatgc gataagtaat gtgaattgca gaattcagtg aatcatcgaa 300
tctttgaacg cacattgcgc ccgccggtat tccggcgggc atgcctgtcc gagcgtcatt 360
tcaccactca agcccagctt ggtgttgggg cacccggccg cccggcggtc ggggccccca 420
agtacatcgg cggtcctgct ggggctccga gcgcagtaac acgcggtaaa acgcgccctc 480
gctcggcggc ctcctcgggc ttccagccgc taaaccccca gtgacgtttt tcgagttgac 540
ctcggatcag gtaggaatac ccgctgaact taagcatatc aata 584

<210> SEQ ID NO 195
<211> LENGTH: 573
<212> TYPE: DNA
<213> ORGANISM: Periconia macrospinosa

<400> SEQUENCE: 195
tgatatgctt aagttcagcg ggtatcccta cctgatccga ggtcaagtcg tgaaaggtct 60
tgctggagcg cggatccgcc gggcctccga gaagcgcaaa tgtgctgcgc gagggggccg 120
gcacgaccgc cgccaatgac tttgaggcga gtccgcgcgc gagaacggcg ggacagacgc 180
ccaacaccaa gctaggcttg agggtgtaaa tgacgctcga acaggcatgg ccaaaggaat 240
acctatggcc gcaatgtgcg ttcaaagatt cgatgattca ctgaattctg caattcacac 300
tacttatcgc atttcgctgc gttcttcatc gatgccagaa ccaagagatc cattgttgaa 360
agttgtgata atttaggttt gttatcagaa gttttcgcgt ataatgcaag ggtttcgtg 420 ggttcctggc ggcgggcgag cccgccgagg aagctataga ggtacacgta ggcagagggt 480
gggtgtataa ggagcgccga agcgccccga atgtgtaatg atccttccgc aggttcacct 540
acggaaacct tgttacgact tttacttcct cta 573

<210> SEQ ID NO 196
<211> LENGTH: 569
<212> TYPE: DNA
<213> ORGANISM: Microdochium sp.

<400> SEQUENCE: 196
tagaggaagt aaaagtcgta acaaggtctc cgtaggtgaa cctgcggagg gatcattact 60
gagttttcaa ctctccaaac catgtgaact taccactgtt gcctcggtgg ttagtgctct 120
ccctcggggg ggtgctgccg ccggtggact actaaactct tgttaattta tggcattctg 180
aatcataact aagaaataag ttaaaacttt caacaacgga tctcttggtt ctggcatcga 240
tgaagaacgc agcgaaatgc gataagtaat gtgaattgca gaattcagtg aatcatcgaa 300

```
tctttgaacg cacattgcgc ccattagtat tctagtgggc atgcctgttc gagcgtcatt    360

tcaaccctta agcctagctt agcgttggga gactgcgcta aaccgcagct cctcaaaacc    420

agtggcggag tcctctcgtg ctctgagcgt agtaattctt tatctcgctt ctgcaagtac    480

ggttgacgac agccataaac cgcaccctct cggggggcac tttttaatgg ttgacctcgg    540

atcaggtagg aatacccgct gaacttaag                                      569


<210> SEQ ID NO 197
<211> LENGTH: 573
<212> TYPE: DNA
<213> ORGANISM: Periconia macrospinosa

<400> SEQUENCE: 197

tgatatgctt aagttcagcg ggtatcccta cctgatccga ggtcaagtcg tgaaaggtct     60

tgctggagcg cggatccgcc gggcctccga gaagcgcaaa tgtgctgcgc gagggggccg    120

gcacgaccgc cgccaatgac tttgaggcga gtccgcgcgc gagaacggcg ggacagacgc    180

ccaacaccaa gctaggcttg agggtgtaaa tgacgctcga acaggcatgg ccaaaggaat    240

acctatggcc gcaatgtgcg ttcaaagatt cgatgattca ctgaattctg caattcacac    300

tacttatcgc atttcgctgc gttcttcatc gatgccagaa ccaagagatc cattgttgaa    360

agttgtgata atttaggttt gttatcagaa gttttcgcgt ataatgcaag ggtttcgtg     420

ggttcctggc ggcgggcgag cccgccgagg aagctataga ggtacacgta ggcagagggt    480

gggtgtataa ggagcgccga agcgccccga atgtgtaatg atccttccgc aggttcacct    540

acggaaacct tgttacgact tttacttcct cta                                 573


<210> SEQ ID NO 198
<211> LENGTH: 589
<212> TYPE: DNA
<213> ORGANISM: Anthostomella brabeji

<400> SEQUENCE: 198

ttagaggaag taaaagtcgt aacaaggtct ccgttggtga accagcggag ggatcattaa     60

agagttaatt acaactccaa acccatgtga acatacctct tgttgcctcg gcaggtcgtg    120

tctaccctgt agtccctacc cgggaagcac ctacctggta tatacggtaa gcctgtcggc    180

ggcccacgaa aactctgttt ttgattttgg aattctgaat actataacta aataagttaa    240

aactttcaac aacggatctc ttggttctgg catcgatgaa gaacgcagcg aaatgcgata    300

agtaatgtga attgcagaat tcagtgaatc atcgaatctt tgaacgcaca ttgcgcccat    360

tagtattcta gtgggcatgc ctgttcgagc gtcatttcaa cccttaagcc cctgttgctt    420

agcgttggga gcctacagcc ctgctgtaac tcctcaaagt tagtggcgga gttagtttat    480

actctaggcg tagtagatta tttttatctc gcttttgtag ttgttctatc tcccgccgta    540

aaacacccta tatattaaag gttgacctcg gatcaggtag gaatacccg                589


<210> SEQ ID NO 199
<211> LENGTH: 492
<212> TYPE: DNA
<213> ORGANISM: Gaeumannomyces incrustans

<400> SEQUENCE: 199

ccctgtgaac ataccaattg ttgcctcggc ggatcagccc gctcccggta aaacggaacg     60

gcccgccaga ggacccctaa actctgtttc tatatgtaac ttctgagtaa aaccataaat    120

aaatcaaaac tttcaacaac ggatctcttg gttctggcat cgatgaagaa cgcagcaaaa    180
```

```
tgcgataagt aatgtgaatt gcagaattca gtgaatcatc gaatctttga acgcacattg    240

cgcccgccag tattctggcg ggcatgcctg ttcgagcgtc atttcaaccc tcaagccccc    300

gggtttggtg ttggggatcg gcgagcctca cggcaagccg gccccgaaat acagtggcgg    360

tctcgctgca gcttccattg cgtagtagta aaaccctcgc aactggtacg cggcgcggcc    420

aagccgttaa acccccaact tctgaatgtt gacctcggat caggtaggaa tacccgctga    480

acttaagcat at                                                        492
```

<210> SEQ ID NO 200
<211> LENGTH: 586
<212> TYPE: DNA
<213> ORGANISM: Gaeumannomyces incrustans

<400> SEQUENCE: 200

```
agaggaagta aaagtcgtaa caaggtctcc gttggtgaac cagcggaggg atcattaaag     60

agttgcaaaa ctccaacccc tgtgaacttt acctgtacgt tgcttcggcg gccgacgcca    120

cgcccagccg ggcctggggg acgccgccgg aggtctcaaa ccctgaattc tagtgaatct    180

ctgaggatga aaaaaaccaa ttaaaacttt caacaacgga tctcttggct ctggcatcga    240

tgaagaacgc agcgaaatgc gataagtaat gtgaattgca gaattcagtg aatcatcgaa    300

tctttgaacg cacattgcgc ccgccggtat tccggcgggc atgcctgtcc gagcgtcatt    360

tcaccactca agcactgctt ggtgttgggg cacccggccg cctggcggtc ggggccccca    420

agtacatcgg cggtcctgct ggggctccga gcgcagtaac tcgcggtaaa acgcgccctc    480

gctcggcggc ctcttcgggc ttccagccgc taaacccgtc cactgacgtt tttcgagttg    540

acctcggatc aggtaggaat acccgctgaa cttaagcata tcaata                   586
```

<210> SEQ ID NO 201
<211> LENGTH: 573
<212> TYPE: DNA
<213> ORGANISM: Periconia macrospinosa

<400> SEQUENCE: 201

```
tgatatgctt aagttcagcg ggtatcccta cctgatccga ggtcaagtcg tgaaaggtct     60

tgctggagcg cggatccgcc gggcctccga gaagcgcaaa tgtgctgcgc gagggggccg    120

gcacgaccgc cgccaatgac tttgaggcga gtccgcgcgc gagaacggcg ggacagacgc    180

ccaacaccaa gctaggcttg agggtgtaaa tgacgctcga acaggcatgg ccaaaggaat    240

acctatggcc gcaatgtgcg ttcaaagatt cgatgattca ctgaattctg caattcacac    300

tacttatcgc atttcgctgc gttcttcatc gatgccagaa ccaagagatc cattgttgaa    360

agttgtgata atttaggttt gttatcagaa gttttcgcgt ataatgcaag ggtttcgtg    420

ggttcctggc ggcgggcgag cccgccgagg aagctataga ggtacacgta ggcagagggt    480

gggtgtataa ggagcgccga agcgccccga atgtgtaatg atccttccgc aggttcacct    540

acggaaacct tgttacgact tttacttcct cta                                 573
```

<210> SEQ ID NO 202
<211> LENGTH: 498
<212> TYPE: DNA
<213> ORGANISM: Fusarium nygamai

<400> SEQUENCE: 202

```
ccctgtgaac ataccaattg ttgcctcggc ggatcagccc gctcccggta aaacggaacg     60
```

gcccgccaga ggacccctaa actctgtttc tatatgtaac ttctgagtaa aaccataaat 120
aaatcaaaac tttcaacaac ggatctcttg gttctggcat cgatgaagaa cgcagcaaaa 180
tgcgataagt aatgtgaatt gcagaattca gtgaatcatc gaatctttga acgcacattg 240
cgcccgccag tattctggcg ggcatgcctg ttcgagcgtc atttcaaccc tcaagccccc 300
gggtttggtg ttggggatcg gcgagcctca cggcaagccg gccccgaaat acagtggcgg 360
tctcgctgca gcttccattg cgtagtagta aaaccctcgc aactggtacg cggcgcggcc 420
aagccgttaa acccccaact tctgaatgtt gacctcggat caggtaggaa tacccgctga 480
acttaagcat atcaatag 498

<210> SEQ ID NO 203
<211> LENGTH: 497
<212> TYPE: DNA
<213> ORGANISM: Fusarium nygamai

<400> SEQUENCE: 203
ccctgtgaac ataccaattg ttgcctcggc ggatcagccc gctcccggta aaacggaacg 60
gcccgccaga ggacccctaa actctgtttc tatatgtaac ttctgagtaa aaccataaat 120
aaatcaaaac tttcaacaac ggatctcttg gttctggcat cgatgaagaa cgcagcaaaa 180
tgcgataagt aatgtgaatt gcagaattca gtgaatcatc gaatctttga acgcacattg 240
cgcccgccag tattctggcg ggcatgcctg ttcgagcgtc atttcaaccc tcaagccccc 300
gggtttggtg ttggggatcg gcgagcctca cggcaagccg gccccgaaat acagtggcgg 360
tctcgctgca gcttccattg cgtagtagta aaaccctcgc aactggtacg cggcgcggcc 420
aagccgttaa acccccaact tctgaatgtt gacctcggat caggtaggaa tacccgctga 480
acttaagcat atcaata 497

<210> SEQ ID NO 204
<211> LENGTH: 573
<212> TYPE: DNA
<213> ORGANISM: Periconia macrospinosa

<400> SEQUENCE: 204
tgatatgctt aagttcagcg ggtatcccta cctgatccga ggtcaagtcg tgaaaggtct 60
tgctggagcg cggatccgcc gggcctccga gaagcgcaaa tgtgctgcgc gagggggccg 120
gcacgaccgc cgccaatgac tttgaggcga gtccgcgcgc gagaacggcg ggacagacgc 180
ccaacaccaa gctaggcttg agggtgtaaa tgacgctcga acaggcatgg ccaaaggaat 240
acctatggcc gcaatgtgcg ttcaaagatt cgatgattca ctgaattctg caattcacac 300
tacttatcgc atttcgctgc gttcttcatc gatgccagaa ccaagagatc cattgttgaa 360
agttgtgata atttaggttt gttatcagaa gttttcgcgt ataatgcaag ggtttcgtg 420 ggttcctggc ggcgggcgag cccgccgagg aagctataga ggtacacgta ggcagagggt 480
gggtgtataa ggagcgccga agcgccccga atgtgtaatg atccttccgc aggttcacct 540
acggaaacct tgttacgact tttacttcct cta 573

<210> SEQ ID NO 205
<211> LENGTH: 612
<212> TYPE: DNA
<213> ORGANISM: Halorosellinia sp.

<400> SEQUENCE: 205
tattgatatg cttaagttca gcgggtattc ctacctgatc cgaggtcaac cttgagaaat 60

```
taggggagtt ttacggcagg ggaccggctc atctataggc gagataaaac ctactacgcc    120

tagagtgtga aaccgactcc gccactaact ttaaggaact acagagggtt tctgtaggct    180

cccaacacta agcaacaggg gcttaagggt tgaaatgacg ctcgaacagg catgcccact    240

agaatactaa tgggcgcaat gtgcgttcaa agattcgatg attcactgaa ttctgcaatt    300

cacattactt atcgcatttc gctgcgttct tcatcgatgc cagaaccaag agatccgttg    360

ttgaaagttt taacttattt agttatatca ttcagaataa catatagtaa acagagttta    420

acagaccacc ggcaggcttt accccgcagc taccaggtta ggtccctaca gggtagggac    480

tcacagggta agctgcagac ctgccgaggc aacaaaggta ggttcacatg ggtttaggag    540

ttgtaataac tctttaatga tccctccgct ggttcaccaa cggagacctt gttacgactt    600

ttacttcctc ta                                                        612


<210> SEQ ID NO 206
<211> LENGTH: 510
<212> TYPE: DNA
<213> ORGANISM: Fusarium sp.

<400> SEQUENCE: 206

cctattgata tgcttaagtt cagcgggtat tcctacctga ttcgaggtca acattcagaa     60

gttgggtgtt ttacggcgtg gccgcgccgc tctccagttg cgaggtgtta gctactacgc    120

aatggaagct gcggcgggac cgccactgta tttgggggac ggcgttgtgc ccgcaggggg    180

cttccgccga tccccaacgc caggcccggg ggcctgaggg ttgtaatgac gctcgaacag    240

gcatgcccgc cagaatactg gcgggcgcaa tgtgcgttca aagattcgat gattcactga    300

attctgcaat tcacattact tatcgcattt cgctgcgttc ttcatcgatg ccagagccaa    360

gagatccgtt gttgaaagtt ttaatttatt tgcttgttta ctcagaagaa acattataga    420

aacagagtta gggggtcctc tggcgggggc ggcccgtgtt acggggccgt ctgttcccgc    480

cgaggcaacg ttataggtat gttcacaggg                                     510


<210> SEQ ID NO 207
<211> LENGTH: 612
<212> TYPE: DNA
<213> ORGANISM: Halorosellinia sp.

<400> SEQUENCE: 207

tattgatatg cttaagttca gcgggtattc ctacctgatc cgaggtcaac cttgagaaat     60

taggggagtt ttacggcagg ggaccggctc atctataggc gagataaaac ctactacgcc    120

tagagtgtga aaccgactcc gccactaact ttaaggaact acagagggtt tctgtaggct    180

cccaacacta agcaacaggg gcttaagggt tgaaatgacg ctcgaacagg catgcccact    240

agaatactaa tgggcgcaat gtgcgttcaa agattcgatg attcactgaa ttctgcaatt    300

cacattactt atcgcatttc gctgcgttct tcatcgatgc cagaaccaag agatccgttg    360

ttgaaagttt taacttattt agttatatca ttcagaataa catatagtaa acagagttta    420

acagaccacc ggcaggcttt accccgcagc taccaggtta ggtccctaca gggtagggac    480

tcacagggta agctgcagac ctgccgaggc aacaaaggta ggttcacatg ggtttaggag    540

ttgtaataac tctttaatga tccctccgct ggttcaccaa cggagacctt gttacgactt    600

ttacttcctc ta                                                        612


<210> SEQ ID NO 208
```

<211> LENGTH: 608
<212> TYPE: DNA
<213> ORGANISM: Uncultured root-associated fungus

<400> SEQUENCE: 208
tattgatatg cttaagttca gcgggtatcc ctacctgatc cgaggtcaaa ctgggggggtt 60 gagcttgatg gacgcgggcc caccggtgcc tcgagaagcg caatgtgctg cgcgagaagc 120
tggcacgacc gctgccaata cctttggggc gagtccgcgc gcgaagcggg acagacgccc 180
aacaccaagc ggagcttgag gggtaaatg acgctcgaac aggcatgccc cacggaatac 240
catggggcgc aatgtgcgtt caaagattcg atgattcact gaattctgca attcacacta 300
cttatcgcat ttcgctgcgt tcttcatcga tgccagaacc aagagatcca ttgttaaaag 360
ttgtaaataa tttggtttgt tttcagaagt ttggatgctg ttgcaaaaag gtttgggggg 420
ttcctggcgg cagaggacct gccgaggaaa caacaaaagg tgcacgtagt caaggtgata 480
gtcaagggct aagcgcccaa ggcagcgtcg tcgcgagcga ctggctcccc cgagcggccc 540
aaggccaggt aatgatcctt ccgcaggttc acctacggaa accttgttac gacttttact 600
tcctctaa 608

<210> SEQ ID NO 209
<211> LENGTH: 601
<212> TYPE: DNA
<213> ORGANISM: Penicillium verruculosum

<400> SEQUENCE: 209
tagaggaagt aaaagtcgta acaaggtttc cgtaggtgaa cctgcggaag gatcattacc 60
gagtgcgggc cctcgcggcc caacctccca cccttgtctc tatacacctg ttgctttggc 120
gggcccaccg gggccacctg gtcgccgggg gacgcacgtc cccgggcccg cgcccgccga 180
agcgctctgt gaaccctgat gaagatgggc tgtctgagta ctatgaaaat tgtcaaaact 240
ttcaacaatg gatctcttgg ttccggcatc gatgaagaac gcagcgaaat gcgataagta 300
atgtgaattg cagaattccg tgaatcatcg aatctttgaa cgcacattgc gccccctggc 360
attccggggg gcatgcctgt ccgagcgtca tttctgccct caagcacggc ttgtgtgttg 420
ggtgtggtcc ccccggggac ctgcccgaaa ggcagcggcg acgtccgtct ggtcctcgag 480
cgtatggggc tctgtcactc gctcgggaag gacctgcggg ggttggtcac caccatgttt 540
ttaccacggt tgacctcgga tcaggtagga gttacccgct gaacttaagc atatcatagg 600
c 601

<210> SEQ ID NO 210
<211> LENGTH: 497
<212> TYPE: DNA
<213> ORGANISM: Fusarium nygamai

<400> SEQUENCE: 210
ccctgtgaac ataccaattg ttgcctcggc ggatcagccc gctcccggta aaacggaacg 60
gcccgccaga ggacccctaa actctgtttc tatatgtaac ttctgagtaa aaccataaat 120
aaatcaaaac tttcaacaac ggatctcttg gttctggcat cgatgaagaa cgcagcaaaa 180
tgcgataagt aatgtgaatt gcagaattca gtgaatcatc gaatctttga acgcacattg 240
cgcccgccag tattctggcg ggcatgcctg ttcgagcgtc atttcaaccc tcaagccccc 300
gggtttggtg ttggggatcg gcgagcctca cggcaagccg gccccgaaat acagtggcgg 360
tctcgctgca gcttccattg cgtagtagta aaaccctcgc aactggtacg cggcgcggcc 420
aagccgttaa acccccaact tctgaatgtt gacctcggat caggtaggaa tacccgctga 480
acttaagcat atcaata 497

<210> SEQ ID NO 211
<211> LENGTH: 500
<212> TYPE: DNA
<213> ORGANISM: Gibberella sp.

<400> SEQUENCE: 211
cctattgata tgcttaagtt cagcgggtat tcctacctga tccgaggtca acattcagaa 60
gttgggggtt taacggcttg gccgcgccgc gtaccagttg cgagggtttt actactacgc 120
aatggaagct gcagcgagac cgccactaga tttcggggcc ggcttgccgc aagggctcgc 180
cgatccccaa caccaaaccc gggggcttga gggttgaaat gacgctcgaa caggcatgcc 240
cgccagaata ctggcgggcg caatgtgcgt tcaaagattc gatgattcac tgaattctgc 300
aattcacatt acttatcgca ttttgctgcg ttcttcatcg atgccagaac caagagatcc 360
gttgttgaaa gttttgattt atttatggtt ttactcagaa gttacatata gaaacagagt 420
ttaggggtcc tctggcgggc cgtcccgttt taccgggagc gggctgatcc gccgaggcaa 480
caattggtat gttcacaggg 500

<210> SEQ ID NO 212
<211> LENGTH: 500
<212> TYPE: DNA
<213> ORGANISM: Fusarium moniliformae

<400> SEQUENCE: 212
cttattgata tgcttttgtt cagcgggtat tcctacctga tccgaggtca acattcagaa 60
gttgggggtt taacggcttg gccgcgccgc gttccagttg cgagggtttt actactacgc 120
aatggaggct gcagcgagac cgccactaga tttcggggcc ggcttgccgc aagggctcgc 180
cgatccccaa caccaaaccc gagggcttga gggttgaaat gacgctcgaa caggcatgcc 240
cgccagaata ctggcgggcg caatgtgcgt tcaaagattc gatgattcac tgaattctgc 300
aattcacatt acttatcgca ttttgctgcg ttcttcatcg atgccagaac caagagatcc 360
gttgttgaaa gttttgattt atttatggtt ttactcagaa gttacatata gaaacagagt 420
ttaggggtcc tctggcgggc cgtcccgttt taccgggagc gggctgatcc gccgaggcaa 480
caagtggtat gttcacaggg 500

<210> SEQ ID NO 213
<211> LENGTH: 571
<212> TYPE: DNA
<213> ORGANISM: Periconia macrospinosa

<400> SEQUENCE: 213
tgatatgctt aagttcagcg ggtatcccta cctgatccga ggtcaagtcg tgaaaggtct 60
tgctggagcg cggatccgcc gggcctccga gaagcgcaaa tgtgctgcgc gagggggccg 120
gcacgaccgc cgccaatgac tttgaggcga gtccgcgcgc gagaacggcg ggacagacgc 180
ccaacaccaa gctaggcttg agggtgtaaa tgacgctcga acaggcatgg ccaaaggaat 240
acctatggcc gcaatgtgcg ttcaaagatt cgatgattca ctgaattctg caattcacac 300
tacttatcgc atttcgctgc gttcttcatc gatgccagaa ccaagagatc cattgttgaa 360
agttgtgata atttaggttt gttatcagaa gttttcgcgt ataatgcaag ggtttcgtg 420

```
ggttcctggc ggcgggcgag cccgccgagg aagctataga ggtacacgta ggcagagggt      480

gggtgtataa ggagcgccga agcgccccga atgtgtaatg atccttccgc aggttcacct      540

acggaaacct tgttacgact tttacttcct c                                     571
```

```
<210> SEQ ID NO 214
<211> LENGTH: 573
<212> TYPE: DNA
<213> ORGANISM: Periconia macrospinosa

<400> SEQUENCE: 214

tgatatgctt aagttcagcg ggtatcccta cctgatccga ggtcaagtcg tgaaaggtct       60

tgctggagcg cggatccgcc gggcctccga gaagcgcaaa tgtgctgcgc gagggggccg      120

gcacgaccgc cgccaatgac tttgaggcga gtccgcgcgc gagaacggcg ggacagacgc      180

ccaacaccaa gctaggcttg agggtgtaaa tgacgctcga acaggcatgg ccaaaggaat      240

acctatggcc gcaatgtgcg ttcaaagatt cgatgattca ctgaattctg caattcacac      300

tacttatcgc atttcgctgc gttcttcatc gatgccagaa ccaagagatc cattgttgaa      360

agttgtgata atttaggttt gttatcagaa gttttcgcgt ataatgcaag gggtttcgtg      420

ggttcctggc ggcgggcgag cccgccgagg aagctataga ggtacacgta ggcagagggt      480

gggtgtataa ggagcgccga agcgccccga atgtgtaatg atccttccgc aggttcacct      540

acggaaacct tgttacgact tttacttcct cta                                   573
```

```
<210> SEQ ID NO 215
<211> LENGTH: 573
<212> TYPE: DNA
<213> ORGANISM: Periconia macrospinosa

<400> SEQUENCE: 215

tgatatgctt aagttcagcg ggtatcccta cctgatccga ggtcaagtcg tgaaaggtct       60

tgctggagcg cggatccgcc gggcctccga gaagcgcaaa tgtgctgcgc gagggggccg      120

gcacgaccgc cgccaatgac tttgaggcga gtccgcgcgc gagaacggcg ggacagacgc      180

ccaacaccaa gctaggcttg agggtgtaaa tgacgctcga acaggcatgg ccaaaggaat      240

acctatggcc gcaatgtgcg ttcaaagatt cgatgattca ctgaattctg caattcacac      300

tacttatcgc atttcgctgc gttcttcatc gatgccagaa ccaagagatc cattgttgaa      360

agttgtgata atttaggttt gttatcagaa gttttcgcgt ataatgcaag gggtttcgtg      420

ggttcctggc ggcgggcgag cccgccgagg aagctataga ggtacacgta ggcagagggt      480

gggtgtataa ggagcgccga agcgccccga atgtgtaatg atccttccgc aggttcacct      540

acggaaacct tgttacgact tttacttcct cta                                   573
```

```
<210> SEQ ID NO 216
<211> LENGTH: 573
<212> TYPE: DNA
<213> ORGANISM: Periconia macrospinosa

<400> SEQUENCE: 216

tgatatgctt aagttcagcg ggtatcccta cctgatccga ggtcaagtcg tgaaaggtct       60

tgctggagcg cggatccgcc gggcctccga gaagcgcaaa tgtgctgcgc gagggggccg      120

gcacgaccgc cgccaatgac tttgaggcga gtccgcgcgc gagaacggcg ggacagacgc      180

ccaacaccaa gctaggcttg agggtgtaaa tgacgctcga acaggcatgg ccaaaggaat      240

acctatggcc gcaatgtgcg ttcaaagatt cgatgattca ctgaattctg caattcacac      300
```

tacttatcgc atttcgctgc gttcttcatc gatgccagaa ccaagagatc cattgttgaa 360
agttgtgata atttaggttt gttatcagaa gttttcgcgt ataatgcaag ggtttcgtg 420 ggttcctggc ggcgggcgag cccgccgagg aagctataga ggtacacgta ggcagagggt 480
gggtgtataa ggagcgccga agcgccccga atgtgtaatg atccttccgc aggttcacct 540
acggaaacct tgttacgact tttacttcct cta 573

<210> SEQ ID NO 217
<211> LENGTH: 579
<212> TYPE: DNA
<213> ORGANISM: Periconia macrospinosa

<400> SEQUENCE: 217
ttagaggaag taaaagtcgt aacaaggttt ccgtaggtga acctgcggaa ggatcattac 60
acattcgggg cgcttcggcg ctccttatac acccaccctc tgcctacgtg tacctctata 120
gcttcctcgg cgggctcgcc cgccgccagg aacccacgaa acccccttgca ttatacgcga 180 aaacttctga taacaaacct aaattatcac aactttcaac aatggatctc ttggttctgg 240
catcgatgaa gaacgcagcg aaatgcgata agtagtgtga attgcagaat tcagtgaatc 300
atcgaatctt tgaacgcaca ttgcggccat aggtattcct ttggccatgc ctgttcgagc 360
gtcatttaca ccctcaagcc tagcttggtg ttgggcgtct gtcccgccgt tctcgcgcgc 420
ggactcgcct caaagtcatt ggcggcggtc gtgccggccc cctcgcgcag cacatttgcg 480
cttctcggag gcccggcgga tccgcgctcc agcaagacct ttcacgactt gacctcggat 540
caggtaggga tacccgctga acttaagcat atcaataag 579

<210> SEQ ID NO 218
<211> LENGTH: 541
<212> TYPE: DNA
<213> ORGANISM: Fusarium nygamai

<400> SEQUENCE: 218
cgttggtgaa ccagcggagg gatcattacc gagtttacaa ctcccaaacc cctgtgaaca 60
taccaattgt tgcctcggcg gatcagcccg ctcccggtaa aacggaacgg cccgccagag 120
gacccctaaa ctctgtttct atatgtaact tctgagtaaa accataaata aatcaaaact 180
ttcaacaacg gatctcttgg ttctggcatc gatgaagaac gcagcaaaat gcgataagta 240
atgtgaattg cagaattcag tgaatcatcg aatctttgaa cgcacattgc gcccgccagt 300
attctggcgg gcatgcctgt tcgagcgtca tttcaaccct caagcccccg ggtttggtgt 360
tggggatcgg cgagcctcac ggcaagccgg ccccgaaata cagtggcggt ctcgctgcag 420
cttccattgc gtagtagtaa aaccctcgca actggtacgc ggcgcggcca agccgttaaa 480
cccccaactt ctgaatgttg acctcggatc aggtaggaat acccgctgaa cttaagcata 540
t 541

<210> SEQ ID NO 219
<211> LENGTH: 499
<212> TYPE: DNA
<213> ORGANISM: Fusarium nygamai

<400> SEQUENCE: 219
ccctgtgaac ataccaattg ttgcctcggc ggatcagccc gctcccggta aaacggaacg 60
gcccgccaga ggacccctaa actctgtttc tatatgtaac ttctgagtaa aaccataaat 120

```
aaatcaaaac tttcaacaac ggatctcttg gttctggcat cgatgaagaa cgcagcaaaa    180

tgcgataagt aatgtgaatt gcagaattca gtgaatcatc gaatctttga acgcacattg    240

cgcccgccag tattctggcg ggcatgcctg ttcgagcgtc atttcaaccc tcaagccccc    300

gggtttggtg ttggggatcg gcgagcctca cggcaagccg gccccgaaat acagtggcgg    360

tctcgctgca gcttccattg cgtagtagta aaaccctcgc aactggtacg cggcgcggcc    420

aagccgttaa acccccaact tctgaatgtt gacctcggat caggtaggaa tacccgctga    480

acttaagcat atcaatagc                                                 499
```

<210> SEQ ID NO 220
<211> LENGTH: 497
<212> TYPE: DNA
<213> ORGANISM: Fusarium nygamai

<400> SEQUENCE: 220

```
ctatgatatg cttaagttca gcgggtattc ctacctgatc cgaggtcaac attcagaagt     60

tgggggttta acggcttggc cgcgccgcgt accagttgcg agggttttac tactacgcaa    120

tggaagctgc agcgagaccg ccactgtatt tcggggccgg cttgccgtga ggctcgccga    180

tccccaacac caaacccggg ggcttgaggg ttgaaatgac gctcgaacag gcatgcccgc    240

cagaatactg gcgggcgcaa tgtgcgttca aagattcgat gattcactga attctgcaat    300

tcacattact tatcgcattt tgctgcgttc ttcatcgatg ccagaaccaa gagatccgtt    360

gttgaaagtt ttgatttatt tatggtttta ctcagaagtt acatatagaa acagagttta    420

ggggtcctct ggcgggccgt tccgttttac cgggagcggg ctgatccgcc gaggcaacaa    480

ttggtatgtt cacaggg                                                   497
```

<210> SEQ ID NO 221
<211> LENGTH: 606
<212> TYPE: DNA
<213> ORGANISM: Macrophomina phaseolina

<400> SEQUENCE: 221

```
cttattgata tgcttaagtt cagcgggtat ccctacctga tccgaggtca accttgagaa     60

aagttcagaa ggttcgtccg gcgggcgacg ccttacgctc cgaagcgagg tgtattctac    120

tacgcttgag gcaagacgcc accgccgagg tctttgaggc gcgcccgcaa aggacggtgc    180

ccaataccaa gcagagcttg agggttgaaa tgacgctcga acaggcatgc cccccggaat    240

accaaggggc gcaatgtgcg ttcaaagatt cgatgattca ctgaattctg caattcacat    300

tacttatcgc atttcgctgc gttcttcatc gatgccagaa ccaagagatc cgttgttgaa    360

agttttagtt tatttaatat ttttttcaga ctgcaacgtt tactaactgg agtttgatag    420

tcctctggcg ggcactagcc accccccaaa atcggggggc ggccgcggaa gaccgcggcc    480

cgccaaagca acagaggtag gtatacaaag ggtgggagga tcgggacgga gcccgaatca    540

actcggtaat gatccttccg caggttcacc tacggaaacc ttgttacgac ttttacttcc    600

tctaat                                                               606
```

<210> SEQ ID NO 222
<211> LENGTH: 573
<212> TYPE: DNA
<213> ORGANISM: Periconia macrospinosa

<400> SEQUENCE: 222

```
tgatatgctt aagttcagcg ggtatcccta cctgatccga ggtcaagtcg tgaaaggtct     60
```

-continued tgctggagcg cggatccgcc gggcctccga gaagcgcaaa tgtgctgcgc gagggggccg 120
gcacgaccgc cgccaatgac tttgaggcga gtccgcgcgc gagaacggcg ggacagacgc 180
ccaacaccaa gctaggcttg agggtgtaaa tgacgctcga acaggcatgg ccaaaggaat 240
acctatggcc gcaatgtgcg ttcaaagatt cgatgattca ctgaattctg caattcacac 300
tacttatcgc atttcgctgc gttcttcatc gatgccagaa ccaagagatc cattgttgaa 360
agttgtgata atttaggttt gttatcagaa gttttcgcgt ataatgcaag ggtttcgtg 420 ggttcctggc ggcgggcgag cccgccgagg aagctataga ggtacacgta ggcagagggt 480
gggtgtataa ggagcgccga agcgccccga atgtgtaatg atccttccgc aggttcacct 540
acggaaacct tgttacgact tttacttcct cta 573

<210> SEQ ID NO 223
<211> LENGTH: 573
<212> TYPE: DNA
<213> ORGANISM: Periconia macrospinosa

<400> SEQUENCE: 223
tgatatgctt aagttcagcg ggtatcccta cctgatccga ggtcaagtcg tgaaaggtct 60
tgctggagcg cggatccgcc gggcctccga gaagcgcaaa tgtgctgcgc gagggggccg 120
gcacgaccgc cgccaatgac tttgaggcga gtccgcgcgc gagaacggcg ggacagacgc 180
ccaacaccaa gctaggcttg agggtgtaaa tgacgctcga acaggcatgg ccaaaggaat 240
acctatggcc gcaatgtgcg ttcaaagatt cgatgattca ctgaattctg caattcacac 300
tacttatcgc atttcgctgc gttcttcatc gatgccagaa ccaagagatc cattgttgaa 360
agttgtgata atttaggttt gttatcagaa gttttcgcgt ataatgcaag ggtttcgtg 420 ggttcctggc ggcgggcgag cccgccgagg aagctataga ggtacacgta ggcagagggt 480
gggtgtataa ggagcgccga agcgccccga atgtgtaatg atccttccgc aggttcacct 540
acggaaacct tgttacgact tttacttcct cta 573

<210> SEQ ID NO 224
<211> LENGTH: 569
<212> TYPE: DNA
<213> ORGANISM: Microdochium sp.

<400> SEQUENCE: 224
tagaggaagt aaaagtcgta acaaggtctc cgtaggtgaa cctgcggagg gatcattact 60
gagttttcaa ctctccaaac catgtgaact taccactgtt gcctcggtgg ttagtgctct 120
ccctcggggg ggtgctgccg ccggtggact actaaactct tgttaattta tggcattctg 180
aatcataact aagaaataag ttaaaacttt caacaacgga tctcttggtt ctggcatcga 240
tgaagaacgc agcgaaatgc gataagtaat gtgaattgca gaattcagtg aatcatcgaa 300
tctttgaacg cacattgcgc ccattagtat tctagtgggc atgcctgttc gagcgtcatt 360
tcaaccctta agcctagctt agcgttggga gactgcgcta aaccgcagct cctcaaaacc 420
agtggcggag tcctctcgtg ctctgagcgt agtaattctt tatctcgctt ctgcaagtac 480
ggttgacgac agccataaac cgcaccctct cggggggcac tttttaatgg ttgacctcgg 540
atcaggtagg aatacccgct gaacttaag 569

<210> SEQ ID NO 225
<211> LENGTH: 500
<212> TYPE: DNA

<213> ORGANISM: Uncultured Nectriaceae

<400> SEQUENCE: 225
ccctgtgaac ataccttact gttgcctcgg cggatcagcc cgcgcccggt aaaacgggac 60
ggcccgccag aggaccccta aactctgttt ttattgtaac ttctgagtaa aaccataaat 120
aaatcaaaac tttcaacaac ggatctcttg gttctggcat cgatgaagaa cgcagcaaaa 180
tgcgataagt aatgtgaatt gcagaattca gtgaatcatc gaatctttga acgcacattg 240
cgcccgccag tattctggcg ggcatgcctg ttcgagcgtc atttcaaccc tcaagccctc 300
gggtttggtg ttggggatcg gcgagccttt ctggcaagcc ggccccgaaa tctagtggcg 360
gtctcactgc agcctccatt gcgtagtagc taacacctcg caactggaac gcggtgcggc 420
caagccgtta aaccccccaa cttctgaatg ttgacctcgg atcaggtagg aatacccgct 480
gaacttaagc atatcaatag 500

<210> SEQ ID NO 226
<211> LENGTH: 601
<212> TYPE: DNA
<213> ORGANISM: Ascomycete sp.

<400> SEQUENCE: 226
tcctcccggc ctattgatat gcttaagttc agcgggtatt cctacctgat ctgaggtcaa 60
ccttggaaag ttgggggttt aacggcaggg gctcgtcgct ctccgatgcg gaatatcact 120
acttcgcaga ggaggccacg acgggtccgc cactagattt aggggccggc cgtccctcgc 180
gggctttggc cgatccccaa caccacgccc taggggcatg agggttgaaa tgacgctcag 240
acaggcatgc ccgccagaat actggcgggc gcaatgtgcg ttcaaagatt cgatgattca 300
ctgaattctg caattcacat tacttatcgc atttcgctgc gttcttcatc gatgccagaa 360
ccaagagatc cgttgttgaa agtttttatt tatttgtaaa aactactcag aagattccaa 420
aataaaacaa gaattaagtt tcctaggcgg gcgcctgatc cggggcacac gaggcgcccg 480
gggcaatccc gccgaagcaa cagtaggtat gttcacatgg gtttgggagt tgtaaactcg 540
gtaatgatcc ctccgctggt tcaccaacgg agaccttgtt acgactttta cttcctctaa 600
t 601

<210> SEQ ID NO 227
<211> LENGTH: 483
<212> TYPE: DNA
<213> ORGANISM: Fusarium nygamai

<400> SEQUENCE: 227
caattgttgc ctcggcggat cagcccgctc ccggtaaaac ggaacggccc gccagaggac 60
ccctaaactc tgtttctata tgtaacttct gagtaaaacc ataaataaat caaaactttc 120
aacaacggat ctcttggttc tggcatcgat gaagaacgca gcaaaatgcg ataagtaatg 180
tgaattgcag aattcagtga atcatcgaat ctttgaacgc acattgcgcc cgccagtatt 240
ctggcgggca tgcctgttcg agcgtcattt caaccctcaa gcccccgggt ttggtgttgg 300
ggatcggcga gcctcacggc aagccggccc cgaaatacag tggcggtctc gctgcagctt 360
ccattgcgta gtagtaaaac cctcgcaact ggtacgcggc gcggccaagc cgttaaaccc 420
ccaacttctg aatgttgacc tcggatcagg taggaatacc cgctgaactt aagcatatca 480
ata 483

<210> SEQ ID NO 228
<211> LENGTH: 485
<212> TYPE: DNA
<213> ORGANISM: Fusarium nygamai

<400> SEQUENCE: 228

```
gcctatgata tgcttaagtt cagcgggtat tcctacctga tccgaggtca acattcagaa      60
gttgggggtt taacggcttg gccgcgccgc gtaccagttg cgagggtttt actactacgc     120
aatgaaagct gcagcgagac cgccactgta tttcggggcc ggcttgccgt gaggctcgcc     180
gatccccaac accaaacccg ggggcttgag ggttgaaatg acgctcgaac aggcatgccc     240
gccagaatac tggcgggcgc aatgtgcgtt caaagattcg atgattcact gaattctgca     300
attcacatta cttatcgcat tttgctgcgt tcttcatcga tgccagaacc aagagatccg     360
ttgttgaaag ttttgattta tttatggttt tactcagaag ttacatatag aaacagagtt     420
taggggtcct ctggcgggcc gttccgtttt accgggagcg ggctgatccg ccgaggcaac     480
aattg                                                                 485
```

<210> SEQ ID NO 229
<211> LENGTH: 573
<212> TYPE: DNA
<213> ORGANISM: Periconia macrospinosa

<400> SEQUENCE: 229

```
tgatatgctt aagttcagcg ggtatcccta cctgatccga ggtcaagtcg tgaaaggtct      60
tgctggagcg cggatccgcc gggcctccga gaagcgcaaa tgtgctgcgc gaggggggccg     120
gcacgaccgc cgccaatgac tttgaggcga gtccgcgcgc gagaacggcg ggacagacgc     180
ccaacaccaa gctaggcttg agggtgtaaa tgacgctcga acaggcatgg ccaaaggaat     240
acctatggcc gcaatgtgcg ttcaaagatt cgatgattca ctgaattctg caattcacac     300
tacttatcgc atttcgctgc gttcttcatc gatgccagaa ccaagagatc cattgttgaa     360
agttgtgata atttaggttt gttatcagaa gttttcgcgt ataatgcaag gggtttcgtg     420
ggttcctggc ggcgggcgag cccgccgagg aagctataga ggtacacgta ggcagagggt     480
gggtgtataa ggagcgccga agcgccccga atgtgtaatg atccttccgc aggttcacct     540
acggaaacct tgttacgact tttacttcct cta                                  573
```

<210> SEQ ID NO 230
<211> LENGTH: 508
<212> TYPE: DNA
<213> ORGANISM: Microdochium sp.

<400> SEQUENCE: 230

```
tagaggaagt aaaagtcgta acaaggtctc cgtaggtgaa cctgcggagg gatcattact      60
gagttttcaa ctctccaaac catgtgaact taccactgtt gcctcggtgg ttagtgctct     120
tcttcggggg agtgctgccg ccggtggact actaaactct tgttaatttt tggcattctg     180
aatcataact aagaaataag ttaaaacttt caacaacgga tctcttggtt ctggcatcga     240
tgaagaacgc agcgaaatgc gataagtaat gtgaattgca gaattcagtg aatcatcgaa     300
tctttgaacg cacattgcgc ccattagtat tctagtggga tgcctgttc gagcgtcatt     360
tcaaccctta agcctagctt agcgttggga gactgcacta aaccgcagct cctcaaaacc     420
agtggcggag tcctcttgtg ctctgagcgt agtaattcat tatctcgctt ctgtaagtac     480
agtggatcac agccataaac cgcaccct                                        508
```

<210> SEQ ID NO 231
<211> LENGTH: 498
<212> TYPE: DNA
<213> ORGANISM: Fusarium nygamai

<400> SEQUENCE: 231
ccctgtgaac ataccaattg ttgcctcggc ggatcagccc gctcccggta aaacggaacg 60
gcccgccaga ggacccctaa actctgtttc tatatgtaac ttctgagtaa aaccataaat 120
aaatcaaaac tttcaacaac ggatctcttg gttctggcat cgatgaagaa cgcagcaaaa 180
tgcgataagt aatgtgaatt gcagaattca gtgaatcatc gaatctttga acgcacattg 240
cgcccgccag tattctggcg ggcatgcctg ttcgagcgtc atttcaaccc tcaagccccc 300
gggtttggtg ttggggatcg gcgagcctca cggcaagccg gccccgaaat acagtggcgg 360
tctcgctgca gcttccattg cgtagtagta aaaccctcgc aactggtacg cggcgcggcc 420
aagccgttaa acccccaact tctgaatgtt gacctcggat caggtaggaa tacccgctga 480
acttaagcat atcaatag 498

<210> SEQ ID NO 232
<211> LENGTH: 581
<212> TYPE: DNA
<213> ORGANISM: Uncultured Leptosphaeriaceae

<400> SEQUENCE: 232
cttggtctat tagaggaagt aaaagtcgta acaaggtttc cgtaggtgaa cctgcggaag 60
gatcattaat tacgaaagct atagcccctc cgggggttat tgcacccacc ctttgtctac 120
ttgtacctct tgttgtttcc tcggcaggct tgcctgccgc caggaacccc ttaaaccctt 180
gcatctacag tatttaaatc tgataactat ttaaattatc acaactttta acaatggatc 240
tcttggttct ggcatcgatg aagaacgcag cgaaatgcga aaagtagtgt gaattgcaga 300
attccgtgaa tcatcgaatc tttgaacgca cattgcgccc ctcggtattc cgtggggcat 360
gcctgttcga gcgtcattta caccctcaag ctctgcttgg tgttgggcgt ctgtcctgct 420
ttatgcgtgg actcgcccca aagtcattgg cagcggtcgt gccagcttct cgcgcagcac 480
atttgcgttt cttgaagttt ggtggatcag cgtccagtaa gctcttttat aacttgacct 540
cggatcaggt agggataccc gctgaactta agcatatcat g 581

<210> SEQ ID NO 233
<211> LENGTH: 573
<212> TYPE: DNA
<213> ORGANISM: Periconia macrospinosa

<400> SEQUENCE: 233
tgatatgctt aagttcagcg ggtatcccta cctgatccga ggtcaagtcg tgaaaggtct 60
tgctggagcg cggatccgcc gggcctccga gaagcgcaaa tgtgctgcgc gagggggccg 120
gcacgaccgc cgccaatgac tttgaggcga gtccgcgcgc gagaacggcg ggacagacgc 180
ccaacaccaa gctaggcttg agggtgtaaa tgacgctcga acaggcatgg ccaaaggaat 240
acctatggcc gcaatgtgcg ttcaaagatt cgatgattca ctgaattctg caattcacac 300
tacttatcgc atttcgctgc gttcttcatc gatgccagaa ccaagagatc cattgttgaa 360
agttgtgata atttaggttt gttatcagaa gttttcgcgt ataatgcaag ggtttcgtg 420 ggttcctggc ggcgggcgag cccgccgagg aagctataga ggtacacgta ggcagagggt 480
gggtgtataa ggagcgccga agcgccccga atgtgtaatg atccttccgc aggttcacct 540
acggaaacct tgttacgact tttacttcct cta 573

<210> SEQ ID NO 234
<211> LENGTH: 579
<212> TYPE: DNA
<213> ORGANISM: Codinaeopsis sp.

<400> SEQUENCE: 234
ggaagtaaaa gtcgtaacaa ggtctccgtt ggtgaaccag cggagggatc attacaggac 60
tcgcaagact cccgtaaacc actgtgaact tacctacaac ccgttgcctc ggcgggtgct 120
ccgggcgcgt cttcgggcgc tccggggcgc tccagcccgc cggcggcccc taaactctgt 180
ctctgtaacg ttggcatctc cgagcagact ataaacgagt caaaactttc aacaacggat 240
ctcttggttc tggcatcgat gaagaacgca gcgaaatgcg ataagtaatg tgaattgcag 300
aattcagtga atcatcgaat ctttgaacgc acattgcgcc cgccagcact ctggcgggca 360
tgcctgtccg agcgtcattt caaccctcag gccccgcctg gcgttggagc cctgcgcagc 420
gcaggctccc aaagacagcg gcgggcgcgc cccggaaccg agcgcagtaa tgctttctcg 480
ttctggtccg gcgcgcgctc cggccgtaaa acccccaact ttctaagtgg ttgacctcgg 540
atcaggtagg aatacccgct gaacttaagc atatcaata 579

<210> SEQ ID NO 235
<211> LENGTH: 498
<212> TYPE: DNA
<213> ORGANISM: Fusarium nygamai

<400> SEQUENCE: 235
ccctgtgaac ataccaattg ttgcctcggc ggatcagccc gctcccggta aaacggaacg 60
gcccgccaga ggacccctaa actctgtttc tatatgtaac ttctgagtaa aaccataaat 120
aaatcaaaac tttcaacaac ggatctcttg gttctggcat cgatgaagaa cgcagcaaaa 180
tgcgataagt aatgtgaatt gcagaattca gtgaatcatc gaatctttga acgcacattg 240
cgcccgccag tattctggcg ggcatgcctg ttcgagcgtc atttcaaccc tcaagccccc 300
gggtttggtg ttggggatcg gcgagcctca cggcaagccg gccccgaaat acagtggcgg 360
tctcgctgca gcttccattg cgtagtagta aaaccctcgc aactggtacg cggcgcggcc 420
aagccgttaa acccccaact tctgaatgtt gacctcggat caggtaggaa tacccgctga 480
acttaagcat atcaatag 498

<210> SEQ ID NO 236
<211> LENGTH: 497
<212> TYPE: DNA
<213> ORGANISM: Fusarium nygamai

<400> SEQUENCE: 236
ctatgatatg cttaagttca gcgggtattc ctacctgatc cgaggtcaac attcagaagt 60
tgggggttta acggcttggc cgcgccgcgt accagttgcg agggttttac tactacgcaa 120
tggaagctgc agcgagaccg ccactgtatt tcggggccgg cttgccgtga ggctcgccga 180
tccccaacac caaacccggg ggcttgaggg ttgaaatgac gctcgaacag gcatgcccgc 240
cagaatactg gcgggcgcaa tgtgcgttca aagattcgat gattcactga attctgcaat 300
tcacattact tatcgcattt tgctgcgttc ttcatcgatg ccagaaccaa gagatccgtt 360
gttgaaagtt ttgatttatt tatggtttta ctcagaagtt acatatagaa acagagttta 420
ggggtcctct ggcgggccgt tccgttttac cgggagcggg ctgatccgcc gaggcaacaa 480
ttggtatgtt cacaggg 497

<210> SEQ ID NO 237
<211> LENGTH: 498
<212> TYPE: DNA
<213> ORGANISM: Fusarium nygamai

<400> SEQUENCE: 237
ccctgtgaac ataccaattg ttgcctcggc ggatcagccc gctcccggta aaacggaacg 60
gcccgccaga ggacccctaa actctgtttc tatatgtaac ttctgagtaa aaccataaat 120
aaatcaaaac tttcaacaac ggatctcttg gttctggcat cgatgaagaa cgcagcaaaa 180
tgcgataagt aatgtgaatt gcagaattca gtgaatcatc gaatctttga acgcacattg 240
cgcccgccag tattctggcg ggcatgcctg ttcgagcgtc atttcaaccc tcaagccccc 300
gggtttggtg ttggggatcg gcgagcctca cggcaagccg gccccgaaat acagtggcgg 360
tctcgctgca gcttccattg cgtagtagta aaaccctcgc aactggtacg cggcgcggcc 420
aagccgttaa acccccaact tctgaatgtt gacctcggat caggtaggaa tacccgctga 480
acttaagcat atcaatag 498

<210> SEQ ID NO 238
<211> LENGTH: 517
<212> TYPE: DNA
<213> ORGANISM: Ascomycete sp.

<400> SEQUENCE: 238
gtttccgtag gtgaacctgc ggaaggatca ttatcaaaag tcaagtcggg ggctgcaaag 60
ccttcgtcta caccccatgt cttttgcgta cttcttgttt cctcggtggc gcaagccgcc 120
gattggacaa accaaaacct tttttgtaat tgcaatcagc gtctgaaaat aatctaatta 180
tttacaactt tcaacaacgg atctcttggt tctggcatcg atgaagaacg cagcgaaatg 240
cgataagtag tgtgaattgc agaattcagt gaatcatcga atctttgaac gcacattgcg 300
ccccttggta ttccatgggg catgcctgtt cgagcgtcat ttgtaccctc aagctttgct 360
tggtgttggg cgtcttgtcg tattacgact cgccttaaat acattggcag ccggcacttt 420
ggcctaggag cgccgcacat tttgcgatcg tagcccgttg tactggcgtc catcaagaac 480
atttaccacg tttgacctcg gatcaggtag ggatacc 517

<210> SEQ ID NO 239
<211> LENGTH: 584
<212> TYPE: DNA
<213> ORGANISM: Codinaeopsis sp.

<400> SEQUENCE: 239
ttagaggaag taaaagtcgt aacaaggtct ccgttggtga accagcggag ggatcattac 60
aggactcgca agactcccgt aaaccactgt gaacttacct acaacccgtt gcctcggcgg 120
gtgctccggg cgcgtcttcg ggcgctccgg ggcgctccag cccgccggcg gcccctaaac 180
tctgtctctg taacgttggc atctccgagc agactataaa cgagtcaaaa ctttcaacaa 240
cggatctctt ggttctggca tcgwtgaaga acgcagcgaa atgcgataag taatgtgaat 300
tgcagaattc agtgaatcat cgaatctttg aacgcacatt gcgcccgcca gcactctggc 360
gggcatgcct gtccgagcgt catttcaacc ctcaggcccc gcctggcgtt ggagccctgc 420
gcagcgcagg ctcccaaaga cagcggcggg cgcgccccgg aaccgagcgc agtaatgctt 480
tctcgttctg gtccggcgcg cgctccggcc gtaaaacccc caactttcta agtggttgac 540
ctcggatcag gtaggaatac ccgctgaact taagcatatc atag 584

<210> SEQ ID NO 240
<211> LENGTH: 483
<212> TYPE: DNA
<213> ORGANISM: Fusarium nygamai

<400> SEQUENCE: 240
caattgttgc ctcggcggat cagcccgctc ccggtaaaac ggaacggccc gccagaggac 60
ccctaaactc tgtttctata tgtaacttct gagtaaaacc ataaataaat caaaactttc 120
aacaacggat ctcttggttc tggcatcgat gaagaacgca gcaaaatgcg ataagtaatg 180
tgaattgcag aattcagtga atcatcgaat ctttgaacgc acattgcgcc cgccagtatt 240
ctggcgggca tgcctgttcg agcgtcattt caaccctcaa gcccccgggt ttggtgttgg 300
ggatcggcga gcctcacggc aagccggccc cgaaatacag tggcggtctc gctgcagctt 360
ccattgcgta gtagtaaaac cctcgcaact ggtacgcggc gcggccaagc cgttaaaccc 420
ccaacttctg aatgttgacc tcggatcagg taggaatacc cgctgaactt aagcatatca 480
ata 483

<210> SEQ ID NO 241
<211> LENGTH: 746
<212> TYPE: DNA
<213> ORGANISM: Uncultured fungus

<400> SEQUENCE: 241
gtttccgtag gtgaacctgc ggaaggatca ttactgaggt taccgggggt gagttgtagt 60
tggactcgct gctggcgtct tacggcgcat gtgcacggtc cgctcgctcg ccttcgttcc 120
ttctatcaac ccctgtgcac tataatcgga tcagagagaa gcgcgcgcat gagccgcatt 180
atgtgggatt aacctagtag ttgtgggtcc gcctgctgcg aaaggttaat cctttgatcg 240
gcgccgcgtg tgtggtacct cgaagtcctt ctttataaac cactatacat gtcttgtcag 300
aatgttcagt ccctcgttgg acgctaatta caatacaact ttcaacaacg gatctcttgg 360
ctctcgcatc gatgaagaac gcagcgaaat gcgataagta atgtgaattg cagaattcag 420
tgaatcatcg aatctttgaa cgcaccttgc gccctttggt attccgaagg gcacgcctgt 480
ttgagtgtca tgttcatctc aatccatcag cttttttta aaggctgctt ggtttggatt 540
tgggagtttt gctggcccgt gtaagggtcg gctctccttg aatgcatgag tgagtgtctg 600
gctcgcgtcg ctggtgtgat agtctcatca ttggcggcgc ttgtctaaag ggcttgcttt 660
cgaaccgtct tctcaacgga gacactactt tgaccaattt gacctcaaat caggtgggac 720
tacccgctga acttaagcat atcata 746

<210> SEQ ID NO 242
<211> LENGTH: 575
<212> TYPE: DNA
<213> ORGANISM: Uncultured Helotiales

<400> SEQUENCE: 242
ttagaggaag taaaagtcgt aacaaggttt ccgtaggtga acctgcggaa ggatcattac 60
agagttcatg cccttcgggg tagatctccc acccttgtgt atcatcatag aatgttgctt 120
tggcgggccg cgcctagtgt gcctggattc gcgttcagcg tgcccgccag aggaccccta 180

```
aactctgaat gttagtgtcg tctgagtact attaaatagt taaaactttc aacaacggat    240

ctcttggttc tggcatcgat gaagaacgca gcgaaatgcg ataagtaatg tgaattgcag    300

aattcagtga atcatcgaat ctttgaacgc acattgcgcc ccctggtatt ccggggggca    360

tgcctgttcg agcgtcattt ataccaatct agcccggcta ggtgttgggc ttcgccgttt    420

ggcgggcctt aaaaccagtg gcggtgctct taggctctac gcgtagtaat ttctcgcta     480

tagggtcctg ggagatgctt gccagcaacc ccaaattttt ctaggttgac ctcggatcag    540

gtagggatac ccgctgaact taagcatatc aatag                               575


<210> SEQ ID NO 243
<211> LENGTH: 836
<212> TYPE: DNA
<213> ORGANISM: Fungal endophyte

<400> SEQUENCE: 243

tttgctaagc aacagtcctt ctgtagcaga gcttaacgga gaccttgcac ccgagagggg     60

ggaggcgact ataaacaagc ttctagcgca agtcagcact cgctggcaac acaatcgaat    120

tgcggggacg ctttaaagcc taccagtacc aacagccccg gccggggctg ggcgagcgca    180

gctcgaggtc acaatctggg aggatgccac aataagcaat ccgcagcggc tctggccgtc    240

cacagactaa gtggttgtgg gtaggagaac cctatctaag atatagtcgg gcccgaggag    300

agatcctcgg ggcttctgcg tccgtaggtg aacctgcgga aggatcatta aaaaaggata    360

ccgggcaacc ggtagacccc acccgtgtct ctctactctt gttgctttgg caggccgtgg    420

cctccaccgc gggctctgcc tgcgtgtgcc tgccagagga ccaaactctg aattttagtg    480

atgtctgagt actatataat agttaaaact ttcaacaacg gatctcttgg ttctggcatc    540

gatgaagaac gcagcgaaat gcgataagta atgtgaattg cagaattcag tgaatcatcg    600

aatctttgaa cgcacattgc gcccggtggt attccgccgg gcatgcctgt tcgagcgtca    660

ttataaccac tcaagcctgg cttggtattg gggctcgcgg ttccgcggcc cctaaaatca    720

gtggcggtgc cggtgggctc taagcgtagt aaatctcctc gctatagggt ccctccggtt    780

gcctgccaga accccccat tttttttagg ttgacctcgg atcaggtagg gatacc         836


<210> SEQ ID NO 244
<211> LENGTH: 582
<212> TYPE: DNA
<213> ORGANISM: Fungal endophyte

<400> SEQUENCE: 244

tagaggaagt aaaagtcgta acaaggtttc cgtaggtgaa cctgcggaag gatcattaca     60

agaaacgagg ccgcgtgcgt gcgctcgccc gcccggcccc gctccttacc ttgcctactg    120

caccgtttgt tgcttcctgg cggcggactg cccgccgcca gggacgttga tacaaccctg    180

tatagaagca ttgaagctct gagaaaacgc gaaatcgtac aactttcaac aatggatctc    240

ttggttctgg catcgatgaa gaacgcagcg aaatgcgata agtagtgtga attgcagaat    300

tcagtgaatc atcgaatctt tgaacgcaca ttgcgcccct tggcattcca tggggcatgc    360

ctgttcgagc gtcatctaaa ccctcaagcc cccggcttgg tgttgggtgc ctgtccccgc    420

tccccgcgcg gactcacccc aaatgcattg gcagccgcct ctcggcttct tgcgcagcac    480

agtgcgcagc gaggcgaggt gaggcgtgcg tccagcaagc aaccacccaa gtttgacctc    540

ggatcaggta gggatacccg ctgaacttaa gcatatcaat ag                       582
```

<210> SEQ ID NO 245
<211> LENGTH: 502
<212> TYPE: DNA
<213> ORGANISM: Uncultured Hypocreales

<400> SEQUENCE: 245
ccctgtgaac atacctttac tgttgcctcg gcggatcagc ccgcgcccgg taaaacggga 60
cggcccgcca gaggacccct aaactctgtt ttttattgta acttctgagt aaaaccataa 120
ataaatcaaa actttcaaca acggatctct tggttctggc atcgatgaag aacgcagcaa 180
aatgcgataa gtaatgtgaa ttgcagaatt cagtgaatca tcgaatcttt gaacgcacat 240
tgcgcccgcc agtattctgg cgggcatgcc tgttcgagcg tcatttcaac cctcaagccc 300
tcgggtttgg tgttggggat cggcgagcct ctctggcaag ccggccccga aatctagtgg 360
cggtctcact gcagcctcca ttgcgtagta gctaacacct cgcaactgga acgcggtgcg 420
gccaagccgt taaacccccc aacttctgaa tgttgacctc ggatcaggta ggaatacccg 480
ctgaacttaa gcatatcaat ag 502

<210> SEQ ID NO 246
<211> LENGTH: 573
<212> TYPE: DNA
<213> ORGANISM: Periconia macrospinosa

<400> SEQUENCE: 246
tgatatgctt aagttcagcg ggtatcccta cctgatccga ggtcaagtcg tgaaaggtct 60
tgctggagcg cggatccgcc gggcctccga gaagcgcaaa tgtgctgcgc gagggggccg 120
gcacgaccgc cgccaatgac tttgaggcga gtccgcgcgc gagaacggcg ggacagacgc 180
ccaacaccaa gctaggcttg agggtgtaaa tgacgctcga acaggcatgg ccaaaggaat 240
acctatggcc gcaatgtgcg ttcaaagatt cgatgattca ctgaattctg caattcacac 300
tacttatcgc atttcgctgc gttcttcatc gatgccagaa ccaagagatc cattgttgaa 360
agttgtgata atttaggttt gttatcagaa gttttcgcgt ataatgcaag ggtttcgtg 420 ggttcctggc ggcgggcgag cccgccgagg aagctataga ggtacacgta ggcagagggt 480
gggtgtataa ggagcgccga agcgccccga atgtgtaatg atccttccgc aggttcacct 540
acggaaacct tgttacgact tttacttcct cta 573

<210> SEQ ID NO 247
<211> LENGTH: 615
<212> TYPE: DNA
<213> ORGANISM: Hypocrea lixii

<400> SEQUENCE: 247
aggtctccgt tggtgaacca gcggagggat cattaccgag tttacaactc ccaaacccaa 60
tgtgaacgtt accaaactgt tgcctcggcg ggatctctgc cccgggtgcg tcgcagcccc 120
ggaccaaggc gcccgccgga ggaccaacct aaaactctta ttgtataccc cctcgcgggt 180
ttttttataa tctgagcctt tctcggcgcc tctcgtaggc gtttcgaaaa tgaatcaaaa 240
ctttcaacaa cggatctctt ggttctggca tcgatgaaga acgcagcgaa atgcgataag 300
taatgtgaat tgcagaattc agtgaatcat cgaatctttg aacgcacatt gcgcccgcca 360
gtattctggc gggcatgcct gtccgagcgt catttcaacc ctcgaacccc tccgggggt 420 cggcgttggg gatcggccct cccttagcgg gtggccgtct ccgaaataca gtggcggtct 480
cgccgcagcc tctcctgcgc agtagtttgc acactcgcat cgggagcgcg gcgcgtccac 540
agccgttaaa cacccaactt ctgaaatgtt gacctcggat caggtaggaa tacccgctga 600
acttaagcat atcat 615

<210> SEQ ID NO 248
<211> LENGTH: 600
<212> TYPE: DNA
<213> ORGANISM: Periconia macrospinosa

<400> SEQUENCE: 248
ttcctccgcc ttatttgata tgcttaagtt cagcgggtat ccctacctga tccgaggtca 60
agtcgtgaaa ggtcttgctg gagcgcggat ccgccgggcc tccgagaagc gcaaatgtgc 120
tgcgcgaggg ggccggcacg accgccgcca atgactttga ggcgagtccg cgcgcgagaa 180
cggcgggaca gacgcccaac accaagctag gcttgagggt gtaaatgacg ctcgaacagg 240
catggccaaa ggaataccta tggccgcaat gtgcgttcaa agattcgatg attcactgaa 300
ttctgcaatt cacactactt atcgcatttc gctgcgttct tcatcgatgc cagaaccaag 360
agatccattg ttgaaagttg tgataattta ggtttgttat cagaagtttt cgcgtataat 420
gcaaggggtt tcgtgggttc ctggcggcgg gcgagcccgc cgaggaagct atagaggtac 480
acgtaggcag agggtgggtg tataaaggag cgccgaagcg ccccgaatgt gtaatgatcc 540
ttccgcaggt tcacctacgg aaaccttgtt acgactttta cttcctctaa atgaccaaga 600

<210> SEQ ID NO 249
<211> LENGTH: 599
<212> TYPE: DNA
<213> ORGANISM: Periconia macrospinosa

<400> SEQUENCE: 249
ttcctccgcc ttattgatat gcttaagttc agcgggtatc cctacctgat ccgaggtcaa 60
gtcgtgaaag gtcttgctgg agcgcggatc cgccgggcct ccgagaagcg caaatgtgct 120
gcgcgagggg gccggcacga ccgccgccaa tgactttgag gcgagtccgc gcgcgagaac 180
ggcgggacag acgcccaaca ccaagctagg cttgagggtg taaatgacgc tcgaacaggc 240
atggccaaag gaatacctat ggccgcaatg tgcgttcaaa gattcgatga ttcactgaat 300
tctgcaattc acactactta tcgcatttcg ctgcgttctt catcgatgcc agaaccaaga 360
gatccattgt tgaaagttgt gataatttag gtttgttatc agaagttttc gcgtataatg 420
caaggggttt cgtgggttcc tggcggcggg cgagcccgcc gaggaagcta tagaggtaca 480
cgtaggcaga gggtgggtgt ataaaggagc gccgaagcgc cccgaatgtg taatgatcct 540
tccgcaggtt cacctacgga aaccttgtta cgacttttac ttcctctaaa tgaccaaga 599

<210> SEQ ID NO 250
<211> LENGTH: 597
<212> TYPE: DNA
<213> ORGANISM: Periconia macrospinosa

<400> SEQUENCE: 250
tcttggtcat ttagaggaag taaaagtcgt aacaaggttt ccgtaggtga acctgcggaa 60
ggatcattac acattcgggg cgcttcggcg ctccttatac acccaccctc tgcctacgtg 120
tacctctata gcttcctcgg cgggctcgcc cgccgccagg aacccacgaa accccttgca 180
ttatacgcga aaacttctga taacaaacct aaattatcac aactttcaac aatggatctc 240
ttggttctgg catcgatgaa gaacgcagcg aaatgcgata agtagtgtga attgcagaat 300
tcagtgaatc atcgaatctt tgaacgcaca ttgcggccat aggtattcct ttggccatgc 360
ctgttcgagc gtcatttaca ccctcaagcc tagcttggtg ttgggcgtct gtcccgccgt 420
tctcgcgcgc ggactcgcct caaagtcatt ggcggcggtc gtgccggccc cctcgcgcag 480
cacatttgcg cttctcggag gcccggcgga tccgcgctcc agcaagacct ttcacgactt 540
gacctcggat caggtaggga tacccgctga acttaagcat atcaataagc ggaggaa 597

<210> SEQ ID NO 251
<211> LENGTH: 596
<212> TYPE: DNA
<213> ORGANISM: Periconia macrospinosa

<400> SEQUENCE: 251
tcctccgctt attgatatgc ttaagttcag cgggtatccc tacctgatcc gaggtcaagt 60
cgtgaaaggt cttgctggag cgcggatccg ccgggcctcc gagaagcgca aatgtgctgc 120
gcgagggggc cggcacgacc gccgccaatg actttgaggc gagtccgcgc gcgagaacgg 180
cgggacagac gcccaacacc aagctaggct tgagggtgta aatgacgctc gaacaggcat 240
ggccaaagga atacctatgg ccgcaatgtg cgttcaaaga ttcgatgatt cactgaattc 300
tgcaattcac actacttatc gcatttcgct gcgttcttca tcgatgccag aaccaagaga 360
tccattgttg aaagttgtga taatttaggt ttgttatcag aagttttcgc gtataatgca 420
aggggtttcg tgggttcctg gcggcgggcg agcccgccga ggaagctata gaggtacacg 480
taggcagagg gtgggtgtat aaggagcgcc gaagcgcccc gaatgtgtaa tgatccttcc 540
gcaggttcac ctacggaaac cttgttacga cttttacttc ctctaaatga ccaaga 596

<210> SEQ ID NO 252
<211> LENGTH: 522
<212> TYPE: DNA
<213> ORGANISM: Fungal endophyte

<400> SEQUENCE: 252
gctaagcaca gtcttctgta gcagagctta acggagacct tgcacccgag agggggGagg 60
cgactataaa caagcttcta gcgcaagtca gcactcgctg gcaacacaat cgaattgcgg 120
ggacgcttta aagcctacca gtaccaacag ccccggccgg ggctgggcga gcgcagctcg 180
aggtcacaat ctgggaggat gccacaataa gcaatccgca gcggctctgg ccgtccacag 240
actaagtggt tgtgggtagg agaaccctat ctaagatata gtcgggcccg aggagagatc 300
ctcggggctt ctgcgtccgt aggtgaacct gcggaaggat cattaaaaaa ggataccggg 360
caaccggtag accccacccg tgtctctcta ctcttgttgc tttggcaggc cgtggcctcc 420
accgcgggct ctgcctgcgt gtgcctgcca gaggaccaaa ctctgaattt tagtgatgtc 480
tgagtactat ataatagtta aaactttcaa caacggatct ct 522

<210> SEQ ID NO 253
<211> LENGTH: 604
<212> TYPE: DNA
<213> ORGANISM: Fusarium nygamai

<400> SEQUENCE: 253
ttccctcccg ctttattgat atgctttaag ttcagcgggt attccctacc tgatccgagg 60
tcaacattca gaagttgggg gtttaacggc ttggccgcgc cgcgtaccag ttgcgagggt 120
tttactacta cgcaatggaa gctgcagcga gaccgccact gtatttcggg gccggcttgc 180
cgtgaggctc gccgatcccc aacaccaaac ccgggggctt gagggttgaa atgacgctcg 240

```
aacaggcatg cccgccagaa tactggcggg cgcaatgtgc gttcaaagat tcgatgattc    300
actgaattct gcaattcaca ttacttatcg cattttgctg cgttcttcat cgatgccaga    360
accaagagat ccgttgttga aagttttgat ttatttatgg ttttactcag aagttacata    420
tagaaacaga gtttaggggt cctctggcgg gccgttccgt tttaccggga gcgggctgat    480
ccgccgaggc aacaattggt atgttcacag ggtttggga gttgtaaact cggtaatgat     540
ccctccgctg gttcaccaac ggagaccttg tttacgacta tatacttcct ctaaatgacc    600
aaga                                                                 604
```

<210> SEQ ID NO 254
<211> LENGTH: 551
<212> TYPE: DNA
<213> ORGANISM: Uncultured root-associated fungus

<400> SEQUENCE: 254

```
ttcctccgct tattgatatg cttaagttca gcgggtattc ctacctgatc cgaggtcaac     60
tcgaaaaacg tcactggggg tttagcggct ggaagcccga ggaggccgcc gagcgagggc    120
gcgttttacc gcgagttact gcgctcggag ccccagcggg accgccgatg tacttggggg    180
ccccgaccgc cgggcggccg ggtgccccaa caccaagctg ggcttgagtg gtgaaatgac    240
gctcggacag gcatgccgcc ggaataccgg cgggcgcaat gtgcgttcaa agattcgatg    300
attcactgaa ttctgcaatt cacattactt atcgcatttc gctgcgttct tcatcgatgc    360
cagagccaag agatccgttg ttgaaagttt taattggtta ttttcgtcct cagagataca    420
ctagaattca gggtttatga cctccggcgg cgtcccccgg gcccggctgg gcgcggcgtc    480
ggccgccgaa gcaacgtaca ggtaaagttc acaggggttg gagttttgca actctttaat    540
gatcccctcc g                                                         551
```

<210> SEQ ID NO 255
<211> LENGTH: 602
<212> TYPE: DNA
<213> ORGANISM: Gaeumannomyces incrustans

<400> SEQUENCE: 255

```
tcttggtcat ttagaggaag taaagtcgta caaggtctcc gtggtgaacc agcggaggga     60
tcattaaaga gttgcaaaac tccaacccct gtgaacttta cctgtacgtt gcttcggcgg    120
ccgacgccgc gcccagccgg gcctggggga cgccgccgga ggttttaaac gctgaattct    180
agtgtatctc tgaggacgaa aaaaaccaat taaaactttc aacaacggat ctcttggctc    240
tggcatcgat gaagaacgca gcgaaatgcg ataagtaatg tgaattgcag aattcagtga    300
atcatcgaat ctttgaacgc acattgcgcc cgccggtatt ccggcgggca tgcctgtccg    360
agcgtcattt caccactcaa gcccagcttg gtgttggggc acccggccgc ccggcggtcg    420
gggcccccaa gtacatcggc ggtcccgctg gggctccgag cgcagtaact cgcggtaaaa    480
cgcgccctcg ctcggcggcc tcctcgggct tccagccgct aaacccccag tgacgttttt    540
cgagttgacc tcggatcagg taggaatacc cgctgaactt aagcatatca ataaggcgga    600
gg                                                                   602
```

<210> SEQ ID NO 256
<211> LENGTH: 553
<212> TYPE: DNA
<213> ORGANISM: Uncultured root-associated fungus

<400> SEQUENCE: 256
gtctggtctc gttggtgaac cagcggaggg atcattaaag agttgcaaaa actccaaccc 60
ctgtgaactt tacctgtacg ttgcttcggc ggccgacgcc gcgcccagac gggcctgggg 120
gacgccgccg gaggtcttaa accctgaatt ctagtgtatc tatgaggacg aaaaaaacca 180
attaaaactt tcaacaacgg atctcttggc tctggcatcg atgaagaacg cagcgaaatg 240
cgataagtaa tgtgaattgc agaattcagt gaatcatcga atctttgaac gcacattgcg 300
cccgccggta ttccggcggg catgcctgtc cgagcgtcat ttcaccactc aagcccagct 360
tggtgttggg gcacccggct gcccggcggt cggggccccc aagtacatcg gcggtcccgc 420
tggggctccg agcgcagtaa ctcgcggtaa aacgcgccct cgctcggcgg cctcctcggg 480
cttccagccg ctaaaccccc agtgacgttt ttcgagttga cctcggatca ggtaggaata 540
cccgctgaac tta 553

<210> SEQ ID NO 257
<211> LENGTH: 563
<212> TYPE: DNA
<213> ORGANISM: Uncultured Hypocreales

<400> SEQUENCE: 257
taaaagtcgt aacaaggtct ccgttggtga accagcggag ggatcattac cgagtttaca 60
actcccaaac ccctgtgaac ataccttact gttgcctcgg cggatcagcc cgcgcccggt 120
aaaacgggac ggcccgccag aggaccccta aactctgttt ttatttgtaa cttctgagta 180
aaaccataaa taaatcaaaa ctttcaacaa cggatctctt ggttctggca tcgatgaaga 240
acgcagcaaa atgcgataag taatgtgaat tgcagaattc agtgaatcat cgaatctttg 300
aacgcacatt gcgcccgcca gtattctggc gggcatgcct gttcgagcgt catttcaacc 360
ctcaagccct cgggtttggt gttggggatc ggcgagcctt atggcaagcc ggccccgaaa 420
tctagtggcg gtctcactgc agcctccatt gcgtagtagc taacacctcg caactggaac 480
gcggtgcggc caagccgtta aacccccaac ttctgaatgt tgacctcgga tcaggtagga 540
atacccgctg aacttaagca tat 563

<210> SEQ ID NO 258
<211> LENGTH: 602
<212> TYPE: DNA
<213> ORGANISM: Fusarium nygamai

<400> SEQUENCE: 258
tcctccgctt attgatatgc ttaagttcag cgggtattcc tacctgatcc gaggtcaaca 60
ttcagaagtt gggggtttaa cggcttggcc gcgccgcgta ccagttgcga gggttttact 120
actacgcaat ggaagctgca gcgagaccgc cactgtattt cggggccggc ttgccgtgag 180
gctcgccgat ccccaacacc aaacccgggg gcttgagggt tgaaatgacg ctcgaacagg 240
catgcccgcc agaatactgg cgggcgcaat gtgcgttcaa agattcgatg attcactgaa 300
ttctgcaatt cacattactt atcgcatttt gctgcgttct tcatcgatgc cagaaccaag 360
agatccgttg ttgaaagttt tgatttattt atggttttac tcagaagtta catatagaaa 420
cagagtttag gggtcctctg gcgggccgtt ccgttttacc gggagcgggc tgatccgccg 480
aggcaacaat tggtatgttc acagggggtt tgggagttgt aaactcggta atgatccctc 540
cgctggttca ccaacggaga accttggtta cgaacttttt acttcctcta aatgaccaaa 600
ga 602

<210> SEQ ID NO 259
<211> LENGTH: 598
<212> TYPE: DNA
<213> ORGANISM: Fusarium moniliformae

<400> SEQUENCE: 259

```
ttcctccgct tattgatatg cttaagttca gcgggtattc ctacctgatc cgaggtcaac     60
attcagaagt tgggggttta acggcttggc cgcgccgcgt accagttgcg agggttttac    120
tactacgcaa tggaagctgc agcgagaccg ccactatatt tcggggccgg cttgccgcga    180
gggctcgccg atccccaaca ccaaacccga gggcttgagg gttgaaatga cgctcgaaca    240
ggcatgcccg ccagaatact ggcgggcgca atgtgcgttc aaagattcga tgattcactg    300
aattctgcaa ttcacattac ttatcgcatt ttgctgcgtt cttcatcgat gccagaacca    360
agagatccgt tgttgaaagt tttgatttat ttatggtttt actcagaagt tacatataga    420
aacagagttt aggggtcctc tggcgggccg tcccgtttta ccgggagcgg gctgatccgc    480
cgaggcaaca attggtatgt tcacaggggt ttgggagttg taaactcggt aatgatccct    540
ccgctggttc accaacggag accttgttac gacttttact tcctataaat gaccaaga      598
```

<210> SEQ ID NO 260
<211> LENGTH: 599
<212> TYPE: DNA
<213> ORGANISM: Sordariomycete sp.

<400> SEQUENCE: 260

```
tcttggtcat ttagaggaag taaaaagtcg taacaaggtc tccgttggtg aacccagcgg     60
agggatcatt accgagttta caactcccaa acccctgtga acataccaat tgttgcctcg    120
gcggatcagc ccgctcccgg taaaacggaa cggcccgcca gaggacccct aaactctgtt    180
tctatatgta acttctgagt aaaaccataa ataaatcaaa actttcaaca acggatctct    240
tggttctggc atcgatgaag aacgcagcaa aatgcgataa gtaatgtgaa ttgcagaatt    300
cagtgaatca tcgaatcttt gaacgcacat tgcgcccgcc agtattctgg cgggcatgcc    360
tgttcgagcg tcatttcaac cctcaagccc ccgggtttgg tgttggggat cggcgagcct    420
cacggcaagc cggccccgaa atacagtggc ggtctcgctg cagcttccat tgcgtagtag    480
taaaaccctc gcaactggta cgcggcgcgg ccaagccgtt aaacccccaa cttctgaatg    540
ttgacctcgg atcaggtagg aatacccgct gaacttaagc atatcaataa gcggaggaa     599
```

<210> SEQ ID NO 261
<211> LENGTH: 614
<212> TYPE: DNA
<213> ORGANISM: Magnaporthe rhizophila

<400> SEQUENCE: 261

```
cctcttggtc atttagaggg aaagtaaaaa gtcgtaaaca aggtctccgt tggtgaacca     60
gcggagggga tcattaaaga gttgcaaaac tccaacccct gtgaacttta cctgtacgtt    120
gcttcggcgg ccgacgccgc gcccagccgg gcccggggga cgccgccgga ggtcataaac    180
cctgaattct agtgtatctc tgaggacgaa aacaaccaat taaaactttc aacaacggat    240
ctcttggctc tggcatcgat gaagaacgca gcgaaatgcg ataagtaatg tgaattgcag    300
aattcagtga atcatcgaat ctttgaacgc acattgcgcc cgccggtatt ccggcgggca    360
tgcctgtccg agcgtcattt caccactcaa gcccagcttg gtgttggggc acccggccgc    420
ctggcggtcg gggcccccaa gtacatcggc ggtcccgctg gggctccgag cgcagtaact    480
```

cgcggtaaaa cgcgccctcg ctcggcggcc tcctcgggct tccagccgct aaacccccca 540
gtgacgtttt tcgagttgac ctcggatcag gtaggaatac ccgctgaact taagcatatc 600
aataagcgga ggaa 614

<210> SEQ ID NO 262
<211> LENGTH: 561
<212> TYPE: DNA
<213> ORGANISM: Fusarium oxysporum

<400> SEQUENCE: 262
ttcctccgct tattgatatg cttaagttca gcgggtattc ctacctgatc cgaggtcaac 60
attcagaagt tggggtttaa cggcgtggcc gcgacgatta ccagtaacga gggttttact 120
actacgctat ggaagctcga cgtgaccgcc aatcaatttg ggaacgcga attaacgcga 180 gtcccaacac caagctgtgc ttgagggttg aaatgacgct cgaacaggca tgcccgccag 240
aatactggcg ggcgcaatgt gcgttcaaag attcgatgat tcactgaatt ctgcaattca 300
cattacttat cgcattttgc tgcgttcttc atcgatgcca gaaccaagag atccgttgtt 360
gaaagttttg atttatttat ggttttactc agaagttaca tatagaaaca gagtttaggg 420
gtcctctggc gggccgtccc gttttaccgg gagcgggctg atccgccgag gcaacaagtg 480
gtatgttcac aggggtttgg gagttgtaaa ctcggtaatg atccctccgc tggttcacca 540
acggagacct tgttacgact t 561

<210> SEQ ID NO 263
<211> LENGTH: 1042
<212> TYPE: DNA
<213> ORGANISM: Mycorrhizal fungal sp.

<400> SEQUENCE: 263
ttccaaaggg ttttgctttc acaattacgt gttagctaaa tagatccttc cacagagtta 60
cttattgaag cctatgtagc ctattcaaat ggctaggtcc cacgacaata aataaagggt 120
accgttgcaa gtcagcttta agcgctggca acatgatcga attgcgggga tctcctaatg 180
cttattagta ccaactattc ttacgagggt agggcctggt ttcaggatgg tcaaaaccta 240
atgagatatt acaatggatt atccgcagcg aagcctttgt gtttaccata aaggaccgtt 300
cacagactaa gtgatcatgg gcagtaaacc tgtctaagat atagtcggtc tcgttgagaa 360
atcaccgagg aaagtcactt gggttctaaa cattatgttt tgcagtttca aagcatcgcg 420
aaggcttgat gtattcgaat ctatagtaac aaatctatct catctccgct cactgggagt 480
accatggtgg aatagaagat ggaaaattcc cgccccaact acccggcgat cccccaaaac 540
taccctcccc caaccgctcc tcggcctcag cctcggtctc atactgtgaa gcctcctctg 600
cttcactgtt gtccttgaaa tctgagagcc atgtgtagaa gtcaacagag cacatcttca 660
tattatggag ctctgcgcaa gtcggcatct tgacatgatc aaattgtcgt tgagcagctt 720
ggactttggg gaggggtgat tttattgtat atatcggtgt agttgacttc ggggcgatac 780
tggcgcttga gaatggtgtc gatgtacaaa aaacaatggt gtcgagccct tgttgtactc 840
cccggcctct gcaatagtat ggtttgggat taatgttact agccaagtta gtggatgata 900
tttgcgcaat gttgtggaaa actttaccgg tgatgtcctc cttgcccgca gagattcgag 960
tggtgagaaa atctcctgat cgggtgcccg aagacatagg taccggtgct gatgggcata 1020
gggccaccag gtaagaccaa at 1042

<210> SEQ ID NO 264
<211> LENGTH: 598
<212> TYPE: DNA
<213> ORGANISM: Sordariomycete sp.

<400> SEQUENCE: 264
ttcctccgcc ttattgatat gcttaagttc agcgggtatt cctacctgat ccgaggtcaa 60
cattcagaag ttgggggttt aacggcttgg ccgcgccgcg taccagttgc gagggtttta 120
ctactacgca atggaagctg cagcgagacc gccactgtat ttcggggccg gcttgccgtg 180
aggctcgccg atccccaaca ccaaacccgg gggcttgagg gttgaaatga cgctcgaaca 240
ggcatgcccg ccagaatact ggcgggcgca atgtgcgttc aaagattcga tgattcactg 300
aattctgcaa ttcacattac ttatcgcatt ttgctgcgtt cttcatcgat gccagaacca 360
agagatccgt tgttgaaagt tttgatttat ttatggtttt actcagaagt tacatataga 420
aacagagttt aggagtcctc tggcgggccg ttccgtttta ccgggagcgg gctgatccgc 480
cgaggcaaca attggtatgt tcacaggggt ttgggagttg taaactcggt aatgatccct 540
ccgctggttc accaacggag accttgttac gacttttact tcctctaaat gaccaaga 598

<210> SEQ ID NO 265
<211> LENGTH: 598
<212> TYPE: DNA
<213> ORGANISM: Uncultured Hypocreales

<400> SEQUENCE: 265
tcttggtcat ttagaggaag taaaagtcgt aacaaggtct ccgttggtga accagcggag 60
ggatcattac cgagtttaca actcccaaac ccctgtgaac ataccttact gttgcctcgg 120
cggatcagcc cgcgcccggt aaaacgggac ggcccgccag aggaccccta aactctgttt 180
ttatttgtaa cttctgagta aaaccataaa taaatcaaaa ctttcaacaa cggatctctt 240
ggttctggca tcgatgaaga acgcagcaaa atgcgataag taatgtgaat tgcagaattc 300
agtgaatcat cgaatctttg aacgcacatt gcgcccgcca gtattctggc gggcatgcct 360
gttcgagcgt catttcaacc ctcaagccct cgggtttggt gttggggatc ggcgagcctt 420
atggcaagcc ggccccgaaa tctagtggcg gtctcactgc agcctccatt gcgtagtagc 480
taacacctcg caactggaac gcggtgcggc caagccgtta aacccccaac ttctgaatgt 540
tgacctcgga tcaggtagga atacccgctg aacttaagca tatcaataag cggaggaa 598

<210> SEQ ID NO 266
<211> LENGTH: 581
<212> TYPE: DNA
<213> ORGANISM: Fusarium nygamai

<400> SEQUENCE: 266
tcctccgcct attgatatgc ttaagttcag cgggtattcc tacctgatcc gaggtcaaca 60
ttcagaagtt gggggtttaa cggcttggcc gcgccgcgta ccagttgcga gggttttact 120
actacgcaat ggaagctgca gcgagaccgc cactgtattt cggggccggc ttgccgtgag 180
gctcgccgat ccccaacacc aaacccgggg gcttgagggt tgaaatgacg ctcgaacagg 240
catgcccgcc agaatactgg cgggcgcaat gtgcgttcaa agattcgatg attcactgaa 300
ttctgcaatt cacattactt atcgcatttt gctgcgttct tcatcgatgc cagaaccaag 360
agatccgttg ttgaaagttt tgatttattt atggttttac tcagaagtta catatagaaa 420
cagagtttag ggtcctctgg cgggccgtt ccgttttacc gggagcgggc tgatccgccg 480
aggcaacaat tggtatgttc acaggggttt gggagttgta aactcggtaa tgatccctcc 540
gctggttcac caacggagac cttgttacga cttttactac c 581

<210> SEQ ID NO 267
<211> LENGTH: 586
<212> TYPE: DNA
<213> ORGANISM: Fusarium nygamai

<400> SEQUENCE: 267
agttcagcgg gtattcctac ctgatccgag gtcaacattc agaagttggg ggtttaacgg 60
cttggcccgc gccgcgtacc agttgcgagg gttttactac tacgcaatgg aagctgcagc 120
gagaccgcca ctgtatttcg gggccggctt gccgtggggc tcgccgatcc ccaacaccaa 180
acccgggggc ttgagggttg aaatgacgct cgaacaggca tgcccgccag aatactggcg 240
ggcgcaatgt gcgttcaaag attcgatgat tcactgaatt ctgcaattca cattacttat 300
cgcattttgc tgcgttcttc atcgatgcca gaaccaagag atccgttgtt gaaagttttg 360
atttatttat ggttttactc agaagttaca tatagaaaca gagtttaggg gtcctctggc 420
gggccgttcc gttttaccgg gagcgggctg atccgccgag gcaacaattg gtatgttcac 480
aggggtttgg gagttgtaaa cctcggtaat gatccctccg ctcgggttcc acccaacgga 540 aaccctttt tacgaccttt tactttcctc taaaatgacc aaagaa 586

<210> SEQ ID NO 268
<211> LENGTH: 598
<212> TYPE: DNA
<213> ORGANISM: Fusarium nygamai

<400> SEQUENCE: 268
tcctccgctt attgatatgc ttaagttcag cgggtattcc tacctgatcc gaggtcaaca 60
ttcagaagtt gggggtttaa cggcttggcc gcgccgcgta ccagttgcga gggttttact 120
actacgcaat ggaagctgca gcgagaccgc cactgtattt cggggccggc ttgccgtgag 180
gctcgccgat ccccaacacc aaacccgggg gcttgagggt tgaaatgacg ctcgaacagg 240
catgcccgcc agaatactgg cgggcgcaat gtgcgttcaa agattcgatg attcactgaa 300
ttctgcaatt cacattactt atcgcatttt gctgcgttct tcatcgatgc cagaaccaag 360
agatccgttg ttgaaagttt tgatttattt atggttttac tcagaagtta catatagaaa 420
cagagtttag gggtcctctg gcgggccgtt ccgttttacc gggagcgggc tgatccgccg 480
aggcaacaat tggtatgttc acaggggttt gggagttgta aactcggtaa tgatccctcc 540
gctggttcac caacggagac cttgttacga ctttttactt tcctctaaat gaccaaga 598

<210> SEQ ID NO 269
<211> LENGTH: 500
<212> TYPE: DNA
<213> ORGANISM: Fusarium nygamai

<400> SEQUENCE: 269
tcccaaaccc ctgtgaacat accaattgtt gcctcggcgg atcagcccgc tcccggtaaa 60
acggaacggc ccgccagagg acccctaaac tctgtttcta tatgtaactt ctgagtaaaa 120
ccataaataa atcaaaactt tcaacaacgg atctcttggt tctggcatcg atgaagaacg 180
cagcaaaatg cgataagtaa tgtgaattgc agaattcagt gaatcatcga atctttgaac 240
gcacattgcg cccgccagta ttctggcggg catgcctgtt cgagcgtcat ttcaaccctc 300

```
aagcccccgg gtttggtgtt ggggatcggc gagcctcacg gcaagccggc cccgaaatac    360

agtggcggtc tcgctgcagc ttccattgcg tagtagtaaa accctcgcaa ctggtacgcg    420

gcgcggccaa gccgttaaac ccccaacttc tgaatgttga cctcggatca ggtaggaata    480

cccgctgaac ttaagcatat                                                500
```

<210> SEQ ID NO 270
<211> LENGTH: 597
<212> TYPE: DNA
<213> ORGANISM: Fusarium proliferatum

<400> SEQUENCE: 270

```
ttcctccgct tattgatatg cttaagttca gcgggtattc ctacctgatc cgaggtcaac     60

attcagaagt tgggggttta acggcttggc cgcgccgcgt accagttgcg agggttttac    120

tactacgcaa tggaagctgc agcgagaccg ccactgtatt tcggggccgg cttgccgtga    180

ggctcgccga tccccaacac caaacccggg ggcttgaggg ttgaaatgac gctcgaacag    240

gcatgcccgc cagaatactg gcgggcgcaa tgtgcgttca aagattcgat gattcactga    300

attctgcaat tcacattact tatcgcattt tgctgcgttc ttcatcgatg ccagaaccaa    360

gagatccgtt gttgaaagtt ttgatttatt tatggtttta ctcagaagtt acatatagaa    420

acagagttta ggggtcctct ggcgggccgt tccgttttac cgggagcggg ctgatccgcc    480

gaggcaacaa ttggtatgtt cacaggggtt tgggagttgt aaactcggta atgatccctc    540

cgctggttca ccaacggaga ccttgttacg acttttactt cctctaaatg accaaga       597
```

<210> SEQ ID NO 271
<211> LENGTH: 556
<212> TYPE: DNA
<213> ORGANISM: Magnaporthe rhizophila

<400> SEQUENCE: 271

```
taggtctcgt tggtgaccag cggagggatc attaaagagt tgcaaaactc caacccctgt     60

gaactttacc tgtacgttgc ttcggcggcc gacgcctcgc ccagccgggc ctgggggacg    120

ccgccggagg ttttaaaccc tgaattctag tgtatctctg aggacgaaaa tagccaatta    180

aaactttcaa caacggatct cttggctctg gcatcgatga agaacgcagc gaaatgcgat    240

aagtaatgtg aattgcagaa ttcagtgaat catcgaatct ttgaacgcac attgcgcccg    300

ccggtattcc ggcgggcatg cctgtccgag cgtcatttca ccactcaagc ccagcttggt    360

gttggggcac ccggccgcct ggcggtcggg gcccccaagt acatcggcgg tcctgctggg    420

gctccgagcg cagtaactcg cggtaaaacg cgccctcgct cggcggcctc ctcgggcttc    480

cagccgctaa acccccagtg acgtttttcg agttgacctc ggatcaggta ggaatacccg    540

ctgaacttaa gcatat                                                    556
```

<210> SEQ ID NO 272
<211> LENGTH: 597
<212> TYPE: DNA
<213> ORGANISM: Magnaporthe rhizophila

<400> SEQUENCE: 272

```
ttcctccgct tattgatatg cttaagttca gcgggtattc ctacctgatc cgaggtcaac     60

attcagaagt tgggggttta acggcttggc cgcgccgcgt accagttgcg agggttttac    120

tactacgcaa tggaagctgc agcgagaccg ccactatatt tcggggccgg cttgccgtga    180

ggctcgccga tccccaacac caaacccgag ggcttgaggg ttgaaatgac gctcgaacag    240
```

gcatgcccgc cagaatactg gcgggcgcaa tgtgcgttca aagattcgat gattcactga 300
attctgcaat tcacattact tatcgcattt tgctgcgttc ttcatcgatg ccagaaccaa 360
gagatccgtt gttgaaagtt ttgatttatt tatggtttta ctcagaagtt acatatagaa 420
acagagttta ggggtcctct ggcgggccgt cccgttttac cgggagcggg ctgatccgcc 480
gaggcaacaa ttggtatgtt cacaggggtt tgggagttgt aaactcggta atgatccctc 540
cgctggttca ccaacggaga ccttgttacg acttttactt cctctaaatg accaaga 597

<210> SEQ ID NO 273
<211> LENGTH: 597
<212> TYPE: DNA
<213> ORGANISM: Fusarium moniliformae

<400> SEQUENCE: 273
ttcctccgct tattgatatg cttaagttca gcgggtattc ctacctgatc cgaggtcaac 60
attcagaagt tgggggttta acggcttggc cgcgccgcgt accagttgcg agggttttac 120
tactacgcaa tggaagctgc agcgagaccg ccactatatt tcggggccgg cttgccgtga 180
ggctcgccga tccccaacac caaacccgag ggcttgaggg ttgaaatgac gctcgaacag 240
gcatgcccgc cagaatactg gcgggcgcaa tgtgcgttca aagattcgat gattcactga 300
attctgcaat tcacattact tatcgcattt tgctgcgttc ttcatcgatg ccagaaccaa 360
gagatccgtt gttgaaagtt ttgatttatt tatggtttta ctcagaagtt acatatagaa 420
acagagttta ggggtcctct ggcgggccgt cccgttttac cgggagcggg ctgatccgcc 480
gaggcaacaa ttggtatgtt cacaggggtt tgggagttgt aaactcggta atgatccctc 540
cgctggttca ccaacggaga ccttgttacg acttttactt cctctaaatg accaaga 597

<210> SEQ ID NO 274
<211> LENGTH: 542
<212> TYPE: DNA
<213> ORGANISM: Fusarium nygamai

<400> SEQUENCE: 274
tatgcttaag ttcagcgggt attcctacct gatccgaggt caacattcag aagttggggg 60
tttaacggct tggccgcgcc gcgtaccagt tgcgagggtt ttactactac gcaatggaag 120
ctgcagcgag accgccactg tatttcgggg ccggcttgcc gtgaggctcg ccgatcccca 180
acaccaaacc cgggggcttg agggttgaaa tgacgctcga acaggcatgc ccgccagaat 240
actggcgggc gcaatgtgcg ttcaaagatt cgatgattca ctgaattctg caattcacat 300
tacttatcgc attttgctgc gttcttcatc gatgccagaa ccaagagatc cgttgttgaa 360
agttttgatt tatttatggt tttactcaga agttacatat agaaacagag tttaggggtc 420
ctctggcggg ccgttccgtt ttaccgggag cgggctgatc cgccgaggca acaattggta 480
tgttcacagg ggtttgggag ttgtaaactc ggtaatgatc cctccgctgg ttcaccaacg 540
ga 542

<210> SEQ ID NO 275
<211> LENGTH: 541
<212> TYPE: DNA
<213> ORGANISM: Uncultured root-associated fungus

<400> SEQUENCE: 275
gtctccgttg gtgaccagcg gagggatcat taaagagttg caaaactcca acccctgtga 60

```
actttacctg taacgttgct tcggcggccg acgccgcgcc cagccgggcc tgggggacgc    120

cgccggaggt tttaaaccct gaattctagt gtatctctga ggacggaaaa aaacacaatt    180

aaaactttca acaacggatc tcttggctct ggcatcgatg aagaacgcag cgaaatgcga    240

taagtaatgt gaattgcaga attcagtgaa tcatcgaatc tttgaacgca cattgcgccc    300

gccggtattc cggcgggcat gcctgtccga gcgtcatttc accactcaag cccagcttgg    360

tgttggggca cccggccgcc tggcggtcgg ggcccccaag tacatcggcg gtcctgctgg    420

ggctccgagc gcagtaactc gcgggtaaaa cgcgccctcg ctcggcggcc tcctcgggct    480

tccagccgct aaaccccag tgacgttttt cgagttgacc tcggatcagg taggaatacc    540

c                                                                    541
```

<210> SEQ ID NO 276
<211> LENGTH: 584
<212> TYPE: DNA
<213> ORGANISM: Fusarium sp.

<400> SEQUENCE: 276

```
ttcctccgct tattgatatg cttaagtttc agcgggtatt cctacctgat ccgaggtcaa     60

cattcagaag ttggggttta acggcgtggc cgcgacgatt accagtaacg agggttttac    120

tactacgcta tggaagctcg acgtgaccgc caatcaattt ggggaacgcg aattaacgcg    180

agtcccaaca ccaagctgtg cttgagggtt gaaatgacgc tcgaacaggc atgcccgcca    240

gaatactggc gggcgcaatg tgcgttcaaa gattcgatga ttcactgaat tctgcaattc    300

acattactta tcgcattttg ctgcgttctt catcgatgcc agaaccaaga gatccgttgt    360

tgaaagtttt gatttattta tggttttact cagaagttac atatagaaac agagtttagg    420

ggtcctctgg cgggccgtcc cgttttaccg ggagcgggct gatccgccga ggcaacaagt    480

ggtatgttca caggggtttg ggagttgtaa actcggtaat gatccctccg ctggttcacc    540

aacggagacc ttgttacgac ttttacttcc tctaatgacc aaga                     584
```

<210> SEQ ID NO 277
<211> LENGTH: 538
<212> TYPE: DNA
<213> ORGANISM: Fusarium oxysporum f. ciceris

<400> SEQUENCE: 277

```
gccgagttta caactcccaa acccctgtga acataccaat tgttgcctcg gcggatcagc     60

ccgctcccgg taaaacggaa cggcccgcca gaggacccct aaactctgtt tctatatgta    120

acttctgagt aaaaacataa ataaatcaaa actttcaaca acggatctct tggttctggc    180

atcgatgaag aacgcagcaa aatgcgataa gtaatgtgaa ttgcagaatt cagtgaatca    240

tcgaatcttt gaacgcacat tgcgcccgcc agtattctgg cgggcatgcc tgttcgagcg    300

tcatttcaac cctcaagccc ccgggtttgg tgttggggat cggcgagcct cacggcaagc    360

cggccccgaa aatacagtgg cggtctcgct gcagcttcca ttgcgtagta gtaaaaccct    420

cgcaactggt acgcggggcg gccaaagccg ttaaaccccc caacttctga atgttgacct    480

cgggatccag gtagggaata cccgctgaac tttaagcata tcaataaggc ggaggaaa      538
```

<210> SEQ ID NO 278
<211> LENGTH: 604
<212> TYPE: DNA
<213> ORGANISM: Microdochium sp.

<400> SEQUENCE: 278

```
tcttggtcat ttagaggaag taaaagtcgt aacaaggtct ccgtaggtga acctgcggag    60
ggatcattac tgagttttca actctccaaa ccatgtgaac ttaccactgt tgcctcggtg   120
gttagtgctc tccctcgggg gggggtgctg ccgccggtgg actactaaac tcttgttaat   180
ttatggcatt ctgaatcata actaagaaat aagttaaaac tttcaacaac ggatctcttg   240
gttctggcat cgatgaagaa cgcagcgaaa tgcgataagt aatgtgaatt gcagaattca   300
gtgaatcatc gaatctttga acgcacattg cgcccattag tattctagtg ggcatgcctg   360
ttcgagcgtc atttcaaccc ttaagcctag cttagcgttg ggagactgcg ctaaaccgca   420
gctcctcaaa accagtggcg gagtcctctc gtgctctgag cgtagtaatt ctttatctcg   480
cttctgcaag tacggttgac gacagccata aaccgcaccc tctcgggggg cactttttaa   540
tggttgacct cggatcaggt aggaataccc gctgaactta agcatatcaa taagcggagg   600
aaaa                                                                604
```

<210> SEQ ID NO 279
<211> LENGTH: 526
<212> TYPE: DNA
<213> ORGANISM: Fusarium acuminatum

<400> SEQUENCE: 279

```
gggttctact gaatccgagt caactcgaaa aacgtcactg ggggtttagc ggctggaagc    60
ccgaggaggc cgccgagcga gggcgcgttt taccgcgagt tactgcgctc ggagccccag   120
cgggaccgcc gatgtacttg ggggccccga ccgccgggcg gccgggtgcc ccaacaccaa   180
gctgggcttg agtggtgaaa tgacgctggg acaggcatgc ccgccggaat accggcgggc   240
gcaatgtgcg ttcaaagatt cgatgattca ctgaattctg caattcacat tacttatcgc   300
atttcgctgc gttcttcatc gatgccagag ccaagagatc cgttgttgaa agttttaatt   360
ggtttttttc gtcctcagag atacactaga attcagggtt taaaacctcc ggcggcgtcc   420
cccaggcccg gctgggcgcg gcgtcggccg ccgaagcaac gtacaggtaa agttcacagg   480
ggttggagtt ttgcaactct ttaatgatcc ctccgctggt caccaa                  526
```

<210> SEQ ID NO 280
<211> LENGTH: 589
<212> TYPE: DNA
<213> ORGANISM: Fusarium proliferatum

<400> SEQUENCE: 280

```
tcttggtcat ttagaggaag taaaagtcgt aacaaggtct cccgttggtg aaccagcgga    60
gggatcatta ccgagtttac aactcccaaa cccctgtgaa catacettta tgttgcctcg   120
gcggatcagc ccgcgccccg taaaacggga cggcccgccg caggaaaccc taaactctgt   180
ttttagtgga acttctgagt ataaaaaaca aataaatcaa aactttcaac aacggatctc   240
ttggttctgg catcgatgaa gaacgcagca aaatgcgata agtaatgtga attgcagaat   300
tcagtgaatc atcgaatctt tgaacgcaca ttgcgcccgc cagtattctg gcgggcatgc   360
ctgttcgagc gtcatttcaa ccctcaagcc cagcttggtg ttgggatctg tttgtcacaa   420
aacagtcctc aaattgattg gcggtcacgt cgagcttcca tagcgtagta atttacacat   480
cgttactggt aatcgtcgcg gccacgccgt taaaccccaa cttctgaatg ttgacctcgg   540
atcaggtagg aatacccgct gaacttaagc atatcaataa gcggaggaa               589
```

<210> SEQ ID NO 281

-continued

<211> LENGTH: 882
<212> TYPE: DNA
<213> ORGANISM: Fusarium moniliformae

<400> SEQUENCE: 281
ttcctcccgc ttattgatat gcttaagttc agcgggtagt cctaccaatc tgaggccgat 60
gaattattaa aatcccttct ttgcaagaag caaagcatgg gcggggttca gaagcacgcc 120
aaacagcaag atcgttgcgt ccagctcttg ccctttctcc gcctccgaag tcctgatatt 180
atcaaatctt ctccgggaat ggagagcgta aggttagctg ggtatcgctc ccggatccga 240
gatcaacatt cagaagttgg gggtttaacg gcttggccgc gccgcgtacc agttgcgagg 300
gttttmctac tacgcaatgg aagctgcagc gagaccgcca ctgtatttcg gggccggctt 360
gccgtgagga acgccgatcc ccaacaccaa acccgggggc ttgagggttg aaatgacgct 420
cgaacaggca tgcccgccag aatactggcg ggcgcaatgt gcgttcaaag attcgatgat 480
tcactgaatt ctgcaattca cattacttat cgcattttgc tgcgttcttc atcgatgcca 540
gaaccaagag atccgttgtt gaaagttttg atttatttat ggttttactc agaagttaca 600
tatagaaaca gagtttaggg gacctctggc gggccgttcc gttttaccgg gagcgggctg 660
atccgccgag gcaacaattg gtatgttcac aggggtttgg gagttgtaaa ctcggtaatg 720
atccctccgc tggttcacca acggagacct tgttacgact tttacttccc gtaaatgacc 780
aagaggacac ctttcgcgtt ctttgacagg ctctcaaccg atgcaaccgt gttaaaaagg 840
tagctcaagt ttagttggac aggtgcgagc cacacctcag aa 882

<210> SEQ ID NO 282
<211> LENGTH: 579
<212> TYPE: DNA
<213> ORGANISM: Uncultured root-associated fungus

<400> SEQUENCE: 282
ttcctccgcc ttattgatat gcttaagttc agcgggtatt cctacctgat ccgaggtcaa 60
cattcagaag ttgggggttt aacggcttgg ccgcgccgcg ttccagttgc gagggtttta 120
ctactacgca atggaggctg cagcgagacc gccactagat ttcggggccg gcttgccgca 180
agggctcgcc gatccccaac accaaacccg agggcttgag ggttgaaatg acgctcgaac 240
aggcatgccc gccagaatac tggcgggcgc aatgtgcgtt caaagattcg atgattcact 300
gaattctgca attcacatta cttatcgcat tttgctgcgt tcttcatcga tgccagaacc 360
aagagatccg ttgttgaaag ttttgattta tttatggttt tactcagaag ttacatatag 420
aaacagagtt taggggtcct ctggcgggcc gtcccgtttt accgggagcg ggctgatccg 480
ccgaggcaac aagtggtatg ttcacagggg tttgggagtt gtaaactcgg taatgatccc 540
tccgctggtt caccaacgga gaccttgtta cgacttttta 579

<210> SEQ ID NO 283
<211> LENGTH: 519
<212> TYPE: DNA
<213> ORGANISM: Uncultured root-associated fungus

<400> SEQUENCE: 283
agttgcaaaa ctccaacccc tgtgaacttt acctgtacgt tgcttcggcg gccgacgccg 60
cgcccagccg ggcccggggg acgccgccgg aggtcataaa ccctgaattc tagtgtatct 120
ctgaggacga aaataaccaa ttaaaacttt caacaacgga tctcttggct ctggcatcga 180
tgaagaacgc agcgaaatgc gataagtaat gtgaattgca gaattcagtg aatcatcgaa 240
tctttgaacg cacattgcgc ccgccggtat tccggcgggc atgcctgtcc gagcgtcatt 300
tcaccactca agcccagctt ggtgttgggg cacccggccg cccggcggtc ggggccccca 360
agtacatcgg cggtcccgct ggggctccga gcgcagtaac tcgcggtaaa acgcgccctc 420
gctcggcggc ctcctcgggc ttccagccgc taaacccccca gtgacgtttt tcgagttgac 480
ctcggatcag gtaggaatac ccgctgaact taagcatat 519

<210> SEQ ID NO 284
<211> LENGTH: 547
<212> TYPE: DNA
<213> ORGANISM: Fusarium nygamai

<400> SEQUENCE: 284
accagcggag ggatcattac cgagtttaca actcccaaac ccctgtgaac ataccaattg 60
ttgcctcggc ggatcagccc gctcccggta aaacgggacg gcccgccaga ggacccctaa 120
actctgtttc tatatgtaac ttctgagtaa aaccataaat aaatcaaaac tttcaacaac 180
ggatctcttg gttctggcat cgatgaagaa cgcagcaaaa tgcgataagt aatgtgaatt 240
gcagaattca gtgaatcatc gaatctttga acgcacattg cgcccgccag tattctggcg 300
ggcatgcctg ttcgagcgtc atttcaaccc tcaagccccc gggtttggtg ttggggatcg 360
gcgagcctca cggcaagccg gccccgaaat acagtggcgg tctcgctgca gcttccattg 420
cgtagtagta aaaccctcgc aactggtacg cggcgcggcc aagccgttaa acccccaact 480
tctgaatgtt gacctcggat caggtaggaa tacccgctga acttaagcat atcaataagc 540
ggaggaa 547

<210> SEQ ID NO 285
<211> LENGTH: 472
<212> TYPE: DNA
<213> ORGANISM: Fusarium nygamai

<400> SEQUENCE: 285
aagttggggg tttaacggct tggccgcgcc gcgtaccagt tgcgagggtt ttactactac 60
gcaatggaag ctgcagcgag accgccactg tatttcgggg ccggcttgcc gtgaggctcg 120
ccgatcccca acaccaaacc cgggggcttg agggttgaaa tgacgctcga acaggcatgc 180
ccgccagaat actggcgggc gcaatgtgcg ttcaaagatt cgatgattca ctgaattctg 240
caattcacat tacttatcgc attttgctgc gttcttcatc gatgccagaa ccaagagatc 300
cgttgttgaa agttttgatt tatttatggt tttactcaga agttacatat agaaacagag 360
tttaggggtc ctctggcggg ccgttccgtt ttaccgggag cgggctgatc cgccgaggca 420
acaattggta tgttcacagg ggtttgggag ttgtaaactc ggtaatgatc cc 472

<210> SEQ ID NO 286
<211> LENGTH: 548
<212> TYPE: DNA
<213> ORGANISM: Magnaporthe rhizophila

<400> SEQUENCE: 286
gagggatcat taaagagttg caaaactcca acccctgtga actttacctg tacgttgctt 60
cggcggccga cgccgcgccc agccgggcct gggggacgcc gccggaggtt ttaaaccctg 120
aattctagtg tatctctgag gacgaaaata accaattaaa actttcaaca acggatctct 180
tggctctggc atcgatgaag aacgcagcga aatgcgataa gtaatgtgaa ttgcagaatt 240
cagtgaatca tcgaatcttt gaacgcacat tgcgcccgcc ggtattccgg cgggcatgcc 300
tgtccgagcg tcatttcacc actcaagccc agcttggtgt tggggcaccc ggccgcctgg 360
cggtcggggc ccccaagtac atcggcggtc ctgctggggc tccgagcgca gtaactcgcg 420
gtaaaacgcg ccctcgctcg gcggcctcct cgggcttcca gccgctaaac cccagtgac 480 gtttttcgag ttgacctcgg atcaggtagg aatacccgct gaacttaagc atatcaataa 540
gcggagga 548

<210> SEQ ID NO 287
<211> LENGTH: 583
<212> TYPE: DNA
<213> ORGANISM: Uncultured Hypocreales

<400> SEQUENCE: 287
ttcctccgct tattgatatg cttaagttca gcgggtattc ctacctgatc cgaggtcaac 60
attcagaagt tgggggttta acggcttggc cgcaccgcgt tccagttgcg aggtgttagc 120
tactacgcaa tggaggctgc agtgagaccg ccactagatt tcggggccgg cttgccataa 180
ggctcgccga tccccaacac caaacccgag ggcttgaggg ttgaaatgac gctcgaacag 240
gcatgcccgc cagaatactg gcgggcgcaa tgtgcgttca aagattcgat gattcactga 300
attctgcaat tcacattact tatcgcattt tgctgcgttc ttcatcgatg ccagaaccaa 360
gagatccgtt gttgaaagtt ttgatttatt tatggtttta ctcagaagtt acaaataaaa 420
acagagttta ggggtcctct ggcgggccgt cccgttttac cgggcgcggg ctgatccgcc 480
gaggcaacag taaggtatgt tcacaggggt ttgggagttg taaactcggt aatgatccct 540
ccgctggttc accaacggag accttgttac gacttttact tcc 583

<210> SEQ ID NO 288
<211> LENGTH: 549
<212> TYPE: DNA
<213> ORGANISM: Magnaporthe rhizophila

<400> SEQUENCE: 288
gggatcatta aagagttgca aaactccaac ccctgtgaac tttacctgta cgttgcttcg 60
gcggccgacg ccgcgcccag ccgggcccgg gggacgccgc cggaggtcat aaaccctgaa 120
ttctagtgta tctctgagga cgaaaataac caattaaaac tttcaacaac ggatctcttg 180
gctctggcat cgatgaagaa cgcagcgaaa tgcgataagt aatgtgaatt gcagaattca 240
gtgaatcatc gaatctttga acgcacattg cgcccgccgg tattccggcg ggcatgcctg 300
tccgagcgtc atttcaccac tcaagcccag cttggtgttg gggcacccgg ccgcccggcg 360
gtcggggccc ccaagtacat cggcggtccc gctggggctc cgagcgcagt aacacgcggt 420
aaaacgcgcc ctcgctcggc ggcctcctcg ggcttccagc cgctaaaacc cccagtgacg 480
tttttcgagt tgacctcgga tcaggtagga atacccgctg aacttaagca tatcaataag 540
cgggaggaa 549

<210> SEQ ID NO 289
<211> LENGTH: 581
<212> TYPE: DNA
<213> ORGANISM: Uncultured soil fungus

<400> SEQUENCE: 289
tcttggtcat ttagaggaag taaaagtcgt aacaaggtct ccgttggtga accagcggag 60
ggatcattac cgagtttaca actcccaaac ccctgtgaac ataccacttg ttgcctcggc 120

```
ggatcagccc gctcccggta aaacgggacg gcccgccaga ggacccctaa actctgtttc    180

tatatgtaac ttctgagtaa aaccataaat aaatcaaaac tttcaacaac ggatctcttg    240

gttctggcat cgatgaagaa cgcagcaaaa tgcgataagt aatgtgaatt gcagaattca    300

gtgaatcatc gaatctttga acgcacattg cgcccgccag tattctggcg ggcatgcctg    360

ttcgagcgtc atttcaaccc tcaagcacag cttggtgttg ggactcgcgt taattcgcgt    420

tccccaaatt gattggcggt cacgtcgagc ttccatagcg tagtagtaaa accctcgtta    480

ctggtaatcg tcgcggccac gccgttaaac cccaacttct gaatgttgac ctcggatcag    540

gtaggaatac ccgctgaact taagcatatc aataagcgga g                        581

<210> SEQ ID NO 290
<211> LENGTH: 589
<212> TYPE: DNA
<213> ORGANISM: Gaeumannomyces incrustans

<400> SEQUENCE: 290

tcttggtcat ttagaggaag taaaagtcgt aaacaaggtc tccgtttggt gaaccagcgg     60

agggatcatt aaagagttgc aaaactccaa cccctgtgaa ctttacctgt acgttgcttc    120

ggcggccgac gccgcgccca gccgggcccg ggggacgccg ccggaggtca taaaccctga    180

attctagtgt atctctgagg acgaaaataa ccaattaaaa ctttcaacaa cggatctctt    240

ggctctggca tcgatgaaga acgcagcgaa atgcgataag taatgtgaat tgcagaattc    300

agtgaatcat cgaatctttg aacgcacatt gcgcccgccg gtattccggc gggcatgcct    360

gtccgagcgt catttcacca ctcaagccca gcttggtgtt ggggcacccg gccgcccggc    420

ggtcggggcc cccaagtaca tcggcggtcc cgctggggct ccgagcgcag taacacgcgg    480

taaaacgcgc cctcgctcgg cggcctcctc gggcttccag ccgctaaaac ccccagtgac    540

gtttttcgag ttgacctcgg atcaggtagg aatacccgct gaacttaag                589

<210> SEQ ID NO 291
<211> LENGTH: 613
<212> TYPE: DNA
<213> ORGANISM: Uncultured root-associated fungus

<400> SEQUENCE: 291

tcttggtcat ttagaggaag taaaaagtcg taacaaggtc tccgttggtg aaccagcgga     60

gggatcatta aagagttgca aaactccaac cctgtgaact ttacctgtac gttgcttcgg    120

cggccgacgc cgcgccccag ccgggggacg ccgccggagg tcttaaaccc tgaattctag    180

tgtatctctg aggacgaaaa aaaccaatta aaactttcaa caacggatct cttggctctg    240

gcatcgatga agaacgcagc gaaatgcgat aagtaatgtg aattgcagaa ttcagtgaat    300

catcgaatct ttgaacgcac attgcgcccg ccggtattcc ggcgggcatg cctgtccgag    360

cgtcatttca ccactcaagc ccagcttggt gtttggggca cccggccgcc tggcggtcgg    420

ggcccccaag tacatcggcg gtcccgctgg ggctctgagc gcagttaact cgcggtaaaa    480

cgcgccctcg ctcggcggcc tcctcgggct tccagccgct aaaccccccca gtgacgtttt    540

tcgagttgac ctcggaatca gggtaggaat accccgctgg aacttaagca tatcaaataa    600

gcgggaggaa agg                                                       613

<210> SEQ ID NO 292
<211> LENGTH: 592
<212> TYPE: DNA
```

<213> ORGANISM: Dothideomycete sp.

<400> SEQUENCE: 292
ttcctccgct tattgatatg cttaagttca gcgggtatcc ctacctgatc cgaggtcaac 60
cttagaaatg ggtttgtttt acggcgtagc ctcccgagca ccctttagcg aatagtttcc 120
acaacgctta ggggacagaa gacccagccg gtcgatttga ggcacgcggc ggaccgcgtt 180
gcccaatacc aagcgaggct tgagtggtga aatgacgctc gaacaggcat gccccccgga 240
ataccagggg gcgcaatgtg cgttcaaaga ttcgatgatt cactgaattc tgcaattcac 300
attacttatc gcatttcgct gcgttcttca tcgatgccag aaccaagaga tccgttgtta 360
aaagttttaa tttattaatt aagtttactc agactgcaaa gttacgcaag agtttgaagt 420
gtccacccgg agcccccgcc cgaaggcagg gtcgccccgg aggcaacaga gtcggacaac 480
aaagggttat gaacatcccg gtggttagac cggggtcact tgtaatgatc cctccgcagg 540
ttcacctacg ggagaccttg ttacgacttt tacttcctct aaatgaccaa ga 592

<210> SEQ ID NO 293
<211> LENGTH: 515
<212> TYPE: DNA
<213> ORGANISM: Uncultured root-associated fungus

<400> SEQUENCE: 293
cgttgtgacc agcggaggga tcattaaaga gttgcaaaac tccaacccct gtgaacttta 60
cctgtacgtt gcttcggcgg ccgacgccgc gcccagccgg gggacgccgc cggaggtctt 120
aaaccctgaa ttctagtgta tctctgagga cgaaaaaaac caattaaaac tttcaacaac 180
ggatctcttg gctctggcat cgatgaagaa cgcagcgaaa tgcgataagt aatgtgaatt 240
gcagaattca gtgaatcatc gaatctttga acgcacattg cgcccgccgg tattccggcg 300
ggcatgcctg tccgagcgtc atttcaccac tcaagcccag cttggtgttg ggcacccgg 360 ccgcctggcg gtcggggccc ccaagtacat cggcggtccc gctggggctc tgagcgcagt 420
aactcgcggt aaaacgcgcc ctcgctcggc ggcctcctcg ggcttccagc cgctaaaccc 480
cccagtgacg ttttcgagtg actcggatca gtagg 515

<210> SEQ ID NO 294
<211> LENGTH: 580
<212> TYPE: DNA
<213> ORGANISM: Didymella fabae

<400> SEQUENCE: 294
ctcttggtca tttagaggaa gtaaaagtcg taacaaggtt tccgtaggtg aacctgcgga 60
aggatcatta cctagagttg taggctttgc ctgctatctc ttacccatgt cttttaagta 120
ccttcgtttc ctcggcgggt tcgcccgccg attggacaat ttaaaccatt tgcagttgca 180
atcagcgtct gaaaaaactt aatagttaca actttcaaca acggatctct tggttctggc 240
atcgatgaag aacgcagcga aatgcgataa gtagtgtgaa ttgcagaatt cagtgaatca 300
tcgaatcttt gaacgcacat tgcgcccctt ggtattccat ggggcatgcc tgttcgagcg 360
tcatttgtac cttcaagctc tgcttggtgt tgggtgtttg tctcgcctct gcgtgtagac 420
tcgcctcaaa acaattggca gccggcgtat tgatttcgga gcgcagtaca tctcgcgctt 480
tgcactcata acgacgacgt ccaaaagtac atttttacac tcttgacctc ggatcaggta 540
gggatacccg ctgaacttaa gcatatcaat aagcggagga 580

<210> SEQ ID NO 295
<211> LENGTH: 522
<212> TYPE: DNA
<213> ORGANISM: Uncultured root-associated fungus

<400> SEQUENCE: 295
ttcctacctg atcgagtcaa ctcgaaaacg tcactggggg gtttagcggc tggaagcccg 60
assaggccgc cgagcgaggg cgcgttttac cgcgagttac tgcgctcgga gccccagcgg 120
gaccgccgat gtacttgggg gccccgaccg cccggcggcc gggtgcccca acaccaagct 180
gggcttgagt ggtgaaatga cgctcggaca ggcatgcccg ccggaatacc ggcgggcgca 240
atgtgcgttc aaagattcga tgattcactg aattctgcaa ttcacattac ttatcgcatt 300
tcgctgcgtt cttcatcgat gccagagcca agagatccgt tgttgaaagt tttaattggt 360
ttttttcgtc ctcagagata cactagaatt cagggtttaa gacctccggc ggcgtccccc 420
ggctgggcgc ggcgtcggcc gccgaagcaa cgtacaggta aagttcacag gggttggagt 480
tttgcaactc tttaatgatc cctccgctgg tcaccaacga ga 522

<210> SEQ ID NO 296
<211> LENGTH: 626
<212> TYPE: DNA
<213> ORGANISM: Macrophomina phaseolina

<400> SEQUENCE: 296
ttcctccgct tattgatatg cttaagttca gcgggtatcc ctacctgatc cgaggtcaac 60
cttgagaaaa gttcagaagg ttcgtccggc gggcgacgcc ttacgctccg aagcgaggtg 120
tattctacta cgcttgaggc aagacgccac cgccgaggtc tttgaggcgc gcccgcaaag 180
gacggtgccc aataccaagc agagcttgag ggttgaaatg acgctcgaac aggcatgccc 240
cccggaatac caaggggcgc aatgtgcgtt caaagattcg atgattcact gaattctgca 300
attcacatta cttatcgcat ttcgctgcgt tcttcatcga tgccagaacc aagagatccg 360
ttgttgaaag ttttagttta tttaatattt ttttcagact gcaacgttta ctgactggag 420
tttgatagtc ctctggcggg cactagccac cccccaaaat cggggggcgg ccgcggaaag 480
accgcggccc gccaaagcaa cagaggtagg tatacaaagg gtgggaggat cggggacgga 540
gccccgaatc aactcggtaa tgatccttcc gcaggttcac ctacggaaac cttgttacga 600
cttttacttc ctctaaatga ccaaga 626

<210> SEQ ID NO 297
<211> LENGTH: 923
<212> TYPE: DNA
<213> ORGANISM: Rhizopycnis sp.

<400> SEQUENCE: 297
tagctcagta cgggacagct tgaccgccag gtcaaggtga tccttccgcg taacacttgc 60
cgaagcctta gcagcccgaa agggtgcagt tccgcgactc aaagaaagga ggactgctga 120
aatgctagtc tgcagaagca ggcaacacta tcaaattgcg ggaacaccct aaagacctca 180
acaccaagcg tcatgggaaa ccatggcgtg gccgagctaa tagccctggg tatggtaaca 240
gcttgaggta tgaagccttc gcaaggaggc cgaaatgggc aatccgcagc caagtcctaa 300
cgtgctcgaa accgagtgcc atggatgctg ttcacaggcc aaatggtagt gggtgactct 360
tgcgagttgc ttaagatatg gtcgggcccc ttcagaaatg tgggggataa gcttacgctt 420
ctccaaaccg ttccgtaggt gaacctgcgg aaggatcatt aacgatttcg gtgtaaaaaa 480

```
ccgttttcta cctatgtcta cgcgtaccac atgtttcctc ggggggcttg ccccccgcta    540

ggacccttta tcaaaccttt ttgtaatagc agtcagcgtc tgatactaag ttaattatta    600

aaactttcaa caatggatct cttggttctg gcatcgatga agaacgcagc gaaatgcgat    660

aagtagtgtg aattgcagaa ttcagtgaat catcgaatct ttgaacgcac attgcgcccc    720

ttggtattcc atggggcatg cctgttcgag cgtcatttga accctcaagc tctgcttggt    780

gttgggtgtt tgtcccgcca ttgcgcgtgg actcgcctta aagcaattgg cagccatgta    840

atccggcttt gagcgcagca cattgcgtac tctctactgg gacatgggca tccagaagcc    900

ttattttta ctcttgactc gga                                             923
```

<210> SEQ ID NO 298
<211> LENGTH: 889
<212> TYPE: DNA
<213> ORGANISM: Uncultured root-associated fungus

<400> SEQUENCE: 298

```
cctgatccga gtcaactggg ggggtgagct tgatggacgc gggcccaccg gtgcctcgag     60

aagcgcaatg tgctgcgcga gaagctggca cgaccgctgc caataccttt ggggcgagtc    120

cgcgcgcgaa gcgggacaga cgcccaacac caagcggagc ttgagggggt aaatgacgct    180

cgaacaggca tgccccacgg aataccatgg ggcgcaatgt gcgttcaaag attcgatgat    240

tcactgaatt ctgcaattca cactacttat cgcatttcgc tgcgttcttc atcgatgcca    300

gaaccaagag atccattgtt aaaagttgta aatgatttgg tttgttttca gaagtttgga    360

tgctgttgca aaagggtttg gggggttcct ggcggcagag gacctgccga ggaaacaaca    420

aaaggtgcac gtagtcaagg tgatagtcaa gggctaagcg cccaaggcag cgtcatcgcg    480

agcgactggc tcccccgagc ggcccaaggc caggtaatga tccttccgca ggttcaccta    540

cggaacggtt accagaaggc tttgcgtctc caagatttct cagggagccc gactatatct    600

taagcggaga taccaaggac tccacccact tccgcttagt ctgtgaacgt tccccatgcc    660

ttacaagaag ggggaggggc ttcgctgcgg ataatccatt tccccagaga cgctctggtt    720

catacctttc ctctgttacc ataccccgat agtttcccac gggccgccag cgggtttccc    780

cggctggttt ggtgtgaagg tctttaggac gtccccggca attcgaaagt gtcgccagcg    840

agagctgact tgcatcaagg ccgaattatt tactgtcgct cagccaacc               889
```

<210> SEQ ID NO 299
<211> LENGTH: 611
<212> TYPE: DNA
<213> ORGANISM: Uncultured root-associated fungus

<400> SEQUENCE: 299

```
tcttggtcat ttagaggaaa gtaaaagtcg taacaaggtc tccgttggtg aacccagcgg     60

agggatcatt aaaggagttg caaaaactcc aacccctgtg aactttacct gtacgttgct    120

tcggcggccg acgccgcgcc cagacgggcc tgggggacgc cgccggaggt cttaaaccca    180

gaattctagt gtatctatga ggacgaaaaa aaccaattaa aactttcaac aacggatctc    240

ttggctctgg catcgatgaa gaacgcagcg aaatgcgata agtaatgtga attgcagaat    300

tcagtgaatc atcgaatctt tgaacgcaca ttgcgcccgc cggtattccg gcgggcatgc    360

ctgtccgagc gtcatttcac cactcaagcc cagcttggtg ttggggcacc cggccgcccg    420

gcggtcgggg cccccaagta catcggcggt cccgctgggg ctccgagcgc agtaactcgc    480

ggtaaaacgc gccctcgctc ggcggcctcc tcgggcttcc agccgctaaa cccccagtga    540
```

cgtttttcga gttgacctcg gatcaggtag gaatacccgc tgaacttaaa gcatatcaat 600
aagcggagga a 611

<210> SEQ ID NO 300
<211> LENGTH: 510
<212> TYPE: DNA
<213> ORGANISM: Uncultured root-associated fungus

<400> SEQUENCE: 300
cggtctccgt tgtgaaccag cggagggatc attaaagagt tgcaaaaact ccaacccctg 60
tgaactttac ctgtacgttg cttcggcggc cgacgccgcg cccagacggg cctgggggac 120
gccgccggag gtcttaaacc cagaattcta gtgtatctat gaggacgaaa aaaaccaatt 180
aaaactttca acaacggatc tcttggctct ggcatcgatg aagaacgcag cgaaatgcga 240
taagtaatgt gaattgcaga attcagtgaa tcatcgaatc tttgaacgca cattgcgccc 300
gccggtattc cggcgggcat gcctgtccga gcgtcatttc accactcaag cccagcttgg 360
tgttggggca cccggccgcc cggcggtcgg ggcccccaag tacatcggcg gtcccgctgg 420
gggctccgag cgcagtaact cgcggtaaaa cgcgccctcg ctcggcggcc tcctcgggct 480
tccagccgct aaaccccag tgacgttttt 510

<210> SEQ ID NO 301
<211> LENGTH: 544
<212> TYPE: DNA
<213> ORGANISM: Phoma medicaginis

<400> SEQUENCE: 301
ttgtaaaagt cgtaacaagg tttccgtagg tgaacctgcg gaaggatcat tacctagagt 60
tgcgggcttt gcctgctatc tcttacccat gtcttttgag tacttacgtt tcctcggcgg 120
gtccgcccgc cgaagacaaa ctataaaacc tttgcagttg caatcagcgt ctgaacaaat 180
ttaaatattt acaactttca acaacggatc tcttggttct ggcatcgatg aagaacgcag 240
cgaaatgcga taagtagtgt gaattgcaga attcagtgaa tcatcgaatc tttgaacgca 300
cattgcgccc cttggtattc catggggcat gcctgttcga gcgtcatttg taccttcaag 360
ctttgcttgg tgttgggtgt ttgtctcgcc tctgcgtgta gactcgcctc aaaacaattg 420
gcagccggcg tattgatttc ggagcgcagt acatctcgcg ctttgcactc ataacgacga 480
cgtccaaaag tacattttta cactcttgac ctcggatcag gtagggatac ccgctgaact 540
taag 544

<210> SEQ ID NO 302
<211> LENGTH: 597
<212> TYPE: DNA
<213> ORGANISM: Fusarium proliferatum

<400> SEQUENCE: 302
tcctccgcct tattgatatg cttaagttca gcgggtattc ctacctgatc cgaggtcaac 60
attcagaagt tgggggttta acggcttggc cgcgccgcgt accagttgcg agggttttac 120
tactacgcaa tggaagctgc agcgagaccg ccactgtatt tcggggccgg cttgccgtga 180
ggctcgccga tccccaacac caaacccggg ggcttgaggg ttgaaatgac gctcgaacag 240
gcatgcccgc cagaatactg gcgggcgcaa tgtgcgttca aagattcgat gattcactga 300
attctgcaat tcacattact tatcgcattt tgctgcgttc ttcatcgatg ccagaaccaa 360

```
gagatccgtt gttgaaagtt ttgatttatt tatggtttta ctcagaagtt acatatagaa    420

acagagttta ggggtcctct ggcgggccgt tccgttttac cgggagcggg ctgatccgcc    480

gaggcaacaa ttgatatgtt cacaggggtt tgggagttgt aaactcggta atgatccctc    540

cgctggttca ccaacggaga ccttgttacg acttttactt cctctaaatg accaaga       597


<210> SEQ ID NO 303
<211> LENGTH: 596
<212> TYPE: DNA
<213> ORGANISM: Fusarium proliferatum

<400> SEQUENCE: 303

tcttggtcat ttagaggtag taaaagtcgt aacaaggtct ccgttggtga accagcggag     60

ggatcattac cgagtttaca actcccaaac ccctgtgaac atatcaattg ttgcctcggc    120

ggatcagccc gctcccggta aaacggaacg gcccgccaga ggacccctaa actctgtttc    180

tatatgtaac ttctgagtaa aaccataaat aaatcaaaac tttcaacaac ggatctcttg    240

gttctggcat cgatgaagaa cgcagcaaaa tgcgataagt aatgtgaatt gcagaattca    300

gtgaatcatc gaatctttga acgcacattg cgcccgccag tattctggcg ggcatgcctg    360

ttcgagcgtc atttcaaccc tcaagccccc gggtttggtg ttggggatcg gcgagcctca    420

cggcaagccg gccccgaaat acagtggcgg tctcgctgca gcttccattg cgtagtagta    480

aaaccctcgc aactggtacg cggcgcggcc aagccgttaa acccccaact tctgaatgtt    540

gacctcggat caggtaggaa tacccgctga acttaagcat atcaataagc ggagga        596


<210> SEQ ID NO 304
<211> LENGTH: 543
<212> TYPE: DNA
<213> ORGANISM: Fusarium nygamai

<400> SEQUENCE: 304

gcgggggatc attaccgagt ttacaactcc caaacccctg tgaacatacc aattgttgcc     60

tcggcggatc agcccgctcc cggtaaaacg gaacggcccg ccagaggacc cctaaactct    120

gtttctatat gtaacttctg agtaaaacca taaataaatc aaaactttca acaacggatc    180

tcttggttct ggcatcgatg aagaacgcag caaaatgcga taagtaatgt gaattgcaga    240

attcagtgaa tcatcgaatc tttgaacgca cattgcgccc gccagtattc tggcgggcat    300

gcctgttcga gcgtcatttc aaccctcaag cccccgggtt tggtgttggg gatcggcgag    360

cctcacggca agccggcccc gaaatacagt ggcggtctcg ctgcagcttc cattgcgtag    420

tagtaaaacc ctcgcaactg gtacgcggcg cggccaagcc gttaaacccc caacttctga    480

atgttgacct cggatcaggg taggaatacc cgctgaactt aagcatatca ataagcggag    540

gaa                                                                  543


<210> SEQ ID NO 305
<211> LENGTH: 531
<212> TYPE: DNA
<213> ORGANISM: Magnaporthe rhizophila

<400> SEQUENCE: 305

taggtctcgt tggtgaccag cggagggatc attaaagagt tgcaaaactc caacccctgt     60

gaactttacc tgtacgttgc ttcggcggcc gacgccgcgc ccagccgggc ccgggggacg    120

ccgccggagg tcataaaccc tgaattctag tgtatctctg aggacgaaaa taaccaatta    180

aaactttcaa caacggatct cttggctctg gcatcgatga agaacgcagc gaaatgcgat    240
```

aagtaatgtg aattgcagaa ttcagtgaat catcgaatct ttgaacgcac attgcgcccg 300
ccggtattcc ggcgggcatg cctgtccgag cgtcatttca ccactcaagc ccagcttggt 360
gttggggcac ccggccgccc ggcggtcggg gcccccaagt acatcggcgg tcccgctggg 420
gctccgagcg cagtaactcg cggtaaaacg cgccctcgct cggcggcctc ctcgggcttc 480
cagccgctaa acccccagtg acgtttttcg agttgacctc ggatcaggta g 531

<210> SEQ ID NO 306
<211> LENGTH: 583
<212> TYPE: DNA
<213> ORGANISM: Gaeumannomyces incrustans

<400> SEQUENCE: 306
aagtaaaagt cgtaacaagg tctccgttgg tgaaccagcg gagggatcat taaagagttg 60
caaaactcca acccctgtga actttacctg tacgttgctt cggcggccga cgccgcgccc 120
agccgggcct gggggacgcc gccggaggtt ttaaaccctg aattctagtg tatctctgag 180
gacgaaaaaa accaattaaa actttcaaca acggatctct tggctctggc atcgatgaag 240
aacgcagcga aatgcgataa gtaatgtgaa ttgcagaatt cagtgaatca tcgaatcttt 300
gaacgcacat tgcgcccgcc ggtattccgg cgggcatgcc tgtccgagcg tcatttcacc 360
actcaagccc agcttggtgt tggggcaccc ggccgcctgg cggtcggggc ccccaagtac 420
atcggcggtc ctgctggggc tccgagcgca gtaactcgcg gtaaaacgcg ctctcgctcg 480
gcggcctcct cgggcttcca gccgctaaac ccccagtgac gtttttcgag ttgacctcgg 540
atcaggtagg aatacccgct gaacttaagc atatcaataa gcg 583

<210> SEQ ID NO 307
<211> LENGTH: 612
<212> TYPE: DNA
<213> ORGANISM: Gaeumannomyces incrustans

<400> SEQUENCE: 307
ttcctccgct ttattgatat gctttaagtt cagcgggtat tccctacctg atccgaggtc 60
aactcgaaaa aacgtcactg gggggtttagc ggctggaagc ccgaggaggc cgccgagcga 120
gggcgcgttt taccgcgagt tactgcgctc ggagccccag caggaccgcc gatgtacttg 180
ggggccccga ccgccaggcg gccgggtgcc ccaacaccaa gctgggcttg agtggtgaaa 240
tgacgctcgg acaggcatgc ccgccggaat accggcgggc gcaatgtgcg ttcaaagatt 300
cgatgattca ctgaattctg caattcacat tacttatcgc atttcgctgc gttcttcatc 360
gatgccagag ccaagagatc cgttgttgaa agttttaatt ggttattttc gtcctcagag 420
atacactaga attcagggtt taaaacctcc ggcggcgtcc cccaggcccg gctgggcgcg 480
gcgtcggccg ccgaagcaac gtacaggtaa agttcacagg ggttggagtt ttgcaactct 540
ttaaatgatc cctccgctgg ttcaccaacg gagaccttgt tacgactttt acttcctcta 600
aatgaccaag ga 612

<210> SEQ ID NO 308
<211> LENGTH: 596
<212> TYPE: DNA
<213> ORGANISM: Fusarium proliferatum

<400> SEQUENCE: 308
tcttggtcat ttagaggaag taaaagtcgt aacaaggtct ccgttggtga accagcggag 60

```
ggatcattac cgagtttaca actcccaaac ccctgtgaac atatcaattg ttgcctcggc    120

ggatcagccc gctcccggta aaacggaacg gcccgccaga ggacccctaa actctgtttc    180

tatatgtaac ttctgagtaa aaccataaat aaatcaaaac tttcaacaac ggatctcttg    240

gttctggcat cgatgaagaa cgcagcaaaa tgcgataagt aatgtgaatt gcagaattca    300

gtgaatcatc gaatctttga acgcacattg cgcccgccag tattctggcg ggcatgcctg    360

ttcgagcgtc atttcaaccc tcaagccccc gggtttggtg ttggggatcg gcgagcctca    420

cggcaagccg gccccgaaat acagtggcgg tctcgctgca gcttccattg cgtagtagta    480

aaaccctcgc aactggtacg cggcgcggcc aagccgttaa acccccaact tctgaatgtt    540

gacctcggat caggtaggaa tacccgctga acttaagcat atcaataagc ggagga        596
```

<210> SEQ ID NO 309
<211> LENGTH: 589
<212> TYPE: DNA
<213> ORGANISM: Uncultured Ascomycete sp.

<400> SEQUENCE: 309

```
tcctccgctt attgatatgc ttaagttcag cgggtatccc tacctgatcc gaggtcaagt     60

cataaaagag cttactggat gctgatccac caaacttcaa gaaacgcaaa tgtgctgcgc    120

gagaagctgg cacgaccgct gccaatgact ttggggcgag tccacgcatg aagcgggaca    180

gacgcccaac accaagcaga gcttgagggt gtaaatgacg ctcgaacagg catgccccac    240

ggaataccga ggggcgcaat gtgcgttcaa agattcgatg attcacggaa ttctgcaatt    300

cacactactt ttcgcatttc gctgcgttct tcatcgatgc cagaaccaag agatccattg    360

ttgaaagttg taataattta atagttatca gatttcaatg cttttaatac aagggtttat    420

tgggttccta gcgacaggca agcctgccga ggaaacaaca agagtacagt agacaaaggg    480

tggatgcaat aacccccgaa ggggctatag cttgcgtaat taatgatcct tccgcaggtt    540

cacctacgga aaccttgtta cgacttttac ttcctctaaa tgaccaaga                 589
```

<210> SEQ ID NO 310
<211> LENGTH: 568
<212> TYPE: DNA
<213> ORGANISM: Gaeumannomyces incrustans

<400> SEQUENCE: 310

```
cttattgata tgcttaagtt cagcgggtat tcctacctga tccgaggtca actcgagaaa     60

cgtcactggg gggtttagcg gctggaagcc cgaagaggcc gccgagcgag ggcgcgtttt    120

accgcgagat actgcgctcg gagccccagc gggaccgccg atgtacttgg gggccccgac    180

cgccaggcgg ccaggtgccc caacaccaag ctgggcttga gcggtgaaat gacgctcgga    240

caggcatgcc cgccggaata ccggcgggcg caatgtgcgt tcaaagattc gatgattcac    300

tgaattctgc aattcacatt acttatcgca tttcgctgcg ttcttcatcg atgccagagc    360

caagagatcc gttgttgaaa gttttgattg gttctttcca tactcagaga cacactagaa    420

ttcagggttt gagacctccg gcggcgtcct ccacgcccgg ccgggcgcgg cgccggccgc    480

cgaagcaacg tgcaggtaag gttcacaggg gttggagttt tgcaactctt taatgatccc    540

tccgctggtt caccaacgga gaccttgt                                       568
```

<210> SEQ ID NO 311
<211> LENGTH: 283
<212> TYPE: DNA
<213> ORGANISM: Ascomycete sp.

<400> SEQUENCE: 311
cggaggwcat tatcaaaagt caagtcgggg gctgtaaagc tctcgtctac acccatgtct 60
tttgcgtact cttgtttcct cggtggcgca agctgccgat tggacaaacc aaaacctttt 120
ttgtaattgc aatcagcgtc tgaaaataat ctaattattt acaactttca acaacggatc 180
tcttggttca ggcatcgatg aagaacgcag cgaaatgcga taagtagtgt gaattgcaga 240
attcagtgaa tcatcgaatc tttgaacgca cattgcgccc ctt 283

<210> SEQ ID NO 312
<211> LENGTH: 643
<212> TYPE: DNA
<213> ORGANISM: Fungal endophyte

<400> SEQUENCE: 312
tttctccgcc tattgatatg cttaagttca gcgggtattc ctacctgatc cgaggtcaaa 60
ccactgtgtt tcagaaccga ggttctgcgt ttttcttttc acggctggca cccgcctgga 120
cccccgagcg agagagaatt actgcgctcg gtgttcatgg cgggcccgcc actgcttttc 180
agggctcagg gtcggccctt ggtgggccgg cctcctgaag gccccaacga caggctgacg 240
aaggcctggg ggttgaaatg acgctcggac aggcatgcct gccagaatac tggcaggcgc 300
aatgtgcgtt caaagattcg atgactcgcg gaattctgca attcgcatta cttatcgcat 360
ttcgctgcgt tcttcatcga tgctagagcc aagagatccg ttgttgaaag ttttgattat 420
tttgtttgtg tactcagaag acaggtcgaa aacaaaaaga gtttgataaa acctccggcg 480
gggtgccttg cggcctgagg acccccggag aggccacccc accgaagcaa catacaggta 540
ggttcacaat ggtttaggga gtgtttacac tctgtaatga tccctccgct ggttcaccaa 600
cggagacctt gttacgactt ttacttcctc taaatgacca aga 643

<210> SEQ ID NO 313
<211> LENGTH: 551
<212> TYPE: DNA
<213> ORGANISM: Fusarium moniliformae

<400> SEQUENCE: 313
aggaagtaaa agtcgtaaca aggtctccgt tggtgaacca gcggagggat cattaccgag 60
tttacaactc ccaaacccct gtgaacatac cacttgttgc ctcggcggat cagcccgctc 120
ccggtaaaac gggacggccc gccagaggac ccctaaactc tgtttctata tgtaacttct 180
gagtaaaacc ataaataaat caaaactttc aacaacggat ctcttggttc tggcatcgat 240
gaagaacgca gcaaaatgcg ataagtaatg tgaattgcag aattcagtga atcatcgaat 300
ctttgaacgc acattgcgcc cgccagtatt ctggcgggca tgcctgttcg agcgtcattt 360
caaccctcaa gccctcgggt ttggtgttgg ggatcggcga gcccttgcgg caagccggcc 420
ccgaaatcta gtggcggtct cgctgcagcc tccattgcgt agtagtaaaa ccctcgcaac 480
tggaacgcgg cgcggccaag ccgttaaacc cccaacttct gaatgttgac ctcggatcag 540
gtaggaatac c 551

<210> SEQ ID NO 314
<211> LENGTH: 550
<212> TYPE: DNA
<213> ORGANISM: Uncultured Leptosphaeriaceae

<400> SEQUENCE: 314

-continued

```
cctacctgat ccgagtcaag tcataaaaga gcttactgga tgctgatcca ccaaacttca     60

agaaacgcaa atgtgctgcg cgagaagctg gcacgaccgc tgccaatgac tttggggcga    120

gtccacgcat gaagcgggac agacgcccaa caccaagcag agcttgaggg tgtaaatgac    180

gctcgaacag gcatgcccca cggaataccg aggggcgcaa tgtgcgttca aagattcgat    240

gattcacgga attctgcaat tcacactact tttcgcattt cgctgcgttc ttcatcgatg    300

ccagaaccaa gagatccatt gttgaaagtt gtaataattt aatagttatc agatttcaat    360

gcttttaata caagggttta ttgggttcct agcgacaggc aagcctgccg aggaaacaac    420

aagagtacag tagacaaagg gtggatgcaa taacccccga aggggctata gcttgcgtaa    480

ttaatgatcc ttccgcaggt tcacctacgg aaaccttgtt acgactttta cttcctctaa    540

atgaccaaga                                                           550
```

<210> SEQ ID NO 315
<211> LENGTH: 533
<212> TYPE: DNA
<213> ORGANISM: Magnaporthe rhizophila

<400> SEQUENCE: 315

```
acaggtctcg ttgctgacca gcggagggat cattaaagag ttgcaaaact ccaacccctg     60

tgaactttac ctgtacgttg cttcggcggc cgacgccgcg cccagccggg cctgggggac    120

gccgccggag gttttaaacc ctgaattcta gtgtatctct gaggacgaaa ataaccaatt    180

aaaactttca acaacggatc tcttggctct ggcatcgatg aagaacgcag cgaaatgcga    240

taagtaatgt gaattgcaga attcagtgaa tcatcgaatc tttgaacgca cattgcgccc    300

gccggtattc cggcgggcat gcctgtccga gcgtcatttc accactcaag cccagcttgg    360

tgttggggca cccggccgcc tggcggtcgg ggcccccaag tacatcggcg gtcctgctgg    420

ggctccgagc gcagtaactc gcggtaaaac gcgccctcgc tcggcgggcc tcctcgggct    480

tccagccgct aaacccccag tgacgttttt cgagttgact cggatcaggt aga           533
```

<210> SEQ ID NO 316
<211> LENGTH: 564
<212> TYPE: DNA
<213> ORGANISM: Fusarium nygamai

<400> SEQUENCE: 316

```
ttcctccgct tattgatatg cttaagttca gcgggtattc ctacctgatc cgaggtcaac     60

attcagaagt tgggggttta acggcttggc cgcgccgcgt accagttgcg agggttttac    120

tactacgcaa tggaagctgc agcgagaccg ccactgtatt tcggggccgg cttgccgtga    180

ggctcgccga tccccaacac caaacccggg ggcttgaggg ttgaaatgac gctcgaacag    240

gcatgcccgc cagaatactg gcgggcgcaa tgtgcgttca aagattcgat gattcactga    300

attctgcaat tcacattact tatcgcattt tgctgcgttc ttcatcgatg ccagaaccaa    360

gagatccgtt gttgaaagtt ttgatttatt tatggtttta ctcagaagtt acatatagaa    420

acagagttta ggggtcctct ggcgggccgt tccgttttac cgggagcggg ctgatccgcc    480

gaggcaacaa ttgatatgtt cacaggggtt tgggagttgt aaactcggta atgatccctc    540

cgctggttca ccaacggaga cctt                                           564
```

<210> SEQ ID NO 317
<211> LENGTH: 610
<212> TYPE: DNA
<213> ORGANISM: Gaeumannomyces incrustans

<400> SEQUENCE: 317
tcttggtcat ttagaggaag taaaaagtcg taacaaggtc tccgttggtg aaccagcgga 60
gggatcatta aagagttgca aaaactccaa cccctgtgaa ctttacctgt acgttgcttc 120
ggcggccgac gccgcgccca gacgggcctg ggggacgccg ccggaggtct taaaccctga 180
attctagtgt atctatgagg acgaaaaaaa ccaattaaaa ctttcaacaa cggatctctt 240
ggctctggca tcgatgaaga acgcagcgaa atgcgataag taatgtgaat tgcagaattc 300
agtgaatcat cgaatctttg aacgcacatt gcgcccgccg gtattccggc gggcatgcct 360
gtccgagcgt catttcacca ctcaagccca gcttggtgtt ggggcacccg gccgcccggc 420
ggtcggggcc cccaagtaca tcggcggtcc cgctggggct ccgagcgcag taactcgcgg 480
taaaacgcgc cctcgctcgg cggcctcctc gggcttccag ccgctaaacc cccagtgacg 540
tttttcgagt tgacctcgga tcagggtagg aaatacccgc tgaacttaag catatcaata 600
agcggaggaa 610

<210> SEQ ID NO 318
<211> LENGTH: 600
<212> TYPE: DNA
<213> ORGANISM: Uncultured fungus

<400> SEQUENCE: 318
tcctccgctt attgatatgc ttaagttcag cgggtattcc tacctgatcc gaggtcaaca 60
ttcagaagtt ggggggttta acggcttggc cgcaccgcgt tccagttgcg aggtgttagc 120
tactacgcaa tggaggctgc agtgagaccg ccactagatt tcggggccgg cttgccagag 180
aggctcgccg atccccaaca ccaaacccga gggcttgagg gttgaaatga cgctcgaaca 240
ggcatgcccg ccagaatact ggcgggcgca atgtgcgttc aaagattcga tgattcactg 300
aattctgcaa ttcacattac ttatcgcatt ttgctgcgtt cttcatcgat gccagaacca 360
agagatccgt tgttgaaagt tttgatttat ttatggtttt actcagaagt tacaataaaa 420
aacagagttt aggggtcctc tggcgggccg tcccgtttta ccgggcgcgg gctgatccgc 480
cgaggcaaca gtaaaggtat gttcacaggg gtttgggagt tgtaaactcg gtaatgatcc 540
ctccgctggt tcaccaacgg agaccttgtt acgactttta cttcctctaa atgaccaaga 600

<210> SEQ ID NO 319
<211> LENGTH: 474
<212> TYPE: DNA
<213> ORGANISM: Fusarium nygamai

<400> SEQUENCE: 319
gaagttgggg gtttaacggc ttggccgcgc cgcgtaccag ttgcggaggg ttttactact 60
acgcaatgga agctgcagcg agaccgccac tgtatttcgg ggccggcttg ccgtgaggct 120
cgccgatccc caacaccaaa cccgggggct tgagggttga aatgacgctc gaacaggcat 180
gcccgccaga atactggcgg gcgcaatgtg cgttcaaaga ttcgatgatt cactgaattc 240
tgcaattcac attacttatc gcattttgct gcgttcttca tcgatgccag aaccaagaga 300
tccgttgttg aaagttttga tttatttatg gttttactca gaagttacat atagaaacag 360
agtttagggg tcctctggcg ggccgttccg ttttaccggg agcgggctga tccgccgagg 420
caacaattgg tatgttcaca ggggtttggg agttgtaaac tcggtaatga tccc 474

<210> SEQ ID NO 320

<211> LENGTH: 515
<212> TYPE: DNA
<213> ORGANISM: Fusarium oxysporum

<400> SEQUENCE: 320

```
tctactgatc gagtcacatt cagaagttgg gggtttaacg gcttggccgc ccgcgttcca     60

gttgcgaggg ttttactact acgcaatgga ggctgcaggg agaccgccac tagatttcgg    120

ggccggcttg ccgcaagggc tcgccgatcc ccaacaccaa acccgagggc ttgagggttg    180

aaatgacgct cgaacaggca tgcccgccag aatactggcg ggcgcaatgt gcgttcaaag    240

attcgatgat tcactgaatt ctgcaattca cattacttat cgcattttgc tgcgttcttc    300

atcgatgcca gaaccaagag atccgttgtt gaaagttttg atttatttat ggttttactc    360

agaagttaca tatagaaaca gagtttaggg gtcctctggc gggccgtccc gttttaccgg    420

gagcgggctg atccgccgag gcaacaagtg gtatgttcac aggggtttgg gagttgtaaa    480

ctcggtaatg atccctccgc tggtcaccaa cggag                               515
```

<210> SEQ ID NO 321
<211> LENGTH: 606
<212> TYPE: DNA
<213> ORGANISM: Fusarium solani

<400> SEQUENCE: 321

```
ttcctccgct tattgatatg cttaagttca gcgggtattc ctacctgatt cgaggtcaac     60

ttcagaagag ttgggtgttt tacggcgtgg ccgcgccgct ctccagtcgc gaggtgttag    120

ctactacgcg atggaagctg cggcgggacc gccactgtat ttgggggacg gcgtgtgccc    180

acgggggggct ccgccgatcc ccaacgccag gcccgggggc ctgagggttg taatgacgct    240

cgaacaggca tgcccgccag aatactggcg ggcgcaatgt gcgttcaaag attcgatgat    300

tcactgaatt ctgcaattca cattacttat cgcatttcgc tgcgttcttc atcgatgcca    360

gagccaagag atccgttgtt gaaagtttta atttatttgc ttgttttact cagaagaaac    420

attatagaaa cagagttagg ggtcctctgg cgggggcggc ccgtttcacg gggccgtctg    480

ttcccgccga agcaacgttt aggtatgttc acagggttga tgagttgaat aactcggtaa    540

tgatccctcc gctggttcac caacggagac cttgttacga cttttacttc ctctaaatga    600

ccaaga                                                               606
```

<210> SEQ ID NO 322
<211> LENGTH: 597
<212> TYPE: DNA
<213> ORGANISM: Fusarium proliferatum

<400> SEQUENCE: 322

```
tcttggtcat ttagaggaag taaaagtcgt aacaaggtct ccgttggtga accagcggag     60

ggatcattac cgagtttaca actcccaaac ccctgtgaac ataccaattg ttgcctcggc    120

ggatcagccc gctcccggta aaacggaacg gcccgccaga ggacccctaa actctgtttc    180

tatatgtaac ttctgagtaa aaccataaat aaatcaaaac tttcaacaac ggatctcttg    240

gttctggcat cgatgaagaa cgcagcaaaa tgcgataagt aatgtgaatt gcagaattca    300

gtgaatcatc gaatctttga acgcacattg cgcccgccag tattctggcg ggcatgcctg    360

ttcgagcgtc atttcaaccc tcaagccccc gggtttggtg ttggggatcg gcgagcctca    420

cggcaagccg gccccgaaat acagtggcgg tctcgctgca gcttccattg cgtagtagta    480

aaaccctcgc aactggtacg cggcgcggcc aagccgttaa acccccaact tctgaatgtt    540
```

gacctcggat caggtaggaa tacccgctga acttaagcat atcaataagc ggaggaa 597

<210> SEQ ID NO 323
<211> LENGTH: 604
<212> TYPE: DNA
<213> ORGANISM: Fusarium proliferatum

<400> SEQUENCE: 323
tcttggtcat ttagaggaag taaaagtcgt aacaaggtct ccgttggtga accagcggag 60
ggatcattac cgagtttaca actcccaaac ccctgtgaac ataccaattg ttgcctcggc 120
ggatcagccc gctcccggta aaacggaacg gcccgccaga ggacccctaa actctgtttc 180
tatatgtaac ttctgagtaa aaccataaat aaatcaaaac tttcaacaac ggatctcttg 240
gttctggcat cgatgaagaa cgcagcaaaa tgcgataagt aatgtgaatt gcagaattca 300
gtgaatcatc gaatctttga acgcacattg cgcccgccag tattctggcg ggcatgcctg 360
ttcgagcgtc atttcaaccc tcaagccccc gggtttggtg ttggggatcg gcgagcctca 420
cggcaagccg gccccgaaat acagtggcgg gtctcgctgc agcttccatt gcgtagtagt 480
aaaaccctcg caactggtac gcgggcgcgg ccaagccgtt taaaccccca acttctgaat 540
gttgacctcg gatcagggta gggaataccc gctgaacttt aagcatatca ataagcggga 600
ggaa 604

<210> SEQ ID NO 324
<211> LENGTH: 599
<212> TYPE: DNA
<213> ORGANISM: Myrothecium cinctum

<400> SEQUENCE: 324
ttcctccgcc ttattgatat gcttaagttc agcgggtatt cctacctgat ccgaggtcaa 60
ctttcagaag tcggggggttt tccggcgtgg ccgccgccgc gctcccaggc tgcgaggtgt 120
gtgctactac gcagaggagg tctacggcgg ggccgccact gtatttcggg gccggccggt 180
gaaggccgat ccccaacgcc aggcgcggga gcctgagggt tgaaatgacg ctcggacagg 240
catgcccgcc agaatgctgg cgggcgcaat gtgcgttcaa agattcgatg attcactgaa 300
ttctgcaatt cacattactt atcgcatttc gctgcgttct tcatcgatgc cagagccaag 360
agatccgttg ttgaaagttt tgatttattt gtataaaatc cactcagagg agaattcata 420
ataaaacaga ggtttgggtc cctgcggcgg gcgcctggtt ccggtgccgg tgagggcgcc 480
ggggcggtcc cgcccgaggca acgtcaaggt aatgttcaca ttgggtttgg gagttgtaaa 540
ctcggtaatg atccctccgc tgggttcacc aacggaggac cttggttacg acttttact 599

<210> SEQ ID NO 325
<211> LENGTH: 612
<212> TYPE: DNA
<213> ORGANISM: Gaeumannomyces incrustans

<400> SEQUENCE: 325
tcttggtcat ttagaggaag taaaagtcgt aacaaaggtc tccgttggtg aaccagcgga 60
ggggatcatt aaagagtttg caaaactcca acccctgtga actttacctg tacgttgctt 120
cggcggccga cgccgcgccc agccgggccc gggggacgcc gccggaggtc ataaaccctg 180
aattctagtg tatctctgag gacgaaaata accaattaaa actttcaaca acggatctct 240
tggctctggc atcgatgaag aacgcagcga aatgcgataa gtaatgtgaa ttgcagaatt 300

```
cagtgaatca tcgaatcttt gaacgcacat tgcgcccgcc ggtattccgg cgggcatgcc    360

tgtccgagcg tcatttcacc actcaagccc agcttggtgt tggggcaccc ggccgcccgg    420

cggtcggggc ccccaagtac atcggcggtc ccgctggggc tccgagcgca gtaactcgcg    480

gtaaaacgcg ccctcgctcg gcggcctcct cgggcttcca gccgctaaac ccccagtgac    540

gtttttcgag ttgacctcgg atcaggtagg aatacccgct gaacttaagc atatcaaata    600

aggcggagga aa                                                        612
```

<210> SEQ ID NO 326
<211> LENGTH: 530
<212> TYPE: DNA
<213> ORGANISM: Fusarium nygamai

<400> SEQUENCE: 326

```
cagcgggtat tcctacctga tccgaggtca acattcagaa gttgggggtt taacggcttg     60

gccgcgccgc gtaccagttg cgagggtttt actactacgc aatggaagct gcagcgagac    120

cgccactgta tttcggggcc ggcttgccgt gaggctcgcc gatccccaac accaaacccg    180

ggggcttgag ggttgaaatg acgctcgaac aggcatgccc gccagaatac tggcgggcgc    240

aatgtgcgtt caaagattcg atgattcact gaattctgca attcacatta cttatcgcat    300

tttgctgcgt tcttcatcga tgccagaacc aagagatccg ttgttgaaag ttttgattta    360

tttatggttt tactcagaag ttacatatag aaacagagtt taggggtcct ctggcgggcc    420

gttccgtttt accgggagcg ggctgatccg ccgaggcaac aattggtatg ttcacagggg    480

tttgggagtt gtaaactcgg taatgatccc tccgctggtt caccaacgga               530
```

<210> SEQ ID NO 327
<211> LENGTH: 541
<212> TYPE: DNA
<213> ORGANISM: Fusarium nygamai

<400> SEQUENCE: 327

```
aattcgtaac aaggtctccg ttggtgaacc agcggaggga tcattaccga gtttacaact     60

cccaaacccc tgtgaacata ccaattgttg cctcggcgga tcagcccgct cccggtaaaa    120

cggaacggcc cgccagagga cccctaaact ctgtttctat atgtaacttc tgagtaaaac    180

cataaataaa tcaaaacttt caacaacgga tctcttggtt ctggcatcga tgaagaacgc    240

agcaaaatgc gataagtaat gtgaattgca gaattcagtg aatcatcgaa tctttgaacg    300

cacattgcgc ccgccagtat tctggcgggc atgcctgttc gagcgtcatt tcaaccctca    360

agcccccggg tttggtgttg gggatcggcg agcctcacgg caagccggcc ccgaaataca    420

gtggcggtct cgctgcagct tccattgcgt agtagtaaaa ccctcgcaac tggtacgcgg    480

cgcggccaag ccgttaaacc cccaacttct gaatgttgac ctcggatcag gtaggaatac    540

c                                                                    541
```

<210> SEQ ID NO 328
<211> LENGTH: 549
<212> TYPE: DNA
<213> ORGANISM: Gaeumannomyces incrustans

<400> SEQUENCE: 328

```
ttaagttcag cgggtattcc tacctgatcc gaggtcaact cgaaaaacgt cactgggggt     60

ttagcggctg gaagcccgag gaggccgccg agcgagggcg cgttttaccg cgagttacta    120

cgctcggagc cccagcggga ccgccgatgt acttgggggc cccgaccgcc aggcggccgg    180
```

gtgccccaac accaagctgg gcttgagtgg tgaaatgacg ctcggacagg catgcccgcc 240
ggaataccgg cgggcgcaat gtgcgttcaa agattcgatg attcactgaa ttctgcaatt 300
cacattactt atcgcatttc gctgcgttct tcatcgatgc cagagccaag agatccgttg 360
ttgaaagttt taattggttt ttttcgtcct cagagataca ctagaattca gggtttaaaa 420
cctccggcgg cgtcccccag gcccggctgg gcgcggcgtc ggccgccgaa gcaacgtaca 480
ggtaaagttc acaggggttg gagttttgca actctttaat gatccctccg ctggttcacc 540
aacggagac 549

<210> SEQ ID NO 329
<211> LENGTH: 569
<212> TYPE: DNA
<213> ORGANISM: Gaeumannomyces incrustans

<400> SEQUENCE: 329
cgggattcta cctgatccga gtcaactcga aaaacgtcac tgggggttta gcggctggaa 60
gcccgaggag gccgccgagc gagggcgcgt tttaccgcga gttactacgc tcggagcccc 120
agcgggaccg ccgatgtact tgggggcccc gaccgccagg cggccgggtg ccccaacacc 180
aagctgggct tgagtggtga aatgacgctc ggacaggcat gcccgccgga ataccggcgg 240
gcgcaatgtg cgttcaaaga ttcgatgatt cactgaattc tgcaattcac attacttatc 300
gcatttcgct gcgttcttca tcgatgccag agccaagaga tccgttgttg aaagttttaa 360
ttggtttttt tcgtcctcag agatacacta gaattcaggg tttaaaacct ccggcggcgt 420
cccccaggcc cggctgggcg cggcgtcggc cgccgaagca acgtacaggt aaagttcaca 480
ggggttggag ttttgcaact ctttaatgat ccctccgctg gttcaccaac ggagaccttg 540
ttacgactta tacttcctct aaatgacca 569

<210> SEQ ID NO 330
<211> LENGTH: 609
<212> TYPE: DNA
<213> ORGANISM: Magnaporthe rhizophila

<400> SEQUENCE: 330
cttggtcatt tagaggaagt aaaagttcgt aacaaaggtc tccgttggtg aaccagcgga 60
ggggatcatt aaagagttgc aaaactccaa cccctgtgaa ctttacctgt acgttgcttc 120
ggcggccgac gccgcgccca gccgggcgtg ggggacgccg ccggaggttt taaaccctga 180
attctagtgt atctctgagg acgaaaagaa ccaattaaaa ctttcaacaa cggatctctt 240
ggctctggca tcgatgaaga acgcagcgaa atgcgataag taatgtgaat tgcagaattc 300
agtgaatcat cgaatctttg aacgcacatt gcgcccgccg gtattccggc gggcatgcct 360
gtccgagcgt catttcacca ctcaagccca gcttggtgtt ggggcacccg gccgcccggc 420
ggtcggggcc cccaagtaca tcggcggtcc tgctggggct ccgagcgcag taacacgcgg 480
taaaacgcgc cctcgctcgg cggcctcctc gggcttccag ccgctaaacc cccagtgacg 540
tttttcgagt tgacctcgga tcaggtagga atacccgctg aacttaagca tatcaataag 600
cggaggaaa 609

<210> SEQ ID NO 331
<211> LENGTH: 525
<212> TYPE: DNA
<213> ORGANISM: Magnaporthe rhizophila

<400> SEQUENCE: 331
ttctacctga tccgagtcaa ctcgaaaaac gtcactgggg gtttagcggc tggaagcccg 60
aggaggccgc cgagcgaggg cgcgttttac cgcgtgttac tgcgctcgga gccccagcag 120
gaccgccgat gtacttgggg gccccgaccg ccgggcggcc gggtgcccca acaccaagct 180
gggcttgagt ggtgaaatga cgctcggaca ggcatgcccg ccggaatacc ggcgggcgca 240
atgtgcgttc aaagattcga tgattcactg aattctgcaa ttcacattac ttatcgcatt 300
tcgctgcgtt cttcatcgat gccagagcca agagatccgt tgttgaaagt tttaattggt 360
tcttttcgtc ctcagagata cactagaatt cagggtttaa aacctccggc ggcgtccccc 420
acgcccggct gggcgcggcg tcggccgccg aagcaacgta caggtaaagt tcacaggggt 480
tggagttttg caactcttta atgatcccct ccgctggttc accaa 525

<210> SEQ ID NO 332
<211> LENGTH: 584
<212> TYPE: DNA
<213> ORGANISM: Uncultured Ascomycete sp.

<400> SEQUENCE: 332
ttcctccgct tattgatatg cttaagttca gcgggtatcc ctacctgatc cgaggtcaaa 60
cgtggtaaat gttcttgatg gacgccagta caacgggcta cgatcgcaaa atgtgctgcg 120
ctcctaggcc aaagtgccgg ctgccaataa atttaaggcg agtcgtaata cgacaagacg 180
cccaacacca agcaaagctt gagggtacaa atgacgctcg aacaggcatg ccccatggaa 240
taccaagggg cgcaatgtgc gttcaaagat tcgatgattc actgaattct gcaattcaca 300
ctacttatcg catttcgctg cgttcttcat cgatgccaga accaagagat ccgttgttga 360
aagttgtaaa taattagatt attttcagac gctgattgca attacaaaaa aggttttggt 420
ttgtccaatc ggcagcttgc gccaccgagg aaacaagagt acgcaaaaga catgggtgta 480
gacgagagct ttacagcccc cgacttgact tttgataatg atccttccgc aggttcacct 540
acggaaacct tgttacgact tttacttcct ctaaatgacc aaga 584

<210> SEQ ID NO 333
<211> LENGTH: 597
<212> TYPE: DNA
<213> ORGANISM: Fusarium proliferatum

<400> SEQUENCE: 333
tttcctccgc ttattgatat gcttaagttc agcgggtatt cctacctgat ccgaggtcaa 60
cattcagaag ttgggggttt aacggcttgg ccgcgccgcg taccagttgc gagggtttta 120
ctactacgca atggaagctg cagcgagacc gccactgtat ttcggggccg gcttgccgtg 180
aggctcgccg atccccaaca ccaaacccgg gggcttgagg gttgaaatga cgctcgaaca 240
ggcatgcccg ccagaatact ggcgggcgca atgtgcgttc aaagattcga tgattcactg 300
aattctgcaa ttcacattac ttatcgcatt ttgctgcgtt cttcatcgat gccagaacca 360
agagatccgt tgttgaaagt tttgatttat ttatggtttt actcagaagt tacatataga 420
aacagagttt aggggtcctc tggcgggccg ttccgtttta ccgggagcgg gctgatccgc 480
cgaggcaaca attggtatgt tcacaggggt ttgggagttg taaactcggt aatgatccct 540
ccgctggttc accaacggag accttgttac gacttttact tcctctaaat gaccaag 597

<210> SEQ ID NO 334
<211> LENGTH: 529

<212> TYPE: DNA
<213> ORGANISM: Magnaporthe rhizophila

<400> SEQUENCE: 334
aaggtctccg ttgtgaccag cggagggatc attaaagagt tgcaaaactc caacccctgt 60
gaactttacc tgtacgttgc ttcggcggcc gacgccgcgc ccagccgggc ccgggggacg 120
ccgccggagg tcataaaccc tgaattctag tgtatctctg aggacgaaaa taaccaatta 180
aaactttcaa caacggatct cttggctctg gcatcgatga agaacgcagc gaaatgcgat 240
aagtaatgtg aattgcagaa ttcagtgaat catcgaatct ttgaacgcac attgcgcccg 300
ccggtattcc ggcgggcatg cctgtccgag cgtcatttca ccactcaagc ccagcttggt 360
gttggggcac ccggccgccc ggcggtcggg gcccccaagt acatcggcgg tcccgctggg 420
gctccgagcg cagtaactcg cggtaaaacg cgccctcgct cggcggcctc ctcgggcttc 480
cagccgctaa acccccagtg acgtttttcg agtgactcgg atcagtaga 529

<210> SEQ ID NO 335
<211> LENGTH: 541
<212> TYPE: DNA
<213> ORGANISM: Uncultured soil fungus

<400> SEQUENCE: 335
gtgaacccag cggagggatc attaccgagt ttacaactcc caaacccctg tgaacatacc 60
tttactgttg cctcggcgga tcagcccgcg cccggtaaaa cgggacggcc cgccagagga 120
cccctaaact ctgtttttat tgtaacttct gagtaaaacc ataaataaat caaaactttc 180
aacaacggat ctcttggttc tggcatcgat gaagaacgca gcaaaatgcg ataagtaatg 240
tgaattgcag aattcagtga atcatcgaat ctttgaacgc acattgcgcc cgccagtatt 300
ctggcgggca tgcctgttcg agcgtcattt caaccctcaa gccctcgggt ttggtgttgg 360
ggatcggcga gcctctctgg caagccggcc ccgaaatcta gtggcggtct cactgcagcc 420
tccattgcgt agtagctaac acctcgcaac tggaacgcgg tgcggccaag ccgttaaacc 480
cccccaactt ctgaatgttg acctcggatc aggtaggaat acccgctgaa cttaagcata 540
t 541

<210> SEQ ID NO 336
<211> LENGTH: 600
<212> TYPE: DNA
<213> ORGANISM: Uncultured fungus

<400> SEQUENCE: 336
tcctccgctt attgatatgc ttaagttcag cgggtattcc tacctgatcc gaggtcaaca 60
ttcagaagtt ggggggtttt aacggcttgg ccgcaccgcg ttccagttgc gaggtgttag 120
ctactacgca atggaggctg cagtgagacc gccactagat ttcggggccg gcttgccaga 180
gaggctcgcc gatccccaac accaaacccg agggcttgag ggttgaaatg acgctcgaac 240
aggcatgccc gccagaatac tggcgggcgc aatgtgcgtt caaagattcg atgattcact 300
gaattctgca attcacatta cttatcgcat tttgctgcgt tcttcatcga tgccagaacc 360
aagagatccg ttgttgaaag ttttgattta tttatggttt tactcagaag ttacaataaa 420
aacagagttt aggggtcctc tggcgggccg tcccgtttta ccgggcgcgg gctgatccgc 480
cgaggcaaca gtaaaggtat gttcacaggg gtttgggagt tgtaaactcg gtaatgatcc 540
ctccgctggt tcaccaacgg agaccttgtt acgactttta cttcctctaa atgaccaaga 600

<210> SEQ ID NO 337
<211> LENGTH: 603
<212> TYPE: DNA
<213> ORGANISM: Periconia macrospinosa

<400> SEQUENCE: 337
ttccctccgc tttattgata tgcttaaagt tcagcgggta tccctacctg atcccgaggt 60
caagtcgtga aaggtcttgc tggagcgcgg atccgccggg cctccgagaa gcgcaaatgt 120
gctgcgcgag ggggccggca cgaccgccgc caatgacttt gaggcgagtc cgcgcgcgag 180
aacggcggga cagacgccca acaccaagct aggcttgagg gtgtaaatga cgctcgaaca 240
ggcatggcca aaggaatacc tatggccgca atgtgcgttc aaagattcga tgattcactg 300
aattctgcaa ttcacactac ttatcgcatt tcgctgcgtt cttcatcgat gccagaacca 360
agagatccat tgttgaaagt tgtgataatt taggtttgtt atcagaagtt ttcgcgtata 420
atgcaagggg tttcgtgggt tcctggcggc gggcgagccc gccgaggaag ctatagaggt 480
acacgtaggc agagggtggg tgtataagga gcgccgaagc gccccgaatg tgtaatgatc 540
cttccgcagg ttcacctacg ggaaaccttg ttacgacttt tacttcctct aaatgaccaa 600
gga 603

<210> SEQ ID NO 338
<211> LENGTH: 597
<212> TYPE: DNA
<213> ORGANISM: Periconia macrospinosa

<400> SEQUENCE: 338
ttcctccgct tattgatatg cttaagttca gcgggtatcc ctacctgatc cgaggtcaag 60
tcgtgaaagg tcttgctgga gcgcggatcc gccgggcctc cgagaagcgc aaatgtgctg 120
cgcgaggggg ccggcacgac cgccgccaat gactttgagg cgagtccgcg cgcgagaacg 180
gcgggacaga cgcccaacac caagctaggc ttgagggtgt aaatgacgct cgaacaggca 240
tggccaaagg aatacctatg gccgcaatgt gcgttcaaag attcgatgat tcactgaatt 300
ctgcaattca cactacttat cgcatttcgc tgcgttcttc atcgatgcca gaaccaagag 360
atccattgtt gaaagttgtg ataatttagg tttgttatca gaagttttcg cgtataatgc 420
aaggggtttc gtgggttcct ggcggcgggc gagcccgccg aggaagctat agaggtacac 480
gtaggcagag ggtgggtgta taaggagcgc cgaagcgccc cgaatgtgta atgatccttc 540
cgcaggttca cctacggaaa ccttgttacg acttttactt cctctaaatg accaaga 597

<210> SEQ ID NO 339
<211> LENGTH: 603
<212> TYPE: DNA
<213> ORGANISM: Fusarium nygamai

<400> SEQUENCE: 339
tcctccgctt attgatatgc ttaagttcag cgggtattcc tacctgatcc gaggtcaaca 60
ttcagaagtt gggggtttaa cggcttggcc gcgccgcgta ccagttgcga gggttttact 120
actacgcaat ggaagctgca gcgagaccgc cactgtattt cggggccggc ttgccgtgag 180
gctcgccgat ccccaacacc aaacccgggg gcttgagggt tgaaatgacg ctcgaacagg 240
catgcccgcc agaatactgg cgggcgcaat gtgcgttcaa agattcgatg attcactgaa 300
ttctgcaatt cacattactt atcgcatttt gctgcgttct tcatcgatgc cagaaccaag 360
agatccgttg ttgaaagttt tgatttattt atggttttac tcagaagtta catatagaaa 420

```
cagagtttag gggtcctctg gcgggccgtt ccgttttacc gggagcgggg ctgatccgcc    480

gaggcaacaa ttggtatgtt cacaggggtt tgggagttgt aaaactcggt aatgatccct    540

ccgctgggtt caccaacgga gaaccttgtt tacgactttt tacttcctct aaatgaccaa    600

gga                                                                  603
```

<210> SEQ ID NO 340
<211> LENGTH: 625
<212> TYPE: DNA
<213> ORGANISM: Eladia saccula

<400> SEQUENCE: 340

```
tcctccgctt attgatatgc ttaagttcag cgggtatccc tacctgatcc gaggtcaacc     60

tggaaaaaag attgatgtgt cggcaagcgc cggccgggcc tacaagagcg ggtgacgaag    120

ccccatacgc tcgaggaccg gacgcggtac cgccgctgcc tttcgggccc gtcccccggg    180

aggaggacgg aggcccaaca cacaagccgt gcttgagggc agcaatgacg ctcggacagg    240

catgcccccc ggaataccag gggcgcaat gtgcgttcaa agactcgatg attcactgaa    300

ttctgcaatt cacattacgt atcgcatttc gctgcgttct tcatcgatgc cggaaccaag    360

agatccgttg ttgaaagttt taacttattt agctaattgc tcagactgca ctcttcagac    420

agcgttcaat ggtgtcttcg gcgggcgcgg gcccgagggg cagaagcccc ccggcggccg    480

tgaggcgggc ccgccgaagc aacaaggtac gataaacacg ggtgggaggt tggacccaga    540

gggccctcac tcggtaatga tccttccgca ggttcaccta cggaaacctt gttacgactt    600

ttacttcctc taaatgacca agatg                                          625
```

<210> SEQ ID NO 341
<211> LENGTH: 586
<212> TYPE: DNA
<213> ORGANISM: Gaeumannomyces incrustans

<400> SEQUENCE: 341

```
gtaaaagtcg taacaaggtc tccgttggtg aaccagcgga gggatcatta aagagttgca     60

aaactccaac ccctgtgaac tttacctgta cgttgcttcg gcggccgacg ccgcgcccag    120

ccgggcccgg gggacgccgc cggaggtcat aaaccctgaa ttctagtgta tctctgagga    180

cgaaaataac caattaaaac tttcaacaac ggatctcttg gctctggcat cgatgaagaa    240

cgcagcgaaa tgcgataagt aatgtgaatt gcagaattca gtgaatcatc gaatctttga    300

acgcacattg cgcccgccgg tattccggcg ggcatgcctg tccgagcgtc atttcaccac    360

tcaagcccag cttggtgttg ggcacccgg ccgcccggcg gtcggggccc ccaagtacat    420

cggcggtccc gctggggctc cgagcgcagt aactcgcggt aaaacgcgcc ctcgctcggc    480

ggcctcctcg ggcttccagc cgctaaaccc ccagtgacgt ttttcgagtt gacctcggat    540

caggtaggaa tacccgctga acttaagcat atcaataagc ggagga                   586
```

<210> SEQ ID NO 342
<211> LENGTH: 565
<212> TYPE: DNA
<213> ORGANISM: Fusarium moniliformae

<400> SEQUENCE: 342

```
aggtctccgt tggtgaacca gcggagggat cattaccgag tttacaactc ccaaacccct     60

gtgaacatac cacttgttgc ctcggcggat cagcccgctc ccggtaaaac gggacggccc    120
```

gccagaggac ccctaaactc tgtttctata tgtaacttct gagtaaaacc ataaataaat 180
caaaactttc aacaacggat ctcttggttc tggcatcgat gaagaacgca gcaaaatgcg 240
ataagtaatg tgaattgcag aattcagtga atcatcgaat ctttgaacgc acattgcgcc 300
cgccagtatt ctggcgggca tgcctgttcg agcgtcattt caaccctcaa gccctcgggt 360
ttggtgttgg ggatcggcga gcccttgcgg caagccggcc ccgaaatcta gtggcggtct 420
cgctgcagcc tccattgcgt agtagtaaaa ccctcgcaac tggaacgcgg cgcggccaag 480
ccgttaaacc cccaacttct gaatgttgac ctcggatcag gtaggaatac ccgctgaact 540
taagcatatc aataagcggg aggaa 565

<210> SEQ ID NO 343
<211> LENGTH: 547
<212> TYPE: DNA
<213> ORGANISM: Gaeumannomyces incrustans

<400> SEQUENCE: 343
gtaacaaggt ctccgttggt gaaccagcgg agggatcatt aaagagttgc aaaactccaa 60
cccctgtgaa ctttacctgt acgttgcttc ggcggccgac gccgcgccca gccgggcctg 120
ggggacgccg ccggaggttt taaaccctga attctagtgt atctctgagg acgaaaaaaa 180
ccaattaaaa ctttcaacaa cggatctctt ggctctggca tcgatgaaga acgcagcgaa 240
atgcgataag taatgtgaat tgcagaattc agtgaatcat cgaatctttg aacgcacatt 300
gcgcccgccg gtattccggc gggcatgcct gtccgagcgt catttcacca ctcaagccca 360
gcttggtgtt ggggcacccg gccgcccggc ggtcggggcc cccaagtaca tcggcggtcc 420
cgctggggct ccgagcgcag taactcgcgg taaaacgcgc cctcgctcgg cggcctcctc 480
gggcttccag ccgctaaacc cccagtgacg tttttcgagt tgacctcgga tcaggtagga 540
atacccg 547

<210> SEQ ID NO 344
<211> LENGTH: 523
<212> TYPE: DNA
<213> ORGANISM: Uncultured root-associated fungus

<400> SEQUENCE: 344
tctactgatc cgagtcaact cgaaaaacgt cactgggggt ttagcggctg gaagcccgag 60
gaggccgccg agcgagggcg cgttttaccg cgagttactg cgctcggagc cccagcggga 120
ccgccgatgt acttgggggc ccccgaccgcc gggcggccgg gtgccccaac accaagctgg 180
gcttgagtgg tgaaatgacg ctcggacagg catgcccgcc ggaataccgg cgggcgcaat 240
gtgcgttcaa agattcgatg attcactgaa ttctgcaatt cacattactt atcgcatttc 300
gctgcgttct tcatcgatgc cagagccaag agatccgttg ttgaaagttt taattggttt 360
ttttcgtcct cagagataca ctagaattca gggtttaaaa cctccggcgg cgtcccccag 420
gcccggctgg gcgcggcgtc ggccgccgaa gcaacgtaca ggtaaagttc acaggggttg 480
gagttttgca actctttaat gatccctccg ctggtcagca acg 523

<210> SEQ ID NO 345
<211> LENGTH: 575
<212> TYPE: DNA
<213> ORGANISM: Fusarium nygamai

<400> SEQUENCE: 345
ttccctccgc ttattgatat gcttaagttc agcgggtatt cctacctgat ccgaggtcaa 60
cattcagaag ttgggggttt aacggcttgg ccgcgccgcg taccagttgc gagggtttta 120
ctactacgca atggaagctg cagcgagacc gccactgtat ttcggggccg gcttgccgtg 180
aggctcgccg atccccaaca ccaaacccgg gggcttgagg gttgaaatga cgctcgaaca 240
ggcatgcccg ccagaatact ggcgggcgca atgtgcgttc aaagattcga tgattcactg 300
aattctgcaa ttcacattac ttatcgcatt ttgctgcgtt cttcatcgat gccagaacca 360
agagatccgt tgttgaaagt tttgatttat ttatggtttt actcagaagt tacatataga 420
aacagagttt aggggtcctc tggcgggccg ttccgtttta ccgggagcgg gctgatccgc 480
cgaggcaaca attggtatgt tccacagggg tttgggagtt gtaaactcgg taatgatccg 540
tccgctggtc agacaacctg aagctcgggc ccccc 575

<210> SEQ ID NO 346
<211> LENGTH: 605
<212> TYPE: DNA
<213> ORGANISM: Fusarium sp.

<400> SEQUENCE: 346
tccatttaga ggaagtaaaa gtcgtaaaca aggtctccgt tggtgaacca gcggagggat 60
cattaccgag ttatacaact catcaaccct gtgaacatac ctataacgtt gcctcggcgg 120
gaacagacgg ccccgtaaca cgggccgccc ccgccagagg acccccctaac tctgtttcta 180 taatgtttct tctgagtaaa caagcaaata aattaaaact ttcaacaacg gatctcttgg 240
ctctggcatc gatgaagaac gcagcgaaat gcgataagta atgtgaattg cagaattcag 300
tgaatcatcg aatctttgaa cgcacattgc gcccgccagt attctggcgg gcatgcctgt 360
tcgagcgtca ttacaaccct caggcccccg ggcctggcgt tggggatcgg cggaagcccc 420
ctgcgggcac aacgccgtcc cccaaataca gtggcggtcc cgccgcagct tccattgcgt 480
agtagctaac acctcgcaac tggagagcgg cgcggccacg ccgtaaaaca cccaacttct 540
gaatgttgac ctcgaatcag gtagggaata cccgctgaac ttaagcatat caataagcgg 600
aggaa 605

<210> SEQ ID NO 347
<211> LENGTH: 528
<212> TYPE: DNA
<213> ORGANISM: Fusarium nygamai

<400> SEQUENCE: 347
tcagcgggta ttcctacctg atccgaggtc aacattcaga agttgggggt ttaacggctt 60
ggccgcgccg cgtaccagtt gcgagggttt tactactacg caatggaagc tgcagcgaga 120
ccgccactgt atttcggggc cggcttgccg tgaggctcgc cgatccccaa caccaaaccc 180
gggggcttga gggttgaaat gacgctcgaa caggcatgcc cgccagaata ctggcgggcg 240
caatgtgcgt tcaaagattc gatgattcac tgaattctgc aattcacatt acttatcgca 300
ttttgctgcg ttcttcatcg atgccagaac caagagatcc gttgttgaaa gttttgattt 360
atttatggtt ttactcagaa gttacatata gaaacagagt ttaggggtcc tctggcgggc 420
cgttccgttt taccgggagc gggctgatcc gccgaggcaa caattggtat gttcacaggg 480
gtttgggagt tgtaaactcg gtaatgatcc ctccgctggt acaccaac 528

<210> SEQ ID NO 348
<211> LENGTH: 573
<212> TYPE: DNA

-continued

<213> ORGANISM: Uncultured endophytic fungus

<400> SEQUENCE: 348

```
tcctccgcct tattgatatg cttaagttca gcgggtattc ctacctgatc cgaggtcaac     60
cttagtgagt gtttcacggc tagcacccgc cgccacgccc agagcgagat acgctactgc    120
gctcggggta acagcgagcc cgccactgca tttagggggc tgcggcagcc gcagggcccc    180
aacacaggcc tggacagggc ctgatggttg aaatgacgct cgaacaggca tgcccgccag    240
aatactggcg ggcgcaatgt gcgttcaaag attcgatgat tcactgaatt ctgcaattca    300
cattacttat cgcatttcgc tgcgttcttc atcgatgcca gaaccaagag atccgttgtt    360
gaaagtttta acttattgaa taagctactc agagatccac tgtaatctag agtttgcatg    420
ctgccggcgg gcggtttcag cgcaccaccc gccgaagcaa ctataacggg ttcgttcaca    480
atggttggga gttttgcaac tctgtaatga tccctccgct ggttcaccaa cggagacctt    540
gttacgactt ttacttcctc taaatgacca aga                                 573
```

<210> SEQ ID NO 349
<211> LENGTH: 779
<212> TYPE: DNA
<213> ORGANISM: Fusarium proliferatum

<400> SEQUENCE: 349

```
tcttggtcat ttagaggaag taaaagtcgt aacaaggtat ctgtaggtga acctgcagat     60
ggatcatttc gatgaaaacc ttttttctga ggtgtggctc gcacctgtcc aactaaactt    120
gagctacctt tttaacacgg ttgcatcggt tgagagcctg tcaaagaacg cgaaagtgtc    180
ctcttggtca tttagaggaa gtaaaagtcg taacaaggtc tccgttggtg aaccagcgga    240
gggatcatta ccgagtttac aactcccaaa cccctgtgaa cataccaatt gttgcctcgg    300
cggatcagcc cgctcccggt aaaacggaac ggcccgccag aggacccct a aactctgttt    360
ctatatgtaa cttctgagta aaaccataaa taaatcaaaa ctttcaacaa cggatctctt    420
ggttctggca tcgatgaaga acgcagcaaa atgcgataag taatgtgaat tgcagaattc    480
agtgaatcat cgaatctttg aacgcacatt gcgcccgcca gtattctggc gggcatgcct    540
gttcgagcgt catttcaacc ctcaagcccc cgggtttggt gttggggatc ggcgagcctc    600
acggcaagcc ggccccgaaa tacagtggcg gtctcgctgc agcttccatt gcgtagtagt    660
aaaaccctcg caactggtac gcggcgcggc caagccgtta aacccccaac ttctgaatgt    720
tgacctcgga tcaggtagga atacccgctg aacttaagca tatcaataag ccggaggaa     779
```

<210> SEQ ID NO 350
<211> LENGTH: 442
<212> TYPE: DNA
<213> ORGANISM: Fusarium oxysporum

<400> SEQUENCE: 350

```
ctacgctatg gaagctcgac gtgaccgcca atcaatttgg ggaacgcgaa ttaacgcgag     60
tcccaacacc aagctgtgct tgagggttga aatgacgctc gaacaggcat gcccgccaga    120
atactggcgg gcgcaatgtg cgttcaaaga ttcgatgatt cactgaattc tgcaattcac    180
attacttatc gcattttgct gcgttcttca tcgatgccag aaccaagaga tccgttgttg    240
aaagttttga tttatttatg gttttactca gaagttacat atagaaacag agtttagggg    300
tcctctggcg ggccgtcccg ttttaccggg agcgggctga tccgccgagg caacaagtgg    360
tatgttccac aggggtttgg gagttgtaaa ctcggtaatg aaccccccgc tggtcaccca    420
```

aacgagaccc tggaagccct ga 442

<210> SEQ ID NO 351
<211> LENGTH: 562
<212> TYPE: DNA
<213> ORGANISM: Fusarium nygamai

<400> SEQUENCE: 351
ggtctccgtt ggtgaaccag cggagggatc attaccgagt ttacaactcc caaacccctg 60
tgaacatacc aattgttgcc tcggcggatc agcccgctcc cggtaaaacg ggacggcccg 120
ccagaggacc cctaaactct gtttctatat gtaacttctg agtaaaacca taaataaatc 180
aaaactttca acaacggatc tcttggttct ggcatcgatg aagaacgcag caaaatgcga 240
taagtaatgt gaattgcaga attcagtgaa tcatcgaatc tttgaacgca cattgcgccc 300
gccagtattc tggcgggcat gcctgttcga gcgtcatttc aaccctcaag cccccgggtt 360
tggtgttggg gatcggcgag cctcacggca agccggcccc gaaatacagt ggcggtctcg 420
ctgcagcttc cattgcgtag tagtaaaacc ctcgcaactg gtacgcggcg cggccaagcc 480
gttaaacccc caacttctga atgttgacct cggatcaggt aggaataccc gctgaactta 540
agcatatcaa taagcggagg aa 562

<210> SEQ ID NO 352
<211> LENGTH: 585
<212> TYPE: DNA
<213> ORGANISM: Uncultured endophytic fungus

<400> SEQUENCE: 352
ttcctccgct tattgatatg cttaagttca gcgggtatcc ctacctgatc cgaggtcaaa 60
cgtggtaaat gttcttgatg gacgccagta caacgggcta cgatcgcaaa atgtgctgcg 120
ctcctaggcc aaagtgccgg ctgccaataa atttaaggcg agtcgtaata cgacaagacg 180
cccaacacca agcaaagctt gagggtacaa atgacgctcg aacaggcatg ccccatggaa 240
taccaagggg cgcaatgtgc gttcaaagat tcgatgattc actgaattct gcaattcaca 300
ctacttatcg catttcgctg cgttcttcat cgatgccaga accaagagat ccgttgttga 360
aagttgtaaa taattagatt attttcagac gctgattgca attacaaaaa aggttttggt 420
ttgtccaatc ggcagcttgc gccaccgagg aaacaagagt acgcaaaaga catgggtgta 480
gacgagagct ttacagcccc cgacttgact tttgataatg atccttccgc aggttcacct 540
accggaarcc kwryymcsac ttttacttcc tctaaatgac caaga 585

<210> SEQ ID NO 353
<211> LENGTH: 515
<212> TYPE: DNA
<213> ORGANISM: Ascomycete sp.

<400> SEQUENCE: 353
ctacctgatc cgaggtcaaa cgtggtaaat gttcttgatg gacgccagta caacgggcta 60
cgatcgcaaa atgtgctgcg ctcctaggcc aaagtgccgg ctgccaataa atttaaggcg 120
agtcgtaata cgacaagacg cccaacacca agcaaagctt gagggtacaa atgacgctcg 180
aacaggcatg ccccatggaa taccaagggg cgcaatgtgc gttcaaagat tcgatgattc 240
actgaattct gcaattcaca ctacttatcg catttcgctg cgttcttcat cgatgccaga 300
accaagagat ccgttgttga aagttgtaaa taattagatt attttcagac gctgattgca 360

```
attacaaaaa aggttttggt ttgtccaatc ggcagcttgc gccaccgagg aaacaagagt    420

acgcaaaaga catgggtgta gacgagagct ttacagcccc cgacttgact tttgataatg    480

atccttccgc aggttcacct acggaaacct tgtta                               515
```

<210> SEQ ID NO 354
<211> LENGTH: 582
<212> TYPE: DNA
<213> ORGANISM: Uncultured Ascomycete sp.

<400> SEQUENCE: 354

```
cttggtcatt tagaggaagt aaaagtcgta acaaggtttc cgtaggtgaa cctgcggaag     60

gatcattatc aaaagtcaag tcgggggctg taaagctctc gtctacaccc atgtcttttg    120

cgtactcttg tttcctcggt ggcgcaagct gccgattgga caaaccaaaa cctttttttgt   180

aattgcaatc agcgtctgaa aataatctaa ttatttacaa ctttcaacaa cggatctctt    240

ggttctggca tcgatgaaga acgcagcgaa atgcgataag tagtgtgaat tgcagaattc    300

agtgaatcat cgaatctttg aacgcacatt gcgccccttg gtattccatg ggcatgcct     360

gttcgagcgt catttgtacc ctcaagcttt gcttggtgtt gggcgtcttg tcgtattacg    420

actcgcctta aatttattgg cagccggcac tttggcctag gagcgcagca cattttgcga    480

tcgtagcccg ttgtactggc gtccatcaag aacatttacc acgtttgacc tcggatcagg    540

tagggatacc cgctgaactt aagcatatca ataagcggag ga                       582
```

<210> SEQ ID NO 355
<211> LENGTH: 607
<212> TYPE: DNA
<213> ORGANISM: Gaeumannomyces incrustans

<400> SEQUENCE: 355

```
tcttggtcat ttagaggaag taaaagtcgt aacaaggtct ccgttggtga accagcggag     60

ggatcattaa agagttgcaa aactccaacc cctgtgaact ttacctgtac gttgcttcgg    120

cggccgacgc cgcgcccagc cgggcctggg ggacgccgcc ggaggtttta aaccctgaat    180

tctagtgtat ctctgaggac gaaaaaaacc aattaaaact ttcaacaacg gatctcttgg    240

ctctggcatc gatgaagaac gcagcgaaat gcgataagta atgtgaattg cagaattcag    300

tgaatcatcg aatctttgaa cgcacattgc gcccgccggt attccggcgg gcatgcctgt    360

ccgagcgtca tttcaccact caagcccagc ttggtgttgg ggcacccggc cgcccggcgg    420

tcggggcccc caagtacatc ggcggtcctg ctggggctcc gagcgcagta acacgcggta    480

aaacgcgccc tcgctcggcg gcctcctcgg gcttccagcc gctaaacccc cagtgacgtt    540

tttcgagttg acctcggatc aggtagggaa tacccgctga acttaagcat atcaataagc    600

ggaggaa                                                              607
```

<210> SEQ ID NO 356
<211> LENGTH: 552
<212> TYPE: DNA
<213> ORGANISM: Uncultured root-associated fungus

<400> SEQUENCE: 356

```
ttcctccgct tattgatatg cttaagttca gcgggtattc ctacctgatc cgaggtcaac     60

tcgaaaaacg tcactggggg tttagcggct ggaagcccga ggaggccgcc gagcgagggc    120

gcgttttacc gcgtgttact gcgctcggag ccccagcagg accgccgatg tacttggggg    180

ccccgaccgc cgggcggccg ggtgccccaa caccaagctg ggcttgagtg gtgaaatgac    240
```

```
gctcggacag gcatgcccgc cggaataccg gcgggcgcaa tgtgcgttca aagattcgat    300

gattcactga attctgcaat tcacattact tatcgcattt cgctgcgttc ttcatcgatg    360

ccagagccaa gagatccgtt gttgaaagtt ttaattggtt tttttcgtcc tcagagatac    420

actagaattc agggtttaaa acctccggcg gcgtccccca ggcccggctg ggcgcggcgt    480

cggccgccga agcaacgtac aggtaaagtt cacaggggtt ggagttttgc aactctttaa    540

tgatccctcc gc                                                        552
```

<210> SEQ ID NO 357
<211> LENGTH: 510
<212> TYPE: DNA
<213> ORGANISM: Uncultured root-associated fungus

<400> SEQUENCE: 357

```
ggtctcgttc tgaccagcgg agggatcatt aaagagttgc aaaactccaa cccctgtgaa     60

ctttacctgt acgttgcttc ggcggccgac gccgcgccca gccgggcctg gggacgccg    120

ccggaggttt taaaccctga attctagtgt atctctgagg acgaaaaaaa ccaattaaaa    180

ctttcaacaa cggatctctt ggctctggca tcgatgaaga acgcagcgaa atgcgataag    240

taatgtgaat tgcagaattc agtgaatcat cgaatctttg aacgcacatt gcgcccgccg    300

gtattccggc gggcatgcct gtccgagcgt catttcacca ctcaagccca gcttggtgtt    360

ggggcacccg gccgcccggc ggtcggggcc cccaagtaca tcggcggtcc tgctggggct    420

ccgagcgcag taacacgcgg taaaacgcgc cctcgctcgg cggcctcctc gggcttccag    480

ccgctaaacc cccagtgacg tttttcgagt                                     510
```

<210> SEQ ID NO 358
<211> LENGTH: 597
<212> TYPE: DNA
<213> ORGANISM: Fusarium proliferatum

<400> SEQUENCE: 358

```
tcttggtcat ttagaggaag taaaagtcgt aacaaggtct ccgttggtga accagcggag     60

ggatcattac cgagtttaca actcccaaac ccctgtgaac ataccaattg ttgcctcggc    120

ggatcagccc gctcccggta aaacggaacg gcccgccaga ggacccctaa actctgtttc    180

tatatgtaac ttctgagtaa aaccataaat aaatcaaaac tttcaacaac ggatctcttg    240

gttctggcat cgatgaagaa cgcagcaaaa tgcgataagt aatgtgaatt gcagaattca    300

gtgaatcatc gaatctttga acgcacattg cgcccgccag tattctggcg ggcatgcctg    360

ttcgagcgtc atttcaaccc tcaagccccc gggtttggtg ttggggatcg gcgagcctca    420

cggcaagccg gccccgaaat acagtggcgg tctcgctgca gcttccattg cgtagtagta    480

aaaccctcgc aactggtacg cggcgcggcc aagccgttaa acccccaact tctgaatgtt    540

gacctcggat caggtaggaa tacccgctga acttaagcat atcaataagc ggaggga       597
```

<210> SEQ ID NO 359
<211> LENGTH: 598
<212> TYPE: DNA
<213> ORGANISM: Fusarium proliferatum

<400> SEQUENCE: 359

```
tcttggtcat tttagaggaa gtaaaagtcg taacaaggtc tccgttggtg aaccagcgga     60

gggatcatta ccgagtttac aactcccaaa cccctgtgaa cataccaatt gttgcctcgg    120
```

```
cggatcagcc cgctcccggt aaaacggaac ggcccgccag aggaccccta aactctgttt    180
ctatatgtaa cttctgagta aaaccataaa taaatcaaaa ctttcaacaa cggatctctt    240
ggttctggca tcgatgaaga acgcagcaaa atgcgataag taatgtgaat tgcagaattc    300
agtgaatcat cgaatctttg aacgcacatt gcgcccgcca gtattctggc gggcatgcct    360
gttcgagcgt catttcaacc ctcaagcccc cgggtttggt gttggggatc ggcgagcctc    420
acggcaagcc ggccccgaaa tacagtggcg gtctcgctgc agcttccatt gcgtagtagt    480
aaaaccctcg caactggtac gcggcgcggc caagccgtta aacccccaac ttctgaatgt    540
tgacctcgga tcaggtagga atacccgctg aacttaagca tatcaataag cggagaga      598
```

<210> SEQ ID NO 360
<211> LENGTH: 602
<212> TYPE: DNA
<213> ORGANISM: Fusarium proliferatum

<400> SEQUENCE: 360

```
ttccctccgc ttattgatat gcttaagttc agcgggtatt tcctacctga tcccgaggtc     60
aacattcaga agttgggggt ttaacggctt ggccgcgccg cgtaccagtt gcgagggttt    120
tactactacg caatggaagc tgcagcgaga ccgccactgt atttcggggc cggcttgccg    180
tgaggctcgc cgatccccaa caccaaaccc gggggcttga gggttgaaat gacgctcgaa    240
caggcatgcc cgccagaata ctggcgggcg caatgtgcgt tcaaagattc gatgattcac    300
tgaattctgc aattcacatt acttatcgca ttttgctgcg ttcttcatcg atgccagaac    360
caagagatcc gttgttgaaa gttttgattt atttatggtt ttactcagaa gttacatata    420
gaaacagagt ttaggggtcc tctggcgggc cgttccgttt taccgggagc gggctgatcc    480
gccgaggcaa caattggtat gttccacagg ggtttgggag ttgtaaactc cggtaatgat    540
ccctccgctg gttcaccaac ggagaccttg ttacgacttt tacttcctct aaatgaccaa    600
ga                                                                   602
```

<210> SEQ ID NO 361
<211> LENGTH: 587
<212> TYPE: DNA
<213> ORGANISM: Uncultured Ascomycete sp.

<400> SEQUENCE: 361

```
cttggtcatt tagaggaagt aaaagtcgta acaaggtttc cgtaggtgaa cctgcggaag     60
gatcattaat tacgcaagct atagcccctt cgggggttat tgcatccacc ctttgtctac    120
tgtactcttg ttgtttcctc ggcaggcttg cctgtcgcta ggaacccaat aaacccttgt    180
attaaaagca ttgaaatctg ataactatta aattattaca actttcaaca atggatctct    240
tggttctggc atcgatgaag aacgcagcga aatgcgaaaa gtagtgtgaa ttgcagaatt    300
ccgtgaatca tcgaatcttt gaacgcacat tgcgcccctc ggtattccgt ggggcatgcc    360
tgttcgagcg tcatttacac cctcaagctc tgcttggtgt tgggcgtctg tcccgcttca    420
tgcgtggact cgccccaaag tcattggcag cggtcgtgcc agcttctcgc gcagcacatt    480
tgcgtttctt gaagtttggt ggatcagcat ccagtaagct cttttatgac ttgacctcgg    540
atcaggtagg gatacccgct gaacttaagc atatcaataa gcggagg                  587
```

<210> SEQ ID NO 362
<211> LENGTH: 552
<212> TYPE: DNA
<213> ORGANISM: Uncultured Hypocreales

<400> SEQUENCE: 362

```
gtaaaagtcg taacaaggtc tccgttggtg aaccagcgga gggatcatta ccgagtttac     60
aactcccaaa cccctgtgaa cataccttac tgttgcctcg gcggatcagc ccgcgcccgg    120
taaaacggga cggcccgcca gaggacccct aaactctgtt tttatttgta acttctgagt    180
aaaaccataa ataaatcaaa actttcaaca acggatctct tggttctggc atcgatgaag    240
aacgcagcaa aatgcgataa gtaatgtgaa ttgcagaatt cagtgaatca tcgaatcttt    300
gaacgcacat tgcgcccgcc agtattctgg cgggcatgcc tgttcgagcg tcatttcaac    360
cctcaagccc tcgggtttgg tgttggggat cggcgagcct tatggcaagc cggccccgaa    420
atctagtggc ggtctcactg cagcctccat tgcgtagtag ctaacacctc gcaactggaa    480
cgcggtgcgg ccaagccgtt aaacccccaa cttctgaatg ttgacctcgg atcaggtagg    540
aatacccgct ga                                                        552
```

<210> SEQ ID NO 363
<211> LENGTH: 514
<212> TYPE: DNA
<213> ORGANISM: Fusarium nygamai

<400> SEQUENCE: 363

```
cattaccgag tttacaactc ccaaacccct gtgaacatac caattgttgc ctcggcggat     60
cagcccgctc ccggtaaaac ggaacggccc gccagaggac ccctaaactc tgtttctata    120
tgtaacttct gagtaaaacc ataaataaat caaaactttc aacaacggat ctcttggttc    180
tggcatcgat gaagaacgca gcaaaatgcg ataagtaatg tgaattgcag aattcagtga    240
atcatcgaat ctttgaacgc acattgcgcc cgccagtatt ctggcgggca tgcctgttcg    300
agcgtcattt caaccctcaa gcccccgggt ttggtgttgg ggatcggcga gcctcacggc    360
aagccggccc cgaaatacag tggcggtctc gctgcagctt ccattgcgta gtagtaaaac    420
cctcgcaact ggtacgcggc gcggccaagc cgttaaaccc ccaacttctg aatgttgacc    480
tcggatcagg taggaatacc cgctgaactt aagc                                514
```

<210> SEQ ID NO 364
<211> LENGTH: 598
<212> TYPE: DNA
<213> ORGANISM: Fungal endophyte

<400> SEQUENCE: 364

```
aaaagtcgta acaaggtctc cgttggtgaa ccagcggagg gatcattatt agagcctaaa     60
aactcaccta aaccattgtg aacttaccta ttcgttgctt cggtgggtgg cccctccggg    120
ggtcctctag gccgcaaggc gcccgccgga ggttatttta aacactatgt cttctactgt    180
acctctgaat aaaaaaataa aaacaatcaa aactttcaac aacggatctc ttggctctag    240
catcgatgaa gaacgcagcg aaatgcgata agtaatgcga attgcagaat tccgcgagtc    300
atcgaatctt tgaacgcaca ttgcgcctgc cagtattctg gcaggcatgc ctgtccgagc    360
gtcatttcaa cccccaggcc ttcgttgcct gttgttgggg cattcagggc ggtccgacgg    420
acccccctgag ccctgaaaat cagtggcggg cctgccaggt caccgagcgc agtaatcact    480
ctcgctcagg ggccctggcg ggagctagcc gtgaaaacac acacctacga acagtggttt    540
gacctcggat caggtaggaa tacccgctga acttaagcat atcaataagg cggaggaa      598
```

<210> SEQ ID NO 365

<211> LENGTH: 595
<212> TYPE: DNA
<213> ORGANISM: Periconia macrospinosa

<400> SEQUENCE: 365
cttggtcatt tagaggaagt aaaagtcgta acaaggtttc cgtaggtgaa cctgcggaag 60
gatcattaca cattcggggc gcttcggcgc tccttataca cccaccctct gcctacgtgt 120
acctctatag cttcctcggc gggctcgccc gccgccagga acccacgaaa ccccttgcat 180
tatacgcgaa aacttctgat aacaaaccta aattatcaca actttcaaca atggatctct 240
tggttctggc atcgatgaag aacgcagcga aatgcgataa gtagtgtgaa ttgcagaatt 300
cagtgaatca tcgaatcttt gaacgcacat tgcggccata ggtattcctt tggccatgcc 360
tgttcgagcg tcatttacac cctcaagcct agcttggtgt tgggcgtctg tcccgccgtt 420
ttcgcgcgcg gactcgcctc aaagtcattg gcggcggtcg tgccggcccc ctcgcgcagc 480
acatttgcgc ttctcggagg cccggcggat ccgcgctcca gcaagacctt tcacgacttg 540
acctcggatc aggtagggat acccgctgaa cttaagcata tcaataagcg gagga 595

<210> SEQ ID NO 366
<211> LENGTH: 582
<212> TYPE: DNA
<213> ORGANISM: Magnaporthe rhizophila

<400> SEQUENCE: 366
cttattgata tgcttaagtt cagcgggtat tcctacctga tccgaggtca actcgaaaaa 60
cgtcactggg ggtttagcgg ctggaagccc gaggaggccg ccgagcgagg gcgcgtttta 120
ccgcgtgtta ctgcgctcgg agccccagca ggaccgccga tgtacttggg ggccccgacc 180
gccgggcggc cgggtgcccc aacaccaagc tgggcttgag tggtgaaatg acgctcggac 240
aggcatgccc gccggaatac cggcgggcgc aatgtgcgtt caaagattcg atgattcact 300
gaattctgca attcacatta cttatcgcat ttcgctgcgt tcttcatcga tgccagagcc 360
aagagatccg ttgttgaaag ttttaattgg ttcttttcgt cctcagagat acactagaat 420
tcagggttta aaacctccgg cggcgtcccc cacgcccggc tgggcgcggc gtcggccgcc 480
gaagcaacgt acaggtaaag ttcacagggg ttggagtttt gcaactcttt aatgatccct 540
ccgctggttc accaacggag accttgttac gacttttact tc 582

<210> SEQ ID NO 367
<211> LENGTH: 579
<212> TYPE: DNA
<213> ORGANISM: Fusarium nygamai

<400> SEQUENCE: 367
aagtaaaagt cgtaacaagg tctccgttgg tgaaccagcg gagggatcat taccgagttt 60
acaactccca aacccctgtg aacataccaa ttgttgcctc ggcggatcag cccgctcccg 120
gtaaaacgga acggcccgcc agaggacccc taaactctgt ttctatatgt aacttctgag 180
taaaaccata aataaatcaa aactttcaac aacggatctc ttggttctgg catcgatgaa 240
gaacgcagca aaatgcgata agtaatgtga attgcagaat tcagtgaatc atcgaatctt 300
tgaacgcaca ttgcgcccgc cagtattctg gcgggcatgc ctgttcgagc gtcatttcaa 360
ccctcaagcc cccgggtttg gtgttgggga tcggcgagcc tcacggcaag ccggccccga 420
aatacagtgg cggtctcgct gcagcttcca ttgcgtagta gtaaaaccct cgcaactggt 480
acgcggcgcg gccaagccgt taaaccccca acttctgaat gttgacctcg gatcaggtag 540
gaatacccgc tgaacttaag catatcaata agcggagga 579

<210> SEQ ID NO 368
<211> LENGTH: 596
<212> TYPE: DNA
<213> ORGANISM: Fusarium proliferatum

<400> SEQUENCE: 368
tcctccgctt attgatatgc ttaagttcag cgggtattcc tacctgatcc gaggtcaaca 60
ttcagaagtt gggggtttaa cggcttggcc gcgccgcgta ccagttgcga gggttttact 120
actacgcaat ggaagctgca gcgagaccgc cactgtattt cggggccggc ttgccgtgag 180
gctcgccgat ccccaacacc aaacccgggg gcttgagggt tgaaatgacg ctcgaacagg 240
catgcccgcc agaatactgg cgggcgcaat gtgcgttcaa agattcgatg attcactgaa 300
ttctgcaatt cacattactt atcgcatttt gctgcgttct tcatcgatgc cagaaccaag 360
agatccgttg ttgaaagttt tgatttattt atggttttac tcagaagtta catatagaaa 420
cagagtttag ggtcctctg gcgggccgtt ccgttttacc gggagcgggc tgatccgccg 480
aggcaacaat tggtatgttc acaggggttt gggagttgta aactcggtaa tgatccctcc 540
gctggttcac caacggagac cttgttacga cttttacttc ctctaaatga ccaaga 596

<210> SEQ ID NO 369
<211> LENGTH: 598
<212> TYPE: DNA
<213> ORGANISM: Fusarium proliferatum

<400> SEQUENCE: 369
tcttggtcat ttagaggtaa gtaaaagtcg taacaaggtc tccgttggtg aaccagcgga 60
gggatcatta ccgagtttac aactcccaaa cccctgtgaa cataccaatt gttgcctcgg 120
cggatcagcc cgctcccggt aaaacggaac ggcccgccag aggacccta aactctgttt 180 ctatatgtaa cttctgagta aaaccataaa taaatcaaaa ctttcaacaa cggatctctt 240
ggttctggca tcgatgaaga acgcagcaaa atgcgataag taatgtgaat tgcagaattc 300
agtgaatcat cgaatctttg aacgcacatt gcgcccgcca gtattctggc gggcatgcct 360
gttcgagcgt catttcaacc ctcaagcccc cgggtttggt gttggggatc ggcgagcctc 420
acggcaagcc ggccccgaaa tacagtggcg gtctcgctgc agcttccatt gcgtagtagt 480
aaaaccctcg caactggtac gcggcgcggc caagccgtta aacccccaac ttctgaatgt 540
tgacctcgga tcaggtagga atacccgctg aacttaagca tatcaataag cggaggaa 598

<210> SEQ ID NO 370
<211> LENGTH: 569
<212> TYPE: DNA
<213> ORGANISM: Uncultured root-associated fungus

<400> SEQUENCE: 370
tttcctccgc ttattgatat gcttaagttc cagcgggtat tccctacctg atccgaggtc 60
aactcgaaaa aacgtcactg ggggtttagc ggctggaagc ccgaggaggc ccgcccgagc 120
gagggcgcgt tttaccgcga gttactgcgc tcggagcccc agcgggaccg ccgatgtact 180
tgggggcccc gaccgccggg cggccgggtg ccccaacacc aagctgggct tgagtggtga 240
aatgacgctc ggacaggcat gcccgccgga ataccggcgg gcgcaatgtg cgttcaaaga 300
ttcgatgatt cactgaattc tgcaattcac attacttatc gcatttcgct gcgttcttca 360
tcgatgccag agccaagaga tccgttgttg aaagttttaa ttggttttat ttcgtcctca 420
gagatacact agaattcagg gtttaagacc tccggcggcg tcccccaggc ccggctgggc 480
gcggcgtcgg ccgccgaagc aacgtacagg taaagttcac aggggttgga gttttgcaac 540
tctttaatga tcccctccgg ctggttcac 569

<210> SEQ ID NO 371
<211> LENGTH: 704
<212> TYPE: DNA
<213> ORGANISM: Fusarium nygamai

<400> SEQUENCE: 371
tgcaattcac actacttatc gcatttcgct gcgttcttca tcgatgccag aaccaagaga 60
tccattgttg aaagttttaa ataattaact tagtatcaga cgctgactgc tattacaaaa 120
aggtttcctc cgcttattga tatgcttaag ttcagcgggt attcctacct gatccgaggt 180
caacattcag aagttggggg tttaacggct tggccgcgcc gcgtaccagt tgcgagggtt 240
ttactactac gcaatggaag ctgcagcgag accgccactg tatttcgggg ccggcttgcc 300
gtgaggctcg ccgatcccca acaccaaacc cgggggcttg agggttgaaa tgacgctcga 360
acaggcatgc ccgccagaat actggcgggc gcaatgtgcg ttcaaagatt cgatgattca 420
ctgaattctg caattcacat tacttatcgc attttgctgc gttcttcatc gatgccagaa 480
ccaagagatc cgttgttgaa agttttgatt tatttatggt tttactcaga agttacatat 540
agaaacagag tttaggggtc ctctggcggg ccgttccgtt ttaccgggag cgggctgatc 600
cgccgaggca acaattggta tgttcacagg ggtttgggag ttgtaaactc ggtaatgatc 660
cctccgctgg ttcaccaacg gagaccttgt tacgactttt actt 704

<210> SEQ ID NO 372
<211> LENGTH: 559
<212> TYPE: DNA
<213> ORGANISM: Fusarium nygamai

<400> SEQUENCE: 372
atatgcttaa gttcagcggg tattcctacc tgatccgagg tcaacattca gaagttgggg 60
gtttaacggc ttggccgcgc cgcgtaccag ttgcgagggt tttactacta cgcaatggaa 120
gctgcagcga gaccgccact gtatttcggg gccggcttgc cgtgaggctc gccgatcccc 180
aacaccaaac ccgggggctt gagggttgaa atgacgctcg aacaggcatg cccgccagaa 240
tactggcggg cgcaatgtgc gttcaaagat tcgatgattc actgaattct gcaattcaca 300
ttacttatcg cattttgctg cgttcttcat cgatgccaga accaagagat ccgttgttga 360
aagttttgat ttatttatgg ttttactcag aagttacata tagaaacaga gtttaggggt 420
cctctggcgg gccgttccgt tttaccggga gcgggctgat ccgccgaggc aacaattggt 480
atgttcacag ggtttggga gttgtaaact cggtaatgat ccctccgctg gttcaccaac 540
ggagaccttg ttacgactt 559

<210> SEQ ID NO 373
<211> LENGTH: 576
<212> TYPE: DNA
<213> ORGANISM: Gaeumannomyces incrustans

<400> SEQUENCE: 373
gcttattgat atgcttaagt tcagcgggta ttcctacctg atccgaggtc aactcggaaa 60
acgtcactgg ggggtttagc ggctggaagc ccgaggaggc cgccgagcga gggcgcgttt 120

```
taccgcgagt tactgcgctc ggagccccag caggaccgcc gatgtacttg ggggccccga    180

ccgccgggcg gccgggtgcc ccaacaccaa gctgggcttg agtggtgaaa tgacgctcgg    240

acaggcatgc ccgccggaat accggcgggc gcaatgtgcg ttcaaagatt cgatgattca    300

ctgaattctg caattcacat tacttatcgc atttcgctgc gttcttcatc gatgccagag    360

ccaagagatc cgttgttgaa agttttaatt ggtttttttc gtcctcagag atacactaga    420

attcagggtt taagacctcc ggcggcgtcc cccaggcccg tctgggcgcg gcgtcggccg    480

ccgaagcaac gtacaggtaa agttcacagg ggttggagtt tttgcaactc tttaatgatc    540

cctccgctgg ttcaccaacg gagaccttgt tacgac                              576
```

<210> SEQ ID NO 374
<211> LENGTH: 503
<212> TYPE: DNA
<213> ORGANISM: Magnaporthe rhizophila

<400> SEQUENCE: 374

```
gagggatcat taaagagttg caaaactcca acccctgtga actttacctg tacgttgctt     60

cggcggccga cgccgcgccc agccgggccc gggggacgcc gccggaggtc ataaaccctg    120

aattctagtg tatctctgag gacgaaaata accaattaaa actttcaaca acggatctct    180

tggctctggc atcgatgaag aacgcagcga aatgcgataa gtaatgtgaa ttgcagaatt    240

cagtgaatca tcgaatcttt gaacgcacat tgcgcccgcc ggtattccgg cgggcatgcc    300

tgtccgagcg tcatttcacc actcaagccc agcttggtgt tggggcaccc ggccgcccgg    360

cggtcggggc ccccaagtac atcggcggtc ccgctggggc tccgagcgca gtaactcgcg    420

gtaaaacgcg ccctcgctcg gcggcctcct cgggcttcca gccgctaaac ccccagtgac    480

gtttttcgag ttgactcgga tca                                            503
```

<210> SEQ ID NO 375
<211> LENGTH: 611
<212> TYPE: DNA
<213> ORGANISM: Gaeumannomyces incrustans

<400> SEQUENCE: 375

```
tcttggtcat ttagaggaag taaaaagtcg taacaaggtc tccgtttggt gaacccagcg     60

gagggatcat taaagagttg caaaactcca acccctgtga actttacctg tacgttgctt    120

cggcggccga cgccgcgccc agccgggcct gggggacgcc gccggaggtt ttaaaccctg    180

aattctagtg tatctctgag gacgaaaaaa accaattaaa actttcaaca acggatctct    240

tggctctggc atcgatgaag aacgcagcga aatgcgataa gtaatgtgaa ttgcagaatt    300

cagtgaatca tcgaatcttt gaacgcacat tgcgcccgcc ggtattccgg cgggcatgcc    360

tgtccgagcg tcatttcacc actcaagccc agcttggtgt tggggcaccc ggccgcccgg    420

cggtcggggc ccccaagtac atcggcggtc ctgctggggc tccgagcgca gtaacacgcg    480

gtaaaacgcg ccctcgctcg gcggcctcct cgggcttcca gccgctaaac ccccagtgat    540

gtttttcgag ttgacctcgg atcaggtagg aatacccgct gaaacttaag catatcaata    600

agcggaggaa a                                                         611
```

<210> SEQ ID NO 376
<211> LENGTH: 554
<212> TYPE: DNA
<213> ORGANISM: Uncultured root-associated fungus

<400> SEQUENCE: 376
gcggagggat cattaaagag ttgcaaaact ccaacccctg tgaactttac ctgtacgttg 60
cttcggcggc cgacgccgcg cccagccggg cctgggggac gccgccggag gttttaaacc 120
ctgaattcta gtgtatctct gaggacgaaa aaaaccaatt aaaactttca acaacggatc 180
tcttggctct ggcatcgatg aagaacgcag cgaaatgcga taagtaatgt gaattgcaga 240
attcagtgaa tcatcgaatc tttgaacgca cattgcgccc gccggtattc cggcgggcat 300
gcctgtccga gcgtcatttc accactcaag cccagcttgg tgttggggca cccggccgcc 360
cggcggtcgg ggcccccaag tacatcggcg gtcctgctgg ggctccgagc gcagtaacac 420
gcggtaaaac gcgccctcgc tcggcggcct cctcgggctt ccagccgcta aaccccagt 480 gatgtttttc gagttgacct cggatcaggt aggaataccc gctgaactta agcatatcaa 540
taagcgggag gaaa 554

<210> SEQ ID NO 377
<211> LENGTH: 497
<212> TYPE: DNA
<213> ORGANISM: Fusarium sp.

<400> SEQUENCE: 377
gagggatcat taccgagttt acaactccca aacccctgtg aacataccaa ttgttgcctc 60
ggcggatcag cccgctcccg gtaaaacgga acggcccgcc agaggacccc taaactctgt 120
ttctatatgt aacttctgag taaaaccata aataaatcaa aactttcaac aacggatctc 180
ttggttctgg catcgatgaa gaacgcagca aaatgcgata agtaatgtga attgcagaat 240
tcagtgaatc atcgaatctt tgaacscaca ttgcgcccgc cagtattctg gcgggcatgc 300
ctgttcgagc gtcatttcaa ccctcaagcc cccgggtttg gtgttgggga tcggcgagcc 360
tcacggcaag ccggccccca aatacagtgg cggtctcgct gcagcttcca ttgcgtagta 420
gtaaaaccct cgcaactggt acgcggcgcg gccaagccgt taaaccccca acttctgaat 480
gtgacctcga tcaggta 497

<210> SEQ ID NO 378
<211> LENGTH: 527
<212> TYPE: DNA
<213> ORGANISM: Fusarium sp.

<400> SEQUENCE: 378
ccagcggagg gatcattacc gagtttacaa ctcccaaacc cctgtgaaca taccaattgt 60
tgcctcggcg gatcagcccg ctcccggtaa aacgggacgg cccgccagag gacccctaaa 120
ctctgtttct atatgtaact tctgagtaaa accataaata aatcaaaact ttcaacaacg 180
gatctcttgg ttctggcatc gatgaagaac gcagcaaaat gcgataagta atgtgaattg 240
cagaattcag tgaatcatcg aatctttgaa cgcacattgc gcccgccagt attctggcgg 300
gcatgcctgt tcgagcgtca tttcaaccct caagcccccg ggtttggtgt tggggatcgg 360
cgagcctcac ggcaagccgg ccccgaaata cagtggcggt ctcgctgcag cttccattgc 420
gtagtagtaa aaccctcgca actggtacgc ggcgcggcca agccgttaaa cccccaactt 480
ctgaatgttg acctcggatc aggtaggaat acccgctgaa cttaagc 527

<210> SEQ ID NO 379
<211> LENGTH: 600
<212> TYPE: DNA
<213> ORGANISM: Fusarium proliferatum

<400> SEQUENCE: 379
tcttggtcat ttagaggaag taaaagtcgt aacaaggtct ccgttggtga accagcggag 60
ggatcattac cgagtttaca actcccaaac ccctgtgaac ataccaattg ttgcctcggc 120
ggatcagccc gctcccggta aaacggaacg gcccgccaga ggacccctaa actctgtttc 180
tatatgtaac ttctgagtaa aaccataaat aaatcaaaac tttcaacaac ggatctcttg 240
gttctggcat cgatgaagaa cgcagcaaaa tgcgataagt aatgtgaatt gcagaattca 300
gtgaatcatc gaatctttga acgcacattg cgcccgccag tattctggcg ggcatgcctg 360
ttcgagcgtc atttcaaccc tcaagccccc gggtttggtg ttggggatcg gcgagcctca 420
cggcaagccg gccccgaaat acagtggcgg tctcgctgca gcttccattg cgtagtagta 480
aaaccctcgc aactggtacg cggcgcggcc aagccgttaa acccccaact tctgaatgtt 540
gacctcggat caggtaggga atacccgctg aacttaagca tatcaataag gcgggaggaa 600

<210> SEQ ID NO 380
<211> LENGTH: 579
<212> TYPE: DNA
<213> ORGANISM: Magnaporthe rhizophila

<400> SEQUENCE: 380
cgtaacaagg tctccgttgg tgaaccagcg gagggatcat taaagagttg caaaactcca 60
acccctgtga actttacctg tacgttgctt cggcggccga cgccgcgccc agccgggcct 120
gggggacgcc gccggaggtt ttaaaccctg aattctagtg tatctctgag gacgaaaata 180
accaattaaa actttcaaca acggatctct tggctctggc atcgatgaag aacgcagcga 240
aatgcgataa gtaatgtgaa ttgcagaatt cagtgaatca tcgaatcttt gaacgcacat 300
tgcgcccgcc ggtattccgg cgggcatgcc tgtccgagcg tcatttcacc actcaagccc 360
agcttggtgt tggggcaccc ggccgcctgg cggtcggggc ccccaagtac atcggcggtc 420
ctgctggggc tccgagcgca gtaactcgcg gtaaaacgcg ctctcgctcg gcggcctcct 480
cgggcttcca gccgctaaac ccccagtgac gtttttcgag ttgacctcgg atcaggtagg 540
aatacccgct gaacttaagc atatcaataa gcggaggaa 579

<210> SEQ ID NO 381
<211> LENGTH: 597
<212> TYPE: DNA
<213> ORGANISM: Fusarium proliferatum

<400> SEQUENCE: 381
tcttggtcat ttagaggaag taaaagtcgt aacaaggtct ccgttggtga accagcggag 60
ggatcattac cgagtttaca actcccaaac ccctgtgaac atatcaattg ttgcctcggc 120
ggatcagccc gctcccggta aaacggaacg gcccgccaga ggacccctaa actctgtttc 180
tatatgtaac ttctgagtaa aaccataaat aaatcaaaac tttcaacaac ggatctcttg 240
gttctggcat cgatgaagaa cgcagcaaaa tgcgataagt aatgtgaatt gcagaattca 300
gtgaatcatc gaatctttga acgcacattg cgcccgccag tattctggcg ggcatgcctg 360
ttcgagcgtc atttcaaccc tcaagccccc gggtttggtg ttggggatcg gcgagcctca 420
cggcaagccg gccccgaaat acagtggcgg tctcgctgca gcttccattg cgtagtagta 480
aaaccctcgc aactggtacg cggcgcggcc aagccgttaa acccccaact tctgaatgtt 540
gacctcggat caggtaggaa tacccgctga acttaagcat atcaataagc ggaggaa 597

<210> SEQ ID NO 382
<211> LENGTH: 597
<212> TYPE: DNA
<213> ORGANISM: Periconia macrospinosa

<400> SEQUENCE: 382
tcttggtcat ttagaggaag taaaagtcgt aacaaggttt ccgtaggtga acctgcggaa 60
ggatcattac acattcgggg cgcttcggcg ctccttatac acccaccctc tgcctacgtg 120
tacctctata gcttcctcgg cgggctcgcc cgccgccagg aacccacgaa accccttgca 180
ttatacgcga aaacttctga taacaaacct aaattatcac aactttcaac aatggatctc 240
ttggttctgg catcgatgaa gaacgcagcg aaatgcgata agtagtgtga attgcagaat 300
tcagtgaatc atcgaatctt tgaacgcaca ttgcggccat aggtattcct ttggccatgc 360
ctgttcgagc gtcatttaca ccctcaagcc tagcttggtg ttgggcgtct gtcccgccgt 420
tctcgcgcgc ggactcgcct caaagtcatt ggcggcggtc gtgccggccc cctcgcgcag 480
cacatttgcg cttctcggag gcccggcgga tccgcgctcc agcaagacct ttcacgactt 540
gacctcggat caggtaggga tacccgctga acttaagcat atcaataagc ggaggaa 597

<210> SEQ ID NO 383
<211> LENGTH: 607
<212> TYPE: DNA
<213> ORGANISM: Codinaeopsis sp.

<400> SEQUENCE: 383
tcctccgcct tattgatatg cttaagttca gcgggtattc ctacctgatc cgaggtcaac 60
cacttagaaa gttgggggtt ttacggccgg agcgcgcgcc ggaccagaac gagaaagcat 120
tactgcgctc ggttccgggg cgcgcccgcc gctgtctttg ggagcctgcg ctgcgcaggg 180
ctccaacgcc aggcggggcc tgagggttga aatgacgctc ggacaggcat gcccgccaga 240
gtgctggcgg gcgcaatgtg cgttcaaaga ttcgatgatt cactgaattc tgcaattcac 300
attacttatc gcatttcgct gcgttcttca tcgatgccag aaccaagaga tccgttgttg 360
aaagttttga ctcgtttata gtctgctcgg agatgccaac gttacagaga cagagtttag 420
gggccgccgg cgggctggag cgccccggag cgcccgaaga cgcgcccgga gcacccgccg 480
aggcaacggg ttgtaggtaa gttcacagtg gtttacggga gtcttgcgag tcctgtaatg 540
atccctccgc tggttcacca acgggagacc ttgttacgac ttttacttcc tctaaatgac 600
caagacg 607

<210> SEQ ID NO 384
<211> LENGTH: 506
<212> TYPE: DNA
<213> ORGANISM: Uncultured root-associated fungus

<400> SEQUENCE: 384
gctgaaccag cggagggatc attaaagagt tgcaaaactc taacccctgt gaactttacc 60
tgtacgttgc ttcggcggcc gacgccgcgc ccagccgggc ctgggggacg ccgccggagg 120
ttttaaaccc tgaattctag tgtatctctg aggacgaaaa aaaccaatta aaactttcaa 180
caacggatct cttggctctg gcatcgatga agaacgcagc gaaatgcgat aagtaatgtg 240
aattgcagaa ttcagtgaat catcgaatct ttgaacgcac attgcgcccg ccggtattcc 300
ggcgggcatg cctgtccgag cgtcatttca ccactcaagc ccagcttggt gttggggcac 360
ccggccgccc ggcggtcggg gcccccaagt acatcggcgg tcccgctggg gctccgagcg 420
cagtaactcg cggtaaaacg cgccctcgct cggcggcctc ctcgggcttc cagccgctaa 480
acccccagtg acgtttttcg agttga 506

<210> SEQ ID NO 385
<211> LENGTH: 597
<212> TYPE: DNA
<213> ORGANISM: Fusarium proliferatum

<400> SEQUENCE: 385
ttcctccgct tattgatatg cttaagttca gcgggtattc ctacctgatc cgaggtcaac 60
attcagaagt tgggggttta acggcttggc cgcgccgcgt accagttgcg agggttttac 120
tactacgcaa tggaagctgc agcgagaccg ccactgtatt tcggggccgg cttgccgtga 180
ggctcgccga tccccaacac caaacccggg ggcttgaggg ttgaaatgac gctcgaacag 240
gcatgcccgc cagaatactg gcgggcgcaa tgtgcgttca aagattcgat gattcactga 300
attctgcaat tcacattact tatcgcattt tgctgcgttc ttcatcgatg ccagaaccaa 360
gagatccgtt gttgaaagtt ttgatttatt tatggtttta ctcagaagtt acatatagaa 420
acagagttta ggggtcctct ggcgggccgt tccgttttac cgggagcggg ctgatccgcc 480
gaggcaacaa ttggtatgtt cacaggggtt tgggagttgt aaactcggta atgatccctc 540
cgctggttca ccaacggaga ccttgttacg acttttactt cctctaaatg accaaga 597

<210> SEQ ID NO 386
<211> LENGTH: 608
<212> TYPE: DNA
<213> ORGANISM: Gaeumannomyces incrustans

<400> SEQUENCE: 386
tttcctcccg cttattgata tgcttaagtt cagcgggtat tccctacctg atccgaggtc 60
aactcgaaaa acgtcactgg gggtttagcg gctggaagcc cgaggaggcc gccgagcgag 120
agcgcgtttt accgcgagtt actgcgctcg gagccccagc aggaccgccg atgtacttgg 180
gggccccgac cgccaggcgg ccgggtgccc caacaccaag ctgggcttga gtggtgaaat 240
gacgctcgga caggcatgcc cgccggaata ccggcgggcg caatgtgcgt tcaaagattc 300
gatgattcac tgaattctgc aattcacatt acttatcgca tttcgctgcg ttcttcatcg 360
atgccagagc caagagatcc gttgttgaaa gttttaattg gttattttcg tcctcagaga 420
tacactagaa ttcagggttt aaaacctccg gcggcgtccc ccaggcccgg ctgggcgcgg 480
cgtcggccgc cgaagcaacg tacaggtaaa gttcacaggg gttggagttt tgcaactctt 540
taatgatccc tccgctggtt caccaacgga gaccttgtta cgacttttac ttcctctaaa 600
tgaccaag 608

<210> SEQ ID NO 387
<211> LENGTH: 548
<212> TYPE: DNA
<213> ORGANISM: Fusarium nygamai

<400> SEQUENCE: 387
catgcttaag ttcagcgggt attcctacct gatccgaggt caacattcag aagttggggg 60
tttaacggct tggccgcgcc gcgtaccagt tgcgagggtt ttactactac gcaatggaag 120
ctgcagcgag accgccactg tatttcgggg ccggcttgcc gtgaggctcg ccgatcccca 180
acaccaaacc cgggggcttg agggttgaaa tgacgctcga acaggcatgc ccgccagaat 240

```
actggcgggc gcaatgtgcg ttcaaagatt cgatgattca ctgaattctg caattcacat    300

tacttatcgc attttgctgc gttcttcatc gatgccagaa ccaagagatc cgttgttgaa    360

agttttgatt tatttatggt tttactcaga agttacatat agaaacagag tttaggggtc    420

ctctggcggg ccgttccgtt ttaccgggag cgggctgatc cgccgaggca acaattggta    480

tgttcacagg ggtttgggag ttgtaaactc ggtaatgatc cctccgctgg ttcaccaacg    540

gagacctt                                                              548


<210> SEQ ID NO 388
<211> LENGTH: 576
<212> TYPE: DNA
<213> ORGANISM: Magnaporthe rhizophila

<400> SEQUENCE: 388

ttcctccgct tattgatatg cttaagttca gcgggtattc cctacctgat ccgaggtcaa     60

ctccgaaaaa cgtcactggg ggtttagcgg ctggaagccc gaggaggccg ccgagcgaga    120

gcgcgtttta ccgcgagtta ctgcgctcgg agccccagca ggaccgccga tgtacttggg    180

ggccccgacc gccaggcggc cgggtgcccc aacaccaagc tgggcttgag tggtgaaatg    240

acgctcggac aggcatgccc gccggaatac cggcgggcgc aatgtgcgtt caaagattcg    300

atgattcact gaattctgca attcacatta cttatcgcat ttcgctgcgt tcttcatcga    360

tgccagagcc aagagatccg ttgttgaaag ttttaattgg ttattttcgt cctcagagat    420

acactagaat tcagggttta aaacctccgg cggcgtcccc caggcccggc tgggcgcggc    480

gtcggccgcc gaagcaacgt acaggtaaag ttcacagggg ttggagtttt gcaactcttt    540

aatgatccct ccgctggtca cccaaccgga aagcta                              576


<210> SEQ ID NO 389
<211> LENGTH: 596
<212> TYPE: DNA
<213> ORGANISM: Fusarium proliferatum

<400> SEQUENCE: 389

tcttggtcat ttagaggaag taaaagtcgt aacaaggtct ccgttggtga accagcggag     60

ggatcattac cgagtttaca actcccaaac ccctgtgaac atatcaattg ttgcctcggc    120

ggatcagccc gctcccggta aaacggaacg gcccgccaga ggacccctaa actctgtttc    180

tatatgtaac ttctgagtaa aaccataaat aaatcaaaac tttcaacaac ggatctcttg    240

gttctggcat cgatgaagaa cgcagcaaaa tgcgataagt aatgtgaatt gcagaattca    300

gtgaatcatc gaatctttga acgcacattg cgcccgccag tattctggcg ggcatgcctg    360

ttcgagcgtc atttcaaccc tcaagccccc gggtttggtg ttggggatcg gcgagcctca    420

cggcaagccg gccccgaaat acagtggcgg tctcgctgca gcttccattg cgtagtagta    480

aaaccctcgc aactggtacg cggcgcggcc aagccgttaa acccccaact tctgaatgtt    540

gacctcggat caggtaggaa tacccgctga acttaagcat atcaataagc ggagga        596


<210> SEQ ID NO 390
<211> LENGTH: 600
<212> TYPE: DNA
<213> ORGANISM: Fusarium proliferatum

<400> SEQUENCE: 390

tcttggtcat ttagaggaag taaaagtcgt aacaaaggtc tccgttggtg aaccagcgga     60

gggatcatta cccgagttta caactcccaa acccctgtga acataccaat tgttgcctcg    120
```

gcggatcagc ccgctcccgg taaaacggaa cggcccgcca gaggacccct aaactctgtt 180
tctatatgta acttctgagt aaaaccataa ataaatcaaa actttcaaca acggatctct 240
tggttctggc atcgatgaag aacgcagcaa aatgcgataa gtaatgtgaa ttgcagaatt 300
cagtgaatca tcgaatcttt gaacgcacat tgcgcccgcc agtattctgg cgggcatgcc 360
tgttcgagcg tcatttcaac cctcaagccc ccgggtttgg tgttggggat cggcgagcct 420
cacggcaagc cggccccgaa atacagtggc ggtctcgctg cagcttccat tgcgtagtag 480
taaaaccctc gcaactggta cgcggcgcgg ccaagccgtt aaacccccaa cttctgaatg 540
ttgacctcgg atcaggtagg aatacccgct gaacttaagc atatcaataa gcggaggaaa 600

<210> SEQ ID NO 391
<211> LENGTH: 596
<212> TYPE: DNA
<213> ORGANISM: Fusarium proliferatum

<400> SEQUENCE: 391
tcttggtcat ttagaggaag taaaagtcgt aacaaggtct ccgttggtga accagcggag 60
ggatcattac cgagtttaca actcccaaac ccctgtgaac ataccaattg ttgcctcggc 120
ggatcagccc gctcccggta aaacggaacg gcccgccaga ggacccctaa actctgtttc 180
tatatgtaac ttctgagtaa aaccataaat aaatcaaaac tttcaacaac ggatctcttg 240
gttctggcat cgatgaagaa cgcagcaaaa tgcgataagt aatgtgaatt gcagaattca 300
gtgaatcatc gaatctttga acgcacattg cgcccgccag tattctggcg ggcatgcctg 360
ttcgagcgtc atttcaaccc tcaagccccc gggtttggtg ttggggatcg gcgagcctca 420
cggcaagccg gccccgaaat acagtggcgg tctcgctgca gcttccattg cgtagtagta 480
aaaccctcgc aactggtacg cggcgcggcc aagccgttaa acccccaact tctgaatgtt 540
gacctcggat caggtaggaa tacccgctga acttaagcat atcaataagc ggagga 596

<210> SEQ ID NO 392
<211> LENGTH: 579
<212> TYPE: DNA
<213> ORGANISM: Fusarium proliferatum

<400> SEQUENCE: 392
tcctccgctt attgatatgc ttaagttcag cgggtattcc tacctgatcc gaggtcaaca 60
ttcagaagtt gggggtttaa cggcttggcc gcgccgcgta ccagttgcga gggttttact 120
actacgcaat ggaagctgca gcgagaccgc cactagattt cggggccggc ttgccgcaag 180
ggctcgccga tccccaacac caaacccggg ggcttgaggg ttgaaatgac gctcgaacag 240
gcatgcccgc cagaatactg gcgggcgcaa tgtgcgttca aagattcgat gattcactga 300
attctgcaat tcacattact tatcgcattt tgctgcgttc ttcatcgatg ccagaaccaa 360
gagatccgtt gttgaaagtt ttgatttatt tatggtttta ctcagaagtt acatatagaa 420
acagagttta ggggtcctct ggcgggccgt cccgttttac cgggagcggg ctgatccgcc 480
gaggcaacaa ttggtatgtt cacaggggtt tgggagttgt aaactcggta atgatccctc 540
cgctggttca ccaacggaga ccttgttacg acttttact 579

<210> SEQ ID NO 393
<211> LENGTH: 610
<212> TYPE: DNA
<213> ORGANISM: Gaeumannomyces incrustans

<400> SEQUENCE: 393
tcttggtcat ttagaggaag taaaagtcgt aacaaggtct ccgttggtga accagcggag 60
ggatcattaa agagttgcaa aaactccaac ccctgtgaac tttacctgta cgttgcttcg 120
gcggccgacg ccgcgcccag acgggcctgg gggacgccgc cggaggtctt aaaccctgaa 180
ttctagtgta tctctgagga cgaaaaaaac caattaaaac tttcaacaac ggatctcttg 240
gctctggcat cgatgaagaa cgcagcgaaa tgcgataagt aatgtgaatt gcagaattca 300
gtgaatcatc gaatctttga acgcacattg cgcccgccgg tattccggcg ggcatgcctg 360
tccgagcgtc atttcaccac tcaagcccag cttggtgttg gggcacccgg ccgcccggcg 420
gtcggggccc ccaagtacat cggcggtcct gctggggctc cgagcgcagt aactcgcggt 480
aaaacgcgcc ctcgctcggc ggcctcctcg ggcttccagc cgctaaaccc cccagtgacg 540
ttttccgagt tgacctcgga tcaggtagga atacccgctg aacttaagca tatcaataaa 600
gcggagggaa 610

<210> SEQ ID NO 394
<211> LENGTH: 518
<212> TYPE: DNA
<213> ORGANISM: Diaporthe phaseolorum

<400> SEQUENCE: 394
gggggtttaa cggcagggca ccgccagggc cttccggagc gagggtttaa ctactgcgct 60
cggggtcctg gcgagctcgc cactgaattt caggccatgc cctgtgacag gcaggggccc 120
aacaccaagc caggcttgag ggttgaaatg acgctcgaac aggcatgccc tccggaatac 180
cagagggcgc aatgtgcgtt caaagattcg atgattcact gaattctgca attcacatta 240
cttatcgcat ttcgctgcgt tcttcatcga tgccagaacc aagagatccg ttgttgaaag 300
ttttgattca tttgtgtttt gtactcagag tttcggtgta aaaacaagag ttggctgggc 360
caccggccgg cctgctcctc gtctccgagg ggcccccggg ggggccggcc tgcgccgagg 420
caacagtaag gtatgagttc acaaagggtt tctgggtgcg cctagggcgc gttccagcaa 480
tgatccctcc gctggttcac caacggagac cttgttac 518

<210> SEQ ID NO 395
<211> LENGTH: 597
<212> TYPE: DNA
<213> ORGANISM: Fusarium moniliformae

<400> SEQUENCE: 395
tcctccgctt attgatatgc ttaagttcag cgggtattcc tacctgatcc gaggtcaaca 60
ttcagaagtt gggggtttaa cggcttggcc gcgccgcgtt ccagttgcga gggttttact 120
actacgcaat ggaggctgca gcgagaccgc cactagattt cggggccggc ttgccgcaag 180
ggctcgccga tccccaacac caaacccgag ggcttgaggg ttgaaatgac gctcgaacag 240
gcatgcccgc cagaatactg gcgggcgcaa tgtgcgttca aagattcgat gattcactga 300
attctgcaat tcacattact tatcgcattt tgctgcgttc ttcatcgatg ccagaaccaa 360
gagatccgtt gttgaaagtt ttgatttatt tatggtttta ctcagaagtt acatatagaa 420
acagagttta ggggtcctct ggcgggccgt cccgttttac cgggagcggg ctgatccgcc 480
gaggcaacaa gtggtatgtt cacaggggtt tgggagttgt aaactcggta atgatccctc 540
cgctggttca ccaacggaga ccttgttacg acttttactt ccactaaatg accaaga 597

<210> SEQ ID NO 396
<211> LENGTH: 533
<212> TYPE: DNA
<213> ORGANISM: Uncultured fungus

<400> SEQUENCE: 396
aggtttccgt aggtgaacct gcggaaggat cattaaaaaa ggataccggg caaccggtag 60
accccacccg tgtctctcta ctcttgttgc tttggcaggc cgtggcctcc actgcgggct 120
ccgcctgcgt gtgcctgtca gaggaccaaa ctctgaattt cagtgatgtc tgagtactat 180
ataatagtta aaactttcaa caacggatct cttggttctg gcatcgatga agaacgcagc 240
gaaatgcgat aagtaatgtg aattgcagaa ttcagtgaat catcgaatct ttgaacgcac 300
attgcgcccg gtggtattcc gccgggcatg cctgttcgag cgtcattata accactcaag 360
ccttggcttg gtattggggt tcgcggttcc gcggccctta aaatcagtgg cggtgccggt 420
gggctctaag cgtagtaaat ctcctcgcta tagggtccct ccggttgcct gccagaaccc 480
cccatttttt caggttgacc tcggatcagg tagggatacc cgctgaactt aag 533

<210> SEQ ID NO 397
<211> LENGTH: 628
<212> TYPE: DNA
<213> ORGANISM: Trichoderma koningiopsis

<400> SEQUENCE: 397
aaagtcgtaa caaggtctcc cgttgggtgg acccagcgga gggatccatt accgagttta 60
ccaactccca aacccaatgt gaaccatacc aaactgttgc ctcggcgggg tcacgccccg 120
ggtgcgtcgc agccccggaa ccaggcgccc gccggaggga ccaaccaaac tctttctgta 180
gtcccctcgc ggacgttatt tcttacagct ctgagcaaaa attcaaaatg aatcaaaact 240
ttcaacaacg gatctcttgg ttctggcatc gatgaagaac gcagcgaaat gcgataagta 300
atgtgaattg cagaattcag tgaatcatcg aatctttgaa cgcacattgc gcccgccagt 360
attctggcgg gcatgcctgt ccgagcgtca tttcaaccct cgaacccctc cgggggtcg 420 gcgttgggga tcgggaaccc ctaagacggg atcccggccc cgaaatacag tggcggtctc 480
gccgcagcct ctcctgcgca gtagtttgca caactcgcac cgggagcgcg gcgcgtccac 540
gtccgtaaaa cacccaactt ctgaaatgtt gacctcggat caggtaggaa tacccgctga 600
acttaagcat atcaataagc ggaggaaa 628

<210> SEQ ID NO 398
<211> LENGTH: 593
<212> TYPE: DNA
<213> ORGANISM: Uncultured Helotiales

<400> SEQUENCE: 398
tcctccgctt attgatatgc ttaagttcag cgggtatccc tacctgatcc gaggtcaacc 60
tagaaaaatt tggggttgct ggccagcatc tcccaggacc ctatagcgag aaaattacta 120
cgcgtagagc ctaagagcac cgccactagt tttaaggccc gccagacggc gaagcccaac 180
acctagccag gctagattgg tataaatgac gctcgaacag gcatgccccc cggaatacca 240
gggggcgcaa tgtgcgttca aagattcgat gattcactga attctgcaat tcacattact 300
tatcgcattt cgctgcgttc ttcatcgatg ccagaaccaa gagatccgtt gttgaaagtt 360
ttaactattt aatagtactc agacgacact aacattcaga gtttaggggt cctctggcgg 420
gcacgctaga cgcgaatcta ggcgcacgag gcgcggcccg ccaaagcaac attctataat 480
gatacacaag ggtgggagat ctaccctgaa gggcatgaac tctgtaatga tccttccgca 540
ggttcaccta cggaaacctt gttacgactt ttacttcctc taaatgacca aga 593

<210> SEQ ID NO 399
<211> LENGTH: 582
<212> TYPE: DNA
<213> ORGANISM: Periconia macrospinosa

<400> SEQUENCE: 399
ggaagtaaaa gtcgtaacaa ggtttccgta ggtgaacctg cggaaggatc attacacatt 60
cggggcgctt cggcgctcct tatacaccca ccctctgcct acgtgtacct ctatagcttc 120
ctcggcgggc tcgcccgccg ccaggaaccc acgaaacccc ttgcattata cgcgaaaact 180
tctgataaca aacctaaatt atcacaactt tcaacaatgg atctcttggt tctggcatcg 240
atgaagaacg cagcgaaatg cgataagtag tgtgaattgc agaattcagt gaatcatcga 300
atctttgaac gcacattgcg gccataggta ttcctttggc catgcctgtt cgagcgtcat 360
ttacaccctc aagcctagct tggtgttggg cgtctgtccc gccgttctcg cgcgcggact 420
cgcctcaaag tcattggcgg cggtcgtgcc ggccccctcg cgcagcacat ttgcgcttct 480
cggaggcccg gcggatccgc gctccagcaa gacctttcac gacttgacct cggatcaggt 540
agggataccc gctgaactta agcatatcaa taagcggagg aa 582

<210> SEQ ID NO 400
<211> LENGTH: 589
<212> TYPE: DNA
<213> ORGANISM: Ascomycete sp.

<400> SEQUENCE: 400
cgtaggtgac ctgcggagga tcattacaag aaacgaggct gcgtgcgctc atccgcccag 60
ccccgctcct taccttgcct actgcaccgt ttgttgcttc ctggcggcag actgcctgcc 120
gccagggaca ttgacataac cttgtatgag cattgaagac ctgaaatacg cgaaatcgta 180
caactttcaa caatggatct cttggttctg gcatcgatga agaacgcagc gaaatgcgat 240
aagtagtgtg aattgcagaa ttcagtgaat catcgaatct ttgaacgcac attgcgcccc 300
ttggtattcc atggggcatg cctgttcgag cgtcatctga accctcaagc ctcctgggtg 360
ttgtcccgcc tcgtgcgttg gacctcgccc ggcttggtgt tgggtgcctg tccctgcccc 420
tcgcgcggac tcaccccaaa tgcattggca gccgcccccc ggcttcttgc gcagcacatt 480
gcgtagcaag gcgaagcgag gcgcgcgtcc agcaagcaac cgctccaagt ttgacctcgg 540
atcaggtagg gatacccgct gaacttaagc atatcaataa gcggaggaa 589

<210> SEQ ID NO 401
<211> LENGTH: 559
<212> TYPE: DNA
<213> ORGANISM: Fusarium nygamai

<400> SEQUENCE: 401
tctcgttggt gaccagcgga gggatcatta ccgagtttac aactcccaaa cccctgtgaa 60
catatcaatt gttgcctcgg cggatcagcc cgctcccggt aaaacggaac ggcccgccag 120
aggaccccta aactctgttt ctatatgtaa cttctgagta aaaccataaa taaatcaaaa 180
ctttcaacaa cggatctctt ggttctggca tcgatgaaga acgcagcaaa atgcgataag 240
taatgtgaat tgcagaattc agtgaatcat cgaatctttg aacgcacatt gcgcccgcca 300
gtattctggc gggcatgcct gttcgagcgt catttcaacc ctcaagcccc cgggtttggt 360
gttggggatc ggcgagcctc acggcaagcc ggccccgaaa tacagtggcg gtctcgctgc 420
agcttccatt gcgtagtagt aaaaccctcg caactggtac gcggcgcggc caagccgtta 480
aacccccaac ttctgaatgt tgacctcgga tcaggtagga atacccgctg aacttaagca 540
tatcaataag gcggaggaa 559

<210> SEQ ID NO 402
<211> LENGTH: 571
<212> TYPE: DNA
<213> ORGANISM: Fusarium nygamai

<400> SEQUENCE: 402
gggaatgcag ggtctccgtt ggtgaccagc ggagggatca ttaccgagtt tacaactccc 60
aaacccctgt gaacatacca attgttgcct cggcggatca gcccgctccc ggtaaaacgg 120
aacggcccgc cagaggaccc ctaaactctg tttctatatg taacttctga gtaaaaccat 180
aaataaatca aaactttcaa caacggatct cttggttctg gcatcgatga agaacgcagc 240
aaaatgcgat aagtaatgtg aattgcagaa ttcagtgaat catcgaatct ttgaacgcac 300
attgcgcccg ccagtattct ggcgggcatg cctgttcgag cgtcatttca accctcaagc 360
ccccgggttt ggtgttgggg atcggcgagc ctcacggcaa gccggccccg aaatacagtg 420
gcggtctcgc tgcagcttcc attgcgtagt agtaaaaccc tcgcaactgg tacgcggcgc 480
ggccaagccg ttaaaccccc aacttctgaa tgttgacctc ggatcaggta ggaatacccg 540
ctgaacttaa gcatatcaat aagcggagga a 571

<210> SEQ ID NO 403
<211> LENGTH: 621
<212> TYPE: DNA
<213> ORGANISM: Gaeumannomyces incrustans

<400> SEQUENCE: 403
tcttggtcat ttagaggaag taaaagtcgt aacaaggtct ccgttggtga accagcggag 60
ggatcattaa agagttgcaa aactccaacc cctgtgaatt ttacctgtac gttgcttcgg 120
cggccgacgc cgcgcccagc cgggcctggg ggacgccgcc ggaggtctta aaccctgaat 180
tctagtgtat ctctgaggac gaaaaaaacc aattaaaact ttcaacaacg gatctcttgg 240
ctctggcatc gatgaagaac gcagcgaaat gcgataagta atgtgaattg cagaattcag 300
tgaatcatcg aatctttgaa cgcacattgc gcccgccggt attccggcgg gcatgcctgt 360
ccgagcgtca tttcaccact caagcccagc ttggtgttgg ggcacccggc cgcctggcgg 420
tcggggcccc taagtacatc ggcggtcccg ctggggctcc gagcgcagta actcgcggta 480
aaacgcgccc tcgctcggcg gcctcctcgg gcttccagcc gctaaacccc cagtgacgtt 540
tttcgagttg acctcggatc aggtaggaat acccgctgaa cttaagcata tcaatagcgg 600
aggaagccgc cgagcgaggc g 621

<210> SEQ ID NO 404
<211> LENGTH: 608
<212> TYPE: DNA
<213> ORGANISM: Gaeumannomyces incrustans

<400> SEQUENCE: 404
tcttggtcat ttagaggaag taaaagtcgt aacaaggtct ccgttggtga accagcggag 60
ggatcattaa agagttgcaa aactccaacc cctgtgaatt ttacctgtac gttgcttcgg 120

```
cggccgacgc cgcgcccagc cgggcctggg ggacgccgcc ggaggtctta aaccctgaat    180

tctagtgtat ctctgaggac gaaaaaaacc aattaaaact ttcaacaacg gatctcttgg    240

ctctggcatc gatgaagaac gcagcgaaat gcgataagta atgtgaattg cagaattcag    300

tgaatcatcg aatctttgaa cgcacattgc gcccgccggt attccggcgg gcatgcctgt    360

ccgagcgtca tttcaccact caagcccagc ttggtgttgg ggcacccggc cgcctggcgg    420

tcggggcccc taagtacatc ggcggtcccg ctggggctcc gagcgcagta actcgcggta    480

aaacgcgccc tcgctcggcg gcctcctcgg gcttccagcc gctaaacccc cagtgacgtt    540

tttcgagttg acctcggatc aggtaggaat acccgctgaa cttaagcata tcaataggcc    600

ggaggaaa                                                              608
```

<210> SEQ ID NO 405
<211> LENGTH: 567
<212> TYPE: DNA
<213> ORGANISM: Fusarium nygamai

<400> SEQUENCE: 405

```
accattaggt ctcgttggtg accagcggag ggatcattac cgagtttaca actcccaaac     60

ccctgtgaac ataccaattg ttgcctcggc ggatcagccc gctcccggta aaacggaacg    120

gcccgccaga ggacccctaa actctgtttc tatatgtaac ttctgagtaa aaccataaat    180

aaatcaaaac tttcaacaac ggatctcttg gttctggcat cgatgaagaa cgcagcaaaa    240

tgcgataagt aatgtgaatt gcagaattca gtgaatcatc gaatctttga acgcacattg    300

cgcccgccag tattctggcg ggcatgcctg ttcgagcgtc atttcaaccc tcaagccccc    360

gggtttggtg ttggggatcg gcgagcctca cggcaagccg gccccgaaat acagtggcgg    420

tctcgctgca gcttccattg cgtagtagta aaaccctcgc aactggtacg cggcgcggcc    480

aagccgttaa acccccaact tctgaatgtt gacctcggat caggtaggaa tacccgctga    540

acttaagcat atcaatagac ggaggaa                                         567
```

<210> SEQ ID NO 406
<211> LENGTH: 541
<212> TYPE: DNA
<213> ORGANISM: Fusarium nygamai

<400> SEQUENCE: 406

```
ggagggatca ttaccgagtt tacaactccc aaacccctgt gaacatacca attgttgcct     60

cggcggatca gcccgctccc ggtaaaacgg aacggcccgc cagaggaccc ctaaactctg    120

tttctatatg taacttctga gtaaaaccat aaataaatca aaactttcaa caacggatct    180

cttggttctg gcatcgatga agaacgcagc aaaatgcgat aagtaatgtg aattgcagaa    240

ttcagtgaat catcgaatct ttgaacgcac attgcgcccg ccagtattct ggcgggcatg    300

cctgttcgag cgtcatttca accctcaagc ccccgggttt ggtgttgggg atcggcgagc    360

ctcacggcaa gccggccccg aaatacagtg gcggtctcgc tgcagcttcc attgcgtagt    420

agtaaaaccc tcgcaactgg tacgcggcgc ggccaagccg ttaaaccccc aacttctgaa    480

tgttgacctc ggatcaggta ggaatacccg ctgaacttaa gcatatcaat aggcggagga    540

a                                                                     541
```

<210> SEQ ID NO 407
<211> LENGTH: 596
<212> TYPE: DNA
<213> ORGANISM: Sordariomycete sp.

<400> SEQUENCE: 407
tcttggtcaa ttagaggaag taaaagtcgt aacaaggtct ccgttggtga accagcggag 60
ggatcattac cgagtttaca actcccaaac ccctgtgaac ataccaattg ttgcctcggc 120
ggatcagccc gctcccggta aaacggaacg gcccgccaga ggacccctaa actctgtttc 180
tatatgtaac ttctgagtaa aaccataaat aaatcaaaac tttcaacaac ggatctcttg 240
gttctggcat cgatgaagaa cgcagcaaaa tgcgataagt aatgtgaatt gcagaattca 300
gtgaatcatc gaatctttga acgcacattg cgcccgccag tattctggcg ggcatgcctg 360
ttcgagcgtc atttcaaccc tcaagccccc gggtttggtg ttggggatcg gcgagcctca 420
cggcaagccg gccccgaaat acagtggcgg tctcgctgca gcttccattg cgtagtagta 480
aaaccctcgc aactggtacg cggcgcggcc aagccgttaa acccccaact tctgaatgtt 540
gacctcggat caggtaggaa tacccgctga acttaagcat atcaatagcg gaggaa 596

<210> SEQ ID NO 408
<211> LENGTH: 585
<212> TYPE: DNA
<213> ORGANISM: Grass root mycorrhizal sp.

<400> SEQUENCE: 408
ttcctccgct tattgatatg cttaagttca gcgggtatcc ctacctgatc cgaggtcaac 60
ctgaaaaaat ggggggttct ggcgggcaac cggggggacc ctatagcgag gagatttact 120
acgcttagag cccaccggca ccgccactga ttttaggggc cgcggaaccg cgagccccaa 180
taccaagcca ggcttgagtg gttataatga cgctcgaaca ggcatgcccg gcggaatacc 240
accgggcgca atgtgcgttc aaagattcga tgattcactg aattctgcaa ttcacattac 300
ttatcgcatt tcgctgcgtt cttcatcgat gccagaacca agagatccgt tgttgaaagt 360
tttaactatt atatagtact cagacatcac taaagttcag agtttggtcc tctggcaggc 420
acacgcaggc agagcccgcg gtggaggcca cggcctgcca aagcaacaag agtagataga 480
cacgggtggg gtctaccggt tgcccggtat cctttttaat gatccttccg caggttcacc 540
tacggaaacc ttgttacgac ttttacttcc tctaaatgac caaga 585

<210> SEQ ID NO 409
<211> LENGTH: 597
<212> TYPE: DNA
<213> ORGANISM: Periconia macrospinosa

<400> SEQUENCE: 409
tcttggtcat ttagaggaag taaaagtcgt aacaaggttt ccgtaggtga acctgcggaa 60
ggatcattac acattcgggg cgcttcggcg ctccttatac acccaccctc tgcctacgtg 120
tacctctata gcttcctcgg cgggctcgcc cgccgccagg aacccacgaa accccttgca 180
ttatacgcga aaacttctga taacaaacct aaattatcac aactttcaac aatggatctc 240
ttggttctgg catcgatgaa gaacgcagcg aaatgcgata agtagtgtga attgcagaat 300
tcagtgaatc atcgaatctt tgaacgcaca ttgcggccat aggtattcct ttggccatgc 360
ctgttcgagc gtcatttaca ccctcaagcc tagcttggtg ttgggcgtct gtcccgccgt 420
tctcgcgcgc ggactcgcct caaagtcatt ggcggcggtc gtgccggccc cctcgcgcag 480
cacatttgcg cttctcggag gcccggcgga tccgcgctcc agcaagacct ttcacgactt 540
gacctcggat caggtaggga tacccgctga acttaagcat atcaataagc ggaagaa 597

<210> SEQ ID NO 410
<211> LENGTH: 573
<212> TYPE: DNA
<213> ORGANISM: Periconia macrospinosa

<400> SEQUENCE: 410
ttattgatat gcttaagttc agcgggtatc cctacctgat ccgaggtcaa gtcgtgaaag 60
gtcttgctgg agcgcggatc cgccgggcct ccgagaagcg caaatgtgct gcgcgagggg 120
gccggcacga ccgccgccaa tgactttgag gcgagtccgc gcgcgagaac ggcgggacag 180
acgcccaaca ccaagctagg cttgagggtg taaatgacgc tcgaacaggc atggccaaag 240
gaatacctat ggccgcaatg tgcgttcaaa gattcgatga ttcactgaat tctgcaattc 300
acactactta tcgcatttcg ctgcgttctt catcgatgcc agaaccaaga gatccattgt 360
tgaaagttgt gataatttag gtttgttatc agaagttttc gcgtataatg caaggggttt 420
cgtgggttcc tggcggcggg cgagcccgcc gaggaagcta tagaggtaca cgtaggcaga 480
gggtgggtgt ataaggagcg ccgaagcgcc ccgaatgtgt aatgatcctt ccgcaggttc 540
acctacggaa accttgttac gacttttact tcc 573

<210> SEQ ID NO 411
<211> LENGTH: 553
<212> TYPE: DNA
<213> ORGANISM: Fusarium nygamai

<400> SEQUENCE: 411
ttggtgacca gcggagggat cattaccgag tttacaactc ccaaacccct gtgaacatac 60
caattgttgc ctcggcggat cagcccgctc ccggtaaaac ggaacggccc gccagaggac 120
ccctaaactc tgtttctata tgtaacttct gagtaaaacc ataaataaat caaaactttc 180
aacaacggat ctcttggttc tggcatcgat gaagaacgca gcaaaatgcg ataagtaatg 240
tgaattgcag aattcagtga atcatcgaat ctttgaacgc acattgcgcc cgccagtatt 300
ctggcgggca tgcctgttcg agcgtcattt caaccctcaa gcccccgggt ttggtgttgg 360
ggatcggcga gcctcacggc aagccggccc cgaaatacag tggcggtctc gctgcagctt 420
ccattgcgta gtagtaaaac cctcgcaact ggtacgcggc gcggccaagc cgttaaaccc 480
ccaacttctg aatgttgacc tcggatcagg taggaatacc cgctgaactt aagcatatca 540
ataagcggag gaa 553

<210> SEQ ID NO 412
<211> LENGTH: 553
<212> TYPE: DNA
<213> ORGANISM: Fusarium nygamai

<400> SEQUENCE: 412
ttggtgacag cggagggatc attaccgagt ttacaactcc caaacccctg tgaacatacc 60
aattgttgcc tcggcggatc agcccgctcc cggtaaaacg gaacggcccg ccagaggacc 120
cctaaactct gtttctatat gtaacttctg agtaaaacca taaataaatc aaaactttca 180
acaacggatc tcttggttct ggcatcgatg aagaacgcag caaaatgcga taagtaatgt 240
gaattgcaga attcagtgaa tcatcgaatc tttgaacgca cattgcgccc gccagtattc 300
tggcgggcat gcctgttcga gcgtcatttc aaccctcaag cccccgggtt tggtgttggg 360
gatcggcgag cctcacggca agccggcccc gaaatacagt ggcggtctcg ctgcagcttc 420
cattgcgtag tagtaaaacc ctcgcaactg gtacgcggcg cggccaagcc gttaaacccc 480 caactttctga atgttgacct cggatcaggt aggaataccc gctgaactta agcatatcaa 540
taaggcggag gaa 553

<210> SEQ ID NO 413
<211> LENGTH: 547
<212> TYPE: DNA
<213> ORGANISM: Fusarium nygamai

<400> SEQUENCE: 413
accagcggag ggatcattac cgagtttaca actcccaaac ccctgtgaac ataccaattg 60
ttgcctcggc ggatcagccc gctcccggta aaacggaacg gcccgccaga ggacccctaa 120
actctgtttc tatatgtaac ttctgagtaa aaccataaat aaatcaaaac tttcaacaac 180
ggatctcttg gttctggcat cgatgaagaa cgcagcaaaa tgcgataagt aatgtgaatt 240
gcagaattca gtgaatcatc gaatctttga acgcacattg cgcccgccag tattctggcg 300
ggcatgcctg ttcgagcgtc atttcaaccc tcaagccccc gggtttggtg ttggggatcg 360
gcgagcctca cggcaagccg gccccgaaat acagtggcgg tctcgctgca gcttccattg 420
cgtagtagta aaaccctcgc aactggtacg cggcgcggcc aagccgttaa acccccaact 480
tctgaatgtt gacctcggat caggtaggaa tacccgctga acttaagcat atcaataagc 540
ggaggaa 547

<210> SEQ ID NO 414
<211> LENGTH: 606
<212> TYPE: DNA
<213> ORGANISM: Gaeumannomyces incrustans

<400> SEQUENCE: 414
tcttggtcat ttagaggaag taaaagtcgt aacaaggtct ccgttggtga accagcggag 60
ggatcattaa agagttgcaa aactccaacc cctgtgaact ttacctgtac gttgcttcgg 120
cggccgacgc cgcgcccagc cgggcccggg ggacgccgcc ggaggtcata aaccctgaat 180
tctagtgtat ctctgaggac gaaaataacc aattaaaact ttcaacaacg gatctcttgg 240
ctctggcatc gatgaagaac gcagcgaaat gcgataagta atgtgaattg cagaattcag 300
tgaatcatcg aatctttgaa cgcacattgc gcccgccggt attccggcgg gcatgcctgt 360
ccgagcgtca tttcaccact caagcccagc ttggtgttgg ggcacccggc cgcccggcgg 420
tcggggcccc caagtacatc ggcggtcccg ctggggctcc gagcgcagta actcgcggta 480
aaacgcgccc tcgctcggcg gcctcctcgg gcttccagcc gctaaacccc cagtgacgtt 540
tttcgagttg acctcggatc aggtaggaat acccgctgaa cttaagcata tcaataagag 600
gaggaa 606

<210> SEQ ID NO 415
<211> LENGTH: 569
<212> TYPE: DNA
<213> ORGANISM: Magnaporthe rhizophila

<400> SEQUENCE: 415
tctccgttgg tgaccagcgg agggatcatt aaagagttgc aaaactccaa cccctgtgaa 60
ctttacctgt acgttgcttc ggcggccgac gccgcgccca gccgggcccg gggacgccg 120 ccggaggtca taaaccctga attctagtgt atctctgagg acgaaaataa ccaattaaaa 180
ctttcaacaa cggatctctt ggctctggca tcgatgaaga acgcagcgaa atgcgataag 240

```
taatgtgaat tgcagaattc agtgaatcat cgaatctttg aacgcacatt gcgcccgccg    300

gtattccggc gggcatgcct gtccgagcgt catttcacca ctcaagccca gcttggtgtt    360

ggggcacccg gccgcccggc ggtcggggcc cccaagtaca tcggcggtcc cgctggggct    420

ccgagcgcag taactcgcgg taaaacgcgc cctcgctcgg cggcctcctc gggcttccag    480

ccgctaaacc cccagtgacg tttttcgagt tgacctcgga tcaggtagga atacccgctg    540

aacttaagca tatcaataag gcggaggaa                                      569


<210> SEQ ID NO 416
<211> LENGTH: 607
<212> TYPE: DNA
<213> ORGANISM: Gaeumannomyces incrustans

<400> SEQUENCE: 416

tcttggtcat ttagaggaag taaaagtcgt aacaaggtct ccgttggtga accagcggag     60

ggatcattaa agagttgcaa aactccaacc cctgtgaact ttacctgtac gttgcttcgg    120

cggccgacgc cgcgcccagc cgggcccggg ggacgccgcc ggaggtcata aaccctgaat    180

tctagtgtat ctctgaggac gaaaataacc aattaaaact ttcaacaacg gatctcttgg    240

ctctggcatc gatgaagaac gcagcgaaat gcgataagta atgtgaattg cagaattcag    300

tgaatcatcg aatctttgaa cgcacattgc gcccgccggt attccggcgg gcatgcctgt    360

ccgagcgtca tttcaccact caagcccagc ttggtgttgg ggcacccggc cgcccggcgg    420

tcggggcccc caagtacatc ggcggtcccg ctggggctcc gagcgcagta actcgcggta    480

aaacgcgccc tcgctcggcg gcctcctcgg gcttccagcc gctaaacccc cagtgacgtt    540

tttcgagttg acctcggatc aggtaggaat acccgctgaa cttaagcata tcaataagac    600

ggaggaa                                                              607


<210> SEQ ID NO 417
<211> LENGTH: 566
<212> TYPE: DNA
<213> ORGANISM: Magnaporthe rhizophila

<400> SEQUENCE: 417

tctcgttggt gaccagcgga gggatcatta aagagttgca aaactccaac ccctgtgaac     60

tttacctgta cgttgcttcg gcggccgacg ccgcgcccag ccgggcccgg gggacgccgc    120

cggaggtcat aaaccctgaa ttctagtgta tctctgagga cgaaaataac caattaaaac    180

tttcaacaac ggatctcttg gctctggcat cgatgaagaa cgcagcgaaa tgcgataagt    240

aatgtgaatt gcagaattca gtgaatcatc gaatctttga acgcacattg cgcccgccgg    300

tattccggcg ggcatgcctg tccgagcgtc atttcaccac tcaagcccag cttggtgttg    360

gggcacccgg ccgcccggcg gtcggggccc ccaagtacat cggcggtccc gctggggctc    420

cgagcgcagt aactcgcggt aaaacgcgcc ctcgctcggc ggcctcctcg ggcttccagc    480

cgctaaaccc ccagtgacgt ttttsgagtt gacctcggat caggtaggaa tacccgctga    540

acttaagcat atcaataaga ggagga                                         566


<210> SEQ ID NO 418
<211> LENGTH: 591
<212> TYPE: DNA
<213> ORGANISM: Fusarium proliferatum

<400> SEQUENCE: 418

ttggtcattt agagtaagta aaagtcgtaa caaggtctcc cgttggtgaa ccagcggagg     60
```

gatcattacc gagtttacaa ctcccaaacc cctgtgaaca tatcaattgt tgcctcggcg 120
gatcagcccg ctcccggtaa aacggaacgg cccgccagag gacccctaaa ctctgtttct 180
atatgtaact tctgagtaaa accataaata aatcaaaact ttcaacaacg gatctcttgg 240
ttctggcatc gatgaagaac gcagcaaaat gcgataagta atgtgaattg cagaattcag 300
tgaatcatcg aatctttgaa cgcacattgc gcccgccagt attctggcgg gcatgcctgt 360
tcgagcgtca tttcaaccct caagcccccg ggtttggtgt tggggatcgg cgagcctcac 420
ggcaagccgg ccccgaaata cagtggcggt ctcgctgcag cttccattgc gtagtagtaa 480
aaccctcgca actggtacgc ggcgcggcca agccgttaaa cccccaactt ctgaatgttg 540
acctcggatc aggtaggaat acccgctgaa cttaagcata tcaataagcg g 591

<210> SEQ ID NO 419
<211> LENGTH: 589
<212> TYPE: DNA
<213> ORGANISM: Fusarium proliferatum

<400> SEQUENCE: 419
cttggtcaat ttagaggaag taaaagtcgt aacaaggtct ccgttggtga accagcggag 60
ggatcattac cgagtttaca actcccaaac ccctgtgaac ataccaattg ttgcctcggc 120
ggatcagccc gctcccggta aaacggaacg gcccgccaga ggacccctaa actctgtttc 180
tatatgtaac ttctgagtaa aaccataaat aaatcaaaac tttcaacaac ggatctcttg 240
gttctggcat cgatgaagaa cgcagcaaaa tgcgataagt aatgtgaatt gcagaattca 300
gtgaatcatc gaatctttga acgcacattg cgcccgccag tattctggcg ggcatgcctg 360
ttcgagcgtc atttcaaccc tcaagccccc gggtttggtg ttggggatcg gcgagcctca 420
cggcaagccg gccccgaaat acagtggcgg tctcgctgca gcttccattg cgtagtagta 480
aaaccctcgc aactggtacg cggcgcggcc aagccgttaa acccccaact tctgaatgtt 540
gacctcggat caggtaggaa tacccgctga acttaagcat atcaataag 589

<210> SEQ ID NO 420
<211> LENGTH: 568
<212> TYPE: DNA
<213> ORGANISM: Magnaporthe rhizophila

<400> SEQUENCE: 420
tctcgttggt gaccagcgga gggatcatta aagagttgca aaactccaac ccctgtgaac 60
tttacctgta cgttgcttcg gcggccgacg ccgcgcccag ccgggcgtgg gggacgccgc 120
cggaggtttt aaaccctgaa ttctagtgta tctctgagga cgaaaagaac caattaaaac 180
tttcaacaac ggatctcttg gctctggcat cgatgaagaa cgcagcgaaa tgcgataagt 240
aatgtgaatt gcagaattca gtgaatcatc gaatctttga acgcacattg cgcccgccgg 300
tattccggcg ggcatgcctg tccgagcgtc atttcaccac tcaagcccag cttggtgttg 360
gggcacccgg ccgcccggcg gtcggggccc ccaagtacat cggcggtcct gctggggctc 420
cgagcgcagt aacacgcggt aaaacgcgcc ctcgctcggc ggcctcctcg ggcttccagc 480
cgctaaaccc ccagtgacgt ttttcgagtt gacctcggat caggtaggaa tacccgctga 540
acttaagcat atcaataaga cggaggaa 568

<210> SEQ ID NO 421
<211> LENGTH: 568
<212> TYPE: DNA

-continued

<213> ORGANISM: Magnaporthe rhizophila

<400> SEQUENCE: 421
tctcgttggt gaccagcgga gggatcatta aagagttgca aaactccaac ccctgtgaac 60
tttacctgta cgttgcttcg gcggccgacg ccgcgcccag ccgggcctgg gggacgccgc 120
cggaggtttt aaaccctgaa ttctagtgta tctctgagga cgaaaagaac caattaaaac 180
tttcaacaac ggatctcttg gctctggcat cgatgaagaa cgcagcgaaa tgcgataagt 240
aatgtgaatt gcagaattca gtgaatcatc gaatctttga acgcacattg cgcccgccgg 300
tattccggcg ggcatgcctg tccgagcgtc atttcaccac tcaagcccag cttggtgttg 360
gggcacccgg ccgcccggcg gtcggggccc ccaagtacat cggcggtccc gctggggctc 420
cgagcgcagt aactcgcggt aaaacgcgcc ctcgctcggc ggcctcctcg ggcttccagc 480
cgctgaaccc ccagtgacgt ttttcgagtt gacctcggat caggtaggaa tacccgctga 540
acttaagcat atcaataagg cggaggaa 568

<210> SEQ ID NO 422
<211> LENGTH: 568
<212> TYPE: DNA
<213> ORGANISM: Gaeumannomyces incrustans

<400> SEQUENCE: 422
atcctactga tccgaggtca actcgaaaaa cgtcactggg ggtttagcgg ctggaagccc 60
gaggaggccg ccgagcgagg gcgcgtttta ccgcgtgtta ctgcgctcgg agccccagca 120
ggaccgccga tgtacttggg ggccccgacc gccgggcggc cgggtgcccc aacaccaagc 180
tgggcttgag tggtgaaatg acgctcggac aggcatgccc gccggaatac cggcgggcgc 240
aatgtgcgtt caaagattcg atgattcact gaattctgca attcacatta cttatcgcat 300
ttcgctgcgt tcttcatcga tgccagagcc aagagatccg ttgttgaaag ttttaattgg 360 ttttttcgt cctcagagat atgctagaat tcagggttta aaacctccgg cggcgtcccc 420
caggcccggc tgggcgcggc gtcggccgcc gaagcaacgt acaggtaaag ttcacagggg 480
ttggagtttt gcaactcttt aatgatccct ccgctggttc accaacggag accttgttac 540
gacttttact tcctctaaat gaccaaga 568

<210> SEQ ID NO 423
<211> LENGTH: 546
<212> TYPE: DNA
<213> ORGANISM: Fusarium nygamai

<400> SEQUENCE: 423
tcgttggtga ccagcggagg gatcattacc gagtttacaa ctcccaaacc cctgtgaaca 60
tatcaattgt tgcctcggcg gatcagcccg ctcccggtaa aacggaacgg cccgccagag 120
gacccctaaa ctctgtttct atatgtaact tctgagtaaa accataaata aatcaaaact 180
ttcaacaacg gatctcttgg ttctggcatc gatgaagaac gcagcaaaat gcgataagta 240
atgtgaattg cagaattcag tgaatcatcg aatctttgaa cgcacattgc gcccgccagt 300
attctggcgg gcatgcctgt tcgagcgtca tttcaaccct caagcccccg ggtttggtgt 360
tggggatcgg cgagcctcac ggcaagccgg ccccgaaata cagtggcggt ctcgctgcag 420
cttccattgc gtagtagtaa aaccctcgca actggtacgc ggcgcggcca agccgttaaa 480
cccccaactt ctgaatgttg acctcggatc aggtaggaat acccgctgaa cttaagcata 540
tcaata 546

<210> SEQ ID NO 424
<211> LENGTH: 558
<212> TYPE: DNA
<213> ORGANISM: Fusarium nygamai

<400> SEQUENCE: 424
gtctcgttgt gaccagcgga gggatcatta ccgagtttac aactcccaaa cccctgtgaa 60
cataccaatt gttgcctcgg cggatcagcc cgctcccggt aaaacggaac ggcccgccag 120
aggaccccta aactctgttt ctatatgtaa cttctgagta aaaccataaa taaatcaaaa 180
ctttcaacaa cggatctctt ggttctggca tcgatgaaga acgcagcaaa atgcgataag 240
taatgtgaat tgcagaattc agtgaatcat cgaatctttg aacgcacatt gcgcccgcca 300
gtattctggc gggcatgcct gttcgagcgt catttcaacc ctcaagcccc cgggtttggt 360
gttggggatc ggcgagcctc acggcaagcc ggccccgaaa tacagtggcg gtctcgctgc 420
agcttccatt gcgtagtagt aaaaccctcg caactggtac gcggcgcggc caagccgtta 480 aaccccccaac ttctgaatgt tgacctcgga tcaggtagga atacccgctg aacttaagca 540
tatcaataag cggaggaa 558

<210> SEQ ID NO 425
<211> LENGTH: 862
<212> TYPE: DNA
<213> ORGANISM: Uncultured Lachnum

<400> SEQUENCE: 425
cctgatccga ggtcaaccta gaaaaatttg gggttgctgg ccagtatctc ccaggaccct 60
atagcgagaa aattactacg cgtagagcct aagagcaccg ccactagttt taaggcccgc 120
cagacagcga agcccaacac ctagccaagc tagattggta taaatgacgc tcgaacaggc 180 atgcccccccg gaataccagg gggcgcaatg tgcgttcaaa gattcgatga ttcactgaat 240
tctgcaattc acattactta tcgcatttcg ctgcgttctt catcgatgcc agaaccaaga 300
gatccgttgt tgaaagtttt aactatttaa tagtactcag acgacactaa cattcagagt 360
ttaggggtcc tctggcgggc acgctagacg cgaatctagg cgcacgaggc gcggcccgcc 420
aaagcaacat tctataatga tacacaaggg tgggagatct accccaaagg gcatgaactc 480
tgtaatgatc cttccgcagg ttcacctacg gaacggttga ccgctgtagt ttcctagagc 540
gcccgactat atcttaagca ggacttgcct acccacgacc acctagtctg tgaacgttcc 600
ccgtaggcct gggccggtag gggcttcgct gcggattgtc cattgtagca tcctagcaga 660
ttctgacctc cagtggggtt agcactggcc cacactgcat ttctacagcg tgttggtacc 720
gctaggcttt aggagatccc cgcaattcga tcatgttgcc gccatagcga cttgcatcct 780
atatttatag tcgcggaccc tggtgaggtt gcataggctt ccacaagcta cccggaagga 840
tactgttcga atgaaaccta tg 862

<210> SEQ ID NO 426
<211> LENGTH: 603
<212> TYPE: DNA
<213> ORGANISM: Trichoderma aureoviride

<400> SEQUENCE: 426
tattgatatg cttaagttca gcgggtattc ctacctgatc cgaggtcaac atttcagaag 60
ttgggtgttt aacggctgtg gacgcgccgc gctcccgatg cgagtgtgca aactactgcg 120

-continued caggagaggc tgcggcgaga ccgccactgt atttcggaga cggccaccgc caaggcaggg 180
ccgatcccca acgccgaccc cccggagggg ttcgagggtt gaaatgacgc tcggacaggc 240
atgcccgcca gaatactggc gggcgcaatg tgcgttcaaa gattcgatga ttcactgaat 300
tctgcaattc acattactta tcgcatttcg ctgcgttctt catcgatgcc agaaccaaga 360
gatccgttgt tgaaagtttt gattcatttt cgaaacgcct acgagaggcg ccgagaaggc 420
tcagattata aaaaaacccg cgagggggta tacaataaga gttttggttg gtcctccggc 480
gggcgccttg gtccggggct gcgacgcacc cggggcagag atcccgccga ggcaacagtt 540
tggtaacgtt cacattgggt ttgggagttg taaactcggt aatgatccct ccgctggtca 600
caa 603

<210> SEQ ID NO 427
<211> LENGTH: 561
<212> TYPE: DNA
<213> ORGANISM: Magnaporthe rhizophila

<400> SEQUENCE: 427
cgttggtgac cagcggaggg atcattaaag agttgcaaaa ctccaacccc tgtgaacctt 60
acctttactg ttgcttcggc ggttggcgcc ggtgcccaga tgggcctgga ggtcgccgcc 120
ggaggttcga aaccctgaat tctagtgtgt ctctgagaaa agaataaaac aaatcaaaac 180
tttcaacaac ggatctcttg gttctggcat cgatgaagaa cgcagcgaaa tgcgataagt 240
aatgtgaatt gcagaattca gtgaatcatc gaatctttga acgcacattg cgcccgccgg 300
tattccggcg ggcatgcctg tccgagcgtc atttcaccac tcaagcacag cttggtgttg 360
gggcacccgg ccgcctggcg gtcggggccc ccaagtacat cggcggtccc gctgggggct 420
ccgagcgcag tagcacgcgg taaaacgcgc cctcgctcgg cggcctcttc gggcttccag 480
ccgctaaacc cgtccaccga cgcccttcga gttgacctcg gatcaggtag gaatacccgc 540
tgaacttaag catatcaata a 561

<210> SEQ ID NO 428
<211> LENGTH: 552
<212> TYPE: DNA
<213> ORGANISM: Fusarium nygamai

<400> SEQUENCE: 428
ttgtgaccag cggagggatc attaccgagt ttacaactcc caaacccctg tgaacatacc 60
aattgttgcc tcggcggatc agcccgctcc cggtaaaacg gaacggcccg ccagaggacc 120
cctaaactct gtttctatat gtaacttctg agtaaaacca taaataaatc aaaactttca 180
acaacggatc tcttggttct ggcatcgatg aagaacgcag caaaatgcga taagtaatgt 240
gaattgcaga attcagtgaa tcatcgaatc tttgaacgca cattgcgccc gccagtattc 300
tggcgggcat gcctgttcga gcgtcatttc aaccctcaag cccccgggtt tggtgttggg 360
gatcggcgag cctcacggca agccggcccc gaaatacagt ggcggtctcg ctgcagcttc 420
cattgcgtag tagtaaaacc ctcgcaactg gtacgcggcg cggccaagcc gttaaacccc 480
caacttctga atgttgacct cggatcaggt aggaataccc gctgaactta agcatatcaa 540
taagcggagg aa 552

<210> SEQ ID NO 429
<211> LENGTH: 546
<212> TYPE: DNA
<213> ORGANISM: Fusarium nygamai

<400> SEQUENCE: 429
ccagcggagg gatcattacc gagtttacaa ctcccaaacc cctgtgaaca tatcaattgt 60
tgcctcggcg gatcagcccg ctcccggtaa aacggaacgg cccgccagag gacccctaaa 120
ctctgtttct atatgtaact tctgagtaaa accataaata aatcaaaact ttcaacaacg 180
gatctcttgg ttctggcatc gatgaagaac gcagcaaaat gcgataagta atgtgaattg 240
cagaattcag tgaatcatcg aatctttgaa cgcacattgc gcccgccagt attctggcgg 300
gcatgcctgt tcgagcgtca tttcaaccct caagcccccg ggtttggtgt tggggatcgg 360
cgagcctcac ggcaagccgg ccccgaaata cagtggcggt ctcgctgcag cttccattgc 420
gtagtagtaa aaccctcgca actggtacgc ggcgcggcca agccgttaaa cccccaactt 480
ctgaatgttg acctcggatc aggtaggaat acccgctgaa cttaagcata tcaataagcg 540
gaggaa 546

<210> SEQ ID NO 430
<211> LENGTH: 597
<212> TYPE: DNA
<213> ORGANISM: Sordariomycete sp.

<400> SEQUENCE: 430
tcttggtcat ttagaggaag taaaagtcgt aacaaggtct ccgttggtga accagcggag 60
ggatcattac cgagtttaca actcccaaac ccctgtgaac ataccaattg ttgcctcggc 120
ggatcagccc gctcccggta aaacggaacg gcccgccaga ggacccctaa actctgtttc 180
tatatgtaac ttctgagtaa aaccataaat aaatcaaaac tttcaacaac ggatctcttg 240
gttctggcat cgatgaagaa cgcagcaaaa tgcgataagt aatgtgaatt gcagaattca 300
gtgaatcatc gaatctttga acgcacattg cgcccgccag tattctggcg ggcatgcctg 360
ttcgagcgtc atttcaaccc tcaagccccc gggtttggtg ttggggatcg gcgagcctca 420
cggcaagccg gccccgaaat acagtggcgg tctcgctgca gcttccattg cgtagtagta 480
aaaccctcgc aactggtacg cggcgcggcc aagccgttaa acccccaact tctgaatgtt 540
gacctcggat caggtaggaa tacccgctga acttaagcat atcaataagc ggaggaa 597

<210> SEQ ID NO 431
<211> LENGTH: 606
<212> TYPE: DNA
<213> ORGANISM: Gaeumannomyces incrustans

<400> SEQUENCE: 431
tcttggtcat ttagaggaag taaaagtcgt aacaaggtct ccgttggtga accagcggag 60
ggatcattaa agagttgcaa aactccaacc cctgtgaact ttacctgtac gttgcttcgg 120
cggccgacgc cgcgcccagc cgggcccggg ggacgccgcc ggaggtcata aaccctgaat 180
tctagtgtat ctctgaggac gaaaataacc aattaaaact ttcaacaacg gatctcttgg 240
ctctggcatc gatgaagaac gcagcgaaat gcgataagta atgtgaattg cagaattcag 300
tgaatcatcg aatctttgaa cgcacattgc gcccgccggt attccggcgg gcatgcctgt 360
ccgagcgtca tttcaccact caagcccagc ttggtgttgg ggcacccggc cgcccggcgg 420
tcggggcccc caagtacatc ggcggtcctg ctggggctcc gagcgcagta acacgcggta 480
aaacgcgccc tcgctcggcg gcctcctcgg gcttccagcc gctaaacccc cagtgacgtt 540
tttcgagttg acctcggatc aggtaggaat acccgctgaa cttaagcata tcaatagccg 600
gaggaa 606

<210> SEQ ID NO 432
<211> LENGTH: 558
<212> TYPE: DNA
<213> ORGANISM: Fusarium moniliformae

<400> SEQUENCE: 432
ctcgttggtg accagcggag ggatcattac cgagtttaca actcccaaac ccctgtgaac 60
ataccaattg ttgcctcggc ggatcagccc gctcccggta aaacgggacg gcccgccaga 120
ggacccctaa actctgtttc tatatgtaac ttctgagtaa aaccataaat aaatcaaaac 180
tttcaacaac ggatctcttg gttctggcat cgatgaagaa cgcagcaaaa tgcgataagt 240
aatgtgaatt gcagaattca gtgaatcatc gaatctttga acgcacattg cgcccgccag 300
tattctggcg ggcatgcctg ttcgagcgtc atttcaaccc tcaagccctc gggtttggtg 360
ttggggatcg gcgagccctc gcggcaagcc ggccccgaaa tatagtggcg gtctcgctgc 420
agcttccatt gcgtagtagt aaaaccctcg caactggtac gcggcgcggc caagccgtta 480
aacccccaac ttctgaatgt tgacctcgga tcaggtagra ayacccgctg aacttaagca 540
tatcaataag cggaggaa 558

<210> SEQ ID NO 433
<211> LENGTH: 511
<212> TYPE: DNA
<213> ORGANISM: Fusarium nygamai

<400> SEQUENCE: 433
cagcggaggg atcattaccg agtttacaac tcccaaaccc ctgtgaacat accaattgtt 60
gcctcggcgg atcagcccgc tcccggtaaa acggaacggc ccgccagagg acccctaaac 120
tctgtttcta tatgtaactt ctgagtaaaa ccataaataa atcaaaactt tcaacaacgg 180
atctcttggt tctggcatcg atgaagaacg cagcaaaatg cgataagtaa tgtgaattgc 240
agaattcagt gaatcatcga atctttgaac gcacattgcg cccgccagta ttctggcggg 300
catgcctgtt cgagcgtcat ttcaaccctc aagcccccgg gtttggtgtt ggggatcggc 360
gagcctcacg gcaagccggc cccgaaatac agtggcggtc tcgctgcagc ttccattgcg 420
tagtagtaaa accctcgcaa ctggtacgcg gcgcggccaa gccgttaaac ccccaacttc 480
tgaatgttga cctcggatca ggtaggaata c 511

<210> SEQ ID NO 434
<211> LENGTH: 608
<212> TYPE: DNA
<213> ORGANISM: Gaeumannomyces incrustans

<400> SEQUENCE: 434
tcttggtcaa ttagaggaag taaaagtcgt aacaaggtct ccgttggtga accagcggag 60
ggatcattaa agagttgcaa aaactccaac ccctgtgaac tttacctgta cgttgcttcg 120
gcggccgacg ccgcgcccag acgggcctgg gggacgccgc cggaggtctt aaaccctgaa 180
ttctagtgta tctatgagga cgaaaaaaac caattaaaac tttcaacaac ggatctcttg 240
gctctggcat cgatgaagaa cgcagcgaaa tgcgataagt aatgtgaatt gcagaattca 300
gtgaatcatc gaatctttga acgcacattg cgcccgccgg tattccggcg ggcatgcctg 360
tccgagcgtc atttcaccac tcaagcccag cttggtgttg gggcacccgg ccgcccggcg 420
gtcggggccc ccgagtacat cggcggtccc gctggggctc cgagcgcagt aactcgcggt 480
aaaacgcgcc ctcgctcggc ggcctcctcg ggcttccagc cgctaaaccc ccagtgacgt 540
ttttcgagtt gacctcggat caggtaggaa tacccgctga acttaagcat atcaataggc 600
ggaggaaa 608

<210> SEQ ID NO 435
<211> LENGTH: 609
<212> TYPE: DNA
<213> ORGANISM: Gaeumannomyces incrustans

<400> SEQUENCE: 435
tcttggtcat ttagaggaag taaaagtcgt aacaaggtct ccgttggtga accagcggag 60
ggatcattaa agagttgcaa aaactccaac ccctgtgaac tttacctgta cgttgcttcg 120
gcggccgacg ccgcgcccag acgggcctgg gggacgccgc cggaggtctt aaaccctgaa 180
ttctagtgta tctatgagga cgaaaaaaac caattaaaac tttcaacaac ggatctcttg 240
gctctggcat cgatgaagaa cgcagcgaaa tgcgataagt aatgtgaatt gcagaattca 300
gtgaatcatc gaatctttga acgcacattg cgcccgccgg tattccggcg ggcatgcctg 360
tccgagcgtc atttcaccac tcaagcccag cttggtgttg gggcacccgg ccgcccggcg 420
gtcggggccc ccaagtacat cggcggtccc gctggggctc cgagcgcagt aactcgcggt 480
aaaacgcgcc ctcgctcggc ggcctcctcg ggcttccagc cgctaaaccc ccagtgacgt 540
ttttcgagtt gacctcggat caggtaggaa tacccgctga acttaagcat atcaataggc 600
cggaggaaa 609

<210> SEQ ID NO 436
<211> LENGTH: 608
<212> TYPE: DNA
<213> ORGANISM: Gaeumannomyces incrustans

<400> SEQUENCE: 436
tcttgctcac ttagaggaag taaaaagtcg taacaaggtc tccgttggtg aaccagcgga 60
gggatcatta aagagttgca aaactccaac ccctgtgaac tttacctgta cgttgcttcg 120
gcggccgacg ccgcgcccag ccgggcctgg gggacgccgc cggaggtttt aaaccctgaa 180
ttctagtgta tctctgagga cgaaaaaaac caattaaaac tttcaacaac ggatctcttg 240
gctctggcat cgatgaagaa cgcagcgaaa tgcgataagt aatgtgaatt gcagaattca 300
gtgaatcatc gaatctttga acgcacattg cgcccgccgg tattccggcg ggcatgcctg 360
tccgagcgtc atttcaccac tcaagcccag cttggtgttg gggcacccgg ccgcccggcg 420
gtcggggccc ccaagtacat cggcggtcct gctggggctc cgagcgcagt aacacgcggt 480
aaaacgcgcc ctcgctcggc ggcctcctcg ggcttccagc cgctaaaccc ccagtgacgt 540
ttttcgagtt gacctcggat caggtaggaa tacccgctga acttaagcat atcaataagc 600
gggaggaa 608

<210> SEQ ID NO 437
<211> LENGTH: 535
<212> TYPE: DNA
<213> ORGANISM: Fusarium sp.

<400> SEQUENCE: 437
ccagcggagg gatcattacc gagtttacaa ctcccaaacc cctgtgaaca taccacttgt 60
tgcctcggcg gatcagcccg ctcccggtaa aacgggacgg cccgccagag gacccctaaa 120
ctctgtttct atatgtaact tctgagtaaa accataaata aatcaaaact ttcaacaacg 180
gatctcttgg ttctggcatc gatgaagaac gcagcaaaat gcgataagta atgtgaattg 240
cagaattcag tgaatcatcg aatctttgaa cgcacattgc gcccgccagt attctggcgg 300
gcatgcctgt tcgagcgtca tttcaaccct caagcacagc ttggtgttgg gactcgcgtt 360
aattcgcgtt cctcaaattg attggcggtc acgtcgagct tccatagcgt agtagtaaaa 420
ccctcgttac tggtaatcgt cgcggccacg ccgttaaacc ccaacttctg aatgttgacc 480
tcggatcagg taggaatacc cgctgaactt aagcatatca ataaggcgga ggaac 535

<210> SEQ ID NO 438
<211> LENGTH: 585
<212> TYPE: DNA
<213> ORGANISM: Ascomycete sp.

<400> SEQUENCE: 438
tcttggtcaa ttagaggaag taaaagtcgt aacaaggttt ccgtaggtga acctgcggaa 60
ggatcattat caaaagtcaa gtcgggggct gtaaagctct cgtctacacc catgtctttt 120
gcgtactctt gtttcctcgg tggcgcaagc tgccgattgg acaaaccaaa accttttttg 180
taattgcaat cagcgtctga aaataatcta attatttaca actttcaaca acggatctct 240
tggttctggc atcgatgaag aacgcagcga aatgcgataa gtagtgtgaa ttgcagaatt 300
cagtgaatca tcgaatcttt gaacgcacat tgcgcccctt ggtattccat ggggcatgcc 360
tgttcgagcg tcatttgtac cctcaagctt tgcttggtgt tgggcgtctt gtcgtattac 420
gactcgcctt aaatttattg gcagccggca ctttggccta ggagcgcagc acattttgcg 480
atcgtagccc gttgtactgg cgtccatcaa gaacatttac cacgtttgac ctcggatcag 540
gtagggatac ccgctgaact taagcatatc aatagccgga ggaaa 585

<210> SEQ ID NO 439
<211> LENGTH: 585
<212> TYPE: DNA
<213> ORGANISM: Ascomycete sp.

<400> SEQUENCE: 439
tcttggtcat ttagaggaag taaaagtcgt aacaaggttt ccgtaggtga acctgcggaa 60
ggatcattat caaaagtcaa gtcgggggct gtaaagctct cgtctacacc catgtctttt 120
gcgtactctt gtttcctcgg tggcgcaagc tgccgattgg acaaaccaaa accttttttg 180
taattgcaat cagcgtctga aaataatcta attatttaca actttcaaca acggatctct 240
tggttctggc atcgatgaag aacgcagcga aatgcgataa gtagtgtgaa ttgcagaatt 300
cagtgaatca tcgaatcttt gaacgcacat tgcgcccctt ggtattccat ggggcatgcc 360
tgttcgagcg tcatttgtac cctcaagctt tgcttggtgt tgggcgtctt gtcgtattac 420
gactcgcctt aaatttattg gcagccggca ctttggccta ggagcgcagc acattttgcg 480
atcgtagccc gttgtactgg cgtccatcaa gaacatttac cacgtttgac ctcggatcag 540
gtagggatac ccgctgaact taagcatatc aatagccgga ggaaa 585

<210> SEQ ID NO 440
<211> LENGTH: 545
<212> TYPE: DNA
<213> ORGANISM: Fusarium nygamai

<400> SEQUENCE: 440
tttgtgacca gcggagggat cattaccgag tttacaactc ccaaacccct gtgaacatac 60
caattgttgc ctcggcggat cagcccgctc ccggtaaaac ggaacggccc gccagaggac 120
ccctaaactc tgtttctata tgtaacttct gagtaaaacc ataaataaat caaaactttc 180
aacaacggat ctcttggttc tggcatcgat gaagaacgca gcaaaatgcg ataagtaatg 240
tgaattgcag aattcagtga atcatcgaat ctttgaacgc acattgcgcc cgccagtatt 300
ctggcgggca tgcctgttcg agcgtcattt caaccctcaa gccccgggt ttggtgttgg 360 ggatcggcga gcctcacggc aagccggccc cgaaatacag tggcggtctc cctgcagctt 420
ccattgcgta ataataaaac cctcgcaact ggtacgcggc gcggccaaac cgttaaaccc 480
ccaacttctg aatgttgacc tcggatcagg taggaatacc ccgtgaactt aaacatatca 540
ataag 545

<210> SEQ ID NO 441
<211> LENGTH: 568
<212> TYPE: DNA
<213> ORGANISM: Fusarium nygamai

<400> SEQUENCE: 441
gcgttcggat ctcgttgtga ccagcggagg gatcattacc gagtttacaa ctcccaaacc 60
cctgtgaaca taccaattgt tgcctcggcg gatcagcccg ctcccggtaa aacggaacgg 120
cccgccagag gacccctaaa ctctgtttct atatgtaact tctgagtaaa accataaata 180
aatcaaaact ttcaacaacg gatctcttgg ttctggcatc gatgaagaac gcagcaaaat 240
gcgataagta atgtgaattg cagaattcag tgaatcatcg aatctttgaa cgcacattgc 300
gcccgccagt attctggcgg gcatgcctgt tcgagcgtca tttcaaccct caagcccccg 360
ggtttggtgt tggggatcgg cgagcctcac ggcaagccgg ccccgaaata cagtggcggt 420
ctcgctgcag cttccattgc gtagtagtaa aaccctcgca actggtacgc ggcgcggcca 480
agccgttaaa cccccaactt ctgaatgttg acctcggatc aggtaggaat acccgctgaa 540
cttaagcata tcaataaggc ggagaaaa 568

<210> SEQ ID NO 442
<211> LENGTH: 552
<212> TYPE: DNA
<213> ORGANISM: Fusarium nygamai

<400> SEQUENCE: 442
tctcgttggt gaccagcgga gggatcatta ccgagtttac aactcccaaa cccctgtgaa 60
cataccaatt gttgcctcgg cggatcagcc cgctcccggt aaaacggaac ggcccgccag 120
aggaccccta aactctgttt ctatatgtaa cttctgagta aaaccataaa taaatcaaaa 180
ctttcaacaa cggatctctt ggttctggca tcgatgaaga acgcagcaaa atgcgataag 240
taatgtgaat tgcagaattc agtgaatcat cgaatctttg aacgcacatt gcgcccgcca 300
gtattctggc gggcatgcct gttcgagcgt catttcaacc ctcaagcccc cgggtttggt 360
gttggggatc ggcgagcctc acggcaagcc ggccccgaaa tacagtggcg gtctcgctgc 420
agcttccatt gcgtagtagt aaaaccctcg caactggtac gcggcgcggc caagccgtta 480
aacccccaac ttctgaatgt tgacctcgga tcaggtagga atacccgctg aacttaagca 540
tatcaataag cg 552

<210> SEQ ID NO 443
<211> LENGTH: 578
<212> TYPE: DNA

<213> ORGANISM: Magnaporthe rhizophila

<400> SEQUENCE: 443
tggtctaacg gttctcgttg gtgaccagcg gaggatcatt aaagagttgc aaaactccaa 60
cccctgtgaa ctttacctgt acgttgcttc ggcggccgac gccgcgccca gccgggcctg 120
ggggacgccg ccggaggttt taaaccctga attctagtgt atctctgagg acgaaaataa 180
ccaattaaaa ctttcaacaa cggatctctt ggctctggca tcgatgaaga acgcagcgaa 240
atgcgataag taatgtgaat tgcagaattc agtgaatcat cgaatctttg aacgcacatt 300
gcgcccgccg gtattccggc gggcatgcct gtccgagcgt catttcacca ctcaagccca 360
gcttggtgtt ggggcacccg gccgcctggc ggtcggggcc cccaagtaca tcggcggtcc 420
tgctggggct ccgagcgcag taactcgcgg taaaacgcgc cctcgctcgg cgggcctcct 480
cgggcttcca gccgctaaac ccccagtgac gtttttcgag ttgacctcgg atcaggtagg 540
aatacccgct gaacttaagc atatcagtaa gcggagga 578

<210> SEQ ID NO 444
<211> LENGTH: 611
<212> TYPE: DNA
<213> ORGANISM: Alternaria alternata

<400> SEQUENCE: 444
ttcctccgct tattgatatg cttacttctc agcgggtatc cctacctgat ccgaggtcaa 60
aagttgaaaa aaaggcttaa tggatgctag acctttgctg atagagagtg cgacttgtgc 120
tgcgctccga aaccagtagg ccggctgcca attactttaa ggcgagtctc cagcaaagct 180
agagacaaga cgcccaacac caagcaaagc ttgagggtac aaatgacgct cgaacaggca 240
tgccctttgg aataccaaag ggcgcaatgt gcgttcaaag attcgatgat tcactgaatt 300
ctgcaattca cactacttat cgcatttcgc tgcgttcttc atcgatgcca gaaccaagag 360
atccgttgtt gaaagttgta attattaatt tgttactgac gctgattgca attacaaaag 420
gtttatgttt gtcctagtgg tgggcgaacc caccaaggaa acaagaagta cgcaaaagac 480
aagggtgaat aattcagcaa ggctgtaacc ccgagaggtt ccagcccgcc ttcatatttg 540
tgtaatgatc cctccgcagg ttcacctacg gagaccttgt tacgactttt acttcctcta 600
attgaccaag a 611

<210> SEQ ID NO 445
<211> LENGTH: 598
<212> TYPE: DNA
<213> ORGANISM: Sordariomycete sp.

<400> SEQUENCE: 445
tcttggtcat ttagaggaag taaaagtcgt aacaaggtct ccgttggtga accagcggag 60
ggatcattac cgagtttaca actcccaaac ccctgtgaac ataccaattg ttgcctcggc 120
ggatcagccc gctcccggta aaacggaacg gcccgccaga ggacccctaa actctgtttc 180
tatatgtaac ttctgagtaa aaccataaat aaatcaaaac tttcaacaac ggatctcttg 240
gttctggcat cgatgaagaa cgcagcaaaa tgcgataagt aatgtgaatt gcagaattca 300
gtgaatcatc gaatctttga acgcacattg cgcccgccag tattctggcg ggcatgcctg 360
ttcgagcgtc atttcaaccc tcaagccccc gggtttggtg ttggggatcg gcgagcctca 420
cggcaagccg gccccgaaat acagtggcgg tctcgctgca gcttccattg cgtagtagta 480
aaaccctcgc aactggtacg cggcgcggcc aagccgttaa acccccaact tctgaatgtt 540

-continued gacctcggat caggtaggaa tacccgctga acttaagcat atcaataggc ggagagaa 598

<210> SEQ ID NO 446
<211> LENGTH: 598
<212> TYPE: DNA
<213> ORGANISM: Sordariomycete sp.

<400> SEQUENCE: 446
tcttggtcat ttagtggaag taaaagtcgt aacaaggtct ccgttggtga accagcggag 60
ggatcattac cgagtttaca actcccaaac ccctgtgaac ataccaattg ttgcctcggc 120
ggatcagccc gctcccggta aaacggaacg gcccgccaga ggacccctaa actctgtttc 180
tatatgtaac ttctgagtaa aaccataaat aaatcaaaac tttcaacaac ggatctcttg 240
gttctggcat cgatgaagaa cgcagcaaaa tgcgataagt aatgtgaatt gcagaattca 300
gtgaatcatc gaatctttga acgcacattg cgcccgccag tattctggcg ggcatgcctg 360
ttcgagcgtc atttcaaccc tcaagccccc gggtttggtg ttggggatcg gcgagcctca 420
cggcaagccg gccccgaaat acagtggcgg tctcgctgca gcttccattg cgtagtagta 480
aaaccctcgc aactggtacg cggcgcggcc aagccgttaa acccccaact tctgaatgtt 540
gacctcggat caggtaggaa tacccgctga acttaagcat atcaataggc ggagagaa 598

<210> SEQ ID NO 447
<211> LENGTH: 605
<212> TYPE: DNA
<213> ORGANISM: Gaeumannomyces incrustans

<400> SEQUENCE: 447
tcttggtcat ttagaggaag taaaagtcgt aacaaggtct ccgttggtga accagcggag 60
ggatcattaa agagttgcaa aactccaacc cctgtgaact ttacctgtac gttgcttcgg 120
cggccgacgc cgcgcccagc cgggcctggg ggacgccgcc ggaggtttta aaccctgaat 180
tctagtgtat ctctgaggac gaaaaaaacc aattaaaact ttcaacaacg gatctcttgg 240
ctctggcatc gatgaagaac gcagcgaaat gcgataagta atgtgaattg cagaattcag 300
tgaatcatcg aatttttgaa cgcacattgc gcccgccggt attccggcgg gcatgcctgt 360
ccgagcgtca tttcaccact caagcccagc ttggtgttgg ggcacccggc cgcccggcgg 420
tcggggcccc caagtacatc ggcggtcctg ctggggctcc gagcgcagta acacgcggta 480
aaacgcgccc tcgctcggcg gcctcctcgg gcttccagcc gctaaacccc cagtgacgtt 540
tttcgagttg acctcggatc aggtaggaat acccgctgaa cttaagcata tcaatagccg 600
gagga 605

<210> SEQ ID NO 448
<211> LENGTH: 609
<212> TYPE: DNA
<213> ORGANISM: Gaeumannomyces incrustans

<400> SEQUENCE: 448
tcttggtcaa tttagaggaa gtaaaagtcg taacaaggtc tccgttggtg aaccagcgga 60
gggatcatta aagagttgca aaactccaac ccctgtgaac tttacctgta cgttgcttcg 120
gcggccgacg ccgcgcccag ccgggcctgg gggacgccgc cggaggtttt aaaccctgaa 180
ttctagtgta tctctgagga cgaaaaaaac caattaaaac tttcaacaac ggatctcttg 240
gctctggcat cgatgaagaa cgcagcgaaa tgcgataagt aatgtgaatt gcagaattca 300

```
gtgaatcatc gaatttttga acgcacattg cgcccgccgg tattccggcg ggcatgcctg    360

tccgagcgtc atttcaccac tcaagcccag cttggtgttg gggcacccgg ccgcccggcg    420

gtcggggccc ccaagtacat cggcggtcct gctggggctc cgagcgcagt aacacgcggt    480

aaaacgcgcc ctcgctcggc ggcctcctcg ggcttccagc cgctaaaccc ccagtgacgt    540

ttttcgagtt gacctcggat caggtaggaa tacccgctga acttaagcat atcaataggc    600

cggaggaaa                                                            609
```

<210> SEQ ID NO 449
<211> LENGTH: 606
<212> TYPE: DNA
<213> ORGANISM: Gaeumannomyces incrustans

<400> SEQUENCE: 449

```
tcttggtcat ttagaggaag taaaagtcgt aacaaggtct ccgttggtga accagcggag     60

ggatcattaa agagttgcaa aactccaacc cctgtgaact ttacctgtac gttgcttcgg    120

cggccgacgc cgcgcccagc cgggcctggg ggacgccgcc ggaggtttta aaccctgaat    180

tctagtgtat ctctgaggac gaaaaaaacc aattaaaact ttcaacaacg gatctcttgg    240

ctctggcatc gatgaagaac gcagcgaaat gcgataagta atgtgaattg cagaattcag    300

tgaatcatcg aatttttgaa cgcacattgc gcccgccggt attccggcgg gcatgcctgt    360

ccgagcgtca tttcaccact caagcccagc ttggtgttgg ggcacccggc cgcccggcgg    420

tcggggcccc caagtacatc ggcggtcctg ctggggctcc gagcgcagta acacgcggta    480

aaacgcgccc tcgctcggcg gcctcctcgg gcttccagcc gctaaacccc cagtgacgtt    540

tttcgagttg acctcggatc aggtaggaat acccgctgaa cttaagcata tcaatagccg    600

gaggaa                                                               606
```

<210> SEQ ID NO 450
<211> LENGTH: 701
<212> TYPE: DNA
<213> ORGANISM: Marasmius nigrobrunneus

<400> SEQUENCE: 450

```
tcttggtcat ttagaggaag taaaagtcgt aacaaggttt ccgtaggtga acctgcggaa     60

ggatcattat tgaaacattg taaaggaagg ttgagctggc tcttcacggg catgtgctcg    120

cctttctttc aatcttcatc cacctgtgca ctttttgtag ggagctttga gaatggacct    180

ctcggggtct tagtattagg ctctctatgt cttcacacac tcttgaatgt atgtcgttga    240

atgtctttta cagggactta attgaccctt taaaaactat acaactttca gcaacggatc    300

tcttggctct cgcatcgatg aagaacgcag cgaaatgcga taagtaatgt gaattgcaga    360

attcagtgaa tcatcgaatc tttgaacgca ccttgcgcct tttggtattc cgagaggcat    420

gcctgtttga gtgtcattaa attctcaact tcaaaagctt ttgtttttga agcttggatg    480

tggaggcttt gctggccctt ctagagtcgg ctcctctgaa atgcattagt ggaaactgtt    540

tgcaatccgc attggtgtga taattatcta cgcttgtgtg tggttgcagc tctttacgag    600

tttagtatct gcttcaaacc gtcctaagtc actggacaac tttgaacctt ttgacctcaa    660

atcaggtagg actaccagct gaacttaagc atatcaataa g                        701
```

<210> SEQ ID NO 451
<211> LENGTH: 646
<212> TYPE: DNA
<213> ORGANISM: Hypocrea lixii

<400> SEQUENCE: 451
tcctccggct tattgatatg cttaagttca gcgggtattc ctacctgatc cgaggtcaac 60
atttcagaag ttgggtgttt aacggctgtg gacgcgccgc gctcccgatg cgagtgtgca 120
aactactgcg caggagaggc tgcggcgaga ccgccactgt atttcggaga cggccaccgc 180
caaggcaggg ccgatcccca acgccgaccc cccggagggg ttcgagggtt gaaatgacgc 240
tcggacaggc atgcccgcca gaatactggc gggcgcaatg tgcgttcaaa gattcgatga 300
ttcactgaat tctgcaattc acattactta tcgcatttcg ctgcgttctt catcgatgcc 360
agaaccaaga gatccgttgt tgaaagtttt gattcatttt cgaaacgcct acgagaggcg 420
ccgagaaggc tcagattata aaaaaaaccc gcgagggggt atacaataag agttttggtt 480
ggtcctccgg cgggcgcctt ggtccggggc tgcgacgcac ccggggcaga gatcccgccg 540
aggcaacagt ttggtaacgt tcacattggg tttgggagtt gtaaactcgg taatgatccc 600
tccgctggtt caccaacggg agaccttgtt acgactttta cttcct 646

<210> SEQ ID NO 452
<211> LENGTH: 594
<212> TYPE: DNA
<213> ORGANISM: Codinaeopsis sp.

<400> SEQUENCE: 452
tattgatatg cttaagttca gcgggtattc ctacctgatc cgaggtcaac cacttagaaa 60
gttgggggtt ttacggccgg agcgcgcgcc ggaccagaac gagaaagcat tactgcgctc 120
ggttccgggg cgcgcccgcc gctgtctttg ggagcctgcg ctgcgcaggg ctccaacgcc 180
aggcggggcc tgagggttga aatgacgctc ggacaggcat gcccgccaga gtgctggcgg 240
gcgcaatgtg cgttcaaaga ttcgatgatt cactgaattc tgcaattcac attacttatc 300
gcatttcgct gcgttcttca tcgatgccag aaccaagaga tccgttgttg aaagttttga 360
ctcgtttata gtctgctcgg agatgccaac gttacagaga cagagtttag gggccgccgg 420
cgggctggag cgccccggag cgcccgaaga cgcgcccggt gcacccgccg aggcaacggg 480
ttgtaggtaa gttcacagtg gtttacggga gtcttgcgag tcctgtaatg atccctccgc 540
tggttcacca acggagacct tgttacgact tttacttcct ctaaatgacc aaga 594

<210> SEQ ID NO 453
<211> LENGTH: 550
<212> TYPE: DNA
<213> ORGANISM: Fusarium nygamai

<400> SEQUENCE: 453
ggtgaccagc ggagggatca ttaccgagtt tacaactccc aaacccctgt gaacatacca 60
attgttgcct cggcggatca gcccgctccc ggtaaaacgg aacggcccgc cagaggaccc 120
ctaaactctg tttctatatg taacttctga gtaaaaccat aaataaatca aaactttcaa 180
caacggatct cttggttctg gcatcgatga agaacgcagc aaaatgcgat aagtaatgtg 240
aattgcagaa ttcagtgaat catcgaatct ttgaacgcac attgcgcccg ccagtattct 300
ggcgggcatg cctgttcgag cgtcatttca accctcaagc ccccgggttt ggtgttgggg 360
atcggcgagc ctcacggcaa gccggccccg aaatacagtg gcggtctcgc tgcagcttcc 420
attgcgtagt agtaaaaccc tcgcaactgg tacgcggcgc ggccaagccg ttaaaccccc 480
aacttctgaa tgttgacctc ggatcaggta ggaatacccg ctgaacttaa gcatatcaat 540
aagcggagga 550

<210> SEQ ID NO 454
<211> LENGTH: 567
<212> TYPE: DNA
<213> ORGANISM: Fusarium nygamai

<400> SEQUENCE: 454
aggtaaaggt ctcgttggtg accagcggag ggatcattac cgagtttaca actcccaaac 60
ccctgtgaac ataccaattg ttgcctcggc ggatcagccc gctcccggta aaacggaacg 120
gcccgccaga ggacccctaa actctgtttc tatatgtaac ttctgagtaa aaccataaat 180
aaatcaaaac tttcaacaac ggatctcttg gttctggcat cgatgaagaa cgcagcaaaa 240
tgcgataagt aatgtgaatt gcagaattca gtgaatcatc gaatctttga acgcacattg 300
cgcccgccag tattctggcg ggcatgcctg ttcgagcgtc atttcaaccc tcaagccccc 360
gggtttggtg ttggggatcg gcgagcctca cggcaagccg gccccgaaat acagtggcgg 420
tctcgctgca gcttccattg cgtagtagta aaaccctcgc aactggtacg cggcgcggcc 480
aagccgttaa acccccaact tctgaatgtt gacctcggat caggtaggaa tacccgctga 540
acttaagcat atcaataagc ggaggaa 567

<210> SEQ ID NO 455
<211> LENGTH: 567
<212> TYPE: DNA
<213> ORGANISM: Gaeumannomyces incrustans

<400> SEQUENCE: 455
tcttggtcaa ttagaggaag taaaagtcgt aacaaggtct ccgttggtga accagcggag 60
ggatcattaa agagttgcaa aactccaacc cctgtgaatt ttacctgtac gttgcttcgg 120
cggccgacgc cgcgcccagc cgggcctggg ggacgccgcc ggaggtctta aaccctgaat 180
tctagtgtat ctctgaggac gaaaaaaacc aattaaaact ttcaacaacg gatctcttgg 240
ctctggcatc gatgaagaac gcagcgaaat gcgataagta atgtgaattg cagaattcag 300
tgaatcatcg aatctttgaa cgcacattgc gcccgccggt attccggcgg gcatgcctgt 360
ccgagcgtca tttcaccact caagcccagc ttggtgttgg ggcacccggc cgcccggcgg 420
tcggggcccc caagtacatc ggcggtcccg ctggggctcc gagcgcagta actcgcggta 480
aaacgcgccc tcgctcggcg gcctcctcgg gcttccagcc gctaaacccc cagtgacgtt 540
tttcgagttg acctcggatc agtagat 567

<210> SEQ ID NO 456
<211> LENGTH: 606
<212> TYPE: DNA
<213> ORGANISM: Gaeumannomyces incrustans

<400> SEQUENCE: 456
tcttggtcat ttagaggaag taaaagtcgt aacaaggtct ccgttggtga accagcggag 60
ggatcattaa agagttgcaa aaactccaac ccctgtgaac tttacctgta cgttgcttcg 120
gcggccgacg ccgcgcccag acgggcctgg gggacgccgc cggaggtctt aaaccctgaa 180
ttctagtgta tctatgagga cgaaaaaaac caattaaaac tttcaacaac ggatctcttg 240
gctctggcat cgatgaagaa cgcagcgaaa tgcgataagt aatgtgaatt gcagaattca 300
gtgaatcatc gaatctttga acgcacattg cgcccgccgg tattccggcg ggcatgcctg 360
tccgagcgtc atttcaccac tcaagcccag cttggtgttg gggcacccgg ccgcccggcg 420

```
gtcggggccc ccaagtacat cggcggtccc gctggggctc cgagcgcagt aactcgcggt    480

aaaacgcgcc cccgctcggc ggcctcctcg ggcttccagc cgttaaaccc ccagtgacgt    540

ttttcgagtt gacctcggat caggtaggaa tacccgctga acttaagcat atcaataggc    600

ggagga                                                               606


<210> SEQ ID NO 457
<211> LENGTH: 598
<212> TYPE: DNA
<213> ORGANISM: Sordariomycete sp.

<400> SEQUENCE: 457

tcttggtcat ttagaggaag taaaagtcgt aacaaggtct ccgttggtga accagcggag     60

ggatcattac cgagtttaca actcccaaac ccctgtgaac ataccaattg ttgcctcggc    120

ggatcagccc gctcccggta aaacggaacg gcccgccaga ggacccctaa actctgtttc    180

tatatgtaac ttctgagtaa aaccataaat aaatcaaaac tttcaacaac ggatctcttg    240

gttctggcat cgatgaagaa cgcagcaaaa tgcgataagt aatgtgaatt gcagaattca    300

gtgaatcatc gaatctttga acgcacattg cgcccgccag tattctggcg ggcatgcctg    360

ttcgagcgtc atttcaaccc tcaagccccc gggtttggtg ttggggatcg gcgagcctca    420

cggcaagccg gccccgaaat acagtggcgg tctcgctgca gcttccattg cgtagtagta    480

aaaccctcgc aactggtacg cggcgcggcc aagccgttaa acccccaact tctgaatgtt    540

gacctcggat caggtaggaa tacccgctga acttaagcat atcaataagc ggaggaag      598


<210> SEQ ID NO 458
<211> LENGTH: 543
<212> TYPE: DNA
<213> ORGANISM: Uncultured root-associated fungus

<400> SEQUENCE: 458

cattaaagag ttgcaaaact ccaacccctg tgaattttac ctgtacgttg cttcggcggc     60

cgacgccgcg cccagccggg cctgggggac gccgccggag gtcttaaacc ctgaattcta    120

gtgtatctct gaggacgaaa aaaaccaatt aaaactttca acaacggatc tcttggctct    180

ggcatcgatg aagaacgcag cgaaatgcga taagtaatgt gaattgcaga attcagtgaa    240

tcatcgaatc tttgaacgca cattgcgccc gccggtattc cggcgggcat gcctgtccga    300

gcgtcatttc accactcaag cccagcttgg tgttggggca cccggccgcc cggcggtcgg    360

ggcccccaag tacatcggcg gtcccgctgg ggctccgagc gcagtaactc gcggtaaaac    420

gcgccctcgc tcggcggcct cctcgggctt ccagccgcta aacccccagt gacgtttttc    480

gagttgacct cggatcaggt aggaataccc gctgaactta agcatatcaa taagacggag    540

gaa                                                                  543


<210> SEQ ID NO 459
<211> LENGTH: 608
<212> TYPE: DNA
<213> ORGANISM: Gaeumannomyces incrustans

<400> SEQUENCE: 459

tcttggtctt tttagaggaa gtaaaagtcg taacaaggtc tccgttggtg aaccagcgga     60

gggatcatta aagagttgca aaactccaac ccctgtgaac tttacctgta cgttgcttcg    120

gcggccgacg ccgcgcccag ccgggcctgg gggacgccgc cggaggtctt aaaccctgaa    180
```

```
ttctagtgta tctctgagga cgaaataaaa ccaattaaaa ctttcaacaa cggatctctt    240

ggctctggca tcgatgaaga acgcagcgaa atgcgataag taatgtgaat tgcagaattc    300

agtgaatcat cgaatctttg aacgcacatt gcgcccgccg gtattccggc gggcatgcct    360

gtccgagcgt catttcacca ctcaagccca gcttggtgtt ggggcacccg gccgcccggc    420

ggtcggggcc cccaagtaca tcggcggtcc cgctggggct ccgagcgcag taactcgcgg    480

taaaacgcgc cctcgctcgg cggcctcctc gggcttccag ccgctaaacc cccagtgacg    540

tttttcgagt tgacctcgga tcaggtagga atacccgctg aacttaagca tatcaatagg    600

cggaggaa                                                             608
```

```
<210> SEQ ID NO 460
<211> LENGTH: 549
<212> TYPE: DNA
<213> ORGANISM: Gaeumannomyces incrustans

<400> SEQUENCE: 460

tcttggtcat ttagaggaag taaaagtcgt aacaaggtct ccgttggtga accagcggag     60

ggatcattaa agagttgcaa aactccaacc cctgtgaact ttacctgtac gttgcttcgg    120

cggccgacgc cgcgcccagc cgggcctggg ggacgccgcc ggaggtttta aaccctgaat    180

tctagtgtat ctctgaggac gaaaaaaacc aattaaaact ttcaacaacg gatctcttgg    240

ctctggcatc gatgaagaac gcagcgaaat gcgataagta atgtgaattg cagaattcag    300

tgaatcatcg aatctttgaa cgcacattgc gcccgccggt attccggcgg gcatgcctgt    360

ccgagcgtca tttcaccact caagcccagc ttggtgttgg ggcacccggc cgcccggcgg    420

tcggggcccc caagtacatc ggcggtcctg ctggggctcc gagcgcagta acacgcggta    480

aaacgcgccc tcgctcggcg gcctcctcgg gcttccagcc gctaaacccc cagtgacgtt    540

tttcgagtg                                                            549
```

```
<210> SEQ ID NO 461
<211> LENGTH: 544
<212> TYPE: DNA
<213> ORGANISM: Gaeumannomyces incrustans

<400> SEQUENCE: 461

tcttggtcat ttagaggaag taaaagtcgt aacaaggtct ccgttggtga accagcggag     60

ggatcattaa agagttgcaa aactccaacc cctgtgaact ttacctgtac gttgcttcgg    120

cggccgacgc cgcgcccagc cgggcctggg ggacgccgcc ggaggtctta aaccctgaat    180

tctagtgtat ctctgaggac gaaataaaac caattaaaac tttcaacaac ggatctcttg    240

gctctggcat cgatgaagaa cgcagcgaaa tgcgataagt aatgtgaatt gcagaattca    300

gtgaatcatc gaatctttga acgcacattg cgcccgccgg tattccggcg ggcatgcctg    360

tccgagcgtc atttcaccac tcaagcccag cttggtgttg gggcacccgg ccgcccggcg    420

gtcggggccc ccaagtacat cggcggtccc gctggggctc cgagcgcagt aactcgcggt    480

aaaacgcgcc ctcgctcggc ggcctcctcg ggcttccagc cgctaaaccc ccagtgacgt    540

tttt                                                                 544
```

```
<210> SEQ ID NO 462
<211> LENGTH: 725
<212> TYPE: DNA
<213> ORGANISM: Waitea circinata var. zeae

<400> SEQUENCE: 462
```

```
ttcctcccgc ctattgatat gcttaagttc agcgggtagt cctacctgat ttgagatcag     60
atcagaaatt taatttgtcc aagctaatgg actattagaa gcggctcatc ctagagcctg    120
gccacctttt ttacgggtgt cctcagcgag tgataactta tcacgccgag tggaaccaag    180
ttcatggaga tccagctaat gcatttaaga ggagcagagt tttaaaatct gcagacctcc    240
aagtccaaag caaaaagccg attgaattaa caaaagactt gctttgagaa tttcatgata    300
ctcaaacagg catgctccga ggaataccaa ggagcgcaag gtgcgttcaa agattcgatg    360
attcactgaa ttctgcaatt cacattactt atcgcatttc gctgcgttct tcatcgatgc    420
gagagccaag agatccgttg ttgaaacttt gtattagatg cgttacatca aattacattc    480
agatttaatt aaattagatt ttatgtgttg atagacggag ctacaaagtc tcctaatgaa    540
aggaaactga gcttctccgt ctcacaagtg cacagggggt gtgtggatga aagagaaggg    600
gcgtgcacat acctctgggg aggtcagcta caacccgaac tctatattca ttcattaatg    660
atccttccgc aggttcacct acggaaacct tgttacgact tttacttcct ctaaattgac    720
caaga                                                                725
```

<210> SEQ ID NO 463
<211> LENGTH: 598
<212> TYPE: DNA
<213> ORGANISM: Gaeumannomyces incrustans

<400> SEQUENCE: 463

```
tcttggtcat ttagaggaag taaaagtcgt aacaaggtct ccgttggtga accagcggag     60
ggatcattaa agagttgcaa aactccaacc cctgtgaacg ttacctgtac gttgcttcgg    120
cggccgacgc cgcgcccagc cgggcctggg ggacgccgcc ggaggtctta aaccctgaat    180
tctagtgtat ctctgaggac gaaaagaacc aattaaaact ttcaacaacg gatctcttgg    240
ctctggcatc gatgaagaac gcagcgaaat gcgataagta atgtgaattg cagaattcag    300
tgaatcatcg aatctttgaa cgcacattgc gcccgccggt attccggcgg gcatgcctgt    360
ccgagcgtca tttcaccact caagcccagc ctggtgttgg ggcacccggc cgcccggcgg    420
tcggggcccc caagtacatc ggcggtcctg ctggggctcc gagcgcagta acacgcggta    480
aaacgcgccc tcgctcggcg gcctcctcgg gcttccagcc gctaaacccc cccaatgacg    540
tttttcgagt tgacctcgga tcaggtagga atatccgctg aacttaagca tatcaata      598
```

<210> SEQ ID NO 464
<211> LENGTH: 606
<212> TYPE: DNA
<213> ORGANISM: Gaeumannomyces incrustans

<400> SEQUENCE: 464

```
tcttggtcat ttagaggaag taaaagtcgt aacaaggtct ccgttggtga accagcggag     60
ggatcattaa agagttgcaa aactccaacc cctgtgaact ttacctgtac gttgcttcgg    120
cggccgacgc cgcgcccagc cgggcccggg ggacgccgcc ggaggtcata aaccctgaat    180
tctagtgtat ctctgaggac gaaaataacc aattaaaact ttcaacaacg gatctcttgg    240
ctctggcatc gatgaagaac gcagcgaaat gcgataagta atgtgaattg cagaattcag    300
tgaatcatcg aatctttgaa cgcacattgc gcccgccggt attccggcgg gcatgcctgt    360
ccgagcgtca tttcaccact caagcccagc ttggtgttgg ggcacccggc cgcccggcgg    420
tcggggcccc caagtacatc ggcggtcccg ctggggctcc gagcgcagta actcgcggta    480
```

aaacgcgccc tcgctcggcg gcctcctcgg gcttccagcc gctaaacccc cagtgacgtt 540
tttcgagttg acctcggatc aggtaggaat acccgctgaa cttaagcata tcaataagcg 600
gaggaa 606

<210> SEQ ID NO 465
<211> LENGTH: 556
<212> TYPE: DNA
<213> ORGANISM: Magnaporthe rhizophila

<400> SEQUENCE: 465
ttgtgaccag cggagggatc attaaagagt tgcaaaactc caacccctgt gaactttacc 60
tgtacgttgc ttcggcggcc gacgccgcgc ccagccgggc ccgggggacg ccgccggagg 120
tcataaaccc tgaattctag tgtatctctg aggacgaaaa taaccaatta aaactttcaa 180
caacggatct cttggctctg gcatcgatga agaacgcagc gaaatgcgat aagtaatgtg 240
aattgcagaa ttcagtgaat catcgaatct ttgaacgcac attgcgcccg ccggtattcc 300
ggcgggcatg cctgtccgag cgtcatttca ccactcaagc ccagcttggt gttggggcac 360
ccggccgccc ggcggtcggg gcccccaagt acatcggcgg tcccgctggg gctccgagcg 420
cagtaactcg cggtaaaacg cgccctcgct cggcggcctc ctcgggcttc cagccgctaa 480
acccccagtg acgtttttcg agttgacctc ggatcaggta ggaatacccg ctgaacttaa 540
gcatatcaat agggaa 556

<210> SEQ ID NO 466
<211> LENGTH: 606
<212> TYPE: DNA
<213> ORGANISM: Gaeumannomyces incrustans

<400> SEQUENCE: 466
tcttggtcat ttagaggaag taaaagtcgt aacaaggtct ccgttggtga accagcggag 60
ggatcattaa agagttgcaa aactccaacc cctgtgaact ttacctgtac gttgcttcgg 120
cggccgacgc cgcgcccagc cgggcctggg ggacgccgcc ggaggtttta aaccctgaat 180
tctagtgtat ctctgaggac gaaaaaaacc aattaaaact ttcaacaacg gatctcttgg 240
ctctggcatc gatgaagaac gcagcgaaat gcgataagta atgtgaattg cagaattcag 300
tgaatcatcg aatctttgaa cgcacattgc gcccgccggt attccggcgg gcatgcctgt 360
ccgagcgtca tttcaccact caagcccagc ttggtgttgg ggcacccggc cgcctggcgg 420
tcggggcccc caagtacatc ggcggtcccg ctggggctcc gagcgtagta actcgcggta 480
aaacgcgccc tcgctcggcg gcctcctcgg gcttccagcc gctaaacccc cagtgacgtt 540
tttcgagttg acctcggatc aggtaggaat acccgctgaa cttaagcata tcaataaggc 600
ggagga 606

<210> SEQ ID NO 467
<211> LENGTH: 506
<212> TYPE: DNA
<213> ORGANISM: Penicillium sp.

<400> SEQUENCE: 467
tgacctgcgg aggatcatta ccgagtgcag ggccctcggg gcccaacctc ccacccttgt 60
ctctttacac ctgtggcttt ggggggccca ccgtaactgg ctggtcgccg gggacgcac 120 cgccccgggc ccgcgcccgc cgacccgctc tgtgaaccct gatgaagatg ggctgtctga 180
atactatgtt aattgtcaaa actttcaaca atgcatctct tggctccggc atcgatgaac 240
aacgcagcga aatgcaataa gtaatgtgaa ttgctgaatt ccgtgaatca tcgaatcttt 300
gaacgtacat tgcgcccct ggcattccgg ggggcatgcc tgtccgagcg tcatttctgc 360
cctcaagcac ggcttgtgtg ttgggtgtgg tccccccggg gacctgcccg aaaggcagcg 420
gcgacgtccg tctggtcctc gagcgtatgg ggctctgtca ctcgctcggg agggacctgc 480
gggggttggt caccaccatg tttttt 506

<210> SEQ ID NO 468
<211> LENGTH: 598
<212> TYPE: DNA
<213> ORGANISM: Fusarium nygamai

<400> SEQUENCE: 468
tcttggtcat ttagattttt gtaaaagtcg taacaaggtc tccgttggtg aaccagcgga 60
gggatcatta ccgagtttac aactcccaaa cccctgtgaa catatcaatt gttgcctcgg 120
cggatcagcc cgctcccggt aaaacggaac ggcccgccag aggaccccta aactctgttt 180
ctatatgtaa cttctgagta aaaccataaa taaatcaaaa ctttcaacaa cggatctctt 240
ggttctggca tcgatgaaga acgcagcaaa atgcgataag taatgtgaat tgcagaattc 300
agtgaatcat cgaatctttg aacgcacatt gcgcccgcca gtattctggc gggcatgcct 360
gttcgagcgt catttcaacc ctcaagcccc cgggtttggt gttggggatc ggcgagcctc 420
acggcaagcc ggccccgaaa tacagtggcg gtctcgctgc agcttccatt gcgtagtagt 480
aaaaccctcg caactggtac gcggcgcggc caagccgtta aacccccaac ttctgaatgt 540
tgacctcgga tcaggtagga atacccgctg aacttaagca tatcaataag cggaggaa 598

<210> SEQ ID NO 469
<211> LENGTH: 549
<212> TYPE: DNA
<213> ORGANISM: Magnaporthe rhizophila

<400> SEQUENCE: 469
ttcctccgct tattgatatg cttaagttca gcgggtattc ctacctgatc cgaggtcaac 60
tcgaaaaacg tcactggggg tttagcggct ggaagcccga ggaggccgcc gagcgagggc 120
gcgttttacc gcgagttact gcgctcggag ccccagcggg accgccgatg tacttggggg 180
ccccgaccgc cgggcggccg ggtgccccaa caccaagctg ggcttgagtg gtgaaatgac 240
gctcggacag gcatgcccgc cggaataccg gcgggcgcaa tgtgcgttca aagattcgat 300
gattcactga attctgcaat tcacattact tatcgcattt cgctgcgttc ttcatcgatg 360
ccagagccaa gagatccgtt gttgaaagtt ttaattggtt attttcgtcc tcagagatac 420
actagaattc agggtttatg acctccggcg gcgtccccg ggcccggctg ggcgcggcgt 480
cggccgccga agcaacgtac aggtaaagtt cacaggggtt ggagttttgc aactctttaa 540
tgatcccct 549

<210> SEQ ID NO 470
<211> LENGTH: 557
<212> TYPE: DNA
<213> ORGANISM: Uncultured root-associated fungus

<400> SEQUENCE: 470
gaccagcgga gggatcatta aagagttgca aaactccaac ccctgtgaac tttacctgta 60
cgttgcttcg gcggccgacg ccgcgcccag ccgggcctgg gggacgccgc cggaggtctt 120
aaaccctgaa ttctagtgta tctatgagga cgaaaaaaac caattaaaac tttcaacaac 180
ggatctcttg gctctggcat cgatgaagaa cgcagcgaaa tgcgataagt aatgtgaatt 240
gcagaattca gtgaatcatc gaatctttga acgcacattg cgcccgccgg tattccggcg 300
ggcatgcctg tccgagcgtc atttcaccac tcaagcccag cttggtgttg gggcacccgg 360
ccgcccggcg gtcggggccc ccaagtacat cggcggtccc gctggggctc cgagcgcagt 420
aactcgcggt aaaacgcgcc ctcgctcggc ggcctcctcg ggcttccagc cgctaaaccc 480
ccagtgacgt tttcgagtt gacctcggat caggtaggaa tacccgctga acttaagcat 540
atcaataggc ggaggaa 557

<210> SEQ ID NO 471
<211> LENGTH: 574
<212> TYPE: DNA
<213> ORGANISM: Gaeumannomyces incrustans

<400> SEQUENCE: 471
tcttggtcat ttagaggaag taaaagtcgt aacaaggtct ccgttggtga accagcggag 60
ggatcattaa agagttgcaa aactccaacc cctgtgaact ttacctgtac gttgcttcgg 120
cggccgacgc cgcgcccagc cgggcctggg ggacgccgcc ggaggtttta aaccctgaat 180
tctagtgtat ctctgaggac gaaaaaaacc aattaaaact ttcaacaacg gatctcttgg 240
ctctggcatc gatgaagaac gcagcgaaat gcgataagta atgtgaattg cagaattcag 300
tgaatcatcg aatctttgaa cgcacattgc gcccgccggt attccggcgg gcatgcctgt 360
ccgagcgtca tttcaccact caagcccagc ttggtgttgg ggcacccggc cgcccggcgg 420
tcggggcccc caagtacatc ggcggtcctg ctggggctcc gagcgcagta acacgcggta 480
aaacgcgccc tcgctcggcg gcctcctcgg gcttccagcc gctaaacccc cagtgacgtt 540
tttcgagttg acctcgatca gtagatccca gttt 574

<210> SEQ ID NO 472
<211> LENGTH: 598
<212> TYPE: DNA
<213> ORGANISM: Sordariomycete sp.

<400> SEQUENCE: 472
tcttggtcat ttagaggaag taaaagtcgt aacaaggtct ccgttggtga accagcggag 60
ggatcattac cgagtttaca actcccaaac ccctgtgaac ataccaattg ttgcctcggc 120
ggatcagccc gctcccggta aaacgggacg gcccgccaga ggacccctaa actctgtttc 180
tatatgtaac ttctgagtaa aaccataaat aaatcaaaac tttcaacaac ggatctcttg 240
gttctggcat cgatgaagaa cgcagcaaaa tgcgataagt aatgtgaatt gcagaattca 300
gtgaatcatc gaatctttga acgcacattg cgcccgccag tattctggcg ggcatgcctg 360
ttcgagcgtc atttcaaccc tcaagccccc gggtttggtg ttggggatcg gcgagcctca 420
cggcaagccg gccccgaaat acagtggcgg tctcgctgca gcttccattg cgtagtagta 480
aaaccctcgc aactggtacg cggcgcggcc aagccgttaa acccccaact tctgaatgtt 540
gacctcggat caggtaggaa tacccgctga acttaagcat atcaataagc ggagagaa 598

<210> SEQ ID NO 473
<211> LENGTH: 588
<212> TYPE: DNA
<213> ORGANISM: Sordariomycete sp.

<400> SEQUENCE: 473

```
tcttggtcat ttagaggaag taaaagtcgt aacaaggtct ccgttggtga accagcggag     60

ggatcattac cgagtttaca actcccaaac ccctgtgaac ataccaattg ttgcctcggc    120

ggatcagccc gctcccggta aaacggaacg gcccgccaga ggacccctaa actctgtttc    180

tatatgtaac ttctgagtaa aaccataaat aaatcaaaac tttcaacaac ggatctcttg    240

gttctggcat cgatgaagaa cgcagcaaaa tgcgataagt aatgtgaatt gcagaattca    300

gtgaatcatc gaatctttga acgcacattg cgcccgccag tattctggcg ggcatgcctg    360

ttcgagcgtc atttcaaccc tcaagccccc gggtttggtg ttggggatcg gcgagcctca    420

cggcaagccg gccccgaaat acagtggcgg tctcgctgca gcttccattg cgtagtagta    480

aaaccctcgc aactggtacg cggcgcggcc aagccgttaa acccccaact tctgaatgtt    540

gacctcggat caggtaggaa tacccgctga acttaagcat atcaataa                 588
```

```
<210> SEQ ID NO 474
<211> LENGTH: 556
<212> TYPE: DNA
<213> ORGANISM: Grass root mycorrhizal sp.

<400> SEQUENCE: 474

agcattcggc ttcgtaggtg acctgcggaa ggatcattaa aaaggatacc gggcaaccgg     60

tagaccccac ccgtgtctat ctactcttgt tgctttggca ggccgtggcc tccaccgcgg    120

gctctgcctg cgtgtgcctg ccagaggacc aaactctgaa ctttagtgat gtctgagtac    180

tatataatag ttaaaacttt caacaacgga tctcttggtt ctggcatcga tgaagaacgc    240

agcgaaatgc gataagtaat gtgaattgca gaattcagtg aatcatcgaa tctttgaacg    300

cacattgcgc ccggtggtat tccgccgggc atgcctgttc gagcgtcatt ataaccactc    360

aagcctggct tggtattggg gctcgcggtt ccgcggcccc taaaatcagt ggcggtgccg    420

gtgggctcta agcgtagtaa atctcctcgc tatagggtcc ccccggttgc ccgccagaac    480

cccccatttt ttcaggttga cctcggatca ggtagggata cccgctgaac ttaagcatat    540

caataaggcg gaggaa                                                    556
```

```
<210> SEQ ID NO 475
<211> LENGTH: 585
<212> TYPE: DNA
<213> ORGANISM: Fusarium nygamai

<400> SEQUENCE: 475

aaggaagtaa aagtcgtaac aaggtctccg ttggtgaacc agcggaggga tcattacccg     60

agtttacaac tcccaaaccc ctgtgaacat accaattgtt gcctcggcgg atcagcccgc    120

tcccggtaaa acggaacggc ccgccagagg accccctaaac tctgtttcta tatgtaactt   180

ctgagtaaaa ccataaataa atcaaaactt tcaacaacgg atctcttggt tctggcatcg    240

atgaagaacg cagcaaaatg cgataagtaa tgtgaattgc agaattcagt gaatcatcga    300

atctttgaac gcacattgcg cccgccagta ttctggcggg catgcctgtt cgagcgtcat    360

ttcaaccctc aagcccccgg gtttggtgtt ggggatcggc gagcctcacg gcaagccggc    420

cccgaaatac agtggcggtc tcgctgcagc ttccattgcg tagtagtaaa accctcgcaa    480

ctggtacgcg gcgcggccaa gccgttaaac ccccaacttc tgaatgttga cctcggatca    540

ggtaggaata cccgctgaac ttaagcatat caataagcgg aggaa                    585
```

```
<210> SEQ ID NO 476
```

<211> LENGTH: 536
<212> TYPE: DNA
<213> ORGANISM: Fusarium nygamai

<400> SEQUENCE: 476
atcattaccg agtttacaac tcccaaaccc ctgtgaacat atcaattgtt gcctcggcgg 60
atcagcccgc tcccggtaaa acggaacggc ccgccagagg acccctaaac tctgtttcta 120
tatgtaactt ctgagtaaaa ccataaataa atcaaaactt tcaacaacgg atctcttggt 180
tctggcatcg atgaagaacg cagcaaaatg cgataagtaa tgtgaattgc agaattcagt 240
gaatcatcga atctttgaac gcacattgcg cccgccagta ttctggcggg catgcctgtt 300
cgagcgtcat ttcaaccctc aagcccccgg gtttggtgtt ggggatcggc gagcctcacg 360
gcaagccggc cccgaaatac agtggcggtc tcgctgcagc ttccattgcg tagtagtaaa 420
accctcgcaa ctggtacgcg gcgcggccaa gccgttaaac ccccaacttc tgaatgttga 480
cctcggatca ggtaggaata cccgctgaac ttaagcatat caataaggcg gaggaa 536

<210> SEQ ID NO 477
<211> LENGTH: 607
<212> TYPE: DNA
<213> ORGANISM: Gaeumannomyces incrustans

<400> SEQUENCE: 477
tcttggtcat ttagaggaag taaaagtcgt aacaaggtct ccgttggtga accagcggag 60
ggatcattaa agagttgcaa aactccaacc cctgtgaact ttacctgtac gttgcttcgg 120
cggccgacgc cgcgcccagc cgggcctggg ggacgccgcc ggaggtttta aaccctgaat 180
tctagtgtat ctctgaggac gaaaaaaacc aattaaaact ttcaacaacg gatctcttgg 240
ctctggcatc gatgaagaac gcagcgaaat gcgataagta atgtgaattg cagaattcag 300
tgaatcatcg aatctttgaa cgcacattgc gcccgccggt attccggcgg gcatgcctgt 360
ccgagcgtca tttcaccact caagcccagc ttggtgttgg ggcacccggc cgcccggcgg 420
tcggggcccc caagtacatc ggcggtcctg ctggggctcc gagcgcagta acacgcggta 480
aaacgcgccc tcgctcggcg gcctcctcgg gcttccagcc gctaaacccc cagtgacgtt 540
tttcgagttg acctcggatc aggtaggaat acccgctgaa cttaagcata tcaataaggc 600
ggaggaa 607

<210> SEQ ID NO 478
<211> LENGTH: 605
<212> TYPE: DNA
<213> ORGANISM: Gaeumannomyces incrustans

<400> SEQUENCE: 478
tcttggtcat ttagaggaag taaaagtcgt aacaaggtct ccgttggtga accagcggag 60
ggatcattaa agagttgcaa aactccaacc cctgtgaact ttacctgtac gttgcttcgg 120
cggccgacgc cgcgcccagc cgggcctggg ggacgccgcc ggaggtttta aaccctgaat 180
tctagtgtat ctctgaggac gaaaaaaacc aattaaaact ttcaacaacg gatctcttgg 240
ctctggcatc gatgaagaac gcagcgaaat gcgataagta atgtgaattg cagaattcag 300
tgaatcatcg aatctttgaa cgcacattgc gcccgccggt attccggcgg gcatgcctgt 360
ccgagcgtca tttcaccact caagcccagc ttggtgttgg ggcacccggc cgcccggcgg 420
tcggggcccc caagtacatc ggcggtcctg ctggggctcc gagcgcagta acacgcggta 480
aaacgcgccc tcgctcggcg gcctcctcgg gcttccagcc gctaaacccc cagtgacgtt 540
tttcgagttg acctcggatc aggtaggaat acccgctgaa cttaagcata tcaataagcg 600
gagga 605

<210> SEQ ID NO 479
<211> LENGTH: 603
<212> TYPE: DNA
<213> ORGANISM: Codinaeopsis sp.

<400> SEQUENCE: 479
tcctccgctt attgatatgc ttaagttcag cgggtattcc tacctgatcc gaggtcaacc 60
acttagaaag ttgggggttt tacggccgga gcgcgcgccg gaccagaacg agaaagcatt 120
actgcgctcg gttccggggc gcgcccgccg ctgtctttgg gagcctgcgc tgcgcagggc 180
tccaacgcca ggcggggcct gagggttgaa atgacgctcg gacaggcatg cccgccagag 240
tgctggcggg cgcaatgtgc gttcaaagat tcgatgattc actgaattct gcaattcaca 300
ttacttatcg catttcgctg cgttcttcat cgatgccaga accaagagat ccgttgttga 360
aagttttgac tcgtttatag tctgctcgga gatgccaacg ttacagagac agagtttagg 420
ggccgccggc gggctggagc gccccggagc gcccgaagac gcgcccggag cacccgccga 480
ggcaacgggt tgtaggtaag ttcacagtgg tttacgggag tcttgcgagt cctgtaatga 540
tccctccgct ggttcaccaa cggagacctt gttacgactt ttacttcctc taaatgacca 600
aga 603

<210> SEQ ID NO 480
<211> LENGTH: 606
<212> TYPE: DNA
<213> ORGANISM: Myrothecium melanosporum

<400> SEQUENCE: 480
gcttattgat atgcttaagt tcagcgggta ttcctacctg atccgaggtc aactttcaga 60
agtcgggggt tttccggcgt ggccgccgcc gcgctcccag gctgcgaggt gtgtgctact 120
acgcagagga ggtctacggc ggggccgcca ctgtatttcg gggccggccg gtgaaggccg 180
atccccaacg ccaggcgcgg gagcctgagg gttgaaatga cgctcggaca ggcatgcccg 240
ccagaatgct ggcgggcgca atgtgcgttc aaagattcga tgattcactg aattctgcaa 300
ttcacattac ttatcgcatt tcgctgcgtt cttcatcgat gccagagcca agagatccgt 360
tgttgaaagt tttgatttat ttgtataaaa tccactcaga ggagaattca taataaaaca 420
gaggtttggg tccctgcggc gggcgcctgg ttccggtgcc ggtgagggcg ccggggcggt 480
cccgccgagg caacgtcaag gtatgttcac attgggtttg ggagttgtaa actcggtaat 540
gatccctccg ctggttcacc aacggagacc ttgttacgac ttttacttcc tctaaattga 600
ccaaga 606

<210> SEQ ID NO 481
<211> LENGTH: 558
<212> TYPE: DNA
<213> ORGANISM: Magnaporthe rhizophila

<400> SEQUENCE: 481
ttcctccgct tattgatatg cttaagttca gcgggtatcc ctacctgatc cgaggtcaaa 60
atggagaatg tatcttttgg tcgcagatcc gtagatatca ctcgcaattg tactgcgctt 120
gaagcctaca aaccggccgc caataacttt aaggcgagtc tacatccccg gaaaggggc 180

```
ttagacaaac gcccaacacc aagcagtgct tgagggtgta aatgacgctc gaacaggcat    240

gccctaagga atgccaaagg gcgcaatgtg cgttcaaaga ttcgatgatt cactgaattc    300

tgcaattcac actacttatc gcatttcgct gcgttcttca tcgatgccag aaccaagaga    360

tccgttgttg aaagttttaa tttattgttt tgtttttcag acaggtacta ctagactaca    420

agagtttata gtgtccctaa tggcaggcgg acctgccagg gaaaacgtac ggtgcttgat    480

aaaaggtcaa gggttctatc tcaatggggc cgaagcccca cggtaatgat ccttccgcag    540

ggttcaccta cggaaacc                                                  558


<210> SEQ ID NO 482
<211> LENGTH: 603
<212> TYPE: DNA
<213> ORGANISM: Gaeumannomyces incrustans

<400> SEQUENCE: 482

tggttctttc gaggaagtaa aagtcgtaac aaggtctccg ttggtgaacc agcggaggga     60

tcattaaaga gttgcaaaac tccaacccct gtgaacttta cctgtacgtt gcttcggcgg    120

ccgacgcccg cgcccagccg ggcctggggg acgccgccgg aggttttaaa ccctgaattc    180

tagtgtatct ctgaggacga aaaaaaccaa ttaaaacttt caacaacgga tctcttggct    240

ctggcatcga tgaagaacgc agcgaaatgc gataagtaat gtgaattgca gaattcagtg    300

aatcatcgaa tctttgaacg cacattgcgc ccgccggtat tccggcgggc atgcctgtcc    360

gagcgtcatt tcaccactca agcccagctt ggtgttgggg cacccggccg cccggcggtc    420

ggggccccca agtacatcgg cggtcctgct ggggctccga gcgcagtaac acgcggtaaa    480

acgcgccctc gctcggcggc ctcctcgggc ttccagccgc taaaccccca gtgacgtttt    540

tcgagttgac ctcggatcag gtaggaatac ccgctgaact taagcatatc aatagccgga    600

gga                                                                  603


<210> SEQ ID NO 483
<211> LENGTH: 606
<212> TYPE: DNA
<213> ORGANISM: Gaeumannomyces incrustans

<400> SEQUENCE: 483

cttggtcaat ttagaggaag taaaagtcgt aacaaggtct ccgttggtga accagcggag     60

ggatcattaa agagttgcaa aactccaacc cctgtgaact ttacctgtac gttgcttcgg    120

cggccgacgc cgcgcccagc cgggcctggg ggacgccgcc ggaggtttta aaccctgaat    180

tctagtgtat ctctgaggac gaaaaaaacc aattaaaact ttcaacaacg gatctcttgg    240

ctctggcatc gatgaagaac gcagcgaaat gcgataagta atgtgaattg cagaattcag    300

tgaatcatcg aatctttgaa cgcacattgc gcccgccggt attccggcgg gcatgcctgt    360

ccgagcgtca tttcaccact caagcccagc ttggtgttgg ggcacccggc cgcccggcgg    420

tcggggcccc caagtacatc ggcggtcctg ctggggctcc gagcgcagta acacgcggta    480

aaacgcgccc tcgctcggcg gcctcctcgg gcttccagcc gctaaacccc cagtgacgtt    540

tttcgagttg acctcggatc aggtaggaat acccgctgaa cttaagcata tcaataggcg    600

gaggaa                                                               606


<210> SEQ ID NO 484
<211> LENGTH: 596
<212> TYPE: DNA
<213> ORGANISM: Sordariomycete sp.
```

<400> SEQUENCE: 484
cttggtcatt tagaggtagt aaaagtcgta acaaggtctc cgttggtgaa ccagcggagg 60
gatcattacc gagtttacaa ctcccaaacc cctgtgaaca taccaattgt tgcctcggcg 120
gatcagcccg ctcccggtaa aacggaacgg cccgccagag gacccctaaa ctctgtttct 180
atatgtaact tctgagtaaa accataaata aatcaaaact ttcaacaacg gatctcttgg 240
ttctggcatc gatgaagaac gcagcaaaat gcgataagta atgtgaattg cagaattcag 300
tgaatcatcg aatctttgaa cgcacattgc gcccgccagt attctggcgg gcatgcctgt 360
tcgagcgtca tttcaaccct caagcccccg ggtttggtgt tggggatcgg cgagcctcac 420
ggcaagccgg ccccgaaata cagtggcggt ctcgctgcag cttccattgc gtagtagtaa 480
aaccctcgca actggtacgc ggcgcggcca agccgttaaa cccccaactt ctgaatgttg 540
acctcggatc aggtaggaat acccgctgaa cttaagcata tcaataagcg gaggaa 596

<210> SEQ ID NO 485
<211> LENGTH: 577
<212> TYPE: DNA
<213> ORGANISM: Uncultured root-associated fungus

<400> SEQUENCE: 485
acgttcgggt ctcgttggtg acagcggagg gatcattaaa gagttgcaaa actccaaccc 60
ctgtgaactt tacctgtacg ttgcttcggc ggccgacgcc gcgcccagcc gggcctgggg 120
gacgccgccg gaggttttaa accctgaatt ctagtgtatc tctgaggacg aaaaaaacca 180
attaaaactt tcaacaacgg atctcttggc tctggcatcg atgaagaacg cagcgaaatg 240
cgataagtaa tgtgaattgc agaattcagt gaatcatcga atctttgaac gcacattgcg 300
cccgccggta ttccggcggg catgcctgtc cgagcgtcat ttcaccactc aagcccagct 360
tggtgttggg gcacccggcc gcccggcggt cggggccccc aagtacatcg gcggtcctgc 420
tggggctccg agcgcagtaa cacgcggtaa aacgcgccct cgctcggcgg cctcctcggg 480
cttccagccg ctaaaccccc agtgacgttt ttcgagttga cctcggatca ggtaggaata 540
cccgctgaac ttaagcatat caataggccg gaggaaa 577

<210> SEQ ID NO 486
<211> LENGTH: 554
<212> TYPE: DNA
<213> ORGANISM: Uncultured root-associated fungus

<400> SEQUENCE: 486
cagcggaggg atcattaaag agttgcaaaa ctccaacccc tgtgaacttt acctgtacgt 60
tgcttcggcg gccgacgccg cgcccagccg ggcctggggg acgccgccgg aggttttaaa 120
ccctgaattc tagtgtatct ctgaggacga aaaaaaccaa ttaaaacttt caacaacgga 180
tctcttggct ctggcatcga tgaagaacgc agcgaaatgc gataagtaat gtgaattgca 240
gaattcagtg aatcatcgaa tctttgaacg cacattgcgc ccgccggtat tccggcgggc 300
atgcctgtcc gagcgtcatt tcaccactca agcccagctt ggtgttgggg cacccggccg 360
cccggcggtc ggggccccca agtacatcgg cggtcctgct ggggctccga gcgcagtaac 420
acgcggtaaa acgcgccctc gctcggcggc ctcctcgggc ttccagccgc taaaccccca 480
gtgacgtttt tcgagttgac ctcggatcag gtaggaatac ccgctgaact taagcatatc 540
aataagcgga ggaa 554

<210> SEQ ID NO 487
<211> LENGTH: 549
<212> TYPE: DNA
<213> ORGANISM: Uncultured root-associated fungus

<400> SEQUENCE: 487
tgacagcgga gggatcatta aagagttgca aaactccaac ccctgtgaac tttacctgta 60
cgttgcttcg gcggccgacg ccgcgcccag ccgggcctgg gggacgccgc cggaggtttt 120
aaaccctgaa ttctagtgta tctctgagga cgaaaaaaac caattaaaac tttcaacaac 180
ggatctcttg gctctggcat cgatgaagaa cgcagcgaaa tgcgataagt aatgtgaatt 240
gcagaattca gtgaatcatc gaatctttga acgcacattg cgcccgccgg tattccggcg 300
ggcatgcctg tccgagcgtc atttcaccac tcaagcccag cttggtgttg ggcacccgg 360 ccgcccggcg gtcggggccc ccaagtacat cggcggtcct gctggggctc cgagcgcagt 420
aacacgcggt aaaacgcgcc ctcgctcggc ggcctcctcg ggcttccagc cgctaaaccc 480
ccagtgacgt tttcgagtt gacctcggat caggtaggaa tacccgctga acttaagcat 540
atcaataag 549

<210> SEQ ID NO 488
<211> LENGTH: 554
<212> TYPE: DNA
<213> ORGANISM: Magnaporthe rhizophila

<400> SEQUENCE: 488
gcttggtgac cagcggaggg atcattaaag agttgcaaaa ctccaacccc tgtgaacgtt 60
acctgtacgt tgcttcggcg gccgacgccg cgcccagccg ggcctggggg acgccgccgg 120
aggtcttaaa ccctgaattc tagtgtatct ctgaggacga aaagaaccaa ttaaaacttt 180
caacaacgga tctcttggct ctggcatcga tgaagaacgc agcgaaatgc gataagtaat 240
gtgaattgca gaattcagtg aatcatcgaa tctttgaacg cacattgcgc ccgccggtat 300
tccggcgggc atgcctgtcc gagcgtcatt tcaccactca agcccagcct ggtgttgggg 360
cacccggccg cccggcggtc ggggccccca agtacatcgg cggtcctgct ggggctccga 420
gcgcagtaac acgcggtaaa acgcgccctc gctcggcggc ctcctcgggc ttccagccgc 480
taaacccccc caatgacgtt ttcgagtgac ctcggatcag taggaatacc cgctgaactt 540
aagcatatca ataa 554

<210> SEQ ID NO 489
<211> LENGTH: 599
<212> TYPE: DNA
<213> ORGANISM: Fusarium nygamai

<400> SEQUENCE: 489
ccggtcctct tttttttttg taaaagtcgt aacaaggtct ccgttggtga accagcggag 60
ggatcattac cgagtttaca actccccaaa cccctgtgaa cataccaatt gttgcctcgg 120
cggatcagcc cgctcccggt aaaacggaac ggcccgccag aggaccccta aactctgttt 180
ctatatgtaa cttctgagta aaaccataaa taaatcaaaa ctttcaacaa cggatctctt 240
ggttctggca tcgatgaaga acgcagcaaa atgcgataag taatgtgaat tgcagaattc 300
agtgaatcat cgaatctttg aacgcacatt gcgcccgcca gtattctggc gggcatgcct 360
gttcgagcgt catttcaacc ctcaagcccc cgggtttggt gttggggatc ggcgagcctc 420
acggcaagcc ggccccgaaa tacagtggcg gtctcgctgc agcttccatt gcgtagtagt 480
aaaaccctcg caactggtac gcggcgcggc caagccgtta aacccccaac ttctgaatgt 540
tgacctcgga tcaggtagga atacccgctg aacttaagca tatcaataag gcggaggaa 599

<210> SEQ ID NO 490
<211> LENGTH: 554
<212> TYPE: DNA
<213> ORGANISM: Magnaporthe rhizophila

<400> SEQUENCE: 490
acagcggagg gatcattaaa gagttgcaaa actccaaccc ctgtgaactt tacctgtacg 60
ttgcttcggc ggccgacgcc gcgcccagcc gggcctgggg gacgccgccg gaggttttaa 120
accctgaatt ctagtgtatc tctgaggacg aaaataacca attaaaactt tcaacaacgg 180
atctcttggc tctggcatcg atgaagaacg cagcgaaatg cgataagtaa tgtgaattgc 240
agaattcagt gaatcatcga atctttgaac gcacattgcg cccgccggta ttccggcggg 300
catgcctgtc cgagcgtcat ttcaccactc aagcccagct tgttgttggg gcacccggcc 360
gcctggcggt cggggccccc aagtacatcg gcggtcctgc tggggctccg agcgcagtaa 420
ctcgcggtaa aacgcgccct cgctcggcgg cctcctcggg cttccagccg ctaaaccccc 480
agtgacgttt ttcgagttga cctcggatca ggtaggaata cccgctgaac ttaagcatat 540
caatagacgg agga 554

<210> SEQ ID NO 491
<211> LENGTH: 562
<212> TYPE: DNA
<213> ORGANISM: Uncultured soil fungus

<400> SEQUENCE: 491
ttcctccgct tattgatatg cttaagttca gcgggtatcc ctacctgatc cgaggtcaaa 60
cgtggtaaat gttcttgatg gacgccagta caacgggcta cgatcgcaaa atgtgctgcg 120
ctcctaggcc aaagtgccgg ctgccaatga atttaaggcg agtcgtaata cgacaagacg 180
cccaacacca agcaaagctt gagggtacaa atgacgctcg aacaggcatg ccccatggaa 240
taccaagggg cgcaatgtgc gttcaaagat tcgatgattc actgaattct gcaattcaca 300
ctacttatcg catttcgctg cgttcttcat cgatgccaga accaagagat ccgttgttga 360
aagttgtaaa taattagatt attttcagac gctgattgca attacaaaaa aggttttggt 420
ttgtccaatc ggcagcttgc gccaccgagg aaacaagagt acgcaaaaga catggggtgt 480
agacgagagc tttacagccc ccgacttgac ttttgataat gatccttccg caggttcacc 540
tacggaaacc ttgttacgac tt 562

<210> SEQ ID NO 492
<211> LENGTH: 607
<212> TYPE: DNA
<213> ORGANISM: Gaeumannomyces incrustans

<400> SEQUENCE: 492
tcttggtcaa ttagaggaag taaaagtcgt aacaaggtct ccgttggtga accagcggag 60
ggatcattaa agagttgcaa aactccaacc cctgtgaact ttacctgtac gttgcttcgg 120
cggccgacgc cgcgcccagc cgggcgtggg ggacgccgcc ggaggtttta aaccctgaat 180
tctagtgtat ctctgaggac gaaaagaacc aattaaaact ttcaacaacg gatctcttgg 240
ctctggcatc gatgaagaac gcagcgaaat gcgataagta atgtgaattg cagaattcag 300

```
tgaatcatcg aatctttgaa cgcacattgc gcccgccggt attccggcgg gcatgcctgt    360
ccgagcgtca tttcaccact caagcccagc ttggtgttgg ggcacccggc cgcccggcgg    420
tcggggcccc caagtacatc ggcggtcctg ctggggctcc gagcgcagta acacgcggta    480
aaacgcgccc tcgctcggcg gcctcctcgg gcttccagcc gctaaacccc cagtgacgtt    540
tttcgagttg acctcggatc aggtaggaat acccgctgaa cttaagcata tcaataggcg    600
gaggaaa                                                              607
```

<210> SEQ ID NO 493
<211> LENGTH: 601
<212> TYPE: DNA
<213> ORGANISM: Sordariomycete sp.

<400> SEQUENCE: 493

```
ttcttggtca tttagaggaa gtaaaagtcg ttaacaaggt ctccgttggt gaaccagcgg     60
agggatcatt accgagttta caactcccaa acccctgtga acataccaat tgttgcctcg    120
gcggatcagc ccgctcccgg taaaacggaa cggcccgcca gaggacccct aaactctgtt    180
tctatatgta acttctgagt aaaaccataa ataaatcaaa actttcaaca acggatctct    240
tggttctggc atcgatgaag aacgcagcaa aatgcgataa gtaatgtgaa ttgcagaatt    300
cagtgaatca tcgaatcttt gaacgcacat tgcgcccgcc agtattctgg cgggcatgcc    360
tgttcgagcg tcatttcaac cctcaagccc ccgggtttgg tgttggggat cggcgagcct    420
cacggcaagc cggccccgaa atacagtggc ggtctcgctg cagcttccat tgcgtagtag    480
taaaaccctc gcaactggta cgcggcgcgg ccaagccgtt aaacccccaa cttctgaatg    540
ttgacctcgg atcaggtagg aatacccgct gaacttaagc atatcaataa gcgggaggaa    600
a                                                                    601
```

<210> SEQ ID NO 494
<211> LENGTH: 550
<212> TYPE: DNA
<213> ORGANISM: Fusarium moniliforme

<400> SEQUENCE: 494

```
gaccagcgga gggatcatta ccgagtttac aactcccaaa cccctgtgaa cataccaatt     60
gttgcctcgg cggatcagcc cgctcccggt aaaacgggac ggcccgccag aggaccccta    120
aactctgttt ctatatgtaa cttctgagta aaaccataaa taaatcaaaa ctttcaacaa    180
cggatctctt ggttctggca tcgatgaaga acgcagcaaa atgcgataag taatgtgaat    240
tgcagaattc agtgaatcat cgaatctttg aacgcacatt gcgcccgcca gtattctggc    300
gggcatgcct gttcgagcgt catttcaacc ctcaagccct cgggtttggt gttggggatc    360
ggcgagccct tgcggcaagc cggccccgaa atatagtggc ggtctcgctg cagcttccat    420
tgcgtagtag taaaaccctc gcaactggta cgcggcgcgg ccaagccgtt aaacccccaa    480
cttctgaatg ttgacctcgg atcaggtagg aatacccgct gaacttaagc atatacaata    540
agcggaggaa                                                           550
```

<210> SEQ ID NO 495
<211> LENGTH: 548
<212> TYPE: DNA
<213> ORGANISM: Codinaeopsis sp.

<400> SEQUENCE: 495

```
ggagggatca ttacaggact cgcaagactc ccgtaaacca ctgtgaactt acctacaacc     60
```

cgttgcctcg gcgggtgctc cgggcgcgtc ttcgggcgct ccggggcgct ccagcccgcc 120
ggcggcccct aaactctgtc tctgtaacgt tggcatctcc gagcagacta taaacgagtc 180
aaaactttca acaacggatc tcttggttct ggcatcgatg aagaacgcag cgaaatgcga 240
taagtaatgt gaattgcaga attcagtgaa tcatcgaatc tttgaacgca cattgcgccc 300
gccagcactc tggcgggcat gcctgtccga gcgtcatttc aaccctcagg ccccgcctgg 360
cgttggagcc ctgcgcagcg caggctccca aagacagcgg cgggcgcgcc ccggaaccga 420
gcgcagtaat gctttctcgt tctggtccgg cgcgcgctcc ggccgtaaaa cccccaactt 480
tctaagtggt tgacctcgga tcaggtagga atacccgctg aacttaagca tatcaataag 540
gcggagga 548

<210> SEQ ID NO 496
<211> LENGTH: 556
<212> TYPE: DNA
<213> ORGANISM: Fusarium nygamai

<400> SEQUENCE: 496
tcgttggtga ccagcggagg gatcattaaa gagttgcaaa actccaaccc ctgtgaactt 60
tacctgtacg ttgcttcggc ggccgacgcc gcgcccagcc gggcctgggg gacgccgccg 120
gaggttttaa accctgaatt ctagtgtatc tctgaggacg aaaaaaacca attaaaactt 180
tcaacaacgg atctcttggc tctggcatcg atgaagaacg cagcgaaatg cgataagtaa 240
tgtgaattgc agaattcagt gaatcatcga atctttgaac gcacattgcg cccgccggta 300
ttccggcggg catgcctgtc cgagcgtcat ttcaccactc aagcccagct tggtgttggg 360
gcacccggcc gcctggcggt cggggccccc aagtacatcg gcggtcctgc tggggctccg 420
agcgcagtaa ctcgcggtaa aacgcgccct cgctcggcgg cctcctcggg cttccagccg 480
ctaaaccccc agtgacgttt ttcgagttga cctcggatca ggtaggaata cccgctgaac 540
ttaagcatat caatag 556

<210> SEQ ID NO 497
<211> LENGTH: 605
<212> TYPE: DNA
<213> ORGANISM: Gaeumannomyces incrustans

<400> SEQUENCE: 497
cttggtcatt tagaggaagt aaaagtcgta acaaggtctc cgttggtgaa ccagcggagg 60
gatcattaaa gagttgcaaa actccaaccc ctgtgaactt tacctgtacg ttgcttcggc 120
ggccgacgcc gcgcccagcc gggcgtgggg gacgccgccg gaggttttaa accctgaatt 180
ctagtgtatc tctgaggacg aaaagaacca attaaaactt tcaacaacgg atctcttggc 240
tctggcatcg atgaagaacg cagcgaaatg cgataagtaa tgtgaattgc agaattcagt 300
gaatcatcga atctttgaac gcacattgcg cccgccggta ttccggcggg catgcctgtc 360
cgagcgtcat ttcaccactc aagcccagct tggtgttggg gcacccggcc gcccggcggt 420
cggggccccc aagtacatcg gcggtcctgc tggggctccg agcgcagtaa cacgcggtaa 480
aacgcgccct cgctcggcgg cctcctcggg cttccagccg ctaaaccccc agtgacgttt 540
ttcgagttga cctcggatca ggtaggaata cccgctgaac ttaagcatat caataggccg 600
gagga 605

<210> SEQ ID NO 498

<211> LENGTH: 605
<212> TYPE: DNA
<213> ORGANISM: Gaeumannomyces incrustans

<400> SEQUENCE: 498
tcttggtcat ttagaggaag taaaagtcgt aacaaggtct ccgttggtga accagcggag 60
ggatcattaa agagttgcaa aactccaacc cctgtgaact ttacctgtac gttgcttcgg 120
cggccgacgc cgcgcccagc cgggcgtggg ggacgccgcc ggaggtttta aaccctgaat 180
tctagtgtat ctctgaggac gaaaagaacc aattaaaact ttcaacaacg gatctcttgg 240
ctctggcatc gatgaagaac gcagcgaaat gcgataagta atgtgaattg cagaattcag 300
tgaatcatcg aatctttgaa cgcacattgc gcccgccggt attccggcgg gcatgcctgt 360
ccgagcgtca tttcaccact caagcccagc ttggtgttgg ggcacccggc cgcccggcgg 420
tcggggcccc caagtacatc ggcggtcctg ctggggctcc gagcgcagta acacgcggta 480
aaacgcgccc tcgctcggcg gcctcctcgg gcttccagcc gctaaacccc cagtgacgtt 540
tttcgagttg acctcggatc aggtaggaat acccgctgaa cttaagcata tcaataggcg 600
gagga 605

<210> SEQ ID NO 499
<211> LENGTH: 602
<212> TYPE: DNA
<213> ORGANISM: Gaeumannomyces incrustans

<400> SEQUENCE: 499
gttcatttag aggaagtaaa agtcgtaaca aggtctccgt tggtgaacca gcggagggat 60
cattaaagag ttgcaaaact ccaacccctg tgaactttac ctgtacgttg cttcggcggc 120
cgacgccgcg cccagccggg cgtgggggac gccgccggag gttttaaacc ctgaattcta 180
gtgtatctct gaggacgaaa agaaccaatt aaaactttca acaacggatc tcttggctct 240
ggcatcgatg aagaacgcag cgaaatgcga taagtaatgt gaattgcaga attcagtgaa 300
tcatcgaatc tttgaacgca cattgcgccc gccggtattc cggcgggcat gcctgtccga 360
gcgtcatttc accactcaag cccagcttgg tgttggggca cccggccgcc cggcggtcgg 420
ggcccccaag tacatcggcg gtcctgctgg ggctccgagc gcagtaacac gcggtaaaac 480
gcgccctcgc tcggcggcct cctcgggctt ccagccgcta aacccccagt gacgtttttc 540
gagttgacct cggatcaggt aggaataccc gctgaactta agcatatcaa tagccggagg 600
aa 602

<210> SEQ ID NO 500
<211> LENGTH: 558
<212> TYPE: DNA
<213> ORGANISM: Gibberella sp.

<400> SEQUENCE: 500
tcttggtcat ttagaggaag taaaagtcgt aacaaggtct ccgttggtga accagcggag 60
ggatcattac cgagtttaca actcccaaac ccctgtgaac ataccaattg ttgcctcggc 120
ggatcagccc gctcccggta aaacggaacg gcccgccaga ggacccctaa actctgtttc 180
tatatgtaac ttctgagtaa aaccataaat aaatcaaaac tttcaacaac ggatctcttg 240
gttctggcat cgatgaagaa cgcagcaaaa tgcgataagt aatgtgaatt gcagaattca 300
gtgaatcatc gaatctttga acgcacattg cgcccgccag tattctggcg ggcatgcctg 360
ttcgagcgtc atttcaaccc tcaagccccc gggtttggtg ttggggatcg gcgagcctca 420
cggcaagccg gccccgaaat acagtggcgg tctcgctgca gcttccattg cgtagtagta 480
aaaccctcgc aactggtacg cggcgcggcc aagccgttaa acccccaact tctgaatgtg 540
acctcggatc aggtagga 558

<210> SEQ ID NO 501
<211> LENGTH: 609
<212> TYPE: DNA
<213> ORGANISM: Uncultured root-associated fungu

<400> SEQUENCE: 501
tcttggtcaa ttagaggaag taaaagtcgt aacaaggtct ccgttggtga accagcggag 60
ggatcattaa agagttgcaa aactccaacc cctgtgaact ttacctgtac gttgcttcgg 120
cggccgacgc cgcgcccagc cgggcctggg ggacgccgcc ggaggtctta aaccctgaat 180
tctagtgtat ctctgaggac gaaaaaaaac caattaaaac tttcaacaac ggatctcttg 240
gctctggcat cgatgaagaa cgcagcgaaa tgcgataagt aatgtgaatt gcagaattca 300
gtgaatcatc gaatctttga acgcacattg cgcccgccgg tattccggcg ggcatgcctg 360
tccgagcgtc atttcaccac tcaagcccag cttggtgttg gggcacccgg ccgcccggcg 420
gtcggggccc ccaagtacat cggcggtcct gctggggctc cgagcgcagt aactcgcggt 480
aaaacgcgcc ctcgctcggc ggcctcctcg ggcttccagc cgctaaaccc ccagtgacgt 540
ttttcgagtt gacctcggat caggtaggaa tacccgctga acttaagcat atcaataggc 600
cggaggaaa 609

<210> SEQ ID NO 502
<211> LENGTH: 534
<212> TYPE: DNA
<213> ORGANISM: Uncultured root-associated fungu

<400> SEQUENCE: 502
tcattaaaga gttgcaaaac tccaacccct gtgaacttta cctgtacgtt gcttcggcgg 60
ccgacgccgc gcccagccgg gcctggggga cgccgccgga ggttttaaac cctgaattct 120
agtgtatctc tgaggacgaa aaaaaccaat taaaactttc aacaacggat ctcttggctc 180
tggcatcgat gaagaacgca gcgaaatgcg ataagtaatg tgaattgcag aattcagtga 240
atcatcgaat ctttgaacgc acattgcgcc cgccggtatt ccggcgggca tgcctgtccg 300
agcgtcattt caccactcaa gcccagcttg gtgttggggc acccggccgc ccggcggtcg 360
gggcccccaa gtacatcggc ggtcctgctg gggctccgag cgcagtaaca cgcggtaaaa 420
cgcgccctcg ctcggcggcc tcctcgggct tccagccgct aaacccccag tgacgttttt 480
cgagttgacc tcggatcagg taggaatacc cgctgaactt aagcatatca ataa 534

<210> SEQ ID NO 503
<211> LENGTH: 550
<212> TYPE: DNA
<213> ORGANISM: Uncultured root-associated fungu

<400> SEQUENCE: 503
accagcggag ggatcattaa agagttgcaa aaactccaac ccctgtgaac tttacctgta 60
cgttgcttcg gcggccgacg ccgcgcccag acgggcctgg gggacgccgc cggaggtctt 120
aaaccctgaa ttctagtgta tctatgagga cgaaaaaaac caattaaaac tttcaacaac 180
ggatctcttg gctctggcat cgatgaagaa cgcagcgaaa tgcgataagt aatgtgaatt 240

```
gcagaattca gtgaatcatc gaatctttga acgcacattg cgcccgccgg tattccggcg    300

ggcatgcctg tccgagcgtc atttcaccac tcaagcccag cttggtgttg ggcacccgg     360

ccgcccggcg gtcggggccc ccaagtacat cggcggtccc gctggggctc cgagcgcagt    420

aactcgcggt aaaacgcgcc ctcgctcggc ggcctcctcg ggcttccagc cgctaaaccc    480

ccagtgacgt ttttcgagtt gacctcggat caggtaggaa tacccgctga acttaagcat    540

atcaataagc                                                           550
```

<210> SEQ ID NO 504
<211> LENGTH: 579
<212> TYPE: DNA
<213> ORGANISM: Gaeumannomyces incrustans

<400> SEQUENCE: 504

```
cgtaacaagg tctccgttgg tgaaccagcg gagggatcat taaagagttg caaaactcca     60

acccctgtga actttacctg tacgttgctt cggcggccga cgccgcgccc agccgggcct    120

gggggacgcc gccggaggtt ttaaaccctg aattctagtg tatctctgag gacgaaaaaa    180

accaattaaa actttcaaca acggatctct tggctctggc atcgatgaag aacgcagcga    240

aatgcgataa gtaatgtgaa ttgcagaatt cagtgaatca tcgaatcttt gaacgcacat    300

tgcgcccgcc ggtattccgg cgggcatgcc tgtccgagcg tcatttcacc actcaagccc    360

agcttggtgt tggggcaccc ggccgcccgg cggtcggggc ccccaagtac atcggcggtc    420

ctgctggggc tccgagcgca gtaacacgcg gtaaaacgcg ccctcgctcg gcggcctcct    480

cgggcttcca gccgctaaac ccccagtgac gtttttcgag ttgacctcgg atcaggtagg    540

aatacccgct gaacttaagc atatcaataa gacggagga                           579
```

<210> SEQ ID NO 505
<211> LENGTH: 557
<212> TYPE: DNA
<213> ORGANISM: Fusarium nygamai

<400> SEQUENCE: 505

```
ctcgttggtg accagcggag ggatcattac cgagtttaca actcccaaac ccctgtgaac     60

ataccaattg ttgcctcggc ggatcagccc gctcccggta aaacggaacg gcccgccaga    120

ggaccoctaa actctgtttc tatatgtaac ttctgagtaa aaccataaat aaatcaaaac    180

tttcaacaac ggatctcttg gttctggcat cgatgaagaa cgcagcaaaa tgcgataagt    240

aatgtgaatt gcagaattca gtgaatcatc gaatctttga acgcacattg cgcccgccag    300

tattctggcg ggcatgcctg ttcgagcgtc atttcaaccc tcaagccccc gggtttggtg    360

ttggggatcg gcgagcctca cggcaagccg gccccgaaat acagtggcgg tctcgctgca    420

gcttccattg cgtagtagta aaaccctcgc aactggtacg cggcgcggcc aagccgttaa    480

acccccaact tctgaatgtt gacctcggat caggtaggaa tacccgctga acttaagcat    540

atcaataagc ggaggaa                                                   557
```

<210> SEQ ID NO 506
<211> LENGTH: 608
<212> TYPE: DNA
<213> ORGANISM: Fusarium sp.

<400> SEQUENCE: 506

```
ttggtcattt attttgaagt aaaagtcgta acaaggtctc cgttggtgaa ccagcggagg     60

gatcattacc gagttataca actcatcaac cctgtgaaca tacctataac gttgcctcgg    120
```

cgggaacaga cggccccgta acacgggccg cccccgccag aggacccccct aactctgttt 180 ctataatgtt tcttctgagt aaacaagcaa ataaattaaa actttcaaca acggatctct 240
tggctctggc atcgatgaag aacgcagcga aatgcgataa gtaatgtgaa ttgcagaatt 300
cagtgaatca tcgaatcttt gaacgcacat tgcgcccgcc agtattctgg cgggcatgcc 360
tgttcgagcg tcattacaac cctcaggccc ccgggcctgg cgttggggat cggcggaagc 420
cccctgcggg cacaacgccg tcccccaaat acagtggcgg tcccgccgca gcttccattg 480
cgtagtagct aacacctcgc aactggagag cggcgcggcc acgccgtaaa acacccaact 540
tctgaatgtt gacctcgaat caggtaggaa tacccgctga acttaagcat atcaataggc 600
ggaggaaa 608

<210> SEQ ID NO 507
<211> LENGTH: 567
<212> TYPE: DNA
<213> ORGANISM: Magnaporthe rhizophila

<400> SEQUENCE: 507
tctcgttggt gaccagcgga gggatcatta aagagttgca caaactccaa cccctgtgaa 60
ctttacctgt acgttgcttc ggcggccgac gccgcgccca gccgggcccg ggggacgccg 120
ccggaggtca taaaccctga attctagtgt atctctgagg acgaaaataa ccaattaaaa 180
ctttcaacaa cggatctctt ggctctggca tcgatgaaga acgcagcgaa atgcgataag 240
taatgtgaat tgcagaattc agtgaatcat cgaatctttg aacgcacatt gcgcccgccg 300
gtattccggc gggcatgcct gtccgagcgt catttcacca ctcaagccca gcttggtgtt 360
ggggcacccg gccgcccggc ggtcggggcc cccaagtaca tcggcggtcc cgctggggct 420
ccgagcgcag taactcgcgg taaaacgcgc cctcgctcgg cggcctcctc gggcttccag 480
ccgctaaacc cccagtgacg tttttcgagt tgacctcgga tcaggtagga atacccgctg 540
aacttaagca tatcaatagc ggaggaa 567

<210> SEQ ID NO 508
<211> LENGTH: 564
<212> TYPE: DNA
<213> ORGANISM: Magnaporthe rhizophila

<400> SEQUENCE: 508
cgttgtgacc agcggaggga tcattaaaga gttgcaaaac tccaacccct gtgaacttta 60
cctgtacgtt gcttcggcgg ccgacgccgc gcccagccgg gcctggggga cgccgccgga 120
ggttttaaac cctgaattct agtgtatctc tgaggacgaa aaaaaccaat taaaactttc 180
aacaacggat ctcttggctc tggcatcgat gaagaacgca gcgaaatgcg ataagtaatg 240
tgaattgcag aattcagtga atcatcgaat ctttgaacgc acattgcgcc cgccggtatt 300
ccggcgggca tgcctgtccg agcgtcattt caccactcaa gcccagcttg gtgttggggc 360
acccggccgc ccggcggtcg gggcccccaa gtacatcggc ggtcctgctg gggctccgag 420
cgcagtaaca cgcggtaaaa cgcgccctcg ctcggcggcc tcctcgggct tccagccgct 480
aaacccccag tgacgttttt cgagttgacc tcggatcagg taggaatacc cgctgaactt 540
aagcatatca ataaggcgga ggaa 564

<210> SEQ ID NO 509
<211> LENGTH: 664
<212> TYPE: DNA

<213> ORGANISM: Rhizoctonia praticola

<400> SEQUENCE: 509
ggcatcggtt tccgtagggt gacctgcgga ggatcattat tgaatgaatg tagagttggt 60
tgtcgctggc cctttcgggg gcatgtgcac gccttctctt tcatccacac acacctgtgc 120
acttgtgaga cggagggctt taattagtct tccgtctact taatcacaca aactcattta 180
atttaatttg aatgtaattg atgtaacgca tcatttgaac taagtttcaa caacggatct 240
cttggctctc gcatcgatga agaacgcagc gaaatgcgat aagtaatgtg aattgcagaa 300
ttcagtgaat catcgaatct ttgaacgcac cttgcgctcc ttggtattcc ttggagcatg 360
cctgtttgag tatcatgaaa ttctcaaagt aaatcttttg ttaattcaac tggtttgctt 420
tggacttgga ggtctttgca gatttcacat ctgctcctct taaatgcatt agctggatct 480
cagtatatgc ttggttccac tcggcgtgat aagtatcact cgctgaggac actgtaaaaa 540
gtggccagga aatacagatg aaccgcttct aatagtctat taagttagac aattaattta 600
agatctgatc tcaaatcagg taggactacc cgctgaactt aagcatatca ataaggcgga 660
ggaa 664

<210> SEQ ID NO 510
<211> LENGTH: 555
<212> TYPE: DNA
<213> ORGANISM: Fusarium nygamai

<400> SEQUENCE: 510
cgttggtgac cagcggaggg atcattaccg agtttacaac tcccaaaccc ctgtgaacat 60
accaattgtt gcctcggcgg atcagcccgc tcccggtaaa acggaacggc ccgccagagg 120
acccctaaac tctgtttcta tatgtaactt ctgagtaaaa ccataaataa atcaaaactt 180
tcaacaacgg atctcttggt tctggcatcg atgaagaacg cagcaaaatg cgataagtaa 240
tgtgaattgc agaattcagt gaatcatcga atctttgaac gcacattgcg cccgccagta 300
ttctggcggg catgcctgtt cgagcgtcat ttcaaccctc aagcccccgg gtttggtgtt 360
ggggatcggc gagcctcacg gcaagccggc cccgaaatac agtggcggtc tcgctgcagc 420
ttccattgcg tagtagtaaa accctcgcaa ctggtacgcg gcgcggccaa gccgttaaac 480
ccccaacttc tgaatgttga cctcggatca ggtaggaata cccgctgaac ttaagcatat 540
caataaggcg gagga 555

<210> SEQ ID NO 511
<211> LENGTH: 585
<212> TYPE: DNA
<213> ORGANISM: Ascomycete sp.

<400> SEQUENCE: 511
tcttggtcat ttagaggaag taaaagtcgt aacaaggttt ccgtaggtga acctgcggaa 60
ggatcattat caaaagtcaa gtcgggggct gtaaagctct cgtctacacc ccatgtcttt 120
tgcgtactct tgtttcctcg gtggcgcaag ctgccgattg gacaaaccaa aacctttttt 180
gtaattgcaa tcagcgtctg aaaataatct aattatttac aactttcaac aacggatctc 240
ttggttctgg catcgatgaa gaacgcagcg aaatgcgata agtagtgtga attgcagaat 300
tcagtgaatc atcgaatctt tgaacgcaca ttgcgcccct tggtattcca tggggcatgc 360
ctgttcgagc gtcatttgta ccctcaagct ttgcttggtg ttgggcgtct tgtcgtatta 420
cgactcgcct taaattcatt ggcagccggc actttggcct aggagcgcag cacattttgc 480
gatcgtagcc cgttgtactg gcgtccatca agaacattta ccacgtttga cctcggatca 540
ggtagggata cccgctgaac ttaagcatat caataagccg gagga 585

<210> SEQ ID NO 512
<211> LENGTH: 597
<212> TYPE: DNA
<213> ORGANISM: Sordariomycete sp.

<400> SEQUENCE: 512
tcttggtcat ttagaggaag taaaagtcgt aacaaggtct ccgttggtga accagcggag 60
ggatcattac cgagtttaca actcccaaac ccctgtgaac ataccaattg ttgcctcggc 120
ggatcagccc gctcccggta aaacggaacg gcccgccaga ggacccctaa actctgtttc 180
tatatgtaac ttctgagtaa aaccataaat aaatcaaaac tttcaacaac ggatctcttg 240
gttctggcat cgatgaagaa cgcagcaaaa tgcgataagt aatgtgaatt gcagaattca 300
gtgaatcatc gaatctttga acgcacattg cgcccgccag tattctggcg ggcatgcctg 360
ttcgagcgtc atttcaaccc tcaagccccc gggtttggtg ttggggatcg gcgagcctca 420
cggcaagccg gccccgaaat acagtggcgg tctcgctgca gcttccattg cgtagtagta 480
aaaccctcgc aactggtacg cggcgcggcc aagccgttaa acccccaact tctgaatgtt 540
gacctcggat caggtaggaa tacccgctga acttaagcat atcaataagc ggaggaa 597

<210> SEQ ID NO 513
<211> LENGTH: 606
<212> TYPE: DNA
<213> ORGANISM: Gaeumannomyces graminis var. tritici

<400> SEQUENCE: 513
tcttggtcaa ttagaggaag taaaagtcgt aacaaggtct ccgttggtga accagcggag 60
ggatcattaa agagttgcaa aactccaacc cctgtgaact ttacctgtac gttgcttcgg 120
cggccgacgc cgcgcccagc cgggcctggg ggacgccgcc ggaggtttta aaccctgaat 180
tctagtgtat ctctgaggac gaaaaaaaca aattaaaact ttcaacaacg gatctcttgg 240
ctctggcatc gatgaagaac gcagcgaaat gcgataagta atgtgaattg cagaattcag 300
tgaatcatcg aatctttgaa cgcacattgc gcccgccggt attccggcgg gcatgcctgt 360
ccgagcgtca tttcaccact caagcccagc ttggtgttgg ggcacccggc cgcccggcgg 420
tcggggcccc caagtacatc ggcggtcccg ctggggctcc gagcgcagta actcgcggta 480
aaacgcgccc tcgctcggcg gcctcctcgg gcttccagcc gctaaacccc cagtgacgtt 540
tttcgagttg acctcggatc aggtaggaat acccgctgaa cttaagcata tcaataggcg 600
gaggaa 606

<210> SEQ ID NO 514
<211> LENGTH: 605
<212> TYPE: DNA
<213> ORGANISM: Gaeumannomyces graminis var. tritici

<400> SEQUENCE: 514
tcttggtcat ttagaggaag taaaagtcgt aacaaggtct ccgttggtga accagcggag 60
ggatcattaa agagttgcaa aactccaacc cctgtgaact ttacctgtac gttgcttcgg 120
cggccgacgc cgcgcccagc cgggcctggg ggacgccgcc ggaggtttta aaccctgaat 180
tctagtgtat ctctgaggac gaaaaaaaca aattaaaact ttcaacaacg gatctcttgg 240
ctctggcatc gatgaagaac gcagcgaaat gcgataagta atgtgaattg cagaattcag 300
tgaatcatcg aatctttgaa cgcacattgc gcccgccggt attccggcgg gcatgcctgt 360
ccgagcgtca tttcaccact caagcccagc ttggtgttgg ggcacccggc cgcccggcgg 420
tcggggcccc caagtacatc ggcggtcccg ctggggctcc gagcgcagta actcgcggta 480
aaacgcgccc tcgctcggcg gcctcctcgg gcttccagcc gctaaacccc cagtgacgtt 540
tttcgagttg acctcggatc aggtaggaat acccgctgaa cttaagcata tcaataggcg 600
gagga 605

<210> SEQ ID NO 515
<211> LENGTH: 605
<212> TYPE: DNA
<213> ORGANISM: Gaeumannomyces graminis var. tritici

<400> SEQUENCE: 515
tcttggtcat ttagaggaag taaaagtcgt aacaaggtct ccgttggtga accagcggag 60
ggatcattaa agagttgcaa aactccaacc cctgtgaact ttacctgtac gttgcttcgg 120
cggccgacgc cgcgcccagc cgggcctggg ggacgccgcc ggaggtttta aaccctgaat 180
tctagtgtat ctctgaggac gaaaaaaaca aattaaaact ttcaacaacg gatctcttgg 240
ctctggcatc gatgaagaac gcagcgaaat gcgataagta atgtgaattg cagaattcag 300
tgaatcatcg aatctttgaa cgcacattgc gcccgccggt attccggcgg gcatgcctgt 360
ccgagcgtca tttcaccact caagcccagc ttggtgttgg ggcacccggc cgcccggcgg 420
tcggggcccc caagtacatc ggcggtcccg ctggggctcc gagcgcagta actcgcggta 480
aaacgcgccc tcgctcggcg gcctcctcgg gcttccagcc gctaaacccc cagtgacgtt 540
tttcgagttg acctcggatc aggtaggaat acccgctgaa cttaagcata tcaataggcg 600
gagga 605

<210> SEQ ID NO 516
<211> LENGTH: 555
<212> TYPE: DNA
<213> ORGANISM: Uncultured root-associated fungus

<400> SEQUENCE: 516
ccagcggagg gatcattaca gagttgcaaa actcccaacc cctgggaact ttacctgttc 60
tttgcttcgg gggtcgacgc ggtccccggc cgggcctggg ggacgccgcc ggaggtttta 120
aaccctgaat tctagtgtat ctctgaggac gaaaaaaacc aattaaaact ttcaacaacg 180
gatctcttgg ctctggcatc gatgaagaac gcagcgaaat gcgataagta atgtgaattg 240
cagaattcag tgaatcatcg aatctttgaa cgcacattgc gcccgccggt attccggcgg 300
gcatgcctgt ccgagcgtca tttcaccact caagcccagc ttggtgttgg ggcacccggc 360
cgcccggcgg tcggggcccc caagtacatc ggcggtcctg ctggggctcc gagcgcagta 420
acacgcggta aaacgcgccc tcgctcggcg gcctcctcgg gcttccagcc gctaaacccc 480
cagtgacgtt gttcgagttg acctcggatc aggtaggaat acccgctgaa cttaagcata 540
tcagtagcgg aggaa 555

<210> SEQ ID NO 517
<211> LENGTH: 607
<212> TYPE: DNA
<213> ORGANISM: Gaeumannomyces incrustans

<400> SEQUENCE: 517

```
tcttggtcat ttagaggaag taaaagtcgt aacaaggtct ccgttggtga accagcggag     60

ggatcattaa agagttgcaa aactccaacc cctgtgaact ttacctgtac gttgcttcgg    120

cggccgacgc cgcgcccagc cgggcctggg ggacgccgcc ggaggtttta aaccctgaat    180

tctagtgtat ctctgaggac gaaaaaaacc aattaaaact ttcaacaacg gatctcttgg    240

ctctggcatc gatgaagaac gcagcgaaat gcgataagta atgtgaattg cagaattcag    300

tgaatcatcg aatctttgaa cgcacattgc gcccgccggt attccggcgg gcatgcctgt    360

ccgagcgtca tttcaccact caagcccagc ttggtgttgg ggcacccggc cgcccggcgg    420

tcggggcccc caagtacatc ggcggtcctg ctggggctcc gagcgcagta acacgcggta    480

aaacgcgccc tcgctcggcg gcctcctcgg gcttccagcc gctaaacccc cagtgacgtt    540

tttcgagttg acctcggatc aggtaggaat acccgctgaa cttaagcata tcaataggcg    600

gaggaaa                                                              607
```

<210> SEQ ID NO 518
<211> LENGTH: 441
<212> TYPE: DNA
<213> ORGANISM: Fusarium nygamai

<400> SEQUENCE: 518

```
tcattaccga gtttacaact cccaaacccc tgtgaacata ccaattgttg cctcggcgga     60

tcagcccgct cccggtaaaa cggaacggcc cgccagagga cccctaaact ctgtttctat    120

atgtaacttc tgagtaaaac cataaataaa tcaaaacttt caacaacgga tctcttggtt    180

ctggcatcga tgaagaacgc agcaaaatgc gataagtaat gtgaattgca gaattcagtg    240

aatcatcgaa tctttgaacg cacattgcgc ccgccagtat tctggcgggc atgcctgttc    300

gagcgtcatt tcaaccctca agcccccttg tttggtgttg gggatcggcg agcctcacgg    360

caagccggcc ccgaaataca gtggcggtct cgctgcagct tccattgcgt agtagtaaaa    420

ccctcgcaac tggtacgggg c                                              441
```

<210> SEQ ID NO 519
<211> LENGTH: 594
<212> TYPE: DNA
<213> ORGANISM: Uncultured root associated fungus

<400> SEQUENCE: 519

```
tcatttttag taagttaaag tcgtaacaag gtctccgttg gtgaaccagc ggagggatca     60

ttaccgagtt tacaactccc aaacccctgt gaacatacct tactgttgcc tcggcggatc    120

agcccgcgcc cggtaaaacg ggacggcccg ccagaggacc cctaaactct gtttttattg    180

taacttctga gtaaaaccat aaataaatca aaactttcaa caacggatct cttggttctg    240

gcatcgatga agaacgcagc aaaatgcgat aagtaatgtg aattgcagaa ttcagtgaat    300

catcgaatct ttgaacgcac attgcgcccg ccagtattct ggcgggcatg cctgttcgag    360

cgtcatttca accctcaagc cctcgggttt ggtgttgggg atcggcgagc ctttctggca    420

agccggcccc gaaatctagt ggcggtctca ctgcagcctc cattgcgtag tagctaacac    480

ctcgcaactg gaacgcggtg cggccaagcc gttaaacccc ccaacttctg aatgttgacc    540

tcggatcagg taggaatacc cgctgaactt aagcatatca taagcggaga aaaa          594
```

<210> SEQ ID NO 520
<211> LENGTH: 556
<212> TYPE: DNA

<213> ORGANISM: Magnaporthe rhizophila

<400> SEQUENCE: 520
ttcctccgtc ttattgatat gcttaagttc agcgggtatt cctacctgat ccgaggtcaa 60
ctcgaaaaac gtcactgggg gtttagcggc tggaagcccg aggaggccgc cgagcgaggg 120
cgcgttttac cgcgagttac tgcgctcgga gccccagcgg gaccgccgat gtacttgggg 180
gccccgaccg ccgggcggcc gggtgcccca acaccaagct gggcttgagt ggtgaaatga 240
cgctcggaca ggcatgcccg ccggaatacc ggcgggcgca atgtgcgttc aaagattcga 300
tgattcactg aattctgcaa ttcacattac ttatcgcatt tcgctgcgtt cttcatcgat 360
gccagagcca agagatccgt tgttgaaagt tttaattggt tattttcgtc ctcagagata 420
cactagaatt cagggtttat gacctccggc ggcgtccccc gggcccggct gggcgcggcg 480
tcggccgccg aagcaacgta caggtaaagt tcacaggggt tggagttttg caactcttta 540
atgatccctc cgctgg 556

<210> SEQ ID NO 521
<211> LENGTH: 568
<212> TYPE: DNA
<213> ORGANISM: Gaeumannomyces incrustans

<400> SEQUENCE: 521
catcctactg atccgaggtc aactcgaaaa acgtcactgg gggtttagcg gctggaagcc 60
cgaggaggcc gccgagcgag ggcgcgtttt accgcgtgtt actgcgctcg gagccccagc 120
aggaccgccg atgtacttgg gggccccgac cgccgggcgg ccgggtgccc caacaccaag 180
ctgggcttga gtggtgaaat gacgctcgga caggcatgcc cgccggaata ccggcgggcg 240
caatgtgcgt tcaaagattc gatgattcac tgaattctgc aattcacatt acttatcgca 300
tttcgctgcg ttcttcatcg atgccagagc caagagatcc gttgttgaaa gttttaattg 360
gtttttttcg tcctcagaga tacactagaa ttcagggttt aaaacctccg gcggcgtccc 420
ccaggcccgg ctgggcgcgg cgtcggccgc cgaagcaacg tacaggtaaa gttcacaggg 480
gttggagttt tgcaactctt taatgatccc tccgctggtt caccaacgga gaccttgtta 540
cgacttttac ttcctctaaa tgaccaag 568

<210> SEQ ID NO 522
<211> LENGTH: 548
<212> TYPE: DNA
<213> ORGANISM: Uncultured root-associated fungus

<400> SEQUENCE: 522
gtgaccagcg gagggatcat taaagagttg caaaactcca acccctgtga actttacctg 60
tacgttgctt cggcggccga cgccgcgccc agccgggcct gggggacgcc gccggaggtt 120
ttaaacgctg aattctagtg tatctctgag gacgaaaaaa accaattaaa actttcaaca 180
acggatctct tggctctggc atcgatgaag aacgcagcga aatgcgataa gtaatgtgaa 240
ttgcagaatt cagtgaatca tcgaatcttt gaacgcacat tgcgcccgcc ggtattccgg 300
cgggcatgcc tgtccgagcg tcatttcacc actcaagccc tgcttggtgt tggggcaccc 360
ggccgcccgg cggtcggggc ccccaagtac atcggcggtc ctgctggggc tccgagcgca 420
gtaacacgcg gtaaaacgcg ccctcgctcg gcggcctcct cgggctccca gccgctaaac 480
ccccagtgac gtttttcgag ttgacctcgg atcaggtagg aatacccgct gaacttaagc 540
atatcaat 548

<210> SEQ ID NO 523
<211> LENGTH: 566
<212> TYPE: DNA
<213> ORGANISM: Uncultured root-associated fungus

<400> SEQUENCE: 523
tctcgttgtg accagcggag ggatcattaa agagttgcaa aactccaacc cctgtgaact 60
ttacctgtac gttgcttcgg cggccgacgc cgcgcccagc cgggcctggg ggacgccgcc 120
ggaggtttta aaccctgaat tctagtgtat ctctgaggac gaaaaaaacc aattaaaact 180
ttcaacaacg gatctcttgg ctctggcatc gatgaagaac gcagcgaaat gcgataagta 240
atgtgaattg cagaattcag tgaatcatcg aatctttgaa cgcacattgc gcccgccggt 300
attccggcgg gcatgcctgt ccgagcgtca tttcaccact caagcccagc ttggtgttgg 360
ggcacccggc cgcccggcgg tcggggcccc caagtacatc ggcggtcctg ctggggctcc 420
gagcgcagta acacgcggta aaacgcgccc tcgctcggcg gcctcctcgg gcttccagcc 480
gctaaacccc cagtgacgtt tttcgagttg acctcggatc aggtaggaat acccgctgaa 540
cttaagcata tcaataaggc ggagga 566

<210> SEQ ID NO 524
<211> LENGTH: 558
<212> TYPE: DNA
<213> ORGANISM: Uncultured root-associated fungus

<400> SEQUENCE: 524
tcgttgtgac cagcggaggg atcattaaag agttgcaaaa ctccaacccc tgtgaacttt 60
acctgtacgt tgcttcggcg gccgacgccg cgcccagccg ggcctggggg acgccgccgg 120
aggttttaaa ccctgaattc tagtgtatct ctgaggacga aaaaaaccaa ttaaaacttt 180
caacaacgga tctcttggct ctggcatcga tgaagaacgc agcgaaatgc gataagtaat 240
gtgaattgca gaattcagtg aatcatcgaa tctttgaacg cacattgcgc ccgccggtat 300
tccggcgggc atgcctgtcc gagcgtcatt tcaccactca agcccagctt ggtgttgggg 360
cacccggccg cccggcggtc ggggccccca agtacatcgg cggtcctgct ggggctccga 420
gcgcagtaac acgcggtaaa acgcgccctc gctcggcggc ctcctcgggc ttccagccgc 480
taaaccccca gtgacgtttt tcgagttgac ctcggatcag gtaggaatac ccgctgaact 540
taagcatatc aataaggc 558

<210> SEQ ID NO 525
<211> LENGTH: 598
<212> TYPE: DNA
<213> ORGANISM: Sordariomycete sp.

<400> SEQUENCE: 525
tcttggtcat ttagaggaag taaaagtcgt aacaaggtct ccgttggtga accagcggag 60
ggatcattac cgagtttaca actcccaaac ccctgtgaac ataccaattg ttgcctcggc 120
ggatcagccc gctcccggta aaacggaacg gcccgccaga ggacccctaa actctgtttc 180
tatatgtaac ttctgagtaa aaccataaat aaatcaaaac tttcaacaac ggatctcttg 240
gttctggcat cgatgaagaa cgcagcaaaa tgcgataagt aatgtgaatt gcagaattca 300
gtgaatcatc gaatctttga acgcacattg cgcccgccag tattctggcg ggcatgcctg 360
ttcgagcgtc atttcaaccc tcaagccccc gggtttggtg ttggggatcg gcgagcctca 420
cggcaagccg gccccgaaat acagtggcgg tctcgctgca gcttccattg cgtagtagta 480
aaaccctcgc aactggtacg cggcgcggcc aagccgttaa acccccaact tctgaatgtt 540
gacctcggat caggtaggaa tacccgctga acttaagcat atcaataagg cggaggaa 598

<210> SEQ ID NO 526
<211> LENGTH: 597
<212> TYPE: DNA
<213> ORGANISM: Sordariomycete sp.

<400> SEQUENCE: 526
tcttggtcat ttagaggaag taaaagtcgt aacaaggtct ccgttggtga accagcggag 60
ggatcattac cgagtttaca actcccaaac ccctgtgaac ataccaattg ttgcctcggc 120
ggatcagccc gctcccggta aaacggaacg gcccgccaga ggacccctaa actctgtttc 180
tatatgtaac ttctgagtaa aaccataaat aaatcaaaac tttcaacaac ggatctcttg 240
gttctggcat cgatgaagaa cgcagcaaaa tgcgataagt aatgtgaatt gcagaattca 300
gtgaatcatc gaatctttga acgcacattg cgcccgccag tattctggcg ggcatgcctg 360
ttcgagcgtc atttcaaccc tcaagccccc gggtttggtg ttggggatcg gcgagcctca 420
cggcaagccg gccccgaaat acagtggcgg tctcgctgca gcttccattg cgtagtagta 480
aaaccctcgc aactggtacg cggcgcggcc aagccgttaa acccccaact tctgaatgtt 540
gacctcggat caggtaggaa tacccgctga acttaagcat atcaataagg cggagga 597

<210> SEQ ID NO 527
<211> LENGTH: 566
<212> TYPE: DNA
<213> ORGANISM: Fusarium nygamai

<400> SEQUENCE: 527
gtcagatagg tctcgttgtg acagcggagg gatcattacc gagtttacaa ctcccaaacc 60
cctgtgaaca tatcaattgt tgcctcggcg gatcagcccg ctcccggtaa aacggaacgg 120
cccgccagag gacccctaaa ctctgtttct atatgtaact tctgagtaaa accataaata 180
aatcaaaact ttcaacaacg gatctcttgg ttctggcatc gatgaagaac gcagcaaaat 240
gcgataagta atgtgaattg cagaattcag tgaatcatcg aatctttgaa cgcacattgc 300
gcccgccagt attctggcgg gcatgcctgt tcgagcgtca tttcaaccct caagcccccg 360
ggtttggtgt tggggatcgg cgagcctcac ggcaagccgg ccccgaaata cagtggcggt 420
ctcgctgcag cttccattgc gtagtagtaa aaccctcgca actggtacgc ggcgcggcca 480
agccgttaaa cccccaactt ctgaatgttg acctcggatc aggtaggaat acccgctgaa 540
cttaagcata tcaataagcg gaggaa 566

<210> SEQ ID NO 528
<211> LENGTH: 585
<212> TYPE: DNA
<213> ORGANISM: Ascomycete sp.

<400> SEQUENCE: 528
ttcctccgct tattgatatg cttaagttca gcgggtatcc ctacctgatc cgaggtcaaa 60
cgtggtaaat gttcttgatg gacgccagta caacgggcta cgatcgcaaa atgtgctgcg 120
ctcctaggcc aaagtgccgg ctgccaatga atttaaggcg agtcgtaata cgacaagacg 180
cccaacacca agcaaagctt gagggtacaa atgacgctcg aacaggcatg ccccatggaa 240
taccaagggg cgcaatgtgc gttcaaagat tcgatgattc actgaattct gcaattcaca 300

```
ctacttatcg catttcgctg cgttcttcat cgatgccaga accaagagat ccgttgttga    360

aagttgtaaa taattagatt attttcagac gctgattgca attacaaaaa aggttttggt    420

ttgtccaatc ggcagcttgc gccaccgagg aaacaagagt acgcaaaaga catggggtgt    480

agacgagagc tttacagccc ccgacttgac ttttgataat gatccttccg caggttcacc    540

tacggaaacc ttgttacgac ttttacttcc tctaaatgac caaga                    585


<210> SEQ ID NO 529
<211> LENGTH: 570
<212> TYPE: DNA
<213> ORGANISM: Fusarium sp.

<400> SEQUENCE: 529

aagtaaaagt cgtaaacaag gtctccgttg gtgaaccagc ggagggatca ttaccgagtt     60

atacaactca tcaaccctgt gaacatacct ataacgttgc ctcggcggga acagacggcc    120

ccgtaacacg ggccgccccc gccagaggac cccctaactc tgtttctata atgtttcttc    180

tgagtaaaca agcaaataaa ttaaaacttt caacaacgga tctcttggct ctggcatcga    240

tgaagaacgc agcgaaatgc gataagtaat gtgaattgca gaattcagtg aatcatcgaa    300

tctttgaacg cacattgcgc ccgccagtat tctggcgggc atgcctgttc gagcgtcatt    360

acaaccctca ggcccccggg cctggcgttg gggatcggcg gaagcccccct gcgggcacaa    420

cgccgtcccc caaatacagt ggcggtcccg ccgcagcttc cattgcgtag tagctaacac    480

ctcgcaactg gagagcggcg cggccacgcc gtaaaacacc caacttctga atgttgacct    540

cgaatcaggt aggaataccc gctgaactta                                     570


<210> SEQ ID NO 530
<211> LENGTH: 597
<212> TYPE: DNA
<213> ORGANISM: Sordariomycete sp.

<400> SEQUENCE: 530

tcttggtcat ttagaggaag taaaagtcgt aacaaggtct ccgttggtga accagcggag     60

ggatcattac cgagtttaca actcccaaac ccctgtgaac atatcaattg ttgcctcggc    120

ggatcagccc gctcccggta aaacggaacg gcccgccaga ggacccctaa actctgtttc    180

tatatgtaac ttctgagtaa aaccataaat aaatcaaaac tttcaacaac ggatctcttg    240

gttctggcat cgatgaagaa cgcagcaaaa tgcgataagt aatgtgaatt gcagaattca    300

gtgaatcatc gaatctttga acgcacattg cgcccgccag tattctggcg ggcatgcctg    360

ttcgagcgtc atttcaaccc tcaagccccc gggtttggtg ttggggatcg gcgagcctca    420

cggcaagccg gccccgaaat acagtggcgg tctcgctgca gcttccattg cgtagtagta    480

aaaccctcgc aactggtacg cggcgcggcc aagccgttaa acccccaact tctgaatgtt    540

gacctcggat caggtaggaa tacccgctga acttaagcat atcaataagc ggaggaa       597


<210> SEQ ID NO 531
<211> LENGTH: 555
<212> TYPE: DNA
<213> ORGANISM: Gaeumannomyces incrustans

<400> SEQUENCE: 531

tcttggtcat ttagaggaag taaaagtcgt aacaaggtct ccgttggtga accagcggag     60

ggatcattaa agagttgcaa aactccaacc cctgtgaact ttacctgtac gttgcttcgg    120
```

cggccgacgc cgcgcccagc cgggcctggg ggacgccgcc ggaggtttta aaccctgaat 180
tctagtgtat ctctgaggac gaaaaaaacc aattaaaact ttcaacaacg gatctcttgg 240
ctctggcatc gatgaagaac gcagcgaaat gcgataagta atgtgaattg cagaattcag 300
tgaatcatcg aatctttgaa cgcacattgc gcccgccggt attccggcgg gcatgcctgt 360
ccgagcgtca tttcaccact caagcccagc ttggtgttgg ggcacccggc cgcccggcgg 420
tcggggcccc caagtacatc ggcggtcctg ctggggctcc gagcgcagta acacgcggta 480
aaacgcgccc tcgctcggcg gcctcctcgg gcttccagcc gctaaacccc cagtgacgtt 540
tttcgagttg acctc 555

<210> SEQ ID NO 532
<211> LENGTH: 546
<212> TYPE: DNA
<213> ORGANISM: Gaeumannomyces incrustans

<400> SEQUENCE: 532
aactacctga tccgaggtca actcgaaaac gtcactgggg gtttagcggc tggaagcccg 60
aggaggccgc cgagcgaggg cgcgttttac cgcgtgttac tgcgctcgga gccccagcag 120
gaccgccgat gtacttgggg gccccgaccg ccgggcggcc gggtgcccca acaccaagct 180
gggcttgagt ggtgaaatga cgctcggaca ggcatgcccg ccggaatacc ggcgggcgca 240
atgtgcgttc aaagattcga tgattcactg aattctgcaa ttcacattac ttatcgcatt 300
tcgctgcgtt cttcatcgat gccagagcca agagatccgt tgttgaaagt tttaattggt 360
ttttttcgtc ctcagagata cactagaatt cagggtttaa aacctccggc ggcgtccccc 420
aggcccggct gggcgcggcg tcggccgccg aagcaacgta caggtaaagt tcacaggggt 480
tggagttttg caactcttta atgatccctc cgctggttca ccaacggaga ccttgttacg 540
actttt 546

<210> SEQ ID NO 533
<211> LENGTH: 570
<212> TYPE: DNA
<213> ORGANISM: Fusarium nygamai

<400> SEQUENCE: 533
wcggtaggtc tcgttggtga ccagcggagg gatcattacc gagtttacaa ctcccaaacc 60
cctgtgaaca taccaattgt tgcctcggcg gatcagcccg ctcccggtaa aacggaacgg 120
cccgccagag gacccctaaa ctctgtttct atatgtaact tctgagtaaa accataaata 180
aatcaaaact ttcaacaacg gatctcttgg ttctggcatc gatgaagaac gcagcaaaat 240
gcgataagta atgtgaattg cagaattcag tgaatcatcg aatctttgaa cgcacattgc 300
gcccgccagt attctggcgg gcatgcctgt tcgarcstca twtcaaccct caagcccccg 360
ggtttggtgt tggggatcgg cgagcctcam ggcaagccgg ccccgaaata cagtggcggt 420
ctcgctgcag cttccattgc gtagtagtaa aaccctcscr actggtacgc ggcgcggcca 480
agccgttaaa cccccaactt ctgaatgttg acctcggatc aggtaggaat ccaaacccgc 540
tgaacttaag catatcaata agcggaggaa 570

<210> SEQ ID NO 534
<211> LENGTH: 553
<212> TYPE: DNA
<213> ORGANISM: Fusarium nygamai

<400> SEQUENCE: 534

```
tggtgaccag cggagggatc attaccgagt ttacaactcc caaacccctg tgaacatacc     60

aattgttgcc tcggcggatc agcccgctcc cggtaaaacg gaacggcccg ccagaggacc    120

cctaaactct gtttctatat gtaacttctg agtaaaacca taaataaatc aaaactttca    180

acaacggatc tcttggttct ggcatcgatg aagaacgcag caaaatgcga taagtaatgt    240

gaattgcaga attcagtgaa tcatcgaatc tttgaacgca cattgcgccc gccagtattc    300

tggcgggcat gcctgttcga gcgtcatttc aaccctcaag cccccgggtt tggtgttggg    360

gatcggcgag cctcacggca agccggcccc gaaatacagt ggcggtctcg ctgcagcttc    420

cattgcgtag tagtaaaacc ctcgcaactg gtacgcggcg cggccaagcc gttaaacccc    480

caacttctga atgttgacct cggatcaggt aggaataccc gctgaactta agcatatcaa    540

taaggcggag gaa                                                       553


<210> SEQ ID NO 535
<211> LENGTH: 532
<212> TYPE: DNA
<213> ORGANISM: Magnaporthe rhizophila

<400> SEQUENCE: 535

gagggatcat taaagagttg caaaactcca acccctgtga actttacctg tacgttgctt     60

cggcggccga cgccgcgccc agccgggcct gggggacgcc gccggaggtt ttaaaccctg    120

aattctagtg tatctctgag gacgaaaata accaattaaa actttcaaca acggatctct    180

tggctctggc atcgatgaag aacgcagcga aatgcgataa gtaatgtgaa ttgcagaatt    240

cagtgaatca tcgaatcttt gaacgcacat tgcgcccgcc ggtattccgg cgggcatgcc    300

tgtccgagcg tcatttcacc actcaagccc agcttggtgt tggggcaccc ggccgcctgg    360

cggtcggggc ccccaagtac atcggcggtc ctgctggggc tccgagcgca gtaactcgcg    420

gtaaaacgcg ccctcgctcg gcggcctcct cgggcttcca gccgctaaac cccccagtgac    480

gtttttcgag ttgacctcgg atcaggtagg aatacccgct gaacttaagc at            532


<210> SEQ ID NO 536
<211> LENGTH: 547
<212> TYPE: DNA
<213> ORGANISM: Magnaporthe rhizophila

<400> SEQUENCE: 536

accagcggag ggatcattaa agagttgcaa aactccaacc cctgtgaact ttacctgtac     60

gttgcttcgg cggccgacgc cgcgcccagc cgggcctggg ggacgccgcc ggaggtttta    120

aaccctgaat tctagtgtat ctctgaggac gaaaataacc aattaaaact ttcaacaacg    180

gatctcttgg ctctggcatc gatgaagaac gcagcgaaat gcgataagta atgtgaattg    240

cagaattcag tgaatcatcg aatctttgaa cgcacattgc gcccgccggt attccggcgg    300

gcatgcctgt ccgagcgtca tttcaccact caagcccagc ttggtgttgg ggcacccggc    360

cgcctggcgg tcggggcccc caagtacatc ggcggtcctg ctggggctcc gagcgcagta    420

actcgcggta aaacgcgccc tcgctcggcg gcctcctcgg gcttccagcc gctaaacccc    480

cagtgacgtt tttcgagttg acctcggatc aggtaggaat acccgctgaa cttaagcata    540

tcaatag                                                              547


<210> SEQ ID NO 537
<211> LENGTH: 566
<212> TYPE: DNA
```

<213> ORGANISM: Diaporthe phaseolorum

<400> SEQUENCE: 537
agcggaggga tcattgctgg aacgcgccct aggcgcaccc agaaaccctt tgtgaactca 60
taccttactg ttgcctcggc gcaggccggc ccccccgggg gcccctcgga gacgaggagc 120
aggccggccg gtggcccagc caactcttgt ttttacaccg aaactctgag tacaaaacac 180
aaatgaatca aaactttcaa caacggatct cttggttctg gcatcgatga agaacgcagc 240
gaaatgcgat aagtaatgtg aattgcagaa ttcagtgaat catcgaatct ttgaacgcac 300
attgcgccct ctggtattcc ggagggcatg cctgttcgag cgtcatttca accctcaagc 360
ctggcttggt gttgggcccc tgcctgtcac agggcatggc ctgaaattca gtggcgagct 420
cgccaggacc ccgagcgcag tagttaaacc ctcgctccgg aaggccctgg cggtgccctg 480
ccgttaaacc cccaacttct gaaagtttga cctcggatca ggtaggaata cccgctgaac 540
ttaagcatat caataggccg gaggaa 566

<210> SEQ ID NO 538
<211> LENGTH: 619
<212> TYPE: DNA
<213> ORGANISM: Diaporthe phaseolorum

<400> SEQUENCE: 538
tcttggtcat ttagaggaag taaaagtcgt aacaaggtct ccgttggtga accagcggag 60
ggatcattgc tggaacgcgc cctaggcgca cccagaaacc ctttgtgaac tcatacctta 120
ctgttgcctc ggcgcaggcc ggcccccccg ggggcccctc ggagacgagg agcaggccgg 180
ccggtggccc agccaactct tgtttttaca ccgaaactct gagtacaaaa cacaaatgaa 240
tcaaaacttt caacaacgga tctcttggtt ctggcatcga tgaagaacgc agcgaaatgc 300
gataagtaat gtgaattgca gaattcagtg aatcatcgaa tctttgaacg cacattgcgc 360
cctctggtat tccggagggc atgcctgttc gagcgtcatt tcaaccctca agcctggctt 420
ggtgttgggc ccctgcctgt cacagggcat ggcctgaaat tcagtggcga gctcgccagg 480
accccgagcg cagtagttaa accctcgctc cggaaggccc tggcggtgcc ctgccgttaa 540
acccccaact tctgaaagtt tgacctcgga tcaggtagga atacccgctg aacttaagca 600
tatcaatagc cggaggaaa 619

<210> SEQ ID NO 539
<211> LENGTH: 606
<212> TYPE: DNA
<213> ORGANISM: Magnaporthe rhizophila

<400> SEQUENCE: 539
tggtcttttt gacgaagtaa aagttgtaac aaggtctccc gttggtgaac ccagcggagg 60
gatcattaaa gagttgcaaa actccaaccc ctgtgaactt tacctgtacg ttgcttcggc 120
ggccgacgcc gcgcccagcc gggcctgggg gacgccgccg gaggttttaa accctgaatt 180
ctagtgtatc tctgaggacg aaaataacca attaaaactt tcaacaacgg atctcttggc 240
tctggcatcg atgaagaacg cagcgaaatg cgataagtaa tgtgaattgc agaattcagt 300
gaatcatcga atctttgaac gcacattgcg cccgccggta ttccggcggg catgcctgtc 360
cgagcgtcat ttcaccactc aagcccagct tggtgttggg gcacccggcc gcctggcggt 420
cggggccccc aagtacatcg gcggtcctgc tggggctccg agcgcagtaa ctcgcggtaa 480
aacgcgccct cgctcggcgg cctcctcggg cttccagccg ctaaaccccc agtgacgttt 540
ttcgagttga cctcggatca ggtaggaata cccgctgaac ttaagcatat caataggccg 600
gaggaa 606

<210> SEQ ID NO 540
<211> LENGTH: 565
<212> TYPE: DNA
<213> ORGANISM: Magnaporthe rhizophila

<400> SEQUENCE: 540
tcgttggtga ccagcggagg gatcattaaa gagttgcaaa actccaaccc ctgtgaactt 60
tacctgtacg ttgcttcggc ggccgacgcc gcgcccagcc gggcctgggg gacgccgccg 120
gaggttttaa accctgaatt ctagtgtatc tctgaggacg aaaagaacca attaaaactt 180
tcaacaacgg atctcttggc tctggcatcg atgaagaacg cagcgaaatg cgataagtaa 240
tgtgaattgc agaattcagt gaatcatcga atctttgaac gcacattgcg cccgccggta 300
ttccggcggg catgcctgtc cgagcgtcat ttcaccactc aagcccagct tggtgttggg 360
gcacccggcc gcccggcggt cggggccccc aagtacatcg gcggtcccgc tggggctccg 420
agcgcagtaa ctcgcggtaa aacgcgccct cgctcggcgg cctcctcggg cttccagccg 480
ctgaaccccc agtgacgttt ttcgagttga cctcggatca ggtaggaata cccgctgaac 540
ttaagcatat caataagagg aggaa 565

<210> SEQ ID NO 541
<211> LENGTH: 545
<212> TYPE: DNA
<213> ORGANISM: Magnaporthe rhizophila

<400> SEQUENCE: 541
actgatcgag gtcagctcga agggcgtcgg tggacgggtt tagcggctgg aagcccgaag 60
aggccgccga gcgagggcgc gttttaccgc gtgctactgc gctcggagcc cccagcggga 120
ccgccgatgt acttgggggc cccgaccgcc aggcggccgg gtgccccaac accaagctgt 180
gcttgagtgg tgaaatgacg ctcggacagg catgcccgcc ggaataccgg cgggcgcaat 240
gtgcgttcaa agattcgatg attcactgaa ttctgcaatt cacattactt atcgcatttc 300
gctgcgttct tcatcgatgc cagaaccaag agatccgttg ttgaaagttt tgattgtttt 360
attcttttct cagagacaca ctagaattca gggtttcgaa cctccggcgg cgacctccag 420
gcccatctgg gcaccggcgc caaccgccga agcaacagta aaggtaaggt tcacaggggt 480
tggagttttg caactcttta atgatccctc cgctggttca ccaacggaga ccttgttacg 540
acttt 545

<210> SEQ ID NO 542
<211> LENGTH: 525
<212> TYPE: DNA
<213> ORGANISM: Magnaporthe rhizophila

<400> SEQUENCE: 542
cctactgatc cgaggtcaac tcgaaaaacg tcactggggg tttagcggct ggaagcccga 60
ggaggccgcc gagcgagggc gcgttttacc gcgagttact gcgctcggag ccccagcggg 120
accgccgatg tacttggggg ccccgaccgc cgggcggccg ggtgccccaa caccaagctg 180
ggcttgagtg gtgaaatgac gctcggacag gcatgcccgc cggaataccg gcgggcgcaa 240
tgtgcgttca aagattcgat gattcactga attctgcaat tcacattact tatcgcattt 300
cgctgcgttc ttcatcgatg ccagagccaa gagatccgtt gttgaaagtt ttaattggtt 360
attttcgtcc tcagagatac actagaattc agggtttatg acctccggcg gcgtcccccg 420
ggcccggctg ggcgcggcgt cggccgccga agcaacgtac aggtaaagtt cacaggggtt 480
ggagttttgc aactctttaa tgatccctcc gctggttcac caacg 525

<210> SEQ ID NO 543
<211> LENGTH: 528
<212> TYPE: DNA
<213> ORGANISM: Magnaporthe rhizophila

<400> SEQUENCE: 543
tcgttggtga ccagcggagg gatcattaaa gagttgcaaa actccaaccc ctgtgaactt 60
tacctgtacg ttgcttcggc ggccgacgcc gcgcccagcc gggcccgggg gacgccgccg 120
gaggtcataa accctgaatt ctagtgtatc tctgaggacg aaaataacca attaaaactt 180
tcaacaacgg atctcttggc tctggcatcg atgaagaacg cagcgaaatg cgataagtaa 240
tgtgaattgc agaattcagt gaatcatcga atctttgaac gcacattgcg cccgccggta 300
ttccggcggg catgcctgtc cgagcgtcat ttcaccactc aagcccagct tggtgttggg 360
gcacccggcc gcccggcggt cggggccccc aagtacatcg gcggtcccgc tggggctccg 420
agcgcagtaa ctcgcggtaa aacgcgccct cgctcggcgg cctcctcggg cttccagccg 480
ctaaaccccc agtgacgttt ttcgagttga cctcggatca ggtaggaa 528

<210> SEQ ID NO 544
<211> LENGTH: 557
<212> TYPE: DNA
<213> ORGANISM: Uncultured root-associated fungus

<400> SEQUENCE: 544
accagcggag ggatcattaa agagttgcaa aactccaacc cctgtgaact ttacctgtac 60
gttgcttcgg cggccgacgc cgcgcccagc cgggcctggg ggacgccgcc ggaggtttta 120
aaccctgaat tctagtgtat ctctgaggac gaaaaaaacc aattaaaact ttcaacaacg 180
gatctcttgg ctctggcatc gatgaagaac gcagcgaaat gcgataagta atgtgaattg 240
cagaattcag tgaatcatcg aatctttgaa cgcacattgc gcccgccggt attccggcgg 300
gcatgcctgt ccgagcgtca tttcaccact caagcccagc ttggtgttgg ggcacccggc 360
cgcccggcgg tcggggcccc caagtacatc ggcggtcctg ctggggctcc gagcgcagta 420
acacgcggta aaacgcgccc tcgctcggcg gcctcctcgg gcttccagcc gctaaacccc 480
cagtgacgtt tttcgagttg acctcggatc aggtaggaat acccgctgaa cttaagcata 540
tcaatagacg gaggaaa 557

<210> SEQ ID NO 545
<211> LENGTH: 556
<212> TYPE: DNA
<213> ORGANISM: Uncultured root-associated fungus

<400> SEQUENCE: 545
accagcggag ggatcattaa agagttgcaa aactccaacc cctgtgaact ttacctgtac 60
gttgcttcgg cggccgacgc cgcgcccagc cgggcctggg ggacgccgcc ggaggtttta 120
aaccctgaat tctagtgtat ctctgaggac gaaaaaaacc aattaaaact ttcaacaacg 180
gatctcttgg ctctggcatc gatgaagaac gcagcgaaat gcgataagta atgtgaattg 240
cagaattcag tgaatcatcg aatctttgaa cgcacattgc gcccgccggt attccggcgg 300
gcatgcctgt ccgagcgtca tttcaccact caagcccagc ttggtgttgg ggcacccggc 360
cgcctggcgg tcggggcccc caagtacatc ggcggtcctg ctggggctcc gagcgcagta 420
actcgcggta aaacgcgctc tcgctcggcg gcctcctcgg gcttccagcc gctaaacccc 480
cagtgacgtt tttcgagttg acctcggatc aggtaggaat acccgctgaa cttaagcata 540
tcaataaggc ggagga 556

<210> SEQ ID NO 546
<211> LENGTH: 577
<212> TYPE: DNA
<213> ORGANISM: Fusarium nygamai

<400> SEQUENCE: 546
ttcctccgct tattgatatg cttaagttca gcgggtattc ctacctgatc cgaggtcaac 60
attcagaagt tgggggttta acggcttggc cgcgccgcgt accagttgcg agggttttac 120
tactacgcaa tggaagctgc agcgagaccg ccactgtatt tcggggccgg cttgccgtga 180
ggctcgccga tccccaacac caaacccggg ggcttgaggg ttgaaatgac gctcgaacag 240
gcatgcccgc cagaatactg gcgggcgcaa tgtgcgttca aagattcgat gattcactga 300
attctgcaat tcacattact tatcgcattt tgctgcgttc ttcatcgatg ccagaaccaa 360
gagatccgtt gttgaaagtt ttgatttatt tatggtttta ctcagaagtt acatatagaa 420
acagagttta ggggtcctct ggcgggccgt tccgttttac cgggagcggg ctgatccgcc 480
gaggcaacaa ttggtatgtt cacaggggtt tgggagttgt aaactcggta atgatccctc 540
cgctggttca ccaacgggag accttgttac gactttt 577

<210> SEQ ID NO 547
<211> LENGTH: 585
<212> TYPE: DNA
<213> ORGANISM: Fusarium sp.

<400> SEQUENCE: 547
cttggtcatt tagaggaagt aaaagtcgta acaaggtctc cgttggtgaa ccagcggagg 60
gatcattacc gagtttacaa ctcccaaacc cctgtgaaca tacctatacg ttgcctcggc 120
ggatcagccc gcgccccgta aaacgggacg gcccgcccga ggacccctaa actctgtttt 180
tagtggaact tctgagtaaa acaaacaaat aaatcaaaac tttcaacaac ggatctcttg 240
gttctggcat cgatgaagaa cgcagcaaaa tgcgataagt aatgtgaatt gcagaattca 300
gtgaatcatc gaatctttga acgcacattg cgcccgccag tattctggcg ggcatgcctg 360
ttcgagcgtc atttcaaccc tcaagctcag cttggtgttg ggactcgcgg taacccgcgt 420
tccccaaatc gattggcggt cacgtcgagc ttccatagcg tagtaatcat acacctcgtt 480
actggtaatc gtcgcggcca cgccgtaaaa ccccaacttc tgaatgttga cctcggatca 540
ggtaggaata cccgctgaac ttaagcatat caataaggcg gagga 585

<210> SEQ ID NO 548
<211> LENGTH: 558
<212> TYPE: DNA
<213> ORGANISM: Magnaporthe rhizophila

<400> SEQUENCE: 548
tctcgttggt gaccagcgga gggatcatta aagagttgca aaactccaac ccctgtgaac 60
tttacctgta cgttgcttcg gcggccgacg ccgcgcccag ccgggcgtgg gggacgccgc 120
cggaggtttt aaaccctgaa ttctagtgta tctctgagga cgaaaagaac caattaaaac 180
tttcaacaac ggatctcttg gctctggcat cgatgaagaa cgcagcgaaa tgcgataagt 240
aatgtgaatt gcagaattca gtgaatcatc gaatctttga acgcacattg cgcccgccgg 300
tattccggcg ggcatgcctg tccgagcgtc atttcaccac tcaagcccag cttggtgttg 360
gggcacccgg ccgcccggcg gtcggggccc ccaagtacat cggcggtcct gctggggctc 420
cgagcgcagt aacacgcggt aaaacgcgcc ctcgctcggc ggcctcctcg ggcttccagc 480
cgctaaaccc ccagtgacgt ttttcgagtt gacctcggat caggtaggaa tacccgctga 540
acttaagcat atcaatag 558

<210> SEQ ID NO 549
<211> LENGTH: 572
<212> TYPE: DNA
<213> ORGANISM: Microdiplodia sp.

<400> SEQUENCE: 549
tttcctccgc ttattgatat gcttaagttc agcgggtatc cctacctgat ccgaggtcaa 60
agactaaagg ttgcttcgtg gacgcgaccc gcgcccctca agaaacgcaa tgtgctgcgc 120
gagaggaggc aaggaccact gccaatgaat ttggggcgag tccacgcgca gaggcgggac 180
agacgcccaa caccaagcag agcttgaggg tgtagatgac gctcgaacag gcatgcccca 240
tggaatacca aggggcgcaa tgtgcgttca aagattcgat gattcactga attctgcaat 300
tcacactact tatcgcattt cgctgcgttc ttcatcgatg ccagagccaa gagatccatt 360
gttgaaagtt gtaacgattg tttgtatcag aacaggtaat gctagatgca aaaaaaggtt 420
ttgtttgttc caacggcagg ttgccccacc gaaggagaac gaaaggtgct cgtaaaaaaa 480
ggattcagac gtgcggcgcg tgagggtgtt accccctacca cccgtgttat cgggggccgc 540
gaccgcagct ggtttgagat ggataatgat cc 572

<210> SEQ ID NO 550
<211> LENGTH: 917
<212> TYPE: DNA
<213> ORGANISM: Rhizopycnis sp.

<400> SEQUENCE: 550
ccgtagctca gtacgggaca gcttgaccgc caggtcaagg tgatccttcc gcgtaacact 60
tgccgaagcc ttagcagccc gaaagggtgc agttccgcga ctcaaagaaa ggaggactgc 120
tgaaatgcta gtctgcagaa gcaggcaaca ctatcaaatt gcgggaacac cctaaagacc 180
tcaacaccaa gcgtcatggg aaaccatggc gtggccgagc taatagccct gggtatggta 240
acagcttgag gtatgaagcc ttcacaagga ggccgaaatg ggcaatccgc agccaagtcc 300
taacgtgctc gaaaccgagt gccatggatg ctgttcacag gccaaatggt agtgggtgac 360
tcttgcgagt tgcttaagat atggtcgggc cccttcagaa atgtggggga taagcttacg 420
cttctccaaa ccgttccgta ggtgaacctg cggaaggatc attaacgatt tcggtgtaaa 480
aaaccgtttt ctacctatgt ctacgcgtac cacatgtttc ctcggggggc ttgcccccg 540 ctaggaccct ttatcaaacc tttttgtaat agcagtcagc gtctgatact aagttaatta 600
ttaaaacttt caacaatgga tctcttggtt ctggcatcga tgaagaacgc agcgaaatgc 660
gataagtagt gtgaattgca gaattcagtg aatcatcgaa tctttgaacg cacattgcgc 720
cccttggtat tccatggggc atgcctgttc gagcgtcatt tgaaccctca agctctgctt 780
ggtgttgggt gtttgtcccg ccattgcgcg tggactcgcc ttaaagcaat tggcagccat 840
gtaatccggc tttgagcgca gcacattgcg tactctctac tgggacatgg gcatccagaa 900
gccttatttt ttactct 917

<210> SEQ ID NO 551
<211> LENGTH: 585
<212> TYPE: DNA
<213> ORGANISM: Penicillium camemberti

<400> SEQUENCE: 551
tttcgtaggt gacctgcgga ggatcattac tgagtgaggg ccctctgggt ccaacctccc 60
acccgtgttt atttaccttg ttgcttcggc gggcccgcct taactggccg ccggggggct 120
tacgcccccg ggcccgcgcc cgccgaagac accctcgaac tctgtctgaa gattgtagtc 180
tgagtgaaaa tataaattat ttaaaacttt caacaacgga tctcttggtt ccggcatcga 240
tgaagaacgc agcgaaatgc gatacgtaat gtgaattgca aattcagtga atcatcgagt 300
ctttgaacgc acattgcgcc ccctggtatt ccggggggca tgcctgtccg agcgtcattg 360
ctgccctcaa gcacggcttg tgtgttgggc cccgtcctcc gattccgggg gacgggcccg 420
aaaggcagcg gcggcaccgc gtccggtcct cgagcgtatg gggctttgtc acccgctctg 480
taggcccggc cggcgcttgc cgatcaaccc aaatttttat ccaggttgac ctcggatcag 540
gtagggatac ccgctgaact taagcatatc aataaggcgg aggaa 585

<210> SEQ ID NO 552
<211> LENGTH: 557
<212> TYPE: DNA
<213> ORGANISM: Fusarium moniliformae

<400> SEQUENCE: 552
ctacctgatc cgaggtcaac attcagaagt tgggggttta acggcttggc cgcgccgcgt 60
accagttgcg agggttttac tactacgcaa tggaagctgc agcgagaccg ccactatatt 120
tcggggccgg cttgccgtga ggctcgccga tccccaacac caaacccgag ggcttgaggg 180
ttgaaatgac gctcgaacag gcatgcccgc cagaatactg gcgggcgcaa tgtgcgttca 240
aagattcgat gattcactga attctgcaat tcacattact tatcgcattt tgctgcgttc 300
ttcatcgatg ccagaaccaa gagatccgtt gttgaaagtt ttgatttatt tatggtttta 360
ctcagaagtt acatatagaa acagagttta ggggtcctct ggcgggccgt cccgttttac 420
cgggagcggg ctgatccgcc gaggcaacaa ttggtatgtt cacaggggtt tgggagttgt 480
aaactcggta atgatccctc cgctggttca ccaacggaga ccttgttacg acttttactt 540
cctctaaatg accaaga 557

<210> SEQ ID NO 553
<211> LENGTH: 933
<212> TYPE: DNA
<213> ORGANISM: Rhizopycnis sp.

<400> SEQUENCE: 553
cgtagctcag tacgggacag cttgaccgcc aggtcaaggt gatccttccg cgtaacactt 60
gccgaagcct tagcagcccg aaagggtgca gttccgcgac tcaaagaaag gaggactgct 120
gaaatgctag tctgcagaag caggcaacac tatcaaattg cgggaacacc ctaaagacct 180
caacaccaag cgtcatggga aaccatggcg tggccgagct aatagccctg ggtatggtaa 240
cagcttgagg tatgaagcct tcgcaaggag gccgaaatgg gcaatccgca gccaagtcct 300

-continued

```
aacgtgctcg aaaccgagtg ccatggatgc tgttcacagg ccaaatggta gtgggtgact    360
cttgcgagtt gcttaagata tggtcgggcc ccttcagaaa tgtgggggat aagcttacgc    420
ttctccaaac cgttccgtag gtgaacctgc ggaaggatca ttaacgattt cggtgtaaaa    480
aaccgttttc tacctatgtc tacgcgtacc acatgtttcc tcggggggct tgcccccccgc    540
taggaccctt tatcaaacct ttttgtaata gcagtcagcg tctgatacta agttaattat    600
taaaactttc aacaatggat ctcttggttc tggcatcgat gaagaacgca gcgaaatgcg    660
ataagtagtg tgaattgcag aattcagtga atcatcgaat ctttgaacgc acattgcgcc    720
ccttggtatt ccatggggca tgcctgttcg agcgtcattt gaaccctcaa gctctgcttg    780
gtgttgggtg tttgtcccgc cattgcgcgt ggactcgcct taaagcaatt ggcagccatg    840
taatccggct ttgagcgcag cacattgcgt actctctact gggacatggg catccagaag    900
ccttattttt tactcttgac ctcggatcag gta                                 933
```

<210> SEQ ID NO 554
<211> LENGTH: 604
<212> TYPE: DNA
<213> ORGANISM: Codinaeopsis sp.

<400> SEQUENCE: 554

```
tcttggtcat ttagaggaag taaaagtcgt aacaaggtct ccgttggtga accagcggag     60
ggatcattac aggactcgca agactcccgt aaaccactgt gaacttacct acaacccgtt    120
gcctcggcgg gtgctccggg cgcgtcttcg ggcgctccgg ggcgctccag cccgccggcg    180
gcccctaaac tctgtctctg taacgttggc atctccgagc agactataaa cgagtcaaaa    240
ctttcaacaa cggatctctt ggttctggca tcgatgaaga acgcagcgaa atgcgataag    300
taatgtgaat tgcagaattc agtgaatcat cgaatctttg aacgcacatt gcgcccgcca    360
gcactctggc gggcatgcct gtccgagcgt catttcaacc ctcaggcccc gcctggcgtt    420
ggagccctgc gcagcgcagg ctcccaaaga cagcggcggg cgcgccccgg aaccgagcgc    480
agtaatgctt tctcgttctg gtccggcgcg cgctccggcc gtaaaacccc caactttcta    540
agtggttgac ctcggatcag gtaggaatac ccgctgaact taagcatatc aataagcgga    600
ggaa                                                                 604
```

<210> SEQ ID NO 555
<211> LENGTH: 560
<212> TYPE: DNA
<213> ORGANISM: Uncultured root-associated fungus

<400> SEQUENCE: 555

```
ggtgaccagc ggagggatca ttaaagagtt gcaaaactcc aacccctgtg aactttacct     60
gtacgttgct tcggcggccg acgccgcgcc cagccgggcc tgggggacgc cgccggaggt    120
tttaaaccct gaattctagt gtatctctga ggacgaaaaa aaccaattaa aactttcaac    180
aacggatctc ttggctctgg catcgatgaa gaacgcagcg aaatgcgata agtaatgtga    240
attgcagaat tcagtgaatc atcgaatctt tgaacgcaca ttgcgcccgc cggtattccg    300
gcgggcatgc ctgtccgagc gtcatttcac cactcaagcc cagcttggtg ttggggcacc    360
```

-continued

```
cggccgcccg gcggtcgggg cccccaagta catcggcggt cctgctgggg ctccgagcgc    420

agtaacacgc ggtaaaacgc gccctcgctc ggcggcctcc tcgggcttcc agccgctaaa    480

cccccagtga cgtttttcga gttgacctcg gatcaggtag gaatacccgc tgaacttaag    540

catatcaata agcggaggaa                                                560
```

GRASS FUNGAL ENDOPHYTES AND USES THEREOF

CROSS-REFERENCE TO RELATED APPLICATIONS

This application claims the priority of U.S. Provisional Application No. 61/419,242, filed Dec. 2, 2010, the entire disclosure of which is incorporated herein by reference.

STATEMENT REGARDING FEDERALLY SPONSORED RESEARCH OR DEVELOPMENT

This invention was made with government support under grant number DE-AC05-00OR22725 awarded by the U.S. Department of Energy. The United States government has certain rights in the invention.

INCORPORATION OF SEQUENCE LISTING

The Sequence Listing, which is a part of the present disclosure, includes a computer readable 473 KB file entitled "NBLE076US_ST25.txt" comprising nucleotide and/or amino acid sequences of the present invention submitted via EFS-Web. The subject matter of the Sequence Listing is incorporated herein by reference in its entirety.

BACKGROUND OF THE INVENTION

1. Field of the Invention

The invention relates to fungal endophytes of host plants, such as grass plants. In particular, the invention relates to prairie grass endophytes and combinations of these endophytes with agronomically elite grass plants.

2. Description of the Related Art

Endophytes are fungal or bacterial organisms that live within plants. Fungal endophytes, such as mycorrhiza, survive within various host plant tissues, often colonizing the intercellular spaces of host leaves, stems, flowers or roots. The symbiotic endophyte-host relationships can provide several fitness benefits to the host plant, such as enhancement of nutrition, increased drought tolerance and/or chemical defense from potential herbivores and often enhanced biomass production. Root-colonizing mycorrhizae survive on photosynthetic carbohydrates from the plant, and in return, aid in the solublization and uptake of water and minerals to the host, which can lead to the promotion of seed germination and plant growth. Additionally, the association of a fungal endophyte with a host plant often provides protection from pathogens or tolerance to a variety of biotic and abiotic stresses, such as insect infestation, grazing, water or nutrient deficiency, heat stress, salt or aluminum toxicity, and freezing temperatures. Host growth and fitness promotion and protection are thought to be achieved through multiple beneficial properties of the endophyte-host association. For instance, the endophytic organisms may produce growth-regulating substances to induce biomass production and alkaloids or other metabolites that have anti-insect and anti-herbivore properties. Additionally, fungal endophytes may directly suppress or compete with disease-causing microbes, protecting the plant from potential pathogens.

SUMMARY OF THE INVENTION

In a first embodiment, the invention provides an isolated fungal endophyte that has been initially identified from a prairie grass species. For example, the isolated endophyte may be selected from those provided in Table 2 or may be defined as comprising a ribosomal DNA (rDNA) sequence comprising one of the sequences of SEQ ID NOs: 1-555.

In a further embodiment, the invention provides a synthetic combination of a grass plant and a fungal endophyte provided herein. In one embodiment, the endophyte comprises a rDNA sequence selected from the group consisting of SEQ ID NOs: 1-555. In certain aspects, the fungal endophyte may primarily colonize a root or stem tissue of the plant. In further aspects, the synthetic combination may comprise two or more different fungal endophytes. For example, a grass plant may comprise at least a first fungal endophyte that colonizes a root tissue and at least a first fungal endophyte that colonizes a stem tissue. In some aspects, a grass plant comprises two, three, four, five, six, or more different endophytes, such as bacterial endophytes or fungal endophytes, including one or more of those provided in Table 2.

In certain embodiments, a synthetic combination according to the invention comprises an agronomically elite grass plant and a fungal endophyte. For example, the grass plant may comprise one or more agronomically elite traits, such as drought resistance, insect resistance, fungus resistance, virus resistance, bacteria resistance, cold tolerance, salt tolerance, increased yield, enhanced nutrient use efficiency, increased fermentable carbohydrate content, reduced lignin content, or resistance to biotic or abiotic stress. In certain aspects, the grass plant may comprise a transgene, such as a transgene that confers an agronomic trait. For example, a transgene may confer herbicide tolerance, drought resistance, insect resistance, fungus resistance, virus resistance, bacteria resistance, male sterility, cold tolerance, salt tolerance, increased yield, enhanced nutrient use efficiency, increased fermentable carbohydrate content, or reduced lignin content. Grass plants that may be used in the synthetic endophyte combinations according to the invention include, but are not limited to, switchgrass (*Panicum virgatum*), wheat, durum wheat, tall wheatgrass, western wheatgrass, maize, rice, sorghum, meadow fescue, tall fescue, cereal rye, Russian wild rye, oats, bermudagrass, Kentucky bluegrass, big bluestem, little bluestem, *Miscanthus* sp., *Miscanthus*×*giganteus*, blue grama, black grama, side-oat grama, johnsongrass, buffalograss, creeping bentgrass, or sugarcane. In certain aspects, the host plant is a forage grass host plant. In one embodiment, the host plant is switchgrass (*Panicum virgatum*).

In some further embodiments, combinations of grass plants and fungal endophytes according to the invention display increased biomass, enhanced drought tolerance, increased nitrogen use efficiency, increased phosphorus utilization, disease resistance, and/or increased vigor relative to a host grass plant of the same genotype that lacks the endophyte, when grown under the same conditions. In another aspect, the endophyte protects the host grass plant from biotic stresses such as insect infestation, nematode infestation, and herbivore grazing, and/or abiotic stresses, such as water deficiency, nutrient deficiency, heat stress, fungal infection, salt toxicity, aluminum toxicity, heavy metal toxicity, and freezing temperatures.

In certain embodiments, the host grass plant is artificially inoculated with the endophyte. The endophyte-host combination may be achieved, for example, by introduction of the endophyte to the host grass plant by a method selected from the group consisting of: inoculation, infection, grafting, and combinations thereof.

In a yet another embodiment, the invention provides a seed comprising a grass plant embryo and a fungal endophyte (e.g., an endophyte comprising a rDNA sequence selected from the group consisting of SEQ ID NOs: 1-555). In certain aspects, a fungal endophyte according to the invention is provided into or onto the exterior of the seed. In still yet another aspect, the invention relates to a method for propagating a host grass plant-fungal endophyte combination comprising: a) obtaining a synthetic combination of a fungal endophyte and a host grass plant, and b) vegetatively reproducing the host grass plant tissue colonized by the endophyte.

In still yet another embodiment, the invention provides a method for cultivating a host grass plant comprising: contacting the host grass plant or a seed (or other propagating material) that produces the plant with a fungal endophyte, such that the endophyte colonizes the plant. In one aspect, colonization of the host grass is achieved by a method selected from the group consisting of: inoculation, infection, grafting, and combinations thereof. In another aspect, the host grass plant has enhanced root growth, more tillers, enhanced total biomass, or enhanced seed yield relative to a host grass plant of the same genotype that lacks the endophyte, when grown under the same conditions. In yet other aspects, the host grass plant displays tolerance to stress as relative to a host grass plant of the same genotype that lacks the endophyte, when grown under the same conditions. The stress may be selected from the group consisting of a biotic stress, a pest stress, an insect stress, an abiotic stress, and a water deficit stress. In one embodiment, the stress may be biotic stress caused by at least one organism selected from the group consisting of a mammalian or insect herbivore, or a microbial pathogen (e.g., nematode, fungus, bacteria, or virus). In a further aspect, the stress is abiotic stress selected from the group consisting of: water deficiency, nutrient deficiency, heat stress, salt toxicity, aluminum toxicity, heavy metal toxicity, and freezing temperatures.

In still yet another embodiment, the invention provides a method for cultivating a host grass plant comprising: contacting the host grass plant or a seed thereof with a filtrate of a cultured fungal endophyte strain, wherein the plant has enhanced root growth, more tillers, enhanced total biomass, or enhanced seed yield or germination relative to a host grass plant of the same genotype that lacks the filtrate, when grown under the same conditions. In one aspect, the host grass plant displays tolerance to stress relative to a host grass plant of the same genotype that lacks the endophyte, when grown under the same conditions, wherein the stress is selected from the group consisting of a biotic stress, a pest stress, an insect stress, an abiotic stress, and a water deficit stress.

In another embodiment, the invention relates to a method for increasing the biomass of a plant or increasing the fermentable biomass of a plant comprising: contacting the host grass plant with an endophyte provided herein, such that the endophyte colonizes the plant, wherein the plant exhibits increased biomass relative to a host grass plant of the same genotype that lacks the endophyte, when grown under the same conditions.

In a further embodiment, the invention provides a commodity product obtained from a plant comprising a synthetic combination of the invention, such as comprising an endophyte with a rDNA sequence selected from the group consisting of SEQ ID NOs: 1-555. For example, a commodity product may be an animal feed, a biofuel (e.g., ethanol or biodiesel), a paper or paper pulp, silage, or a fermentable biofuel feedstock. In certain aspects, the invention provides an isolated nucleic acid molecule comprising a sequence selected from the group consisting of SEQ ID NOs: 1-555.

In still a further embodiment, there is provided a method for the manufacture of a commercial product comprising obtaining a grass plant or grass plant part comprising a fungal endophyte according to the invention and producing a commercial product therefrom. For example, a plant or plant part described herein can be manufactured into a product such as paper, paper pulp, ethanol, biodiesel, silage, animal feed, or fermentable biofuel feedstock.

In yet another embodiment, the invention provides a method of producing ethanol comprising: (a) obtaining a grass plant comprising a fungal endophyte according to the invention; (b) treating tissue from the plant to render carbohydrates in the tissue fermentable; and (c) fermenting the carbohydrates to produce ethanol.

In yet another embodiment, the invention provides a method for processing lignocellulosic biomass from a plant or plant part described herein. In one embodiment, the method for processing lignocellulosic biomass from a plant or plant part may comprise acid and/or enzymatic treatment(s). The enzymatic treatment(s) may comprise treatment with one or more cellulolytic enzymes, such as a cellulase. In another embodiment, the method comprises an acid treatment prior to or during a treatment to render carbohydrates in the plant fermentable. In yet another embodiment, no acid treatment is performed.

The use of the word "a" or "an" when used in conjunction with the term "comprising" in the claims and/or the specification may mean "one," but it is also consistent with the meaning of "one or more," "at least one," and "one or more than one."

Other objects, features, and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

Endophytic fungi are ubiquitous in nature, infecting virtually all plants in both natural and agronomic ecosystems. Provided herein are endophytic fungi initially identified from switchgrass and having utility for improving the phenotype of a grass plant. Given the constraints involved in producing a bioenergy crop, for example, these beneficial endophytes can be used to maximize the sustainability and minimize the economic cost of growing biofuel crops, such as switchgrass. Novel combinations of fungal endophytes with grasses can be used to enhance agronomic characteristics of grass, such as nutrient use efficiency and stress tolerance, as well as to increase yield. Combining grass species with fungal endophytes thus represents a technique that can be used in parallel with plant breeding and transgenic technologies to improve yield from grass crops and reduce the cost of cellulosic biofuel production.

Thus, in one aspect, the invention provides a combination (also termed a "symbiotum") of a host plant and an endophyte that allows for improved agronomic properties of host plants. The combination may be achieved by artificial inoculation, application, or other infection of a host plant, such as a grass plant, or host plant tissues, with a fungal endophyte strain of the present invention. Thus, a combination achieved by such an inoculation is termed a "synthetic" combination. The fungal endophyte may be present in intercellular spaces within plant tissue, such as the root. Its presence may also occur or may also be maintained within a grass plant or plant population by means of grafting or other inoculation methods.

These endophytes may also be introduced or maintained by such procedures, into various grasses, such as switchgrass, wheat (*Triticum aestivum*), durum wheat (*Triticum turgidum* ssp. durum), tall wheatgrass (*Thinopyrum ponticum*), western wheatgrass (*Pascopyrum smithii*), maize (*Zea mays*), rice (*Oyrza sativa*), sorghum (*Sorghum bicolor*), meadow fescue (*Festuca pratensis*), tall fescue (*Festuca arundinacea*), cereal rye (*Secale cereale*), Russian wild rye (*Psathyrostachys juncea*), oats (*Avena sativa*), bermudagrass (*Cynodon dactylon*), Kentucky bluegrass (*Poa pratensis*), big bluestem (*Andropogon gerardii*), little bluestem (*Schizachyrium scoparium*), blue grama (*Bouteloua gracilis*), black grama (*Bouteloua eriopoda*), side-oat grama (*Bouteloua curtipendula*), johnsongrass (*Sorghum halepense*), buffalograss (*Buchloe dactyloides*), and creeping bentgrass (*Agrostis stolonifera*). In one embodiment, the host plant is defined as a monocot. In an additional embodiment, the host plant is a forage grass host plant or a cereal. In a particular embodiment, the host plant is a grass host plant such as switchgrass (*Panicum virgatum*).

Endophytes for use according to the invention include any of those provided in Table 2 below. For example, the endophyte may be an endophyte of the Hypocreales order, such as the clavicipitaceous, seed-borne Neotyphodium endophytes, *Fusarium* spp. or *Acremonium* spp. Thus, a combination according to the invention may comprise a grass plant and one of the *Acremonium strictum* endophytes represented Table 2.

In certain embodiments, the agronomic qualities for improvement may be selected from the group consisting of: increased biomass, increased tillering, increased root mass, increased flowering, increased seed yield, and enhanced resistance to biotic and/or abiotic stresses, each of these qualities being rated in relation to plants of the same genotype grown under the same conditions, and differing only with respect to the presence or absence of a fungal endophyte. The stresses may include, for instance, drought (water deficit), cold, heat stress, nutrient deficiency, salt toxicity, aluminum toxicity, heavy metal toxicity, grazing by herbivores, insect infestation, nematode infection, and fungal infection, among others. In a particular embodiment, the enhanced resistance is provided by the endophyte and protects the host plant from subsequent infection by other fungal diseases, such as root rot, powdery mildew, *Fusarium* blight, *Pythium* blight, leaf spot, rust, and snow mold, among others. This resistance may allow for improved biomass or seed yield relative, for instance, to grass plants not colonized by an endophyte. In another embodiment, the invention may be defined as a grass plant seed in combination with an endophyte strain or coated with a fungal endophyte strain of the present invention.

The invention also relates to methods for protecting grass plants from biotic or abiotic stress, by means of introducing an endophyte strain of the present invention into a grass plant, and propagating the plant-endophyte combination by vegetative means. Vegetative propagation of the plant allows for propagation of the combination, since fungal propagules (e.g., mycelia, conidia, and chlamydospores) are present in or on plant tissue, or may infect the plant tissue.

The invention also provides methods for detecting the presence of a fungal endophyte of the present invention within a host plant. This may be accomplished, for instance, by isolation of total DNA from tissues of a potential plant-endophyte combination, followed by PCR, or alternatively, Southern blotting, western blotting, or other methods known in the art, to detect the presence of specific nucleic or amino acid sequences associated with the presence of a fungal endophyte strain of the present invention (Selosse et al. 2007). Alternatively, biochemical methods such as ELISA, HPLC, TLC, or fungal metabolite assays may be utilized to determine the presence of an endophyte strain of the present invention in a given sample of grass plant tissue. Additionally, methods for identification may include microscopic analysis, such as root staining, or culturing methods, such as grow out tests or other methods known in the art (Deshmukh et al. 2006). In particular embodiments, the roots of a potential grass plant-endophyte combination may be stained with fungal specific stains, such as WGA-Alexa 488, and microscopically assayed to determine fungal root associates, as described below.

DEFINITIONS

Agronomically elite plants: Refers to a genotype or cultivar with a phenotype adapted for commercial cultivation. Traits comprised by an agronomically elite plant may include biomass, carbohydrate, and/or seed yield; biotic or abiotic stress resistance, including drought resistance, insect resistance, fungus resistance, virus resistance, bacteria resistance, cold tolerance, and salt tolerance; improved standability, enhanced nutrient use efficiency, and reduced lignin content.

Biofuel crop species: A plant that may be used to provide biomass for production of lignocellulosic-derived ethanol. Examples of such plants include switchgrass (*Panicum virgatum*), giant reed (*Arundo donax*), reed canarygrass (*Phalaris arundinacea*), *Miscanthus×giganteus, Miscanthus* sp., sericea lespedeza (*Lespedeza cuneata*), corn, sugarcane, sorghum, millet, ryegrass (*Lolium multiflorum, Lolium* sp.), timothy, *Kochia* (*Kochia scoparia*), sunn hemp, kenaf, bahiagrass, bermudagrass, dallisgrass, pangolagrass, big bluestem, indiangrass, fescue (*Festuca* sp.), *Dactylis* sp., *Brachypodium distachyon*, smooth bromegrass, orchardgrass, Kentucky bluegrass, and fonio (*Digitaria* sp.), among others.

Biomass: The total mass or weight, at a given time, of a plant or population of plants, usually given as weight per unit area. The term may also refer to all the plants or species in the community (community biomass).

Culture filtrate: Broth or media obtained from cultures inoculated with a strain of fungi and allowed to grow. The media is typically filtered to remove any suspended cells, leaving the nutrients, hormones, or other chemicals.

Endophyte: An organism capable of living within a plant cell. An endophyte may refer to a fungal organism that may confer an increase in yield, biomass, resistance, or fitness in its host plant. Fungal endophytes may occupy the intracellular or extracellular spaces of plant tissue, including the leaves, stems, flowers, or roots.

Genotype: The genetic constitution of a cell or organism.

Host plant: Any plant which an endophytic fungi colonizes.

Increased yield: An increase in biomass or seed weight, seed size, seed number per plant, seed number per unit area, bushels per acre, tons per acre, kilo per hectare, or carbohydrate yield.

Phenotype: The detectable characteristics of a cell or organism, which characteristics are the manifestation of gene expression.

Regeneration: The process of growing a plant from a plant cell (e.g., plant protoplast, callus, or explant).

Synthetic combination: A combination (also termed a "symbiotum") of a host plant and an endophyte. The combination may be achieved, for example, by artificial inoculation, application, or other infection of a host plant, such as a grass plant, or host plant tissues with an endophyte.

Transgene: A segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Isolation of Wild Grass Endophytes

Plant samples were collected from Alfalfa, Grant, Kay, and Osage counties of Northern Oklahoma. The sampling points were located between the GPS coordinates of 36°38'38" to 36°48'48" N latitude and 96°10'26" to 08°16'11" W longitude (Table 1). This region has a sub-humid continental climate, with a mean annual temperature of 15° C. and a growing season of 177 to 220 days. Mean annual precipitation ranges from 76 to 112 cm, of which more than 70% usually falls in April through October (USDA 1985; USDA 2007a; USDA 2007b; USDA 2008). Although all four counties studied are part of the North American tallgrass prairie, sampling sites from Alfalfa, Grant, and Kay counties were from quite diverse habitats (e.g., grassland, pasture, lake shores, salt plains, or marshy land). Conversely, those from Osage county were predominantly composed of natural grassland from the Tallgrass Prairie Preserve (TGPP). Since 1989, the Nature Conservancy has owned and managed the TGPP by recreating a semi-natural grazing and disturbance regime with bison herds and a stochastic fire regime (Hamilton 1996). In addition to habitat differences, Alfalfa, Grant, and the western part of Kay counties receive significantly lower average annual precipitation than Osage county (82 cm versus 112 cm). Sampling sites from Alfalfa, Grant, and Kay counties are henceforth referred to as the west part and those from Osage county are referred to as the east part of the study area.

TABLE 1

Sample collection sites.

| Location | Coordinates | |
|---|---|---|
| ID | Lat. | Lon. |
| E1 | 36.38.38 | 96.23.47 |
| E2 | 36.38.39 | 96.23.50 |
| E3 | 36.38.39 | 96.23.47 |
| E4 | 36.38.40 | 96.23.52 |
| E5 | 36.41.39 | 96.20.02 |
| E6 | 36.41.40 | 96.20.01 |
| E7 | 36.41.40 | 96.20.02 |
| E8 | 36.41.41 | 96.20.00 |
| E9 | 36.44.11 | 96.11.13 |
| E10 | 36.44.12 | 96.11.12 |
| E11 | 36.44.13 | 96.11.11 |
| E12 | 36.44.16 | 96.11.12 |
| E13 | 36.44.31 | 96.21.50 |
| E14 | 36.44.32 | 96.21.50 |
| E15 | 36.44.32 | 96.21.49 |
| E16 | 36.44.33 | 96.21.49 |
| E17 | 36.45.10 | 96.21.47 |
| E18 | 36.45.10 | 96.21.46 |
| E19 | 36.45.10 | 96.21.46 |
| E20 | 36.45.10 | 96.21.47 |
| E21 | 36.45.23 | 96.22.56 |
| E22 | 36.45.24 | 96.22.56 |
| E23 | 36.45.24 | 96.22.56 |
| E24 | 36.45.25 | 96.22.56 |
| E25 | 36.45.45 | 96.10.27 |
| E26 | 36.45.45 | 96.10.29 |
| E27 | 36.45.45 | 96.10.26 |
| E28 | 36.45.47 | 96.10.26 |
| E29 | 36.45.48 | 96.10.26 |
| E30 | 36.46.08 | 96.23.24 |
| E31 | 36.46.08 | 96.23.26 |
| E32 | 36.46.08 | 96.23.26 |
| E33 | 36.46.09 | 96.23.24 |
| E34 | 36.47.10 | 96.23.49 |
| E35 | 36.47.10 | 96.23.49 |
| E36 | 36.47.10 | 96.23.48 |
| E37 | 36.47.11 | 96.23.49 |
| E38 | 36.47.56 | 96.24.48 |
| E39 | 36.47.56 | 96.24.48 |
| E40 | 36.47.57 | 96.24.48 |
| E41 | 36.47.57 | 96.24.48 |
| E42 | 36.48.39 | 96.26.03 |
| E43 | 36.48.39 | 96.26.03 |
| E44 | 36.48.39 | 96.26.02 |
| E45 | 36.48.40 | 96.26.02 |
| E46 | 36.48.48 | 96.26.22 |
| E47 | 36.48.48 | 96.26.23 |
| E48 | 36.48.48 | 96.26.23 |
| W1 | 36.48.44 | 97.18.15 |
| W2 | 36.48.44 | 97.18.15 |
| W3 | 36.48.44 | 97.18.13 |
| W4 | 36.48.40 | 97.27.14 |
| W5 | 36.48.40 | 97.27.14 |
| W6 | 36.48.37 | 97.31.34 |
| W7 | 36.48.37 | 97.31.37 |
| W8 | 36.48.37 | 97.31.40 |
| W9 | 36.48.42 | 97.40.41 |
| W10 | 36.48.41 | 98.01.19 |
| W11 | 36.48.46 | 97.40.41 |
| W12 | 36.48.41 | 98.01.19 |
| W13 | 36.48.42 | 98.01.18 |
| W14 | 36.48.41 | 98.01.15 |
| W15 | 36.48.38 | 98.04.59 |
| W16 | 36.48.36 | 98.05.00 |
| W17 | 36.48.36 | 98.05.01 |
| W18 | 36.45.01 | 98.09.42 |
| W19 | 36.45.04 | 98.09.44 |
| W20 | 36.45.04 | 98.07.45 |
| W21 | 36.45.06 | 98.07.43 |
| W22 | 36.45.06 | 98.07.44 |
| W23 | 36.41.04 | 98.12.09 |
| W24 | 36.41.04 | 98.12.10 |
| W25 | 36.40.51 | 98.14.07 |
| W26 | 36.40.52 | 98.14.08 |

TABLE 1-continued

| Sample collection sites. | | |
|---|---|---|
| Location | Coordinates | |
| ID | Lat. | Lon. |
| W27 | 36.40.52 | 98.14.08 |
| W28 | 36.42.35 | 98.16.10 |
| W29 | 36.42.34 | 98.16.11 |
| W30 | 36.42.34 | 98.16.11 |
| W31 | 36.42.28 | 98.16.10 |
| W32 | 36.42.25 | 98.16.10 |
| W33 | 36.42.22 | 98.16.08 |
| W34 | 36.42.23 | 98.16.11 |
| W35 | 36.42.22 | 98.16.08 |

Plant samples were collected during early vegetative, full reproductive, and senescence stages of switchgrass growth in the months of April, July, and October of 2009, respectively. Each sampling consisted of up to 83 whole plant samples (5 to 10 tillers per sample) from different parts of the tallgrass prairie that included at least 35 samples each from the east and west. GPS coordinates were recorded for each sampling site in the April sampling, and the same general coordinates (within the same field) were used for subsequent samplings. More than 210 total plant samples were collected and all samples were processed for shoot and root inhabiting endophytic fungal communities. Twenty-four representative soil samples from these GPS locations, 12 each from the east and west parts of prairie were collected and analyzed for pH, organic matter, phosphorus, potassium, calcium, magnesium, and sodium content.

Collected plants with approximately 25-35 cm of both above- and below-ground tissues were transported to the laboratory on ice and processed within 24 h of collection. Each plant sample was divided into two parts. The roots from the first half were harvested immediately for endophyte isolation, while the second half was cut back at 10-12 cm above ground level, transplanted into 3.8 L containers with Metromix 350 and maintained in the greenhouse for six weeks prior to endophyte isolation from shoot tissues. This was done to minimize excessive saprophytic fungal contamination.

Processing of the root tissues involved thorough rinsing of multiple roots (5-10/plant), with tap water to remove excess soil. The basal portion of shoots was collected from the plants maintained in the greenhouse. Root and shoot samples were cut into 3-4 cm pieces prior to rigorous surface sterilization (95% ethanol for 30 s, 70% ethanol for 5 min followed by 3% sodium hypochlorite for 25-30 min). Surface sterilized tissue were rinsed three times with sterile water, blot dried, cut into small pieces (1-1.5 cm) and plated on PDA plates amended with 100 ppm ampicillin sodium salt, 50 ppm chloramphenicol, and 50 ppm streptomycin sulfate. Plates were incubated in the dark for up to two months at 24° C. and examined regularly for emerging fungal colonies. Emerging fungal colonies were passed through two rounds of subculture prior to preparing agar slants for long-term storage and collecting fungal materials for DNA extraction.

Example 2

Characterization of Isolated Endophytes

Fungal material for DNA extraction was harvested from 1 to 2 week-old cultures grown on potato dextrose agar (PDA) by cutting an agar block of 1.5 $cm^3$. Agar blocks were placed in a 1.5 ml micro-tube with a single 4.5 mm stainless steel bead. These micro-tubes were arranged in a rack and covered with an AirPore® filter, stored at −80° C. overnight and lyophilized for 24 h. The DNA was extracted from lyophilized tissue using QIAGEN MagAttract® 96 DNA Plant Core Kit according to the manufacturer's instructions.

The internal transcribed spacer (ITS) regions of fungal ribosomal DNA (rDNA) are highly variable in sequence, and thus of great importance in distinguishing fungal species (White et al. 1990). The fungal-specific primers ITS 1F and ITS4, amplifying the highly variable ITS 1 and ITS2 sequences surrounding the 5.8S-coding sequences, were used in this study. These primer sets have been used widely (Gardes & Bruns 1993; Martin & Rygiewicz 2005) and are thus well represented in the NCBI nucleotide database. PCR primers were used to sequence the purified PCR products as described previously (Puckette et al. 2009). Gene sequences were manually inspected, edited, and appended into contigs using DNA sequence assembly software Sequencher® version 4.9 (Gene Code Corporation, Ann Arbor, Michigan). Test sequences were compared to the NCBI fungal database and the top three hits with ≥99% sequence similarities were used to determine the identity of test isolates to the deepest possible taxonomic resolution.

TABLE 2

| Identification of fungal endophytes by rDNA sequence. | | | | |
|---|---|---|---|---|
| SEQ ID NO | Isolate ID | Location* | Plant Part | Initial ID/(Accession No.) |
| 1 | April09_Shoot_13ES1 | W13 | Shoot | *Fusarium nygamai* (X94174) |
| 2 | April09_Shoot_18ES1 | E18 | Shoot | *Emericellopsis terricola* (FJ430737) |
| 3 | April09_Shoot_18ES2 | E18 | Shoot | *Cladosporium colombiae* (FJ936159) |
| 4 | April09_Shoot_19ES2 | E18 | Shoot | Uncultured Ascomycete sp. (EU489902) |
| 5 | April09_Shoot_1WS1 | W14 | Shoot | *Phoma glomerata* (AY183371) |
| 6 | April09_Shoot_20WS3 | W20 | Shoot | *Acremonium* sp. (AM901698) |
| 7 | April09_Shoot_21WS1 | W21 | Shoot | *Stachybotrys elegans* (AF081481) |
| 8 | April09_Shoot_21WS2 | W21 | Shoot | *Myrothecium melanosporum* (FJ235086) |
| 9 | April09_Shoot_22WS1 | W22 | Shoot | *Gibberella* sp. (FJ466715) |
| 10 | April09_Shoot_22WS2 | W22 | Shoot | *Gibberella* sp. (FJ466715) |
| 11 | April09_Shoot_22WS3 | W22 | Shoot | Ascomycete sp. (AY243057) |
| 12 | April09_Shoot_23WS1 | W223 | Shoot | *Emericellopsis terricola* (FJ430737) |
| 13 | April09_Shoot_24WS3 | W24 | Shoot | *Bionectria rossmaniae* (AM944351) |
| 14 | April09_Shoot_26WS1 | W26 | Shoot | *F. oxysporum f.* sp. *vasinfectum* (AF322074) |
| 15 | April09_Shoot_26WS2 | W26 | Shoot | *Emericellopsis terricola* (FJ430737) |
| 16 | April09_Shoot_26WS5 | W27 | Shoot | *F. oxysporum f.* sp. *vasinfectum* (AF322074) |

TABLE 2-continued

Identification of fungal endophytes by rDNA sequence.

| SEQ ID NO | Isolate ID | Location* | Plant Part | Initial ID/(Accession No.) |
|---|---|---|---|---|
| 17 | April09_Shoot_27WS3 | W27 | Shoot | Uncultured endophytic fungus (EF505542) |
| 18 | April09_Shoot_28ES1 | E28 | Shoot | Uncultured endophytic fungus (EF505542) |
| 19 | April09_Shoot_28WS2 | W28 | Shoot | *Myrothecium melanosporum* (FJ235086) |
| 20 | April09_Shoot_29ES1 | E29 | Shoot | *Hypocrea lixii* (EF392760) |
| 21 | April09_Shoot_29ES2 | E29 | Shoot | *Hypocrea lixii* (EF392760) |
| 22 | April09_Shoot_29ES3 | E29 | Shoot | *Hypocrea lixii* (EF392760) |
| 23 | April09_Shoot_29WS1 | W29 | Shoot | *Buergenerula spartinae* (AF422960) |
| 24 | April09_Shoot_29WS2 | W29 | Shoot | *Gibberella acuminata* (U85533) |
| 25 | April09_Shoot_2WS1 | W2 | Shoot | *Emericellopsis terricola* (FJ430737) |
| 26 | April09_Shoot_2WS2 | W2 | Shoot | Ascomycete sp. (AJ279460) |
| 27 | April09_Shoot_30WS2 | W30 | Shoot | *Emericellopsis terricola* (FJ430737) |
| 28 | April09_Shoot_32ES1 | E32 | Shoot | *Fusarium proliferatum* (AF291061) |
| 29 | April09_Shoot_32WS | W32 | Shoot | *Stachybotrys elegans* (AF081481) |
| 30 | April09_Shoot_34ES2 | E34 | Shoot | *Eutypa scoparia* (AF373064) |
| 31 | April09_Shoot_34ES3 | E34 | Shoot | Sordariomycete sp. (EU680539) |
| 32 | April09_Shoot_35WS1 | W35 | Shoot | Uncultured soil fungus (EU479884) |
| 33 | April09_Shoot_35WS4 | W35 | Shoot | *Myrothecium melanosporum* (FJ235086) |
| 34 | April09_Shoot_35WS5 | W35 | Shoot | *Leptosphaeria avenaria f.* sp. *triticea* (U77357) |
| 35 | April09_Shoot_35WS6 | W35 | Shoot | *Acremonium* sp. (AM901698) |
| 36 | April09_Shoot_3WS1 | W3 | Shoot | *Penicillium citreonigrum* (EU497942) |
| 37 | April09_Shoot_44ES1 | E44 | Shoot | Fungal endophyte sp. (EU977213) |
| 38 | April09_Shoot_46ES1 | E46 | Shoot | *Fusarium proliferatum* (AF291061) |
| 39 | April09_Shoot_46ES2 | E46 | Shoot | *Emericellopsis terricola* (FJ430737) |
| 40 | April09_Shoot_4ES1 | E4 | Shoot | *Emericellopsis terricola* (FJ430737) |
| 41 | April09_Shoot_5WS2 | W5 | Shoot | *Acremonium strictum* (EU497953) |
| 42 | April09_Shoot_6ES2 | E6 | Shoot | *Emericellopsis minima* (U57675) |
| 43 | April09_Shoot_6WS2 | W6 | Shoot | *Alternaria mali* (AY154683) |
| 44 | April09_Shoot_8ES1 | E8 | Shoot | *Bipolaris heveae* (AB179834) |
| 45 | April09_Shoot_9ES1 | E9 | Shoot | *Stachybotrys bisbyi* (AF081480) |
| 46 | April09_Shoot_9WS1 | W9 | Shoot | Dothideomycete sp. (EU680559) |
| 47 | July09_Shoot_10WS2 | W10 | Shoot | *Acremonium strictum* (GU219467) |
| 48 | July09_Shoot_12WS1 | W12 | Shoot | *Pleosporaceae* sp. (EU330624) |
| 49 | July09_Shoot_12WS2 | W12 | Shoot | *Alternaria* sp. (FJ210481) |
| 50 | July09_Shoot_12WS3 | W12 | Shoot | *Fusarium moniliformae* (EU364864) |
| 51 | July09_Shoot_12WS4 | W12 | Shoot | *Fusarium moniliformae* (AB369908) |
| 52 | July09_Shoot_12WS5 | W12 | Shoot | *Sporisorium everhartii* (AY740159) |
| 53 | July09_Shoot_16WS2 | W16 | Shoot | *Alternaria* sp. (FJ037742, GQ389617) |
| 54 | July09_Shoot_16WS3 | W16 | Shoot | *Fusarium proliferatum* (AF291061) |
| 55 | July09_Shoot_17ES2 | E17 | Shoot | *Fusarium nygamai* (U34568) |
| 56 | July09_Shoot_17ES3 | E17 | Shoot | *Periconia macrospinosa* (FJ536208) |
| 57 | July09_Shoot_17ES4 | E17 | Shoot | *Codinaeopsis* sp. (EF488392) |
| 58 | July09_Shoot_17WS1 | W17 | Shoot | *Sporisorium everhartii* (AY740159) |
| 59 | July09_Shoot_19ES1 | E19 | Shoot | *Fusarium proliferatum* (AF291061) |
| 60 | July09_Shoot_19ES2 | E19 | Shoot | *Fusarium moniliformae* (AB369908) |
| 61 | July09_Shoot_19ES3 | E19 | Shoot | *Fusarium proliferatum* (EU888923) |
| 62 | July09_Shoot_19ES4 | E19 | Shoot | *Fusarium moniliformae* (EU364864) |
| 63 | July09_Shoot_19WS3 | W19 | Shoot | *Acremonium strictum* (EU497953) |
| 64 | July09_Shoot_1ES1 | E1 | Shoot | *Myrothecium verrucaria* (AY303603) |
| 65 | July09_Shoot_20ES1 | E20 | Shoot | *Fusarium subglutinans* (GQ167234) |
| 66 | July09_Shoot_20ES2 | E20 | Shoot | *Leptosphaeria bicolor* (AF455415) |
| 67 | July09_Shoot_20WS1 | W20 | Shoot | *Acremonium* sp. (AM901698) |
| 68 | July09_Shoot_20WS2 | W20 | Shoot | *Acremonium strictum* (U57671) |
| 69 | July09_Shoot_20WS3 | W20 | Shoot | *Periconia macrospinosa* (FJ536208) |
| 70 | July09_Shoot_22WS1 | W22 | Shoot | *Fusarium pseudograminearum* (DQ4598710) |
| 71 | July09_Shoot_22WS2 | W22 | Shoot | *Acremonium* sp. (AM924149) |
| 72 | July09_Shoot_23ES2 | E23 | Shoot | *Fusarium nygamai* (U34568) |
| 73 | July09_Shoot_25ES1 | E25 | Shoot | *Gibberella* sp. (FJ008984) |
| 74 | July09_Shoot_25ES2 | E25 | Shoot | *Colletotrichum graminicola* (GQ221855) |
| 75 | July09_Shoot_25WS3 | W25 | Shoot | *Sporisorium everhartii* (AY740159) |
| 76 | July09_Shoot_26ES1 | E26 | Shoot | *Monographella* sp. (FJ228195) |
| 77 | July09_Shoot_26ES2 | E26 | Shoot | *Myrothecium verrucaria* (AY303603) |
| 78 | July09_Shoot_27ES1 | E27 | Shoot | *Alternaria arborescens* (AY154706) |
| 79 | July09_Shoot_27ES3 | E27 | Shoot | *Alternaria alternata* (FJ872066) |
| 80 | July09_Shoot_27ES4 | E27 | Shoot | *Parasarcopodium ceratocaryi* (AY344479) |
| 81 | July09_Shoot_27WS1 | W27 | Shoot | *Acremonium* sp. (AM924149) |
| 82 | July09_Shoot_29WS1 | W29 | Shoot | *Acremonium strictum* (EU497953) |
| 83 | July09_Shoot_29WS2 | W29 | Shoot | *Sporisorium everhartii* (AY740159) |
| 84 | July09_Shoot_2ES1 | E2 | Shoot | *Fusarium nygamai* (U34568) |
| 85 | July09_Shoot_2WS2 | W2 | Shoot | *Acremonium* sp. (AM924149) |
| 86 | July09_Shoot_30ES1 | E30 | Shoot | *Alternaria mali* (AY154683) |

TABLE 2-continued

Identification of fungal endophytes by rDNA sequence.

| SEQ ID NO | Isolate ID | Location* | Plant Part | Initial ID/(Accession No.) |
|---|---|---|---|---|
| 87 | July09__Shoot__30ES2 | E30 | Shoot | *Gibberella* sp. (AM901682) |
| 88 | July09__Shoot__30ES3 | E30 | Shoot | *Fusarium proliferatum* (AF291061) |
| 89 | July09__Shoot__30ES4 | E30 | Shoot | *Alternaria mali* (AY154683) |
| 90 | July09__Shoot__31ES1 | E31 | Shoot | *Pseudozyma flocculosa* (DQ411535) |
| 91 | July09__Shoot__32WS1 | W32 | Shoot | *Fusarium nygamai* (U34568) |
| 92 | July09__Shoot__33WS1 | W33 | Shoot | *Fusarium nygamai* (U34568) |
| 93 | July09__Shoot__33WS2 | W33 | Shoot | *Nigrospora oryzae* (EU272488) |
| 94 | July09__Shoot__33WS3 | W33 | Shoot | *Fusarium nygamai* (U34568) |
| 95 | July09__Shoot__33WS4 | W33 | Shoot | *Acremonium strictum* (EU497953) |
| 96 | July09__Shoot__33WS5 | W33 | Shoot | *Fusarium proliferatum* (AF291061) |
| 97 | July09__Shoot__33WS6 | W33 | Shoot | *Sporisorium everhartii* (AY740159) |
| 98 | July09__Shoot__33WS7 | W33 | Shoot | Uncultured root-associated fungus (EU144817) |
| 99 | July09__Shoot__34WS1 | W34 | Shoot | Uncultured endophytic fungus (EF505485) |
| 100 | July09__Shoot__34WS3 | W34 | Shoot | *Gibberella* sp. (FJ008984) |
| 101 | July09__Shoot__34WS4 | W34 | Shoot | *Acremonium strictum* (EU497953) |
| 102 | July09__Shoot__35ES1 | E35 | Shoot | *Fusarium proliferatum* (AF291061) |
| 103 | July09__Shoot__35ES2 | E35 | Shoot | *Fusarium nygamai* (X94174) |
| 104 | July09__Shoot__35ES3 | E35 | Shoot | *Acremonium* sp. (AM901698) |
| 105 | July09__Shoot__35WS1 | W35 | Shoot | *Gibberella* sp. (AM901682) |
| 106 | July09__Shoot__35WS2 | W35 | Shoot | *Gibberella* sp. (FJ008984) |
| 107 | July09__Shoot__35WS3 | W35 | Shoot | *Gibberella* sp. (AM901682) |
| 108 | July09__Shoot__35WS4 | W35 | Shoot | *Gibberella* sp. (AM901682) |
| 109 | July09__Shoot__35WS5 | W35 | Shoot | *Fusarium proliferatum* (EU272509) |
| 110 | July09__Shoot__35WS6 | W35 | Shoot | *Alternaria alternata* (AY433814) |
| 111 | July09__Shoot__36ES1 | E36 | Shoot | *Sporisorium everhartii* (AY740159) |
| 112 | July09__Shoot__42ES2 | E42 | Shoot | Sordariomycete sp. (EU680539) |
| 113 | July09__Shoot__45ES1 | E45 | Shoot | *Fusarium proliferatum* (AF291061) |
| 114 | July09__Shoot__45ES2 | E45 | Shoot | *Fusarium moniliformae* (AB369908) |
| 115 | July09__Shoot__48ES1 | E48 | Shoot | *Fusarium nygamai* (U34568) |
| 116 | July09__Shoot__48ES2 | E48 | Shoot | *Fusarium proliferatum* (AF291061) |
| 117 | July09__Shoot__48ES3 | E48 | Shoot | *Fusarium nygamai* (U34568) |
| 118 | July09__Shoot__4ES1 | E4 | Shoot | *Exserohilum rostratum* (GQ169762) |
| 119 | July09__Shoot__5ES1 | E5 | Shoot | *Fusarium proliferatum* (AF291061) |
| 120 | July09__Shoot__6WS1 | W6 | Shoot | *Fusarium moniliformae* (EU364864) |
| 121 | July09__Shoot__6WS2 | W6 | Shoot | *Fusarium moniliformae* (AB369908) |
| 122 | July09__Shoot__7ES1 | E7 | Shoot | *Bipolaris oryzae* (DQ300203) |
| 123 | July09__Shoot__7ES2 | E7 | Shoot | *Gibberella* sp. (FJ008984) |
| 124 | July09__Shoot__8ES1 | E8 | Shoot | *Colletotrichum graminicola* (EU400146) |
| 125 | July09__Shoot__8ES3 | E8 | Shoot | *Sporisorium everhartii* (AY740159) |
| 126 | July09__Shoot__8ES4 | E8 | Shoot | *Sporisorium everhartii* (AY740159) |
| 127 | July09__Shoot__9ES2 | E9 | Shoot | *Fusarium moniliformae* (AB369908) |
| 128 | July09__Shoot__9ES3 | E9 | Shoot | *Sporisorium everhartii* (AY740159) |
| 129 | July09__Shoot__9ES4 | E9 | Shoot | *Sporisorium everhartii* (AY740159) |
| 130 | Oct09__Shoot__10ES2 | E10 | Shoot | Sordariomycete sp. (EU680539) |
| 131 | Oct09__Shoot__10ES3 | E10 | Shoot | Sordariomycete sp. (EU680539) |
| 132 | Oct09__Shoot__28ES1 | E28 | Shoot | *Fusarium nygamai* (X94174) |
| 133 | Oct09__Shoot__30ES1 | E30 | Shoot | *Fusarium acuminatum* (GQ505462) |
| 134 | Oct09__Shoot__37ES1 | E37 | Shoot | *Fusarium nygamai* (X94174) |
| 135 | Oct09__Shoot__37ES2 | E37 | Shoot | *Fusarium proliferatum* (AF291061) |
| 136 | Oct09__Shoot__48ES1 | E48 | Shoot | Leaf litter ascomycetes (AF502815) |
| 137 | Oct09__Shoot__10WS1 | W10 | Shoot | *Acremonium strictum* (U57671) |
| 138 | Oct09__Shoot__14WS1 | W14 | Shoot | *Fusarium nygamai* (X94174) |
| 139 | Oct09__Shoot__16WS1 | W16 | Shoot | *Fusarium nygamai* (X94174) |
| 140 | Oct09__Shoot__16WS2 | W16 | Shoot | *Fusarium nygamai* (X94174) |
| 141 | Oct09__Shoot__24WS1 | W24 | Shoot | *Stachybotrys elegans* (AF081481) |
| 142 | Oct09__Shoot__24WS2 | W24 | Shoot | *Stachybotrys elegans* (AF081481) |
| 143 | Oct09__Shoot__24WS3 | W24 | Shoot | *Stachybotrys elegans* (AF081481) |
| 144 | April09__Root__10WR1 | W10 | Root | *Periconia macrospinosa* (FJ536207) |
| 145 | April09__Root__10WR2 | W10 | Root | *Codinaeopsis* sp. (EF488392) |
| 146 | April09__Root__11WR1 | W11 | Root | *Fusarium nygamai* (X94174) |
| 147 | April09__Root__12ER1 | E12 | Root | *Gaeumannomyces incrustans* (U17214) |
| 148 | April09__Root__12ER2 | E12 | Root | *Periconia macrospinosa* (FJ536207) |
| 149 | April09__Root__12ER3 | E12 | Root | *Fusarium* sp. (EF453116) |
| 150 | April09__Root__12ER-A | E12 | Root | *Gaeumannomyces incrustans* (U17214) |
| 151 | April09__Root__12WR1 | W12 | Root | *Fusarium annulatum* (AY213654) |
| 152 | April09__Root__13ER1 | E13 | Root | *Fusarium nygamai* (X94174) |
| 153 | April09__Root__14ER2 | E14 | Root | *Periconia macrospinosa* (FJ536207) |
| 154 | April09__Root__15ER1 | E15 | Root | *Gaeumannomyces incrustans* (U17214) |
| 155 | April09__Root__16ER1 | E16 | Root | *Coprinus auricomus* (FM163186) |
| 156 | April09__Root__16ER2 | E16 | Root | *Coprinus auricomus* (FM163186) |
| 157 | April09__Root__16ER-A | E16 | Root | *Amyloathelia crassiuscula* (DQ144610) |
| 158 | April09__Root__16WR1 | W16 | Root | *Alternaria longissima* (EU030349) |
| 159 | April09__Root__18WR2 | W18 | Root | *Kabatiella microsticta* (EU167608) |

TABLE 2-continued

Identification of fungal endophytes by rDNA sequence.

| SEQ ID NO | Isolate ID | Location* | Plant Part | Initial ID/(Accession No.) |
|---|---|---|---|---|
| 160 | April09__Root__19ER1 | E19 | Root | *Fusarium annulatum* (AY213654) |
| 161 | April09__Root__19ER2 | E19 | Root | *Fusarium nygamai* (X94174) |
| 162 | April09__Root__19ER3 | E19 | Root | *Fusarium nygamai* (X94174) |
| 163 | April09__Root__19WR1 | W19 | Root | *Alternaria mali* (AY154683) |
| 164 | April09__Root__19WR-A | W19 | Root | *Fusarium moniliformae* (EU364865) |
| 165 | April09__Root__1ER1 | E1 | Root | *Periconia macrospinosa* (FJ536207) |
| 166 | April09__Root__1ER3 | E1 | Root | Uncultured soil fungus (EU480242) |
| 167 | April09__Root__20ER1 | E20 | Root | *Gaeumannomyces incrustans* (U17214) |
| 168 | April09__Root__20ER2 | E20 | Root | *Fusarium nygamai* (X94174) |
| 169 | April09__Root__20WR2 | W20 | Root | *Eutypella* sp. (FJ172283) |
| 170 | April09__Root__21ER1 | E21 | Root | *Periconia macrospinosa* (FJ536207) |
| 171 | April09__Root__22WR1 | W22 | Root | *Fusarium nygamai* (X94174) |
| 172 | April09__Root__22WR2 | W22 | Root | *Fusarium nygamai* (X94174) |
| 173 | April09__Root__22WR3 | W22 | Root | *Fusarium* sp. (AY143085) |
| 174 | April09__Root__24WR2 | W24 | Root | Fungal endophyte (FJ449944) |
| 175 | April09__Root__26ER1 | E26 | Root | *Fusarium nygamai* (X94174) |
| 176 | April09__Root__26WR1 | W26 | Root | *Alternaria mali* (AY154683) |
| 177 | April09__Root__26WR2 | W26 | Root | *Fusarium nygamai* (X94174) |
| 178 | April09__Root__27ER1 | E27 | Root | *Fusarium nygamai* (X94174) |
| 179 | April09__Root__27WR1 | W27 | Root | *Microdochium* sp. (FJ536210) |
| 180 | April09__Root__29WR1 | W29 | Root | *Fusarium nygamai* (X94174) |
| 181 | April09__Root__29WR2 | W29 | Root | *Fusarium nygamai* (X94174) |
| 182 | April09__Root__29WR3 | W29 | Root | *Fusarium nygamai* (X94174) |
| 183 | April09__Root__2ER1 | E2 | Root | *Periconia macrospinosa* (FJ536207) |
| 184 | April09__Root__2WR1 | W2 | Root | Uncultured Ascomycete sp. (EU358786) |
| 185 | April09__Root__2WR2 | W2 | Root | Uncultured Ascomycete sp. (EU358786) |
| 186 | April09__Root__2WR3 | W2 | Root | Uncultured Ascomycete sp. (EU003079) |
| 187 | April09__Root__2WR4 | W2 | Root | Uncultured Ascomycete sp. (EF154350) |
| 188 | April09__Root__30ER1 | E30 | Root | *Fusarium nygamai* (X94174) |
| 189 | April09__Root__31ER2 | E31 | Root | *Fusarium nygamai* (X94174) |
| 190 | April09__Root__31ER3 | E31 | Root | *Fusarium* sp. (GQ505756) |
| 191 | April09__Root__31ER4 | E31 | Root | *Fusarium nygamai* (X94174) |
| 192 | April09__Root__31WR1 | W31 | Root | *Fusarium nygamai* (X94174) |
| 193 | April09__Root__31WR2 | W31 | Root | *Fusarium nygamai* (X94174) |
| 194 | April09__Root__32WR1 | W32 | Root | *Gaeumannomyces incrustans* (U17214) |
| 195 | April09__Root__33ER1 | E33 | Root | *Periconia macrospinosa* (FJ536207) |
| 196 | April09__Root__33ER2 | E33 | Root | *Microdochium* sp. (FJ536210) |
| 197 | April09__Root__33ER3 | E33 | Root | *Periconia macrospinosa* (FJ536207) |
| 198 | April09__Root__33ER4 | E33 | Root | *Anthostomella brabeji* (EU552098) |
| 199 | April09__Root__33WR1 | W33 | Root | *Gaeumannomyces incrustans* (U17214) |
| 200 | April09__Root__34ER1 | E34 | Root | *Gaeumannomyces incrustans* (U17214) |
| 201 | April09__Root__34ER2 | E34 | Root | *Periconia macrospinosa* (FJ536207) |
| 202 | April09__Root__37ER1 | E37 | Root | *Fusarium nygamai* (X94174) |
| 203 | April09__Root__37ER2 | E37 | Root | *Fusarium nygamai* (X94174) |
| 204 | April09__Root__37ER3 | E37 | Root | *Periconia macrospinosa* (FJ536207) |
| 205 | April09__Root__3ER1 | E3 | Root | *Halorosellinia* sp. (EU715636) |
| 206 | April09__Root__3ER2 | E3 | Root | *Fusarium* sp. (EU750677) |
| 207 | April09__Root__3ER3 | E3 | Root | *Halorosellinia* sp. (EU715636) |
| 208 | April09__Root__3ER-A | E3 | Root | Uncultured root-associated fungus (EU144759) |
| 209 | April09__Root__3WR1 | W3 | Root | *Penicillium verruculosum* (AF510496) |
| 210 | April09__Root__3WR2 | W3 | Root | *Fusarium nygamai* (X94174) |
| 211 | April09__Root__3WR3 | W3 | Root | *Gibberella* sp. (GQ389619) |
| 212 | April09__Root__3WR4 | W3 | Root | *Fusarium moniliformae* (EU364865) |
| 213 | April09__Root__41ER1 | E41 | Root | *Periconia macrospinosa* (FJ536207) |
| 214 | April09__Root__41ER2 | E41 | Root | *Periconia macrospinosa* (FJ536207) |
| 215 | April09__Root__41ER2-Green | E41 | Root | *Periconia macrospinosa* (FJ536207) |
| 216 | April09__Root__41ER3-Ash | E41 | Root | *Periconia macrospinosa* (FJ536207) |
| 217 | April09__Root__41ER-A | E41 | Root | *Periconia macrospinosa* (FJ536207) |
| 218 | April09__Root__42ER1 | E42 | Root | *Fusarium nygamai* (X94174) |
| 219 | April09__Root__44ER1 | E44 | Root | *Fusarium nygamai* (X94174) |
| 220 | April09__Root__45ER1 | E45 | Root | *Fusarium nygamai* (X94174) |
| 221 | April09__Root__45ER2 | E45 | Root | *Macrophomina phaseolina* (EF545133) |
| 222 | April09__Root__45ER3 | E45 | Root | *Periconia macrospinosa* (FJ536207) |
| 223 | April09__Root__46ER1 | E46 | Root | *Periconia macrospinosa* (FJ536207) |
| 224 | April09__Root__46ER2 | E46 | Root | *Microdochium* sp. (FJ536210) |
| 225 | April09__Root__47ER1 | E47 | Root | Uncultured Nectriaceae (EF068175) |
| 226 | April09__Root__47ER2 | E47 | Root | Ascomycete sp. (AJ279488) |
| 227 | April09__Root__4ER1 | E4 | Root | *Fusarium nygamai* (X94174) |
| 228 | April09__Root__4ER2 | E4 | Root | *Fusarium nygamai* (X94174) |
| 229 | April09__Root__4ER3 | E4 | Root | *Periconia macrospinosa* (FJ536207) |
| 230 | April09__Root__4ER4 | E4 | Root | *Microdochium* sp. (FJ536210) |
| 231 | April09__Root__4ER5 | E4 | Root | *Fusarium nygamai* (X94174) |

TABLE 2-continued

Identification of fungal endophytes by rDNA sequence.

| SEQ ID NO | Isolate ID | Location* | Plant Part | Initial ID/(Accession No.) |
|---|---|---|---|---|
| 232 | April09__Root__5ER1 | E5 | Root | Uncultured Leptosphaeriaceae (AY744286) |
| 233 | April09__Root__5ER2 | E5 | Root | *Periconia macrospinosa* (FJ536207) |
| 234 | April09__Root__5ER3 | E5 | Root | *Codinaeopsis* sp. (EF488392) |
| 235 | April09__Root__5WR1 | W5 | Root | *Fusarium nygamai* (X94174) |
| 236 | April09__Root__5WR2 | W5 | Root | *Fusarium nygamai* (X94174) |
| 237 | April09__Root__5WR3 | W5 | Root | *Fusarium nygamai* (X94174) |
| 238 | April09__Root__6ER1 | E6 | Root | Ascomycete sp. (DQ657853) |
| 239 | April09__Root__6ER2 | E6 | Root | *Codinaeopsis* sp. (EF488392) |
| 240 | April09__Root__7ER1 | E7 | Root | *Fusarium nygamai* (X94174) |
| 241 | April09__Root__7ER2 | E7 | Root | Uncultured fungus (FJ776560) |
| 242 | April09__Root__7ER-A | E7 | Root | Uncultured Helotiales (FJ475783) |
| 243 | April09__Root__7WR1 | W7 | Root | Fungal endophyte (DQ979674) |
| 244 | April09__Root__7WR2 | W7 | Root | Fungal endophyte (FN394695) |
| 245 | April09__Root__8ER1 | E8 | Root | Uncultured *Hypocreales* (FJ708608) |
| 246 | April09__Root__8ER2 | E8 | Root | *Periconia macrospinosa* (FJ536207) |
| 247 | April09__Root__8WR1 | W8 | Root | *Hypocrea lixii* (EF392760) |
| 248 | July09__Root__10ER1 | E10 | Root | *Periconia macrospinosa* (FJ536208) |
| 249 | July09__Root__10ER2 | E10 | Root | *Periconia macrospinosa* (FJ536208) |
| 250 | July09__Root__10ER3 | E10 | Root | *Periconia macrospinosa* (FJ536208) |
| 251 | July09__Root__10ER4 | E10 | Root | *Periconia macrospinosa* (FJ536208) |
| 252 | July09__Root__10ER5 | E10 | Root | Fungal endophyte (DQ979674) |
| 253 | July09__Root__10WR1 | W10 | Root | *Fusarium nygamai* (X94174) |
| 254 | July09__Root__10WR2 | W10 | Root | Uncultured root-associated fungus (EU144817) |
| 255 | July09__Root__12WR1 | W12 | Root | *Gaeumannomyces incrustans* (U17214) |
| 256 | July09__Root__12WR10 | W12 | Root | Uncultured root-associated fungus (EU144817) |
| 257 | July09__Root__12WR3 | W12 | Root | Uncultured *Hypocreales* (FJ708608) |
| 258 | July09__Root__13ER1 | E13 | Root | *Fusarium nygamai* (X94174) |
| 259 | July09__Root__13ER2 | E13 | Root | *Fusarium moniliformae* (EU364856) |
| 260 | July09__Root__13ER4 | E13 | Root | Sordariomycete sp. (EU680539) |
| 261 | July09__Root__13WR1 | W13 | Root | *Magnaporthe rhizophila* (DQ528791) |
| 262 | July09__Root__15WR1 | W15 | Root | *Fusarium oxysporum* (FJ478116) |
| 263 | July09__Root__17ER1 | E17 | Root | Mycorrhizal fungal sp. (FJ236025) |
| 264 | July09__Root__17WR2 | W17 | Root | Sordariomycete sp. (EU680539) |
| 265 | July09__Root__17WR3 | W17 | Root | Uncultured *Hypocreales* (FJ708608) |
| 266 | July09__Root__18ER1 | E18 | Root | *Fusarium nygamai* (X94174) |
| 267 | July09__Root__18ER2 | E18 | Root | *Fusarium nygamai* (X94174) |
| 268 | July09__Root__18ER3 | E18 | Root | *Fusarium nygamai* (X94174) |
| 269 | July09__Root__18ER4 | E18 | Root | *Fusarium nygamai* (X94174) |
| 270 | July09__Root__18WR1 | W18 | Root | *Fusarium proliferatum* (AF291061) |
| 271 | July09__Root__18WR2 | W18 | Root | *Magnaporthe rhizophila* (DQ528791) |
| 272 | July09__Root__18WR2 | W18 | Root | *Magnaporthe rhizophila* (DQ528791) |
| 273 | July09__Root__18WR3 | W18 | Root | *Fusarium moniliformae* (EU364856) |
| 274 | July09__Root__18WR4 | W18 | Root | *Fusarium nygamai* (X94174) |
| 275 | July09__Root__19ER1 | E19 | Root | Uncultured root-associated fungus (EU144806) |
| 276 | July09__Root__19WR2 | W19 | Root | *Fusarium* sp. (EU750682) |
| 211 | July09__Root__19WR3 | W19 | Root | *Fusarium oxysporum f. ciceris* (EU442590) |
| 278 | July09__Root__1ER1 | E1 | Root | *Microdochium* sp. (FJ536210) |
| 279 | July09__Root__1ER2 | E1 | Root | *Fusarium acuminatum* (GQ505462) |
| 280 | July09__Root__1WR1 | W1 | Root | *Fusarium proliferatum* (AF291061) |
| 281 | July09__Root__1WR2 | W1 | Root | *Fusarium moniliformae* (EU364865) |
| 282 | July09__Root__1WR3 | W1 | Root | Uncultured root-associated fungus (EU144806) |
| 283 | July09__Root__1WR4 | W1 | Root | Uncultured root-associated fungus (FJ362205) |
| 284 | July09__Root__1WR5 | W1 | Root | *Fusarium nygamai* (X94174) |
| 285 | July09__Root__20ER1 | E20 | Root | *Fusarium nygamai* (U34568) |
| 286 | July09__Root__20ER10 | E20 | Root | *Magnaporthe rhizophila* (DQ528791) |
| 287 | July09__Root__20WR2 | W20 | Root | Uncultured *Hypocreales* (FJ708608) |
| 288 | July09__Root__21ER1 | E21 | Root | *Magnaporthe rhizophila* (DQ528791) |
| 289 | July09__Root__21ER3 | E21 | Root | Uncultured soil fungus (DQ420771) |
| 290 | July09__Root__21ER4 | E21 | Root | *Gaeumannomyces incrustans* (U17214) |
| 291 | July09__Root__21WR1 | W21 | Root | Uncultured root-associated fungus (EU144817) |
| 292 | July09__Root__21WR2 | W21 | Root | Dothideomycete sp. (EU680535) |
| 293 | July09__Root__21WR3 | W21 | Root | Uncultured root-associated fungus (EU144817) |
| 294 | July09__Root__22WR2 | W22 | Root | *Didymella fabae* (GQ305306) |
| 295 | July09__Root__22WR3 | W22 | Root | Uncultured root-associated fungus (EU144817) |
| 296 | July09__Root__23WR1 | W23 | Root | *Macrophomina phaseolina* (EF545133) |

TABLE 2-continued

Identification of fungal endophytes by rDNA sequence.

| SEQ ID NO | Isolate ID | Location* | Plant Part | Initial ID/(Accession No.) |
|---|---|---|---|---|
| 297 | July09__Root__23WR3 | W23 | Root | *Rhizopycnis* sp. (DQ682600) |
| 298 | July09__Root__23WR4 | W23 | Root | Uncultured root-associated fungus (FJ361993) |
| 299 | July09__Root__24WR10 | W24 | Root | Uncultured root-associated fungus (EU144817) |
| 300 | July09__Root__24WR4 | W24 | Root | Uncultured root-associated fungus (EU144817) |
| 301 | July09__Root__24WR5 | W24 | Root | *Phoma medicaginis* (EU167575) |
| 302 | July09__Root__25ER1 | E25 | Root | *Fusarium proliferatum* (AF291061) |
| 303 | July09__Root__25WR4 | W25 | Root | *Fusarium proliferatum* (AF291061) |
| 304 | July09__Root__26ER1 | E26 | Root | *Fusarium nygamai* (X94174) |
| 305 | July09__Root__26ER2 | E26 | Root | *Magnaporthe rhizophila* (DQ528791) |
| 306 | July09__Root__26ER3 | E26 | Root | *Gaeumannomyces incrustans* (U17214) |
| 307 | July09__Root__26WR1 | W26 | Root | *Gaeumannomyces incrustans* (U17214) |
| 308 | July09__Root__26WR2 | W26 | Root | *Fusarium proliferatum* (AF291061) |
| 309 | July09__Root__26WR3 | W26 | Root | Uncultured Ascomycete sp. (EU490093) |
| 310 | July09__Root__27WR2 | W27 | Root | *Gaeumannomyces incrustans* (U17214) |
| 311 | July09__Root__27WR3 | W27 | Root | Ascomycete sp. (EF672299) |
| 312 | July09__Root__27WR5 | W27 | Root | Fungal endophyte (FN392299) |
| 313 | July09__Root__28ER2 | E28 | Root | *Fusarium moniliformae* (EU364865) |
| 314 | July09__Root__28WR1 | W28 | Root | Uncultured Leptosphaeriaceae (AY744286) |
| 315 | July09__Root__29ER1 | E29 | Root | *Magnaporthe rhizophila* (DQ528791) |
| 316 | July09__Root__29WR2 | W29 | Root | *Fusarium nygamai* (X94174) |
| 317 | July09__Root__29WR3 | W29 | Root | *Gaeumannomyces incrustans* (U17214) |
| 318 | July09__Root__2ER2 | E2 | Root | Uncultured fungus (FN397215) |
| 319 | July09__Root__2ER3 | E2 | Root | *Fusarium nygamai* (U34568) |
| 320 | July09__Root__2ER5 | E2 | Root | *Fusarium oxysporum* (AY928417) |
| 321 | July09__Root__2WR3 | W2 | Root | *Fusarium solani* (FJ478128) |
| 322 | July09__Root__31ER1 | E31 | Root | *Fusarium proliferatum* (AF291061) |
| 323 | July09__Root__31ER4 | E31 | Root | *Fusarium proliferatum* (AF291061) |
| 324 | July09__Root__31WR1 | W31 | Root | *Myrothecium cinctum* (DQ135998) |
| 325 | July09__Root__31WR2 | W31 | Root | *Gaeumannomyces incrustans* (U17214) |
| 326 | July09__Root__32WR1 | W32 | Root | *Fusarium nygamai* (U34568) |
| 327 | July09__Root__32WR2 | W32 | Root | *Fusarium nygamai* (U34568) |
| 328 | July09__Root__33WR2 | W33 | Root | *Gaeumannomyces incrustans* (U17214) |
| 329 | July09__Root__33WR3 | W33 | Root | *Gaeumannomyces incrustans* (U17214) |
| 330 | July09__Root__35ER2 | E35 | Root | *Magnaporthe rhizophila* (DQ528791) |
| 331 | July09__Root__35ER4 | E35 | Root | *Magnaporthe rhizophila* (DQ528791) |
| 332 | July09__Root__35WR2 | W35 | Root | Uncultured Ascomycete sp. (EF154351) |
| 333 | July09__Root__35WR3 | W35 | Root | *Fusarium proliferatum* (AF291061) |
| 334 | July09__Root__35WR4 | W35 | Root | *Magnaporthe rhizophila* (DQ528791) |
| 335 | July09__Root__36ER1 | E36 | Root | Uncultured soil fungus (EU480242) |
| 336 | July09__Root__36ER2 | E36 | Root | Uncultured fungus (FN397215) |
| 337 | July09__Root__36ER3 | E36 | Root | *Periconia macrospinosa* (FJ536208) |
| 338 | July09__Root__36ER4 | E36 | Root | *Periconia macrospinosa* (FJ536208) |
| 339 | July09__Root__36WR1 | W36 | Root | *Fusarium nygamai* (X94174) |
| 340 | July09__Root__36WR2 | W36 | Root | *Eladia saccula* (FJ914702) |
| 341 | July09__Root__36WR2-2 | W36 | Root | *Gaeumannomyces incrustans* (U17214) |
| 342 | July09__Root__36WR5 | W36 | Root | *Fusarium moniliformae* (EU364865) |
| 343 | July09__Root__37ER1 | E37 | Root | *Gaeumannomyces incrustans* (U17214) |
| 344 | July09__Root__37ER2 | E37 | Root | Uncultured root-associated fungus (EU144817) |
| 345 | July09__Root__37ER3 | E37 | Root | *Fusarium nygamai* (X94174) |
| 346 | July09__Root__39ER1 | E39 | Root | *Fusarium* sp. (EU750677) |
| 347 | July09__Root__39ER3 | E39 | Root | *Fusarium nygamai* (X94174) |
| 348 | July09__Root__39ER5 | E39 | Root | Uncultured endophytic fungus (FJ524302) |
| 349 | July09__Root__3ER1-2 | E3 | Root | *Fusarium proliferatum* (AF291061) |
| 350 | July09__Root__3ER2 | E3 | Root | *Fusarium oxysporum* (FJ154076) |
| 351 | July09__Root__3ER3 | E3 | Root | *Fusarium nygamai* (X94174) |
| 352 | July09__Root__3WR1 | W3 | Root | Uncultured endophytic fungus (EF505610) |
| 353 | July09__Root__3WR2 | W3 | Root | Ascomycete sp. (EF672299) |
| 354 | July09__Root__3WR3 | W3 | Root | Uncultured Ascomycete sp. (EF154351) |
| 355 | July09__Root__40ER1 | E40 | Root | *Gaeumannomyces incrustans* (U17214) |
| 356 | July09__Root__40ER2 | E40 | Root | Uncultured root-associated fungus (EU144817) |
| 357 | July09__Root__40ER3 | E40 | Root | Uncultured root-associated fungus (EU144817) |
| 358 | July09__Root__41ER1 | E41 | Root | *Fusarium proliferatum* (AF291061) |
| 359 | July09__Root__42ER1 | E42 | Root | *Fusarium proliferatum* (AF291061) |
| 360 | July09__Root__42ER2 | E42 | Root | *Fusarium proliferatum* (AF291061) |
| 361 | July09__Root__43ER1 | E43 | Root | Uncultured Ascomycete sp. (EU490093) |
| 362 | July09__Root__43ER2 | E43 | Root | Uncultured *Hypocreales* (FJ708608) |

TABLE 2-continued

Identification of fungal endophytes by rDNA sequence.

| SEQ ID NO | Isolate ID | Location* | Plant Part | Initial ID/(Accession No.) |
|---|---|---|---|---|
| 363 | July09__Root__43ER3 | E43 | Root | *Fusarium nygamai* (X94174) |
| 364 | July09__Root__43ER4 | E43 | Root | Fungal endophyte (FN392299) |
| 365 | July09__Root__44ER1 | E44 | Root | *Periconia macrospinosa* (FJ536208) |
| 366 | July09__Root__45ER1 | E45 | Root | *Magnaporthe rhizophila* (DQ528791) |
| 367 | July09__Root__45ER4 | E45 | Root | *Fusarium nygamai* (X94174) |
| 368 | July09__Root__47ER1 | E47 | Root | *Fusarium proliferatum* (AF291061) |
| 369 | July09__Root__47ER2 | E47 | Root | *Fusarium proliferatum* (AF291061) |
| 370 | July09__Root__47ER3 | E47 | Root | Uncultured root-associated fungus (EU144817) |
| 371 | July09__Root__47ER4 | E47 | Root | *Fusarium nygamai* (X94174) |
| 372 | July09__Root__48ER1 | E48 | Root | *Fusarium nygamai* (X94174) |
| 373 | July09__Root__48ER2 | E48 | Root | *Gaeumannomyces incrustans* (U17214) |
| 374 | July09__Root__48ER3 | E48 | Root | *Magnaporthe rhizophila* (DQ528791) |
| 375 | July09__Root__4ER1 | E4 | Root | *Gaeumannomyces incrustans* (U17214) |
| 376 | July09__Root__4ER2 | E4 | Root | Uncultured root-associated fungus (EU144817) |
| 377 | July09__Root__4ER3 | E4 | Root | *Fusarium* sp. (GU257897) |
| 378 | July09__Root__4ER4 | E4 | Root | *Fusarium* sp. (AF158312) |
| 379 | July09__Root__4WR1 | W4 | Root | *Fusarium proliferatum* (AF291061) |
| 380 | July09__Root__4WR3 | W4 | Root | *Magnaporthe rhizophila* (DQ528791) |
| 381 | July09__Root__5ER2 | E5 | Root | *Fusarium proliferatum* (AF291061) |
| 382 | July09__Root__5ER3-1 | E5 | Root | *Periconia macrospinosa* (FJ536208) |
| 383 | July09__Root__5ER3-2 | E5 | Root | *Codinaeopsis* sp. (EF488392), |
| 384 | July09__Root__5ER5 | E5 | Root | Uncultured root-associated fungus (EU144817) |
| 385 | July09__Root__5WR1 | W5 | Root | *Fusarium proliferatum* (AF291061) |
| 386 | July09__Root__5WR10 | W5 | Root | *Gaeumannomyces incrustans* (U17214) |
| 387 | July09__Root__5WR2 | W5 | Root | *Fusarium nygamai* (X94174) |
| 388 | July09__Root__5WR20 | W5 | Root | *Magnaporthe rhizophila* (DQ528791) |
| 389 | July09__Root__5WR3 | W5 | Root | *Fusarium proliferatum* (AF291061) |
| 390 | July09__Root__6ER1 | E6 | Root | *Fusarium proliferatum* (AF291061) |
| 391 | July09__Root__6ER2 | E6 | Root | *Fusarium proliferatum* (AF291061) |
| 392 | July09__Root__6WR1 | W6 | Root | *Fusarium proliferatum* (AF291061) |
| 393 | July09__Root__7ER1 | E7 | Root | *Gaeumannomyces incrustans* (U17214) |
| 394 | July09__Root__7ER2 | E7 | Root | *Diaporthe phaseolorum* (AF001016) |
| 395 | July09__Root__7WR1 | W7 | Root | *Fusarium moniliformae* (EU364865) |
| 396 | July09__Root__7WR10 | W7 | Root | Uncultured fungus (AM260913) |
| 397 | July09__Root__8ER1 | E8 | Root | *Trichoderma koningiopsis* (EU280108) |
| 398 | July09__Root__8ER2 | E8 | Root | Uncultured Helotiales (FJ475783) |
| 399 | July09__Root__9ER1 | E9 | Root | *Periconia macrospinosa* (FJ536208) |
| 400 | Oct09__Root__10WR1 | W10 | Root | Ascomycete sp. (EU520609) |
| 401 | Oct09__Root__10WR2 | W10 | Root | *Fusarium nygamai* (X94174) |
| 402 | Oct09__Root__10WR3 | W10 | Root | *Fusarium nygamai* (X94174) |
| 403 | Oct09__Root__11WR1 | W11 | Root | *Gaeumannomyces incrustans* (U17214) |
| 404 | Oct09__Root__11WR2 | W11 | Root | *Gaeumannomyces incrustans* (U17214) |
| 405 | Oct09__Root__11WR5 | W11 | Root | *Fusarium nygamai* (X94174) |
| 406 | Oct09__Root__12WR1 | W12 | Root | *Fusarium nygamai* (X94174) |
| 407 | Oct09__Root__12WR2 | W12 | Root | Sordariomycete sp. (EU680539) |
| 408 | Oct09__Root__12WR4 | W12 | Root | Grass root mycorrhizal sp. (AY599235) |
| 409 | Oct09__Root__13ER1 | E13 | Root | *Periconia macrospinosa* (FJ536208) |
| 410 | Oct09__Root__13ER2 | E13 | Root | *Periconia macrospinosa* (FJ536207) |
| 411 | Oct09__Root__13ER3 | E13 | Root | *Fusarium nygamai* (X94174) |
| 412 | Oct09__Root__13WR1 | W13 | Root | *Fusarium nygamai* (X94174) |
| 413 | Oct09__Root__13WR2 | W13 | Root | *Fusarium nygamai* (X94174) |
| 414 | Oct09__Root__13WR3 | W13 | Root | *Gaeumannomyces incrustans* (U17214) |
| 415 | Oct09__Root__14WR2 | W14 | Root | *Magnaporthe rhizophila* (DQ528791) |
| 416 | Oct09__Root__15WR1 | W15 | Root | *Gaeumannomyces incrustans* (U17214) |
| 417 | Oct09__Root__15WR2 | W15 | Root | *Magnaporthe rhizophila* (DQ528791) |
| 418 | Oct09__Root__16WR2 | W16 | Root | *Fusarium proliferatum* (AF291061) |
| 419 | Oct09__Root__17ER1 | E17 | Root | *Fusarium proliferatum* (AF291061) |
| 420 | Oct09__Root__17WR1 | W17 | Root | *Magnaporthe rhizophila* (DQ528791) |
| 421 | Oct09__Root__17WR2 | W17 | Root | *Magnaporthe rhizophila* (DQ528791) |
| 422 | Oct09__Root__17WR5 | W17 | Root | *Gaeumannomyces incrustans* (U17214) |
| 423 | Oct09__Root__18ER1 | E18 | Root | *Fusarium nygamai* (X94174) |
| 424 | Oct09__Root__18ER2 | E18 | Root | *Fusarium nygamai* (X94174) |
| 425 | Oct09__Root__18ER3 | E18 | Root | Uncultured *Lachnum* (FJ440910) |
| 426 | Oct09__Root__18WR2 | W18 | Root | *Trichoderma aureoviride* (AF194010) |
| 427 | Oct09__Root__18WR3 | W18 | Root | *Magnaporthe rhizophila* (DQ528791) |
| 428 | Oct09__Root__18WR4 | W18 | Root | *Fusarium nygamai* (X94174) |
| 429 | Oct09__Root__19ER1 | E19 | Root | *Fusarium nygamai* (X94174) |
| 430 | Oct09__Root__19ER2 | E19 | Root | Sordariomycete sp. (EU680539) |
| 431 | Oct09__Root__19ER3 | E19 | Root | *Gaeumannomyces incrustans* (U17214) |
| 432 | Oct09__Root__19ER4 | E19 | Root | *Fusarium moniliformae* (EU364856) |
| 433 | Oct09__Root__19WR1 | W19 | Root | *Fusarium nygamai* (U34568) |
| 434 | Oct09__Root__1ER1 | E1 | Root | *Gaeumannomyces incrustans* (U17214) |

TABLE 2-continued

Identification of fungal endophytes by rDNA sequence.

| SEQ ID NO | Isolate ID | Location* | Plant Part | Initial ID/(Accession No.) |
|---|---|---|---|---|
| 435 | Oct09__Root__1ER3 | E1 | Root | *Gaeumannomyces incrustans* (U17214) |
| 436 | Oct09__Root__1ER4 | E1 | Root | *Gaeumannomyces incrustans* (U17214) |
| 437 | Oct09__Root__1WR1 | W1 | Root | *Fusarium* sp. 14018 (EU750682) |
| 438 | Oct09__Root__1WR2 | W1 | Root | Ascomycete sp. (EF672299) |
| 439 | Oct09__Root__1WR3 | W1 | Root | Ascomycete sp. (EF672299) |
| 440 | Oct09__Root__1WR4 | W1 | Root | *Fusarium nygamai* (X94174) |
| 441 | Oct09__Root__21ER2 | E212 | Root | *Fusarium nygamai* (X94174) |
| 442 | Oct09__Root__22ER3 | E22 | Root | *Fusarium nygamai* (X94174) |
| 443 | Oct09__Root__22ER4 | E22 | Root | *Magnaporthe rhizophila* (DQ528791) |
| 444 | Oct09__Root__22WR1 | W22 | Root | *Alternaria alternata* (DQ023279) |
| 445 | Oct09__Root__22WR2 | W22 | Root | Sordariomycete sp. (EU680539) |
| 446 | Oct09__Root__22WR3 | W22 | Root | Sordariomycete sp. (EU680539) |
| 447 | Oct09__Root__23ER1 | E23 | Root | *Gaeumannomyces incrustans* (U17214) |
| 448 | Oct09__Root__23ER2 | E23 | Root | *Gaeumannomyces incrustans* (U17214) |
| 449 | Oct09__Root__23ER4 | E23 | Root | *Gaeumannomyces incrustans* (U17214) |
| 450 | Oct09__Root__23WR1 | W23 | Root | *Marasmius nigrobrunneus* (EU935578) |
| 451 | Oct09__Root__23WR2 | W23 | Root | *Hypocrea lixii* (AF194011) |
| 452 | Oct09__Root__23WR3 | W23 | Root | *Codinaeopsis* sp. (EF488392) |
| 453 | Oct09__Root__23WR4 | W23 | Root | *Fusarium nygamai* (X94174) |
| 454 | Oct09__Root__23WR5 | W23 | Root | *Fusarium nygamai* (X94174) |
| 455 | Oct09__Root__24WR1 | W24 | Root | *Gaeumannomyces incrustans* (U17214) |
| 456 | Oct09__Root__24WR2 | W24 | Root | *Gaeumannomyces incrustans* (U17214) |
| 457 | Oct09__Root__24WR3 | W24 | Root | Sordariomycete sp. (EU680539) |
| 458 | Oct09__Root__24WR4 | W24 | Root | Uncultured root-associated fungus (EU144817) |
| 459 | Oct09__Root__25ER1 | E25 | Root | *Gaeumannomyces incrustans* (U17214) |
| 460 | Oct09__Root__25ER2-1 | E25 | Root | *Gaeumannomyces incrustans* (U17214) |
| 461 | Oct09__Root__25ER2-2 | E25 | Root | *Gaeumannomyces incrustans* (U17214) |
| 462 | Oct09__Root__25ER3 | E25 | Root | *Waitea circinata* var. *zeae* (GQ221863) |
| 463 | Oct09__Root__25WR1 | W25 | Root | *Gaeumannomyces incrustans* (U17214) |
| 464 | Oct09__Root__25WR2 | W25 | Root | *Gaeumannomyces incrustans* (U17214) |
| 465 | Oct09__Root__25WR3 | W25 | Root | *Magnaporthe rhizophila* (DQ528791) |
| 466 | Oct09__Root__25WR4 | W25 | Root | *Gaeumannomyces incrustans* (U17214) |
| 467 | Oct09__Root__25WR5 | W25 | Root | *Penicillium* sp. (FJ571475) |
| 468 | Oct09__Root__26ER1 | E26 | Root | *Fusarium nygamai* (X94174) |
| 469 | Oct09__Root__26ER2 | E26 | Root | *Magnaporthe rhizophila* (DQ528791) |
| 470 | Oct09__Root__26ER3 | E26 | Root | Uncultured root-associated fungus (EU144817) |
| 471 | Oct09__Root__26ER4 | E26 | Root | *Gaeumannomyces incrustans* (U17214) |
| 472 | Oct09__Root__26WR1 | W26 | Root | Sordariomycete sp. (EU680539) |
| 473 | Oct09__Root__26WR2 | W26 | Root | Sordariomycete sp. (EU680539) |
| 474 | Oct09__Root__26WR3 | W26 | Root | Grass root mycorrhizal sp. (AY599235) |
| 475 | Oct09__Root__27WR1 | W27 | Root | *Fusarium nygamai* (X94174) |
| 476 | Oct09__Root__28ER1 | E28 | Root | *Fusarium nygamai* (X94174) |
| 477 | Oct09__Root__28ER2 | E28 | Root | *Gaeumannomyces incrustans* (U17214) |
| 478 | Oct09__Root__28ER4 | E28 | Root | *Gaeumannomyces incrustans* (U17214) |
| 479 | Oct09__Root__28ER5 | E28 | Root | *Codinaeopsis* sp. (EF488392) |
| 480 | Oct09__Root__28WR1 | W28 | Root | *Myrothecium melanosporum* (FJ235086) |
| 481 | Oct09__Root__29ER1 | E29 | Root | *Magnaporthe rhizophila* (DQ528791) |
| 482 | Oct09__Root__2WR1 | W2 | Root | *Gaeumannomyces incrustans* (U17214) |
| 483 | Oct09__Root__2WR2 | W2 | Root | *Gaeumannomyces incrustans* (U17214) |
| 484 | Oct09__Root__2WR3 | W2 | Root | Sordariomycete sp. (EU680539) |
| 485 | Oct09__Root__2WR4 | W2 | Root | Uncultured root-associated fungus (EU144817) |
| 486 | Oct09__Root__2WR5 | W2 | Root | Uncultured root-associated fungus (EU144817) |
| 487 | Oct09__Root__2WR6 | W2 | Root | Uncultured root-associated fungus (EU144817) |
| 488 | Oct09__Root__2WR7 | W2 | Root | *Magnaporthe rhizophila* (DQ528791) |
| 489 | Oct09__Root__2WR8 | W2 | Root | *Fusarium nygamai* (X94174) |
| 490 | Oct09__Root__31ER1 | E31 | Root | *Magnaporthe rhizophila* (DQ528791) |
| 491 | Oct09__Root__32WR2 | W32 | Root | Uncultured soil fungus (EU490117) |
| 492 | Oct09__Root__32WR3 | W32 | Root | *Gaeumannomyces incrustans* (U17214) |
| 493 | Oct09__Root__32WR4 | W32 | Root | Sordariomycete sp. (EU680539) |
| 494 | Oct09__Root__33WR1 | W33 | Root | *Fusarium moniliforme* (EU364856) |
| 495 | Oct09__Root__33WR2 | W33 | Root | *Codinaeopsis* sp. (EF488392) |
| 496 | Oct09__Root__33WR3 | W33 | Root | *Fusarium nygamai* (X94174) |
| 497 | Oct09__Root__34WR2 | W34 | Root | *Gaeumannomyces incrustans* (U17214) |
| 498 | Oct09__Root__34WR4 | W34 | Root | *Gaeumannomyces incrustans* (U17214) |
| 499 | Oct09__Root__34WR5 | W34 | Root | *Gaeumannomyces incrustans* (U17214) |
| 500 | Oct09__Root__35ER1 | E35 | Root | *Gibberella* sp. 1893 (FJ008984) |
| 501 | Oct09__Root__35ER2 | E35 | Root | Uncultured root-associated fungus (EU144817) |
| 502 | Oct09__Root__35ER3 | E35 | Root | Uncultured root-associated fungus (EU144817) |

TABLE 2-continued

Identification of fungal endophytes by rDNA sequence.

| SEQ ID NO | Isolate ID | Location* | Plant Part | Initial ID/(Accession No.) |
|---|---|---|---|---|
| 503 | Oct09__Root__35ER4 | E35 | Root | Uncultured root-associated fungus (EU144817) |
| 504 | Oct09__Root__36ER1 | E36 | Root | *Gaeumannomyces incrustans* (U17214) |
| 505 | Oct09__Root__36ER2 | E36 | Root | *Fusarium nygamai* (X94174) |
| 506 | Oct09__Root__3ER1 | 3E | Root | *Fusarium* sp. (EU750677) |
| 507 | Oct09__Root__3ER2 | 3E | Root | *Magnaporthe rhizophila* (DQ528791) |
| 508 | Oct09__Root__3ER3 | 3E | Root | *Magnaporthe rhizophila* (DQ528791) |
| 509 | Oct09__Root__3ER4 | 3E | Root | *Rhizoctonia praticola* (DQ223780) |
| 510 | Oct09__Root__3WR1 | 3W | Root | *Fusarium nygamai* (X94174) |
| 511 | Oct09__Root__3WR3 | 3W | Root | Ascomycete sp. (EF672299) |
| 512 | Oct09__Root__40ER4 | E40 | Root | Sordariomycete sp. (EU680539) |
| 513 | Oct09__Root__42ER1 | E42 | Root | *Gaeumannomyces graminis* var. *tritici* (AJ246153) |
| 514 | Oct09__Root__42ER2 | E42 | Root | *Gaeumannomyces graminis* var. *tritici* (AJ246153) |
| 515 | Oct09__Root__42ER3 | E42 | Root | *Gaeumannomyces graminis* var. *tritici* (AJ246153) |
| 516 | Oct09__Root__43ER1 | E42 | Root | Uncultured root-associated fungus (EU144817) |
| 517 | Oct09__Root__43ER2 | E42 | Root | *Gaeumannomyces incrustans* (U17214) |
| 518 | Oct09__Root__43ER3 | E43 | Root | *Fusarium nygamai* (U34568) |
| 519 | Oct09__Root__45ER1 | E45 | Root | Uncultured root associated fungus (EU144855) |
| 520 | Oct09__Root__45ER3 | E45 | Root | *Magnaporthe rhizophila* (DQ528791) |
| 521 | Oct09__Root__45ER4 | E45 | Root | *Gaeumannomyces incrustans* (U17214) |
| 522 | Oct09__Root__47ER1 | E47 | Root | Uncultured root-associated fungus (EU144817) |
| 523 | Oct09__Root__48ER1 | E48 | Root | Uncultured root-associated fungus (EU144817) |
| 524 | Oct09__Root__48ER2 | E48 | Root | Uncultured root-associated fungus (EU144817) |
| 525 | Oct09__Root__4ER1 | E4 | Root | Sordariomycete sp. (EU680539) |
| 526 | Oct09__Root__4ER2 | E4 | Root | Sordariomycete sp. (EU680539) |
| 527 | Oct09__Root__4ER3 | E4 | Root | *Fusarium nygamai* (X94174) |
| 528 | Oct09__Root__4WR1 | W4 | Root | Ascomycete sp. (EF672299) |
| 529 | Oct09__Root__4WR2 | W4 | Root | *Fusarium* sp. (EU750677, EU750686) |
| 530 | Oct09__Root__5ER1 | E5 | Root | Sordariomycete sp. (EU680539) |
| 531 | Oct09__Root__5ER2 | E5 | Root | *Gaeumannomyces incrustans* (U17214) |
| 532 | Oct09__Root__5ER3 | E5 | Root | *Gaeumannomyces incrustans* (U17214) |
| 533 | Oct09__Root__5WR1 | W5 | Root | *Fusarium nygamai* (X94174) |
| 534 | Oct09__Root__5WR2 | W5 | Root | *Fusarium nygamai* (X94174) |
| 535 | Oct09__Root__6ER1 | E6 | Root | *Magnaporthe rhizophila* (DQ528791) |
| 536 | Oct09__Root__6ER2 | E6 | Root | *Magnaporthe rhizophila* (DQ528791) |
| 537 | Oct09__Root__6ER3 | E6 | Root | *Diaporthe phaseolorum* (AF001016) |
| 538 | Oct09__Root__6ER4 | E6 | Root | *Diaporthe phaseolorum* (AF001016) |
| 539 | Oct09__Root__6ER5 | E6 | Root | *Magnaporthe rhizophila* (DQ528791) |
| 540 | Oct09__Root__6WR1 | W6 | Root | *Magnaporthe rhizophila* (DQ528791) |
| 541 | Oct09__Root__7ER2 | E7 | Root | *Magnaporthe rhizophila* (DQ528791) |
| 542 | Oct09__Root__7ER3 | E7 | Root | *Magnaporthe rhizophila* (DQ528791) |
| 543 | Oct09__Root__7ER4 | E7 | Root | *Magnaporthe rhizophila* (DQ528791) |
| 544 | Oct09__Root__8ER1 | E8 | Root | Uncultured root-associated fungus (EU144817) |
| 545 | Oct09__Root__8ER2 | E8 | Root | Uncultured root-associated fungus (EU144817) |
| 546 | Oct09__Root__8ER4 | E8 | Root | *Fusarium nygamai* (X94174) |
| 547 | Oct09__Root__8WR1 | W8 | Root | *Fusarium* sp. (EF152423) |
| 548 | Oct09__Root__9ER1 | E9 | Root | *Magnaporthe rhizophila* (DQ528791) |
| 549 | Oct09__Root__9ER2 | E9 | Root | *Microdiplodia* sp. (EF432267) |
| 550 | Oct09__Root__9ER3 | E9 | Root | *Rhizopycnis* sp. (DQ682600) |
| 551 | Oct09__Root__9ER4 | E9 | Root | *Penicillium camemberti* (DQ681326) |
| 552 | Oct09__Root__9ER7 | E9 | Root | *Fusarium moniliformae* (EU364856) |
| 553 | Oct09__Root__9WR1 | W9 | Root | *Rhizopycnis* sp. (DQ682600) |
| 554 | Oct09__Root__9WR2 | W9 | Root | *Codinaeopsis* sp. (EF488392) |
| 555 | Oct09__Root__9WR3 | W9 | Root | Uncultured root-associated fungus (EU144817) |

*GPS coordinates for each location are provided in Table 1.

Example 3

Endophyte Population Analysis

Two comprehensive endophyte species lists, one for shoot and one for root, were generated for each collection date. Comparisons were made between species from the east and west parts of the tallgrass prairie, as well as between sampling dates. In addition, fungal species from shoot and root tissue were grouped according to their higher taxonomic level (ordinal level) to allow ordinal frequencies to be evaluated.

Species diversity in each of these fungal "communities" was estimated using the Shannon diversity index (Bowman et al. 1971) as implemented in the PROC IML program, SAS software version 9.1.3 (SAS 2004). Differences in Shannon diversity indices of any two fungal communities were compared using Student's t-test at a 95% confidence level. The mean organic matter, macronutrients, sodium, and pH content in soils from the east and west parts of the tallgrass prairie were compared using PROC TTEST in SAS software version 9.1.3 (SAS 2004).

A total of 736 culturable fungal taxa were obtained from three collection trips.

Out of these isolates, 69% originated from roots, while 31% came from shoot tissues. Quality ITS sequences were obtained for 555 isolates, representing 75.4% of the total isolates obtained in this study. Of those sequenced, 74% were from root tissue and 26% were from shoot tissues. The results presented below are based on the sequence data from these 555 isolates.

Endophyte Community Structure in Shoot Tissues

The shoot fungal endophyte community was composed of 143 fungal taxa representing at least 51 different species (Table 3). The number of fungal taxa isolated from shoot tissues varied between study months. The numbers of taxa isolated in April, July, and October were 83, 46, and 14, respectively.

Endophyte Community Structure in Root Tissues

The root fungal endophyte community was composed of 412 taxa representing at least 58 different species (Table 4). The number of fungal taxa isolated from root tissue also varied between study months. The numbers of taxa isolated in April, July, and October were 104, 156, and 152, respectively.

Species Diversity in Endophyte Communities in Different Sampling Months

The species diversity in endophyte communities varied between sampling months (Table 5). The shoot community had the highest species diversity in April (HS=3.241), and the lowest in October (HS=1.730). The shoot endophyte community was significantly more diverse than the root community in April, whereas the root community was significantly more diverse than the shoot community in the October sampling date ($P<0.001$; Table 5).

Species Diversity in Fungal Communities from East and West Parts of the Tallgrass Prairie Fungal communities from the east and west parts were similar in species diversity (Table 6). However, a combined analysis of species from three collections revealed that the root endophyte community from the west had significantly higher species diversity than that of the east (HS=2.957 vs. 2.787; $P<0.001$; Table 6).

Soils from East and West Parts of the Tallgrass Prairie

Soils from the east and west parts of tallgrass prairie were significantly different in organic matter, phosphorus, calcium, and sodium contents ($P\leq0.049$; Table 7). The organic matter and calcium content was high in soils from the east part, whereas phosphorus and sodium content was high in the soils from the west part.

Diversity in Endophyte Communities at the Ordinal Level

Endophytic fungal isolates from the 2009 collections belonged to at least 18 orders (Table 8). Isolates from shoot tissues were assigned to nine orders and root isolates to 15 orders. Three orders were unique to shoot tissues, whereas nine orders were unique to root tissues. At least seven orders were common between shoot and root tissues. Members of the order Hypocreales were the most commonly isolated fungi, constituting approximately 64% and 39% of the fungal communities in shoot and root tissue, respectively.

TABLE 3

Temporal distributions of endophytic fungal species in switchgrass shoot tissues from the tallgrass prairie.

| | Month & Species Distribution | | | | |
|---|---|---|---|---|---|
| Species | April | July | October | Total | Percent |
| *Acremonium* sp. | 2 | 5 | 0 | 7 | 4.90 |
| *Acremonium strictum* | 1 | 6 | 1 | 8 | 5.59 |
| *Alternaria alternata* | 0 | 2 | 0 | 2 | 1.40 |
| *Alternaria arborescens* | 0 | 1 | 0 | 1 | 0.70 |
| *Alternaria mali* | 1 | 2 | 0 | 3 | 2.10 |
| *Alternaria* sp. | 0 | 2 | 0 | 2 | 1.40 |
| Ascomycete sp. | 2 | 0 | 0 | 2 | 1.40 |
| *Bionectria rossmaniae* | 1 | 0 | 0 | 1 | 0.70 |
| *Bipolaris heveae* | 1 | 0 | 0 | 1 | 0.70 |
| *Bipolaris oryzae* | 1 | 1 | 0 | 2 | 1.40 |
| *Buergenerula spartinae* | 1 | 0 | 0 | 1 | 0.70 |
| *Cladosporium colombiae* | 1 | 0 | 0 | 1 | 0.70 |
| *Codinaeopsis* sp. | 0 | 1 | 0 | 1 | 0.70 |
| *Colletotrichum graminicola* | 0 | 2 | 0 | 2 | 1.40 |
| Dothideomycete sp. | 1 | 0 | 0 | 1 | 0.70 |
| *Emericellopsis minima* | 1 | 0 | 0 | 1 | 0.70 |
| *Emericellopsis terricola* | 6 | 0 | 0 | 6 | 4.20 |
| *Eutypa scoparia* | 1 | 0 | 0 | 1 | 0.70 |
| *Exserohilum rostratum* | 0 | 1 | 0 | 1 | 0.70 |
| *Fusarium acuminatum* | 0 | 0 | 1 | 1 | 0.70 |
| *Fusarium moniliformae* | 0 | 8 | 0 | 8 | 5.59 |
| *Fusarium nygamai* | 1 | 9 | 5 | 15 | 10.49 |
| *F. oxysporum f.* sp. *vasinfectum* | 2 | 0 | 0 | 2 | 1.40 |
| *Fusarium proliferatum* | 2 | 10 | 1 | 13 | 9.09 |
| *Fusarium pseudograminearum* | 0 | 1 | 0 | 1 | 0.70 |
| *Fusarium subglutinans* | 0 | 1 | 0 | 1 | 0.70 |
| *Gibberella acuminata* | 1 | 0 | 0 | 1 | 0.70 |
| *Gibberella* sp. | 2 | 8 | 0 | 10 | 6.99 |
| *Hypocrea lixii* | 3 | 0 | 0 | 3 | 2.10 |
| Leaf litter ascomycetes | 0 | 0 | 1 | 1 | 0.70 |
| *Leptosphaeria avenaria f.* sp. *triticea* | 1 | 0 | 0 | 1 | 0.70 |
| *Leptosphaeria bicolor* | 0 | 1 | 0 | 1 | 0.70 |
| *Monographella* sp. | 0 | 1 | 0 | 1 | 0.70 |
| *Myrothecium melanosporum* | 3 | 0 | 0 | 3 | 2.10 |
| *Myrothecium verrucaria* | 0 | 2 | 0 | 2 | 1.40 |
| *Nigrospora oryzae* | 0 | 1 | 0 | 1 | 0.70 |
| *Parasarcopodium ceratocaryi* | 0 | 1 | 0 | 1 | 0.70 |
| *Penicillium citreonigrum* | 1 | 0 | 0 | 1 | 0.70 |
| *Periconia macrospinosa* | 0 | 2 | 0 | 2 | 1.40 |
| *Phaeosphaeria* sp. | 1 | 0 | 0 | 1 | 0.70 |
| *Phoma glomerata* | 1 | 0 | 0 | 1 | 0.70 |
| Pleosporaceae sp. | 0 | 1 | 0 | 1 | 0.70 |
| *Pseudozyma flocculosa* | 0 | 1 | 0 | 1 | 0.70 |
| Sordariomycete sp. | 1 | 1 | 2 | 4 | 2.80 |
| *Sporisorium everhartii* | 0 | 10 | 0 | 10 | 6.99 |
| *Stachybotrys bisbyi* | 1 | 0 | 0 | 1 | 0.70 |
| *Stachybotrys elegans* | 2 | 0 | 3 | 5 | 3.50 |
| Uncultured Ascomycete sp. | 1 | 0 | 0 | 1 | 0.70 |
| Uncultured endophytic fungus | 2 | 1 | 0 | 3 | 2.10 |
| Uncultured root-associated fungus | 0 | 1 | 0 | 1 | 0.70 |
| Uncultured soil fungus | 1 | 0 | 0 | 1 | 0.70 |

TABLE 4

Temporal distributions of endophytic fungal species in switchgrass root tissues from the tallgrass prairie.

| | Month & Species Distribution | | | | |
|---|---|---|---|---|---|
| Species | April | July | October | Total | Percent |
| *Alternaria alternata* | 0 | 0 | 1 | 1 | 0.24 |
| *Alternaria longissima* | 1 | 0 | 0 | 1 | 0.24 |
| *Alternaria mali* | 2 | 0 | 0 | 2 | 0.49 |
| *Amyloathelia crassiuscula* | 1 | 0 | 0 | 1 | 0.24 |
| *Anthostomella brabeji* | 1 | 0 | 0 | 1 | 0.24 |
| Ascomycete sp. | 2 | 2 | 5 | 9 | 2.18 |
| *Codinaeopsis* sp. | 3 | 1 | 4 | 8 | 1.94 |

TABLE 4-continued

Temporal distributions of endophytic fungal species in switchgrass root tissues from the tallgrass prairie.

| Species | Month & Species Distribution April | July | October | Total | Percent |
|---|---|---|---|---|---|
| *Coprinus auricomus* | 2 | 0 | 0 | 2 | 0.49 |
| *Diaporthe phaseolorum* | 0 | 1 | 2 | 3 | 0.73 |
| *Didymella fabae* | 0 | 1 | 0 | 1 | 0.24 |
| Dothideomycete sp. | 0 | 1 | 0 | 1 | 0.24 |
| *Eladia saccula* | 0 | 1 | 0 | 1 | 0.24 |
| *Eutypella* sp. | 1 | 0 | 0 | 1 | 0.24 |
| Fungal endophyte | 3 | 3 | 0 | 6 | 1.46 |
| *Fusarium acuminatum* | 2 | 1 | 0 | 3 | 0.73 |
| *Fusarium moniliformae* | 2 | 6 | 3 | 11 | 2.67 |
| *Fusarium nygamai* | 31 | 23 | 29 | 83 | 20.15 |
| *Fusarium oxysporum* | 0 | 3 | 0 | 3 | 0.73 |
| *Fusarium oxysporum f. ciceris* | 0 | 1 | 0 | 1 | 0.24 |
| *Fusarium proliferatum* | 0 | 21 | 2 | 23 | 5.58 |
| *Fusarium solani* | 0 | 1 | 0 | 1 | 0.24 |
| *Fusarium* sp. | 4 | 4 | 4 | 12 | 2.91 |
| *Gaeumannomyces graminis* var. *tritici* | 0 | 0 | 3 | 3 | 0.73 |
| *Gaeumannomyces incrustans* | 7 | 16 | 34 | 57 | 13.83 |
| *Gibberella* sp. | 1 | 0 | 1 | 2 | 0.49 |
| Grass root mycorrhizal sp. | 0 | 0 | 2 | 2 | 0.49 |
| *Halorosellinia* sp. | 2 | 0 | 0 | 2 | 0.49 |
| *Hypocrea lixii* | 1 | 0 | 1 | 2 | 0.49 |
| *Kabatiella microsticta* | 1 | 0 | 0 | 1 | 0.24 |
| *Macrophomina phaseolina* | 1 | 1 | 0 | 2 | 0.49 |
| *Magnaporthe rhizophila* | 0 | 14 | 22 | 36 | 8.74 |
| *Marasmius nigrobrunneus* | 0 | 0 | 1 | | 0.24 |
| *Microdiplodia* sp. | 0 | 0 | 1 | | 0.24 |

TABLE 4-continued

Temporal distributions of endophytic fungal species in switchgrass root tissues from the tallgrass prairie.

| Species | Month & Species Distribution April | July | October | Total | Percent |
|---|---|---|---|---|---|
| *Microdochium* sp. | 4 | 1 | 0 | 5 | 1.21 |
| Mycorrhizal fungal sp. | 0 | 1 | 0 | | 0.24 |
| *Myrothecium cinctum* | 0 | 1 | 0 | | 0.24 |
| *Myrothecium melanosporum* | 0 | 0 | 1 | | 0.24 |
| *Penicillium camemberti* | 0 | 0 | 1 | | 0.24 |
| *Penicillium* sp. | 0 | 0 | 1 | | 0.24 |
| *Penicillium verruculosum* | 1 | 0 | 0 | | 0.24 |
| *Periconia macrospinosa* | 20 | 9 | 2 | 31 | 7.52 |
| *Phoma medicaginis* | 0 | 1 | 0 | | 0.24 |
| *Rhizoctonia praticola* | 0 | 0 | 1 | | 0.24 |
| *Rhizopycnis* sp. | 0 | 1 | 2 | 3 | 0.73 |
| Sordariomycete sp. | 0 | 2 | 13 | 15 | 3.64 |
| *Trichoderma aureoviride* | 0 | 0 | 1 | 1 | 0.24 |
| *Trichoderma koningiopsis* | 0 | 1 | 0 | 1 | 0.24 |
| Uncultured Ascomycete sp. | 4 | 4 | 0 | 8 | 1.94 |
| Uncultured endophytic fungus | 0 | 2 | 0 | 2 | 0.49 |
| Uncultured Fungus | 1 | 3 | 0 | 4 | 0.97 |
| Uncultured Helotiales | 1 | 1 | 0 | 2 | 0.49 |
| Uncultured *Hypocreales* | 1 | 3 | 0 | 4 | 0.97 |
| Uncultured *Lachnum* | 0 | 0 | 1 | 1 | 0.24 |
| Uncultured Leptosphaeriaceae | 1 | 2 | 0 | 3 | 0.73 |
| Uncultured Nectriaceae | 1 | 0 | 0 | 1 | 0.24 |
| Uncultured root-associated fungus | 1 | 17 | 16 | 34 | 8.25 |
| Uncultured soil fungus | 1 | 2 | 1 | 4 | 0.97 |
| *Waitea circinata* var. *zeae* | 0 | 0 | 1 | 1 | 0.24 |

TABLE 5

Fungal taxa, species, and species diversity in switchgrass endophytic fungal communities from the tallgrass prairie.

| Parameter | Comparisons | Number of taxa | Number of species | Shannon Index ($H_S$) | t-value | Degree of freedom | P value |
|---|---|---|---|---|---|---|---|
| Shoot | April vs. July | 46 vs. 83 | 30 vs. 28 | 3.241 vs. 2.898 | 2.775 | 127 | <0.001 |
| Shoot | April vs. October | 46 vs. 14 | 30 vs. 7 | 3.241 vs. 1.730 | 7.158 | 58 | <0.001 |
| Shoot | July vs. October | 83 vs. 14 | 28 vs. 7 | 2.898 vs. 1.730 | 6.167 | 95 | <0.001 |
| Root | April vs. July | 104 vs. 152 | 30 vs. 34 | 2.610 vs. 2.865 | 4.476 | 254 | <0.001 |
| Root | April vs. October | 104 vs. 156 | 30 vs. 28 | 2.610 vs. 2.512 | 1.631 | 258 | >0.100 |
| Root | July vs. October | 152 vs. 156 | 34 vs. 28 | 2.865 vs. 2.512 | 6.920 | 306 | <0.001 |
| April | Shoot vs. Root | 46 vs. 104 | 30 vs. 30 | 3.241 vs. 2.610 | 5.311 | 148 | <0.001 |
| July | Shoot vs. Root | 83 vs. 152 | 28 vs. 34 | 2.898 vs. 2.865 | 0.497 | 233 | >0.500 |
| October | Shoot vs. Root | 14 vs. 156 | 7 vs. 28 | 1.730 vs. 2.512 | 4.237 | 168 | <0.001 |
| All three months | Shoot vs. Root | 143 vs. 412 | 51 vs. 58 | 3.456 vs. 3.006 | 9.857 | 553 | <0.001 |

TABLE 6

Fungal taxa, species, and species diversity in switchgrass endophytic fungal communities from the east and west parts of the tallgrass prairie.

| Month | Plant Part | Part of Prairie | Number of taxa | Number of species | Shannon Index ($H_S$) | t-value | Degree of freedom | P value |
|---|---|---|---|---|---|---|---|---|
| April | Shoot | East vs. West | 18 vs. 28 | 14 vs. 19 | 2.553 vs. 2.818 | 1.060 | 44 | >0.200 |
| | Root | East vs. West | 67 vs. 37 | 20 vs. 17 | 2.292 vs. 2.358 | 0.555 | 102 | >0.500 |
| July | Shoot | East vs. West | 44 vs. 39 | 21 vs. 15 | 2.752 vs. 2.486 | 1.965 | 81 | >0.050 |
| | Root | East vs. West | 82 vs. 70 | 23 vs. 25 | 2.647 vs. 2.770 | 1.477 | 150 | >0.100 |
| October | Shoot | East vs. West | 7 vs. 7 | 5 vs. 3 | 1.550 vs. 1.004 | 1.491 | 12 | >0.100 |
| | Root | East vs. West | 81 vs. 75 | 19 vs. 19 | 2.319 vs. 2.420 | 1.407 | 154 | >0.100 |
| All three months | Shoot | East vs. West | 69 vs. 74 | 33 vs. 29 | 3.166 vs. 3.071 | 0.949 | 141 | >0.300 |
| | Root | East vs. West | 230 vs. 182 | 38 vs. 42 | 2.787 vs. 2.957 | 4.464 | 410 | <0.001 |

TABLE 7

Organic matter, macronutrients and sodium contents, and pH content in the soils from the east and west parts of the tallgrass prairie.

| Parameter | Part of Prairie | Mean | Standard error | t-value (at 22 df) | P value |
|---|---|---|---|---|---|
| Organic matter (%) | East | 4.90 | 0.34 | 4.460 | 0.0002 |
| | West | 2.48 | 0.42 | | |
| Phosphorus (ppm) | East | 9 | 0.99 | 2.370 | 0.0267 |
| | West | 35 | 11 | | |
| Potassium (ppm) | East | 354 | 63 | 0.350 | 0.7310 |
| | West | 395 | 99 | | |
| Calcium (ppm) | East | 7684 | 654 | 3.540 | 0.0018 |
| | West | 4154 | 751 | | |
| Magnesium (ppm) | East | 412 | 41 | 1.540 | 0.1380 |
| | West | 599 | 114 | | |
| Sodium (ppm) | East | 40 | 8 | 2.080 | 0.0491 |
| | West | 96 | 26 | | |
| pH (1 to 14) | East | 7.5 | 0.16 | 0.090 | 0.9310 |
| | West | 7.5 | 0.24 | | |

TABLE 8

Ordinal distributions of switchgrass fungal endophytes in shoot and root tissues at different sampling months.

| | Sampling months & number of taxon | | | | | | Total Number of | | Percentage of | |
|---|---|---|---|---|---|---|---|---|---|---|
| | April | | July | | October | | Isolates | | Population | |
| Order | Shoot | Root | Shoot | Root | Shoot | Root | Shoot | Root | Shoot | Root |
| Agaricales | 0 | 2 | 0 | 0 | 0 | 1 | 0 | 3 | 0.00 | 0.73 |
| Boletales | 0 | 1 | 0 | 0 | 0 | 0 | 0 | 1 | 0.00 | 0.24 |
| Botryosphaeriales | 0 | 7 | 0 | 2 | 0 | 1 | 0 | 10 | 0.00 | 2.43 |
| Cantharellales | 0 | 0 | 0 | 0 | 0 | 1 | 0 | 1 | 0.00 | 0.24 |
| Capnodiales | 1 | 0 | 0 | 0 | 0 | 0 | 1 | 0 | 0.70 | 0.00 |
| Chaetosphaeriales | 0 | 1 | 1 | 1 | 0 | 4 | 1 | 6 | 0.70 | 1.46 |
| Corticiales | 0 | 0 | 0 | 0 | 0 | 1 | 0 | 1 | 0.00 | 0.24 |
| Diaporthales | 0 | 0 | 0 | 1 | 0 | 2 | 0 | 3 | 0.00 | 0.73 |
| Dothideales | 0 | 1 | 0 | 0 | 0 | 0 | 0 | 1 | 0.00 | 0.24 |
| Eurotiales | 1 | 1 | 0 | 1 | 0 | 2 | 1 | 4 | 0.70 | 0.97 |
| Helotiales | 0 | 1 | 0 | 1 | 0 | 1 | 0 | 3 | 0.00 | 0.73 |
| Hypocreales | 28 | 43 | 52 | 75 | 11 | 44 | 91 | 162 | 63.64 | 39.32 |
| Incertae sedis | 1 | 0 | 1 | 2 | 2 | 13 | 4 | 15 | 2.80 | 3.64 |
| Magnaporthales | 0 | 7 | 0 | 19 | 0 | 39 | 0 | 65 | 0.00 | 15.78 |
| Not assigned | 2 | 0 | 2 | 16 | 0 | 22 | 4 | 38 | 2.80 | 9.22 |
| Pleosporales | 6 | 24 | 12 | 12 | 0 | 3 | 18 | 39 | 12.59 | 9.47 |
| Trichosphaeriales | 0 | 0 | 1 | 0 | 0 | 0 | 1 | 0 | 0.70 | 0.00 |
| Unknown | 6 | 12 | 2 | 22 | 1 | 22 | 9 | 56 | 6.29 | 13.59 |
| Ustilaginales | 0 | 0 | 11 | 0 | 0 | 0 | 11 | 0 | 7.69 | 0.00 |
| Xylariales | 1 | 4 | 1 | 0 | 0 | 0 | 2 | 4 | 1.40 | 0.97 |
| Total | 46 | 104 | 83 | 152 | 14 | 156 | 143 | 412 | 100 | 100 |

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit, and scope of the invention. More specifically, it will be apparent that certain agents which are both chemically and physiologically related may be substituted for the agents described herein, while the same or similar results would be achieved. All such similar substitutes and modifications apparent to those skilled in the art are deemed to be within the spirit, scope, and concept of the invention as defined by the appended claims.

REFERENCES

The references listed below are incorporated herein by reference to the extent that they supplement, explain, provide a background for, or teach methodology, techniques, and/or compositions employed herein.

U.S. Pat. No. 6,111,170

International PCT Publication WO 99/29177

Abbott L K, Robson A L (1984) The effect of VA mycorrhizae on plant growth. In: VA Mycorrhiza (eds. Powell C L, Bagyaraj D J), pp. 113-130. CRC Press, Boca Raton, Fla.

Ahmad A, et al. (2001) Fungal endophyte enhances biomass production and essential oil yield of east Indian lemongrass. *Symbiosis* 30, 275-285.

Arnold A E, et al. (2003) Fungal endophytes limit pathogen damage in a tropical tree. *Proc. Natl. Acad. Sci. USA* 100, 15649-15654.

Bischoff K M, et al. (2009) Extracellular hemicellulolytic enzymes from the maize endophyte *Acremonium zeae. Current Microbiology* 58, 499-503.

Bouton J (2007) The economic benefits of forage improvement in the United States. *Euphytica* 154, 263-270.

Bouton J (2008) Improvement of switchgrass as a bioenergy crop. In: Genetic Improvement of Bioenergy Crops (ed. Vermerris W), pp. 295-308. Springer Science and Business Media.

Bowman K O, et al. (1971) Comments on distribution of indices of diversity. In:

Statistical Ecology, Many Species, Populations, Ecosystem and System Analysis (eds. Patil G P, Pielou E C, Waters W E), pp. 315-359. The Pennsylvania State University Press, University Park, Pa.

Bush L P, et al. (1997) Bioprotective alkaloids of grass-fungal endophyte symbioses. *Plant Physiology* 114, 1-7.

Choi G J, et al. (2009) Biocontrol activity of *Acremonium strictum* BCP against Botrytis diseases. *Plant Pathology Journal* 25, 165-171.

Christensen M J, et al. (2000) Infection of tall fescue and perennial ryegrass plants by combinations of different Neotyphodium endophytes. *Mycological Research* 104, 974-978.

Clay K, et al. (1989) Impact of fungus *Balansia henningsiana* on *Panicum agrostoides*: frequency of infection, plant growth and reproduction, and resistance to pests. *Oecologia* 80, 374-380.

Clay K, Schardl C (2002) Evolutionary origins and ecological consequences of endophyte symbiosis with grasses. *American Naturalist* 160, S99-S127.

de Jong E V, et al. (2008) Global genetic diversity of the perennial ryegrass fungal endophyte *Neotyphodium lolii. Crop Science* 48, 1487-1501.

Dongyi H, Kelemu S (2004) *Acremonium implicatum*, a seed-transmitted endophytic fungus in Brachiaria grasses. *Plant Disease* 88, 1252-1254.

Evans J W (2006) Commercialization of AR1 in Australia. In: International Symposium on Fungal Endophytes of Grasses (eds. Popay A J, Thom E R), pp. 241-242. New Zealand Grassland Association, Christchurch, New Zealand.

Gardes M, Bruns T D (1993) ITS primers with enhanced specificity for *Basidimycetes*—application to the identification of mycorrhizae and rusts. *Molecular Ecology* 2, 113-118.

George E, et al. (1995) Role of arbuscular mycorrhizal fungi in uptake of phosphorus and nitrogen from soil. Critical Reviews in *Biotechnology* 15, 257-270.

Ghimire S R, et al. (2009) The mycorrhizal fungus, *Sebacina vermifera*, enhances seed germination and biomass production in switchgrass (*Panicum virgatum* L). *Bioenergy Research* 2, 51-58.

Groth J V, Roelfs A P (1987) The concept of measurement of phenotypic diversity in *Puccinia graminis* on wheat. *Phytopathology* 77, 1395-1399.

Hamilton R G (1996) Using fire and bison to restore a functional tallgrass prairie landscape. In: Transactions of the 61st North American Wildlife and Natural Resource Conference, pp. 208-214. Wildlife Management Institute Tulsa, Okla.

Horinouchi H, et al. (2007) *Fusarium equiseti* GF191 as an effective biocontrol agent against *Fusarium* crown and root rot of tomato in rock wool systems. *Crop Protection* 26, 1514-1523.

Kaur R, et al. (2010) Nonpathogenic *Fusarium* as a biological control agent. *Plant Pathology Journal* 9, 88-100.

Kelemu S, et al. (2001) An endophyte of the tropical forage grass *Brachiaria brizantha*: Isolating, identifying, and characterizing the fungus, and determining its antimycotic properties. *Canadian Journal of Microbiology* 47, 55-62.

Linderman R G, Hendrix J W (1982) Evaluation of plant response to colonization by vascular-arbuscular mycorrhizal fungi: A. Host variables. In: Methods and principles of mycorrhizal research (ed. Schenck N C), pp. 69-76. American Phytopathological Society, St. Paul, Minn.

Martin K J, Rygiewicz P T (2005) Fungal-specific PCR primers developed for analysis of the ITS region of environmental DNA extracts. *BMC Microbiology* 5.

Milne G D (2006) Technology transfer of novel ryegrass endophyte in New Zealand. In: Internation Symposium on Fungal Endophytes of Grasses (eds. Popay A J, Thom E R), pp. 237-239. New Zealand Grassland Association, Christchurch, New Zealand.

National Park Service (2010) Last stand of the tallgrass prairie. Tallgrass Prairie National Preserve Cottonwood Falls, Kans.

Pedersen J F, et al. (1990) A review of the agronomic characteristics of endophyte free and endophyte infected tall fescue. *Applied Agricultural Research* 5, 188-194.

Petrini O (1986) Taxonomy of endophytic fungi of aerial plant tissues. In: Microbiology of the Phyllosphere (eds. Fokkema N J, Van Den Heuvel J), pp. 175-187. Cambridge University Press, New York, USA; London, UK.

Puckette M, et al. (2009) Ozone responsive genes in *Medicago truncatula*: Analysis by suppression subtraction hybridization. *Journal of Plant Physiology* 166, 1284-1295.

Safir G R, Boyer J S (1971) Mycorrhizal enhancement of water transport in soybean. *Science* 172, 581-583.

Sanderson M A, et al. (1996) Switchgrass as a sustainable bioenergy crop. *Bioresource Technology* 56, 83-93.

SAS (2004) PROC IML. SAS Institute Inc., Cary, N.C.

Schardl C L, et al. (2004) Symbioses of grasses with seed borne fungal endophytes. *Annual Review of Plant Biology* 55, 315-340.

Singh A, et al. (2000) Plant productivity determinants beyond minerals, water and light: *Piriformospora indica*—A revolutionary plant growth promoting fungus. *Current Science* 79, 1548-1554.

Stovall M E, Clay K (1988) The effect of the fungus, *Balansia cyperi* on growth and reproduction of purple nutsedge, *Cyperus rotundus. New Phytologist* 109, 351-359.

Sylvia D M, Williams S E (1992) Vesicular-arbuscular mycorrhizae and environmental stress. In: Mycorrhizae in sustainable agriculture (eds. Bethlenfalvay G J, Linderman R G), pp. 101-124. *American Society of Agronomy*, Madison, Wis.

USDA (1985) Soil survey of Grant County, Oklahoma, p. 117. United States Department of Agriculture and Soil Conservation Services.

USDA (2007a) Supplement to the soil survey of Alfalfa County, Oklahoma, p. 107. United States Department of Agriculture and Natural Resources Conservation Services.

USDA (2007b) Supplement to the soil survey of the Kay County, Oklahoma, p. 127. United States Department of Agriculture and Natural Resources Conservation Services.

USDA (2008) Supplement to the soil survey of Osage County, Oklahoma, p. 145. United Stated Department of Agriculture and Natural Resources Conservation Services.

Vogel K P, et al. (2002) Switchgrass biomass production in the Midwest USA: Harvest and nitrogen management. *Agronomy Journal* 94, 413-420.

Waller F, et al. (2005) The endophytic fungus *Piriformospora indica* reprograms barley to salt-stress tolerance, disease resistance, and higher yield. *Proc. Natl. Acad. Sci. USA* 102, 13386-13391.

White T J, et al. (1990) Amplification and direct sequencing of fungal ribosomal RNA genes for phylogenetics. In: PCR Protocols: A guide to methods and applications (eds. Innis M A, Gelfand D H, Sninsky J J, White T J). Academic Press Inc., New York.

Wicklow D T, et al. (2005) A protective endophyte of maize: *Acremonium zeae* antibiotics inhibitory to *Aspergillus flavus* and *Fusarium verticillioides. Mycological Research* 109, 610-618.

Yang J D, et al. (2009) Natural variation for nutrient use and remobilization efficiencies in switchgrass. *Bioenergy Research* 2, 257-266.

What is claimed is:

1. A synthetic combination of a grass plant and an *Acremonium* spp. fungal endophyte, wherein the fungal endophyte comprises a rDNA sequence comprising SEQ ID NO:82, and wherein the fungal endophyte colonizes a root tissue of the grass plant.

2. The synthetic combination of claim 1, wherein the grass plant is an agronomically elite grass plant.

3. The synthetic combination of claim 1, wherein the grass plant is a transgenic grass plant.

4. The synthetic combination of claim 3, wherein the transgenic grass plant comprises a transgene that confers herbicide tolerance, drought resistance, insect resistance, fungus resistance, virus resistance, bacteria resistance, male sterility, cold tolerance, salt tolerance, increased yield, enhanced nutrient use efficiency, increased fermentable carbohydrate content, or reduced lignin content.

5. The synthetic combination of claim 4, wherein the transgenic grass plant comprises a transgene that confers reduced lignin content.

6. The synthetic combination of claim 1, wherein the grass plant is wheat, durum wheat, tall wheatgrass, western wheatgrass, maize, rice, sorghum, meadow fescue, tall fescue, cereal rye, Russian wild rye, oats, bermudagrass, Kentucky bluegrass, big bluestem, little bluestem, *Miscanthus* sp., *Miscanthus×giganteus*, blue grama, black grama, side-oat grama, johnsongrass, buffalograss, creeping bentgrass, switchgrass, or sugarcane.

7. The synthetic combination of claim 6, wherein the grass plant is a switchgrass plant.

8. The synthetic combination of claim 7, wherein the switchgrass plant is an agronomically elite switchgrass plant.

9. The synthetic combination of claim 1, wherein the fungal endophyte colonizes a stem tissue of the grass plant.

10. The synthetic combination of claim 1, wherein the grass plant displays increased biomass or vigor relative to a host grass plant of the same genotype that lacks the endophyte, when grown under the same conditions.

11. The synthetic combination of claim 1, wherein the host grass plant is artificially inoculated with the endophyte.

12. The synthetic combination of claim 1, wherein the endophyte protects the host grass plant from biotic or abiotic stresses.

13. The synthetic combination of claim 12 wherein the abiotic stress is selected from the group consisting of: water deficiency, nutrient deficiency, heat stress, salt toxicity, aluminum toxicity, heavy metal toxicity, and freezing temperatures.

14. The synthetic combination of claim 12 wherein the biotic stress is selected from the group consisting of: insect infestation, rust infection, nematode infestation, and herbivore grazing.

15. The synthetic combination of claim 1, wherein the combination is achieved by introduction of the endophyte to the host grass by a method selected from the group consisting of: inoculation, infection, grafting, and combinations thereof.

16. The synthetic combination of claim 1, wherein the host plant is a forage grass host plant.

17. A commodity product comprising a synthetic combination of a harvested grass plant or part thereof and an *Acremonium* spp. fungal endophyte comprising a rDNA sequence comprising SEQ ID NO:82, and wherein the fungal endophyte colonizes a root tissue of the grass plant.

18. The commodity product of claim 17, wherein the product is a biofuel feedstock or an animal feed.

19. A seed comprising a synthetic combination of an *Acremonium* spp. fungal endophyte and a grass plant embryo, wherein the fungal endophyte comprises a rDNA sequence comprising SEQ ID NO:82, and wherein the fungal endophyte colonizes a root tissue of the grass plant.

20. A grass seed comprising a seed-coat comprising an *Acremonium* spp. fungal endophyte comprising a rDNA sequence comprising SEQ ID NO:82, and wherein the fungal endophyte colonizes a root tissue of the grass plant.

21. A method for propagating a grass plant-fungal endophyte combination, comprising:

a) obtaining a synthetic combination of a grass plant and an *Acremonium* spp. fungal endophyte comprising a rDNA sequence comprising SEQ ID NO:82; and b) vegetatively reproducing the grass plant tissue, wherein the fungal endophyte colonizes a root tissue of the grass plant.

22. A method for cultivating a grass plant comprising: contacting the host grass plant with an *Acremonium* spp. fungal endophyte, such that the endophyte colonizes the plant, wherein the fungal endophyte comprises a rDNA sequence comprising SEQ ID NO:82, and wherein the fungal endophyte colonizes a root tissue of the grass plant.

23. The method of claim 22, wherein the grass plant has enhanced root growth, more tillers, enhanced total biomass, or enhanced seed yield relative to a host grass plant of the same genotype that lacks the endophyte, when grown under the same conditions.

24. The method of claim 22, wherein the grass plant displays tolerance to stress as relative to a host grass plant of the same genotype that lacks the endophyte, when grown under the same conditions.

25. The method of claim 24, wherein said stress is selected from the group consisting of a biotic stress, a pest stress, an insect stress, an abiotic stress, and a water deficit stress.

26. The method of claim 24, wherein the stress is biotic stress caused by at least one organism selected from the group consisting of a mammalian herbivore, a microbial pathogen, and an insect.

27. The method of claim 24, wherein the stress is abiotic stress selected from the group consisting of: water deficiency, nutrient deficiency, heat stress, salt toxicity, aluminum toxicity, heavy metal toxicity, and freezing temperatures.

28. The method of claim 22, wherein colonization of the grass is achieved by introduction of the fungal endophyte to the grass by a method selected from the group consisting of inoculation, infection, grafting, and combinations thereof.

29. A method for increasing the biomass of a grass plant comprising: contacting the grass plant with an *Acremonium* spp. fungal endophyte comprising a rDNA sequence comprising SEQ ID NO:82, wherein the fungal endophyte colonizes a root tissue of the grass plant, and wherein the plant exhibits increased biomass relative to a grass plant of the same genotype that lacks the endophyte, when grown under the same conditions.

30. A method for producing a biofuel comprising: obtaining a grass plant comprising an *Acremonium* spp. fungal endophyte comprising a rDNA sequence comprising SEQ ID NO:82, wherein the fungal endophyte colonizes a root tissue of the grass plant; and producing biofuel therefrom.

31. The method of claim 30, wherein the biofuel is ethanol.

* * * * *